(12) United States Patent
Berman et al.

(10) Patent No.: US 7,790,709 B2
(45) Date of Patent: Sep. 7, 2010

(54) HETEROCYCLIC COMPOUNDS, METHODS OF MAKING THEM AND THEIR USE IN THERAPY

(75) Inventors: Judd M. Berman, Toronto (CA); Peter Sampson, Toronto (CA); Heinz W. Pauls, Toronto (CA); Jailall Ramnauth, Toronto (CA); David Douglas Manning, Duanesburg, NY (US); Matthew D. Surman, Albany, NY (US); Dejian Xie, Glenmount, NY (US); Helene Y. Decornez, Clifton Park, NY (US)

(73) Assignee: Affinium Pharmaceuticals, Inc., Toronto (CA)

( * ) Notice: Subject to any disclaimer, the term of this patent is extended or adjusted under 35 U.S.C. 154(b) by 111 days.

(21) Appl. No.: 10/537,747

(22) PCT Filed: Dec. 5, 2003

(86) PCT No.: PCT/US03/38706

§ 371 (c)(1), (2), (4) Date: Mar. 27, 2006

(87) PCT Pub. No.: WO2004/052890

PCT Pub. Date: Jun. 24, 2004

(65) Prior Publication Data

US 2006/0183908 A1    Aug. 17, 2006

Related U.S. Application Data

(60) Provisional application No. 60/431,406, filed on Dec. 6, 2002, provisional application No. 60/465,583, filed on Apr. 25, 2003.

(51) Int. Cl.

| | |
|---|---|
| A01N 43/00 | (2006.01) |
| A01N 43/62 | (2006.01) |
| A61K 31/55 | (2006.01) |
| C07D 243/00 | (2006.01) |
| C07D 487/22 | (2006.01) |
| C07D 491/00 | (2006.01) |
| C07D 498/00 | (2006.01) |
| C07D 487/00 | (2006.01) |

(52) U.S. Cl. .................. 514/213.01; 514/221; 540/555; 540/577

(58) Field of Classification Search .................. None
See application file for complete search history.

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey et al. |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody et al. |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe et al. |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Cagle et al. |
| 6,399,629 B1 | 6/2002 | Chamberland et al. |
| 6,406,880 B1 | 6/2002 | Thornton |
| 6,423,341 B1 | 7/2002 | Yamaguchi et al. |

(Continued)

FOREIGN PATENT DOCUMENTS

CA    2444597    10/2002

(Continued)

OTHER PUBLICATIONS

Sladowska et al. Farmaco, Edizione Scientifica, 1986, 41(12), 954-963.*

(Continued)

*Primary Examiner*—James O Wilson
*Assistant Examiner*—Noble Jarrell
(74) *Attorney, Agent, or Firm*—Goodwin Procter LLP

(57) ABSTRACT

In part, the present invention is directed to antibacterial compounds of formula (I) wherein A is a bicyclic heteroaryl ring or a tricyclic ring and $R_2$ is an heterocyclic residue; L is a bond, or L is alkyl, alkenyl or cycloalkyl.

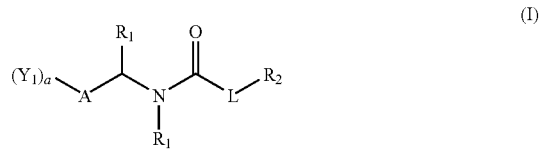

14 Claims, 8 Drawing Sheets

U.S. PATENT DOCUMENTS

| | | |
|---|---|---|
| 6,423,741 B1 | 7/2002 | Khanuja et al. |
| 6,428,579 B1 | 8/2002 | Valentini |
| 6,432,444 B1 | 8/2002 | Fischetti et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe et al. |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw et al. |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki et al. |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 6/2003 | Heerding et al. |
| 6,573,272 B1 | 6/2003 | Miller et al. |
| 6,673,941 B2 | 1/2004 | Heerding et al. |
| 6,673,961 B2 | 1/2004 | Connor et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | Dewolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,524,843 B2 | 4/2009 | Miller et al. |
| 7,557,125 B2 | 7/2009 | Miller et al. |
| 2003/0232850 A1 | 12/2003 | Miller et al. |
| 2004/0053814 A1 | 3/2004 | Brandt et al. |
| 2005/0250810 A1 | 11/2005 | Miller et al. |
| 2006/0116394 A1 | 6/2006 | Burgess et al. |
| 2006/0142265 A1 | 6/2006 | Berman et al. |
| 2006/0183908 A1 | 8/2006 | Berman et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |
| 2009/0275572 A1 | 11/2009 | Miller et al. |

FOREIGN PATENT DOCUMENTS

| | | |
|---|---|---|
| EP | 0407200 | 1/1991 |
| EP | 1000935 | 5/2000 |
| HU | 0203122 | 1/1988 |
| HU | 210679 | 7/1993 |
| WO | WO-93/04035 | 3/1993 |
| WO | WO-9518619 | 7/1995 |
| WO | WO-9600730 | 1/1996 |
| WO | WO-9748696 | 12/1997 |
| WO | WO-9857952 | 12/1998 |
| WO | WO-99/24406 | 5/1999 |
| WO | WO-00/27628 | 5/2000 |
| WO | WO-00/57933 | 10/2000 |
| WO | WO-0126652 | 4/2001 |
| WO | WO-0126654 | 4/2001 |
| WO | WO-0127103 | 4/2001 |
| WO | WO 0127103 * | 4/2001 |
| WO | WO-01/41573 | 6/2001 |
| WO | WO-0148248 | 7/2001 |
| WO | WO-01/70172 | 9/2001 |
| WO | WO-02/10332 | 2/2002 |
| WO | WO-0242273 | 5/2002 |
| WO | WO-0248097 | 6/2002 |
| WO | WO-02/064572 | 8/2002 |
| WO | WO 02064572 * | 8/2002 |
| WO | WO-03/086396 | 10/2003 |
| WO | WO-2004/014869 | 2/2004 |
| WO | WO-2004052890 | 6/2004 |
| WO | WO-2004/082586 | 9/2004 |
| WO | WO-2007/053131 | 5/2007 |
| WO | WO-2007/067416 | 6/2007 |
| WO | WO-2008/009122 | 1/2008 |

OTHER PUBLICATIONS

U.S. Appl. No. 11/628,569, filed Dec. 11, 2009, Sargent et al., Therapeutic Agents and Methods of Making and Using Same, Pending.

PCT/US06/45903, filed Dec. 1, 2006, Therapeutic Agents and Methods of Making and Using Same, Pending.

Claus et al., *Monatsh. Chem.* 97:271-279 (1966).

Hungarian Search Report dated Dec. 31, 2003.

International Search Report dated Oct. 4, 2000 for PCT/US2000/15154.

International Search Report dated Jan. 25, 2001 for PCT/US2000/27844.

International Search Report dated Jan. 29, 2001 for PCT/US2000/27591.

International Search Report dated Feb. 22, 2001 for PCT/US2000/27619.

International Search Report dated Apr. 21, 2004 for PCT/US2003/38706.

International Search Report dated Oct. 13, 2004 for PCT/IB2004/001261.

International Search Report dated Apr. 20, 2005 for PCT/US2002/10332.

International Search Report dated Jun. 14, 2007 for PCT/US2005/019805.

International Search Report dated Sep. 12, 2007 for PCT/US2006/045903.

International Search Report dated Oct. 26, 2007 for PCT/CA2007/001277.

International Search Report dated Apr. 7, 2008 for PCT/CA2008/000300.
Patent Abstract of Japan vol. 2000, No. 02, Feb. 29, 2000, JP 11-302173.
Payne et al., *Drug Discovery Today*, 2008 pp. 537-541.
Seefeld et al., "Indole Naphthyridinones as Inhibitors of Bacterial Enoyl-ACP Reductases FabI and FabK" *J. Med. Chem.* 46:1627-1635 (2003).
Sladowska et al. "Synthesis and properties of amides of 1-benzyl-3-methyl and 1-butyl-3-phenyl-7-methyl-4-oxo-2-thioxo (2,4-dioxo)-1,2,3,4-tetrahydropyrido-[2,3-d]pyrimidine-6-carboxylic acids" *Farmaco Edizione Scientifica* 1986 41:954-963.
Bergler, Helmut, et al., "Protein EnvM is the NADH-dependent Enoyl-ACP Reductase (FabI) of *Escherichia coli*," J. Biological Chemistry, vol. 269, No. 8, Feb. 25, 1994, pp. 5493-5496.
Grassberger, Maximilian, et al., "Preparation and Antibacterial Activities of New 1,2,3-Diazaborine Derivatives and Analogues," J. Med. Chemistry, 1984, 27, 947-953.
Heath, Richard J., et al., "A Triclosan-Resistant Bacterial Enzyme," Nature, vol. 406, Jul. 13, 2000, p. 145-146.
Heath, Richard J., et al., "Regulation of Fatty Acid Elongation and Initiation by Acyl-Acyl Carrier Protein in *Escherichia coli*," J. Biological Chemistry, vol. 271, No. 4, Jan. 26, 1996, pp. 1833-1836.
Heck, Richard F., Organic Reactions, 1982, 27, pp. 345-390.
Levy, Colin W., et al., "Molecular Basis of Triclosan Activity," Nature, vol. 398, Apr. 1, 1999, pp. 383-384.
McMurray, Laura M., et al., "Triclosan Targets Lipid Synthesis," Nature, vol. 394, Aug. 4, 1998, pp. 531-532.
Turnowsky, Friederike, et al., "envM Genes of *Salmonella typhimurium* and *Escherichia coli*," J. Bacteriology, vol. 171, No. 12, Dec. 1989, pp. 6555-6565.
Ward, Walter H.J., et al., "Kinetic and Structural Characteristics of the Inhibition of Enoyl (Acyl Carrier Protein) Reductase by Triclosan," Biochemistry, 1999, vol. 38, No. 38, pp. 12514-12525.
Jossang-Yanagida, Akino, et al., "Tetrahydropyridoazepines and Tetrahydropyridoazepinones from the Corresponding Dihydroquinolones," J. Heterocyclic Chemistry, vol. 15, pp. 249-251.
Abou-Gharbia et al., "Psychotropic Agents: Synthesis and Antipysychotic Activity of Substituted B-Carbolines," J. Med. Chem., 30 (6): 1100-1115 (1987).
Jianxiong et al., "Synthesis and Antistaphylococcal Activity of Nematophin and Its Analogs," Bioorganic & Medicinal Chemistry Letters, Oxford, GB, 7(10): 1349-1352, (May 20, 1977) XP004136332.
Miller et al., Discovery of Aminopyridine-Based Inhibitors of Bacterial Enoyl-ACP Reductase (FABI); J. Med. Chem. 2002, vol. 45, pp. 3246-3256.
Misztal et al., "Synthesis and Pharmacologic Properties of Pyridol Derivatives of 3-Methylaminoindole 2-Methyltryptamine and Isotryptamine," Archivum Immnologiae et Therapiae Experimentalis, 24(6): 851-852 (1976).
Pachter et al., "The Chemistry of Hortiamine and 6-Methoxyhetsinine," J. Amer. Chem., 83:635-642 (1961).
Rehse et al., "Dopaminanaloge 1,2,3,4-Tetrahydro-B-Carboline," Arch. Pharm., 311(1): 11-18 (1978).
Shoji et al., "Two Novel Alkaloids from *Evodia rutaecarpa*," J. Natural Products, 52(5): 1160-1162 (1989).
Database CA on STN, AN 7:66733, Rosenmund et al., "Chemistry of indole II . . . ," *Chem Ber.* 103(2): 496-509.
Database CAOLD on STN, AN CA51:10524d, Hellman et al., "N-Mannich bases (VI) condensation . . . ," *Direct Submission* (1953).
Database CAPLUS on STN, An 1977:439214. Misztal et al., "Synthesis and pharmacologic properties of pyridoyl . . . ," Arch Immuno ther Exp. 24(6): 851-862 (1976).
Database Crossfire Beilstein, 1966, Database accession No. 2819049, 2819050, XP002216033.
Himmer et al., "Synthesis and Antibacterial in Vitro Activity of Novel Analogues of Nematophin," Bioorganic & Medicinal Chemistry Letters, 8(15): 2045-2050 (Aug. 1998).
Database CAPLUS on STN, AN 1986:68547, Stuetz, et al., "Synthesis and Structure Activity . . . ," *J Med Chem.* 29(1): 112-25, (1986).
Database CAPLUS on STN, AN 1991:428908, Fuse, et al., "Preparation of cinnamamide derivatives . . . ," EP407200A1. (1991).
Database CAPLUS on STN, AN 1999; 325910 Aslanian et al., "Preparation of phenylalkylimidazoles . . . ," WO99/24406. (1999).
Stutz et al., "Synthesis and Structure-Activity Relationships of Naftifine-Related Allylamine Antimycotics," Journal of Medicinal Chemistry, 1986, vol. 29, No. 1, 112-125.

\* cited by examiner

HETEROCYCLIC COMPOUNDS, METHODS OF MAKING THEM AND THEIR USE IN THERAPY

GOVERNMENT SUPPORT

This invention was made with support provided by the National Institute of Health; the government, therefore, has certain rights in the invention.

INTRODUCTION

Infections caused by or related to bacteria are a major cause of human illness worldwide, and the frequency of resistance to standard antibiotics has risen dramatically over the last decade. Hence, there exists an unmet medical need and demand for new agents acting against bacterial targets.

Examples of potential bacterial targets are those enzymes involved in fatty acid biosynthesis. While the overall pathway of saturated fatty acid biosynthesis is similar in all organisms, the fatty acid synthase (FAS) systems vary considerably with respect to their structural organization. It is believed that vertebrates and yeast possess a FAS in which all the enzymatic activities are encoded on one or two polypeptide chains, respectively, and the acyl carrier protein (ACP) is an integral part of the complex. In contrast, in bacterial FAS, it is known that each of the reactions is catalyzed by a distinct, monofunctional enzyme and the ACP is a discrete protein. Therefore, it may be possible to achieve selective inhibition of the bacterial system by appropriate agents.

One such potential bacterial target is the FabI protein. FabI (previously designated EnvM) is believed to function as an enoyl-ACP reductase in the final step of the four reactions involved in each cycle of bacterial fatty acid biosynthesis. It is believed that in this pathway, the first step is catalyzed by β-ketoacyl-ACP synthase, which condenses malonyl-ACP with acetyl-CoA (FabH, synthase III). It is believed that in subsequent rounds, malonyl-ACP is condensed with the growing-chain acyl-ACP (FabB and FabF, synthases I and II, respectively). The second step in the elongation cycle is thought to be ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP. Finaly, in step four, trans-2-enoyl-ACP is converted to acyl-ACP by an NADH (or NADPH)-dependent enoyl-ACP reductase (Fab I). Further rounds of this cycle, adding two carbon atoms per cycle, would eventually lead to palmitoyl-ACP (16C), where upon the cycle is stopped largely due to feedback inhibition of Fab I by palmitoyl-ACP. Thus, Fab I is believed to be a major biosynthetic enzyme and is a key regulatory point in the overall synthetic pathway of bacterial fatty acid biosynthesis.

In some bacteria the final step of fatty acid biosynthes is catalyzed by Fab I only, in others by FabK, an NADH and FMN dependent reductase, still others utilize both FabI and FabK. The present invention provides, in part, compounds and compositions with FabI inhibiting properties.

SUMMARY OF INVENTION

In part, the present invention is directed towards compounds with FabI inhibiting properties as well as other enzymes. Other uses for the subject compounds and compositions will be readily discernable to those of skill in the art.

In part, the present invention is directed towards compounds that will affect multiple species, so-called "wide spectrum" anti-bacterials. Alternatively, subject compounds that are selective for one or more bacterial or other non-mammalian species, and not for one or more mammalian species (especially human), may be identified.

In part, the present invention is directed towards pharmaceutical compositions comprising a compound with FabI inhibiting properties.

The subject compositions may be administered by one of a variety of means known to those of skill in the art. The subject compounds may be prepared as described herein and as known to those of skill in the art.

Whole-cell antimicrobial activity for the antibacterial compositions of the present invention may be determined by broth microdilution using the National Committee for Clinical Laboratory Standards (NCCLS) recommended procedure, Document M7-A5, "Methods for Dilution Susceptibility Tests for Bacteria that Grow Aerobically". The compositions of the present invention may be tested, for example, in serial two-fold dilutions ranging from 0.06 to 32 mcg/mL. A panel of up to 12 or more bacterial strains may be evaluated in the assay. A panel may consist of, for example, the following laboratory strains: *Enterococcus faecalis* 29212, *Staphylococcus aureus* 29213, *Staphylococcus aureus* 43300, *Moraxella catarrhalis* 49143, *Haemophilus influenzae* 49247, *Streptococcus pneumoniae* 49619, *Staphylococcus epidermidis* 1024939, *Staphylococcus epidermidis* 1024961, *Escherichia coli* AG100 (AcrAB$^+$), *Escherichia coli* AG 100A (AcrAB$^-$), *Pseudomonas aeruginosa* K767 (MexAB$^+$, OprM$^+$), *Pseudomonas aeruginosa* K1119 (MexAB$^-$, OprM$^-$). The minimum inhibitory concentration (MIC) may then be determined as the lowest concentration of the subject composition that inhibited visible growth. A spectrophotometer may be used to assist in determining the MIC endpoint.

Non-limiting examples of bacteria that the antibacterial compounds or compositions of the present invention may be used to either destroy or inhibit the growth of include a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Francisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus*, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis,* coagulase negative *Staphylococci, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium per-*

*fringens, Clostridium tetani, Clostridium botulinum, Treponema pallidum, Rickettsia rickettsii, Helicobacter pylori* or *Chlamydia trachomitis*.

In another aspect, the subject compounds or compositions may be used to treat bacterial infections.

In certain embodiments, the present invention provides antibacterial compositions of the present invention, and methods of using the same, for the reduction and abatement of at least one of the bacteria caused disorders or conditions based on a therapeutic regimen. In certain aspects, the present invention contemplates monitoring such disorders or conditions as part of any therapeutic regimen, which may be administered over the short-term and/or long-term. These aspects of the invention may be particularly helpful in preventive care regimes.

In another aspect of the present invention, the antibacterial compounds or compositions of the present invention may be used in the manufacture of a medicament to treat any of the foregoing bacteria related conditions or diseases. In certain embodiments, the present invention is directed to a method for formulating compounds of the present invention in a pharmaceutically acceptable carrier or excipient.

In part, the present invention also relates to inhibitors and compositions comprising inhibitors of enzymes similar to FabI either structurally or functionally, such as, for example, FabK which is also believed to play a role in bacterial fatty acid synthesis.

In another aspect of the present invention, the antibacterial compounds of the present invention may be used to disinfect an inanimate surface by administering the antibacterial compound to the inanimate surface.

For continuous intravenous infusion, e.g., drip or push, the antibacterial agent can be provided in a sterile dilute solution or suspension (collectively hereinafter "i.v. injectable solution"). The i.v. injectable solution may be formulated such that the amount of antibacterial agent (or antibacterial agents) provided in a 1 L solution would provide a dose, if administered over 15 minutes or less, of at least the median effective dose, or less than 100 times the $ED_{50}$, or less than 10 or 5 times the $ED_{50}$. The i.v. injectable solution may be formulated such that the total amount of antibacterial agent (or antibacterial agents) provided in 1 L solution administered over 60, 90, 120 or 240 minutes would provide an $ED_{50}$ dose to a patient, or less than 100 times the $ED_{50}$, or less than 10 or 5 times the $ED_{50}$. In other embodiments, a single i.v. "bag" provides about 0.25 mg to 5000 mg of antibacterial agent per liter i.v. solution, or 0.25 mg to 2500 mg, or 0.25 mg to 1250 mg.

In another embodiment of the invention it will be desirable to include monitoring or diagnostic regimes or kits with subject antibacterial compounds or methods based on FabI inhibitors described herein, and instructions for use of these compositions or methods.

In another aspect, the present invention also provides for kits containing at least one dose of a subject composition, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

The dosage may be selected to modulate metabolism of the bacteria in such a way as to inhibit or stop growth of said bacteria or by killing said bacteria. The skilled artisan may identify this amount as provided herein as well as by using other methods known in the art.

As explained herein in greater detail, the invention will readily enable the design and implementation of trials in warm-blooded animals, including humans and mammals, necessary for easily determining or tailoring the form and dose for any composition of the present invention.

These embodiments of the present invention, other embodiments, and their features and characteristics, will be apparent from the description, drawings and claims that follow.

DETAILED DESCRIPTION OF INVENTION

Introduction

The present invention is directed in part towards novel compositions that inhibit bacterial enzymes, and methods of making and using the same. In certain aspects, inhibitors and other compounds of the invention may be found by a structure-guided medicinal chemistry effort.

Figure 1:
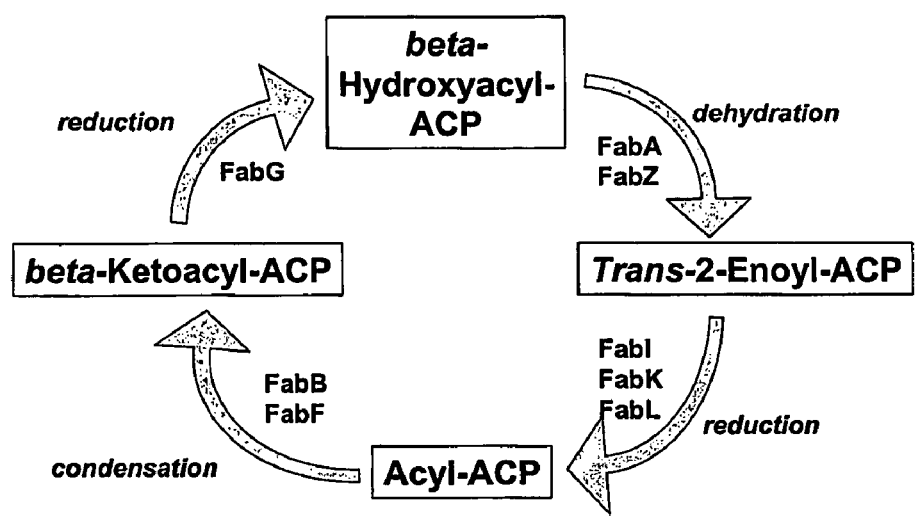
FIG. 1 depicts the bacterial fatty acid biosynthesis cycle via a Type II or dissociated fatty acid synthase system.

Bacterial fatty acid biosynthesis is believed to proceed via a Type II or dissociated fatty acid synthase system, in contrast to the mammalian Type I system. The overall process is believed to proceed in two stages—initiation and cyclical elongation. Enoyl-ACP reductase is part of the elongation cycle, in which malonyl-ACP is condensed with a growing acyl chain by b-ketoacyl-ACP synthase (FabB, FabF, FabH). The β-ketoester is reduced by β-ketoacyl-ACP reductase, which is then dehydrated to the trans-unsaturated acyl-ACP. The trans-unsaturated acyl-ACP is then reduced by enoyl-ACP reductase. (See FIG. 1).

The enoyl-ACP reductase step is believed to be accomplished by FabI in *E. coli* and other gram negative organisms and *Staphylococci*. In certain gram-positive organisms, FabI paralogs exist. In *Streptococcus pneumoniae*, the enzymatic step is believed to be accomplished by the FabK protein, which has limited homology with the *S. aureus* FabI protein. In *B. subtilis* and *E. faecalis*, genes encoding both FabI and FabK exist. In *Mycobacterium tuberculosis* a FabI prolog termed Inca exists.

Enoyl-ACP reductase is believed to be the enzymatic target of the antimicrobial product reclosing.

Figure 2:
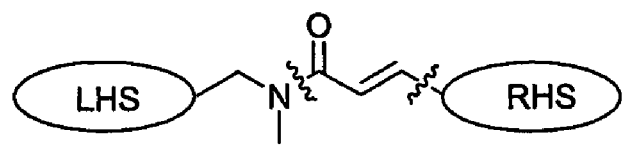
FIG. 2 depicts a simplified view of ene-amide core flanked by LHS (left-hand side) and RHS (right-hand side) moieties.
Figure 3A:
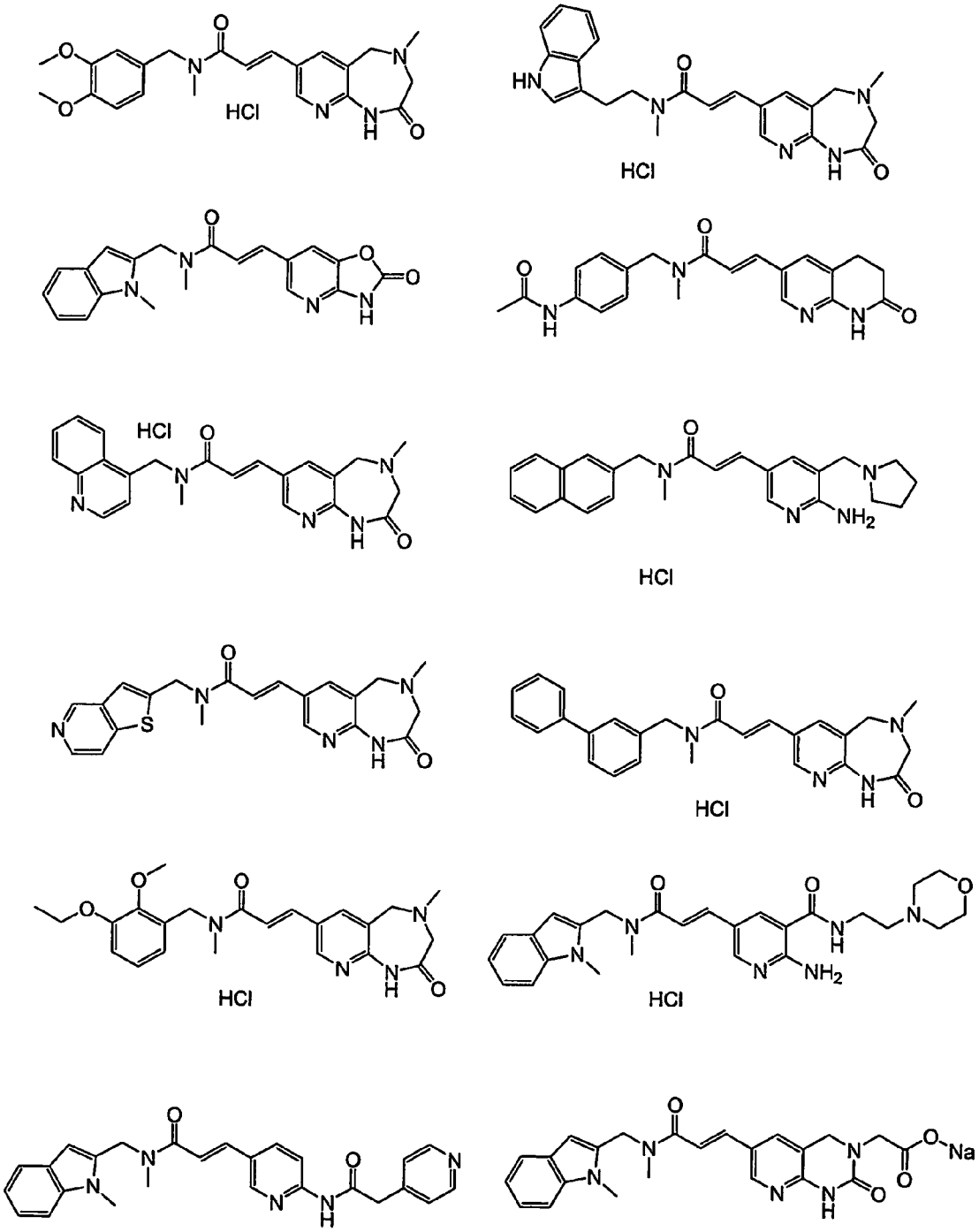
FIGS. 3*a-F* depict the structures of some of the compounds of the present invention from the representative list.
Figure 3B:
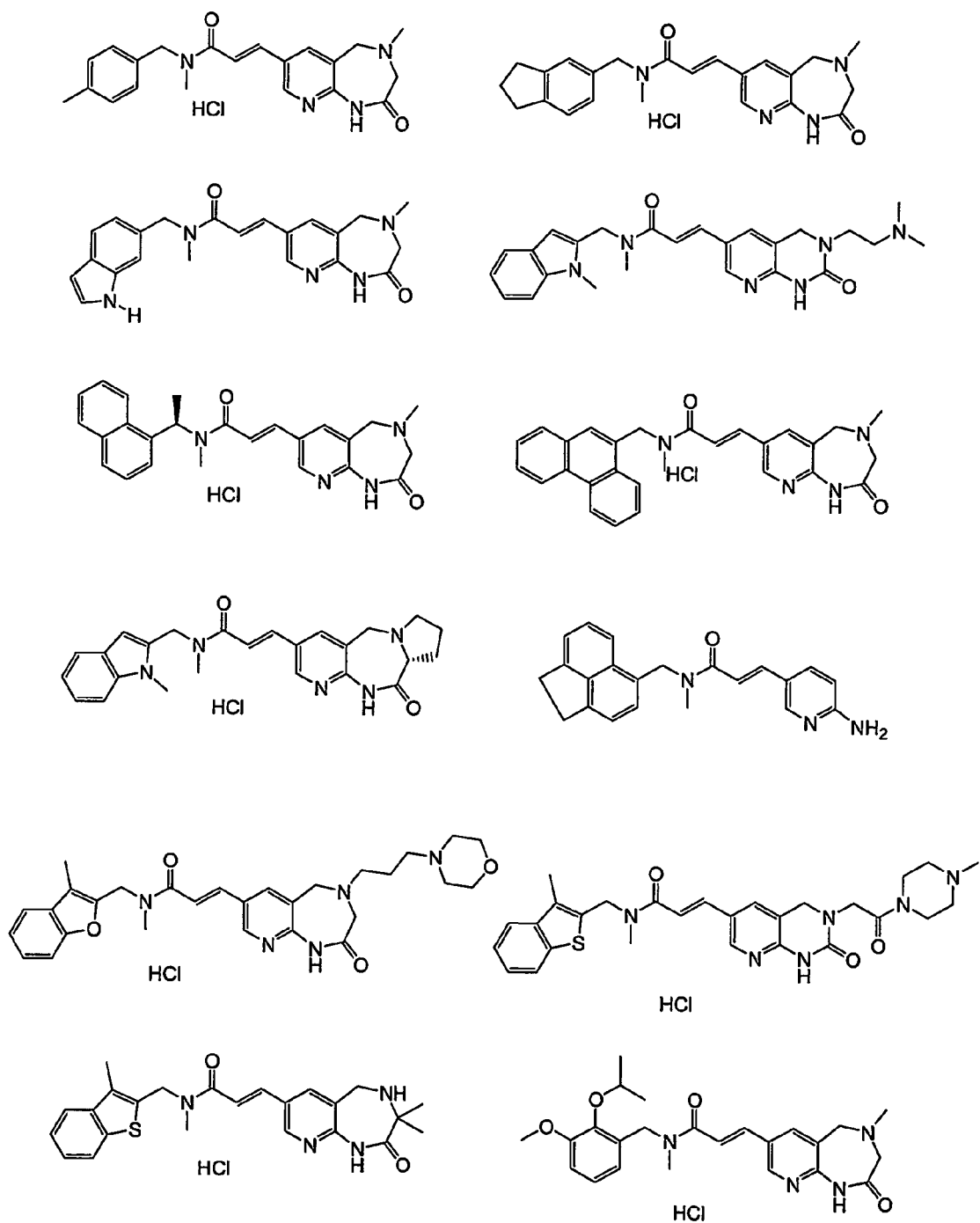
Figure 3C:
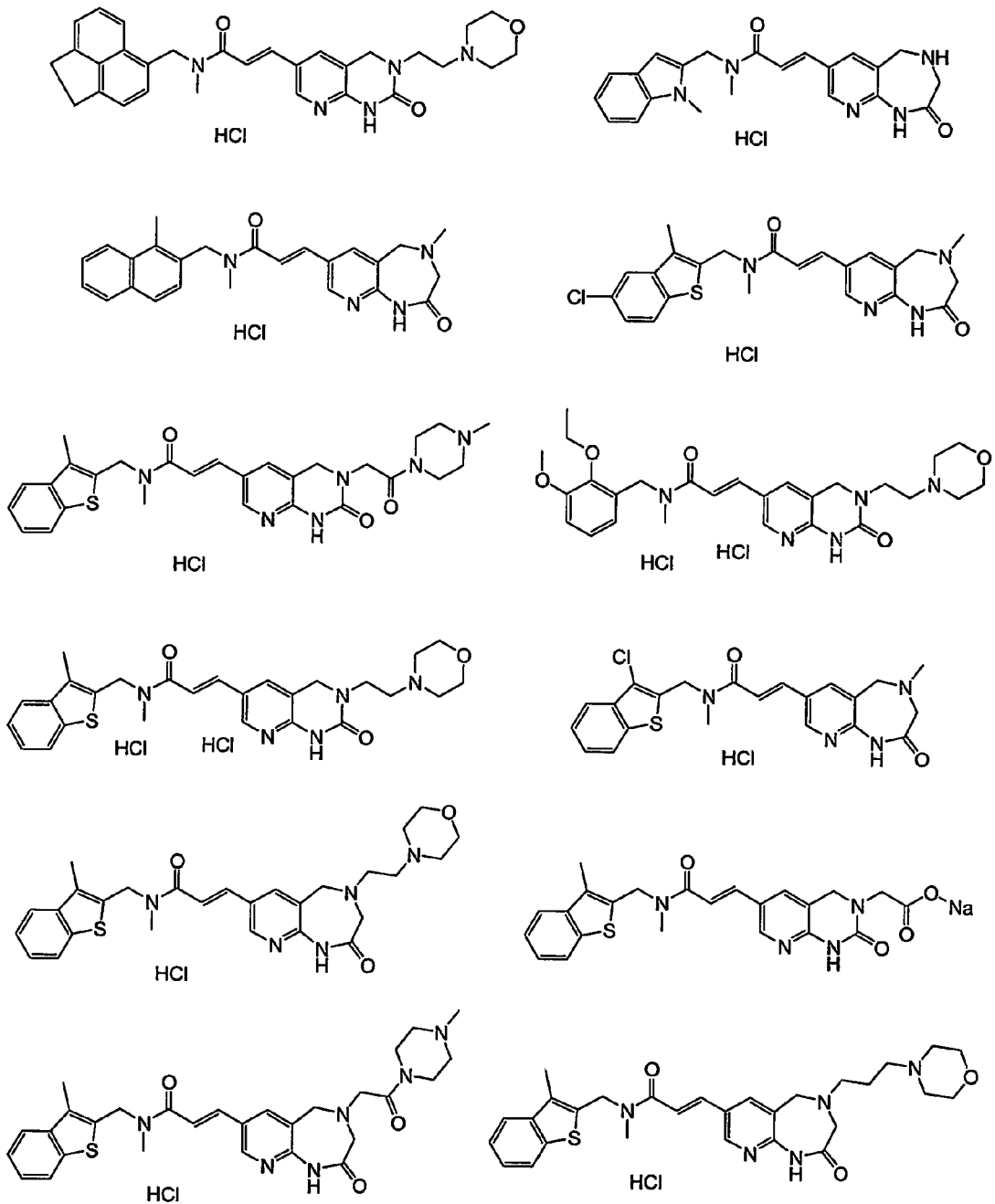
Figure 3D:
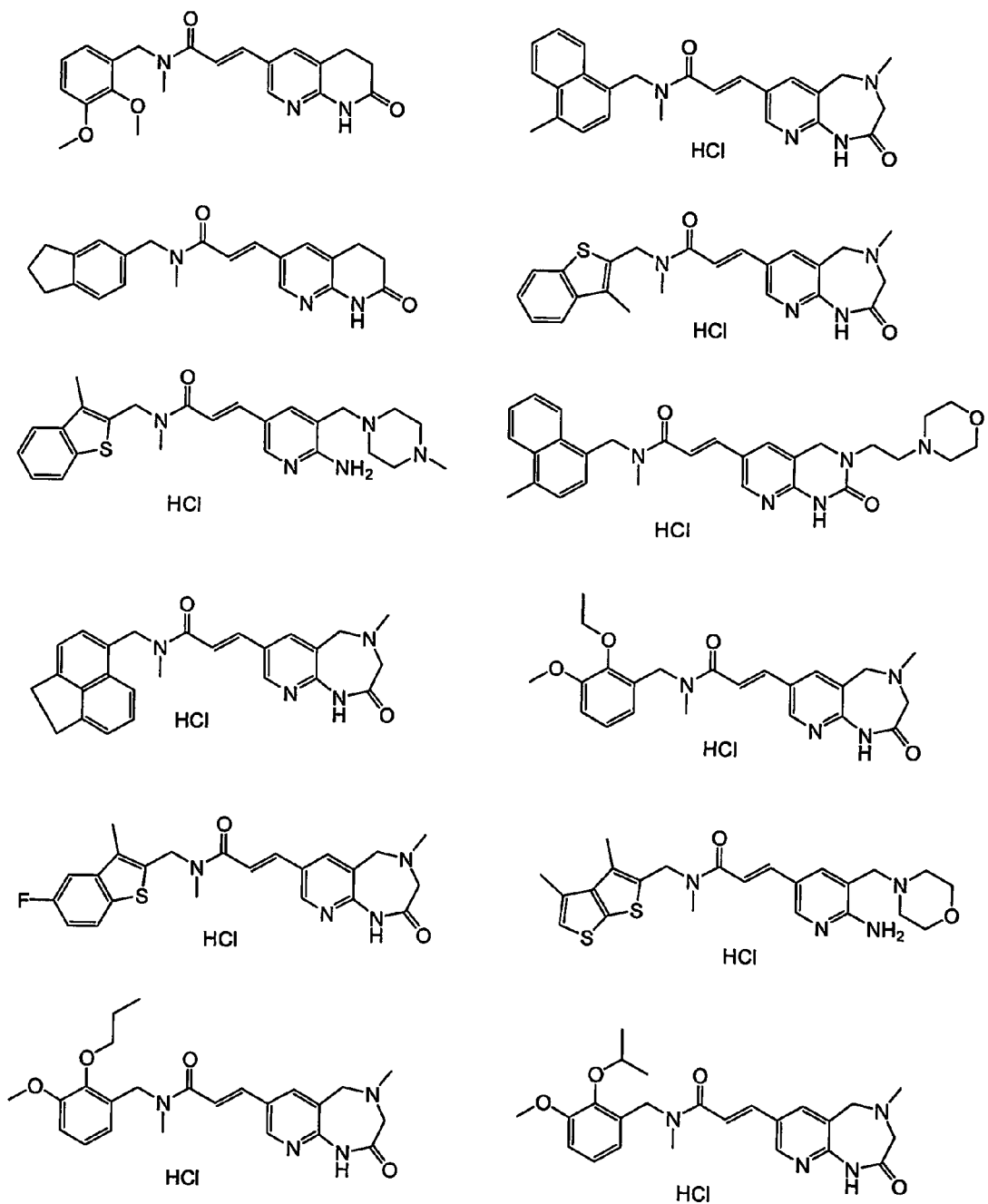
Figure 3E:
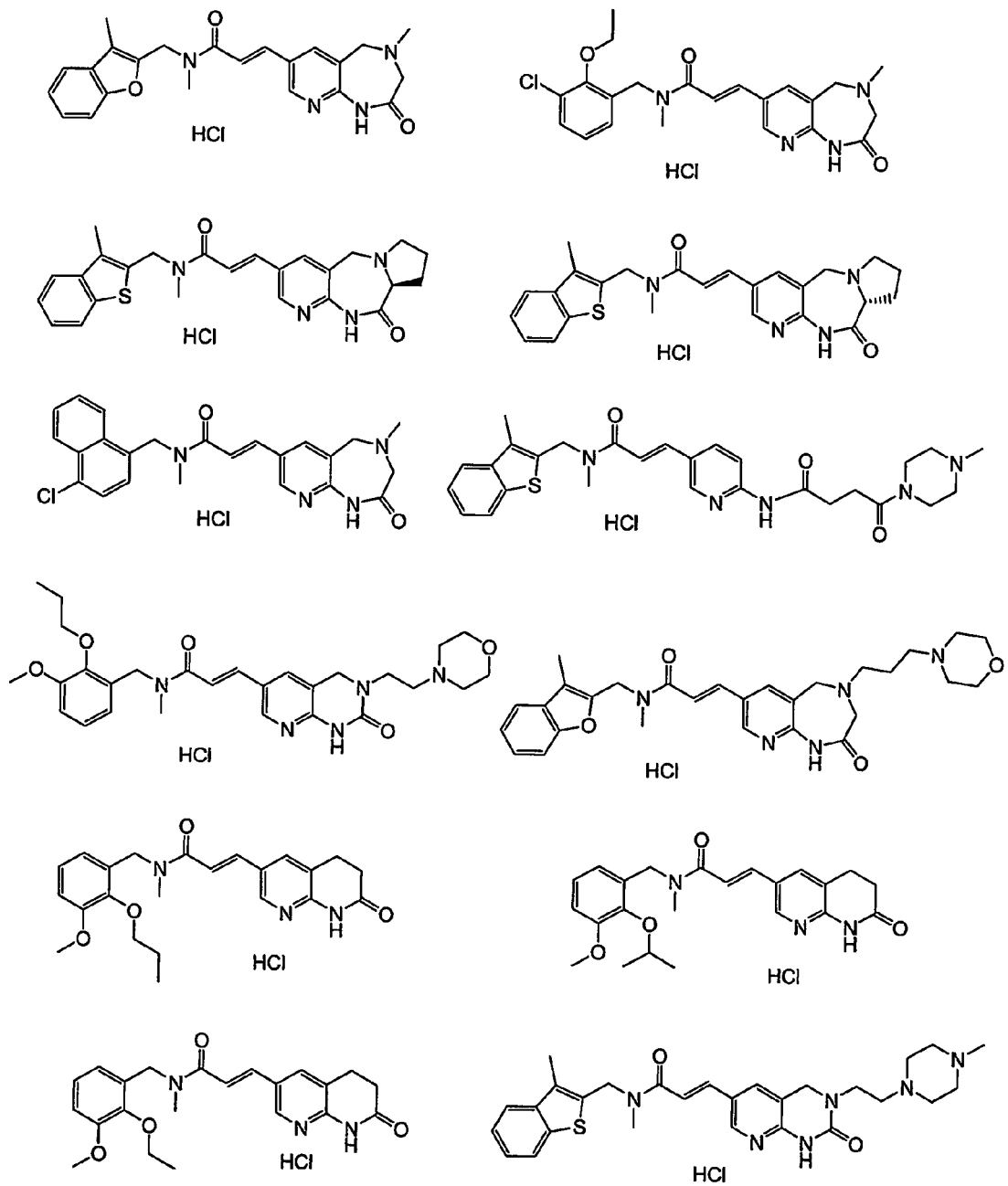
Figure 3F:
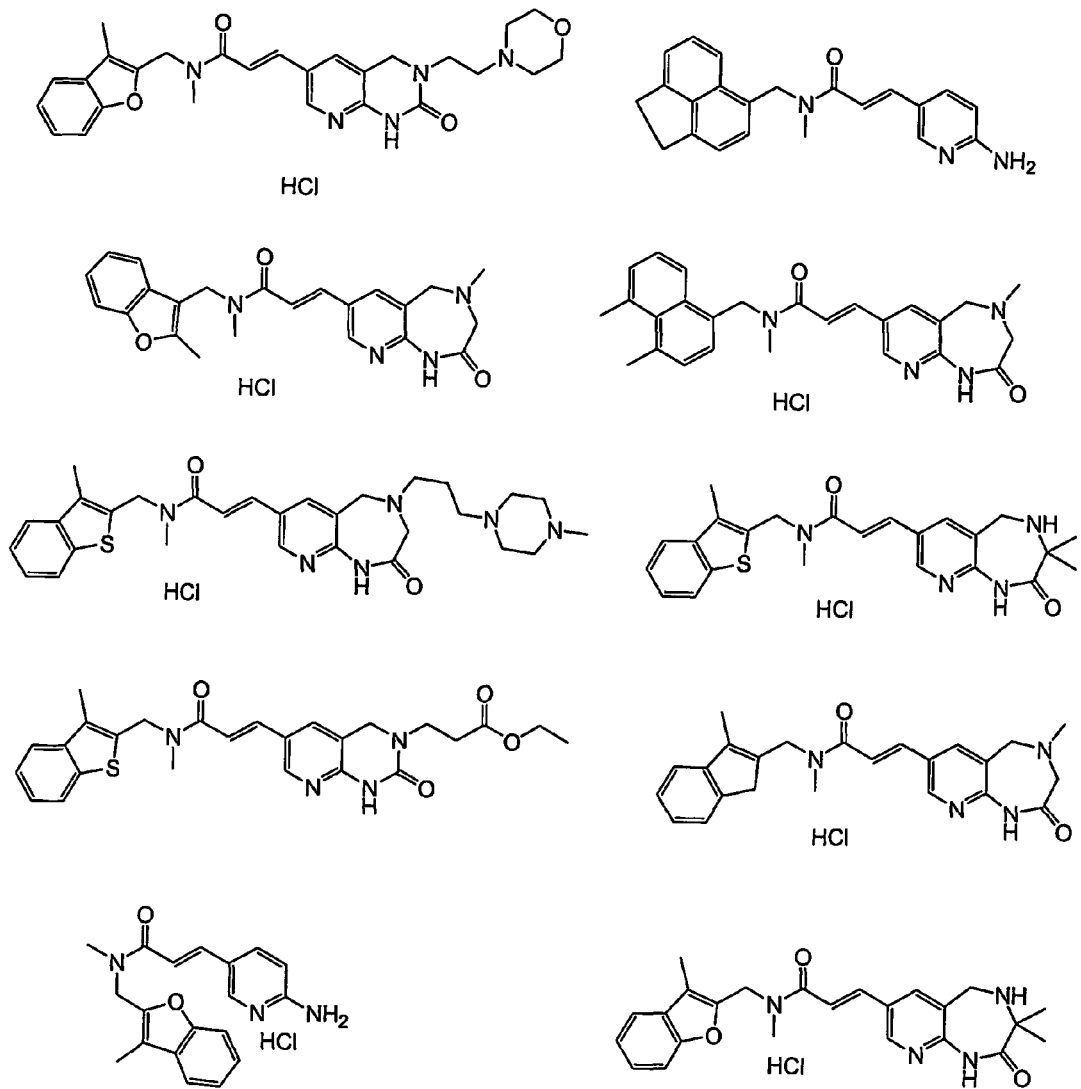

In certain embodiments, the design of new analogs having FabI inhibiting properties is based on viewing the analogs as consisting of a central acrylamide flanked by two relatively hydrophobic groups, conveniently denoted as left-hand side (LHS) and right-hand side (RHS) as put forth in U.S. Provisional Patent Application 60/431,406. Schematically this is depicted in FIG. 2, where a dumbbell like structure provides one way of viewing certain of the subject compositions (the central bond disconnections that is envisioned in a retrosynthetic sense are shown with dashed lines).

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria and plants.

The term "enzyme inhibitor" refers to any compound that prevents an enzyme from effectively carrying out its respective biochemical roles. Therefore a "FabI inhibitor" is any compound that inhibits FabI from carrying out its biochemical role. The amount of inhibition of the enzyme by any such compound will vary and is described herein and elsewhere.

The term "antibiotic agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and the like. Other general categories of antibiotic agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a)("regulatory approved drug"); any agent that is or was subject to a human drug application under 21 U.S.C. §379(g)("human drug"). (All references to statutory code for this definition refer to such code as of the original filing date of this provisional application.) Other antibiotic agents are disclosed herein, and are known to those of skill in the art. In certain embodiments, the term "antibiotic agent" does not include an agent that is a FabI inhibitor, so that the combinations of the present invention in certain instances will include one agent that is a FabI inhibitor and another agent that is not.

The term "synergistic" is art recognized and refers to two or more components working together so that the total effect is greater than the sum of the effect of the components.

The term "illness" as used herein refers to any illness caused by or related to infection by an organism.

The term "bacterial illness" as used herein refers to any illness caused by or related to infection by bacteria.

The term "polynucleotide(s)" is art recognized and refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "polypeptide(s)" is art recognized and refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2$^{nd}$ Ed., T. E. Creighton, W. H. Freeman and Company, New York (1993) and Wold, F., Post-translational Protein Modifications: Perspectives and Prospects, pgs. 1-12 in *POSTTRANSLATIONAL COVALENT MODIFICATION OF PROTEINS*, B. C. Johnson, Ed., Academic Press, New York (1983); Seifter et al., *Meth. Enzymol.* 182:626-646 (1990) and Rattan et al., *Protein Synthesis: Posttranslational Modifications and Aging*, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Antibiotic agents and Fab I/Fab K inhibitors are examples of therapeutic agents.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "$K_i$" is art-recognized and refers to the dissociation constant of the enzyme-inhibitor complex.

The term "antimicrobial" is art-recognized and refers to the ability of the compounds of the present invention to prevent, inhibit or destroy the growth of microbes such as bacteria, fungi, protozoa and viruses.

The term "antibacterial" is art-recognized and refers to the ability of the compounds of the present invention to prevent, inhibit or destroy the growth of microbes of bacteria.

The term "microbe" is art-recognized and refers to a microscopic organism. In certain embodiments the term microbe is applied to bacteria. In other embodiments the term refers to pathogenic forms of a microscopic organism.

The term "prodrug" is art-recognized and is intended to encompass compounds which, under physiological conditions, are converted into the antibacterial agents of the present invention. A common method for making a prodrug is to select moieties which are hydrolyzed under physiological conditions to provide the desired compound. In other embodiments, the prodrug is converted by an enzymatic activity of the host animal or the target bacteria.

The term "structure-activity relationship" or "(SAR)" is art-recognized and refers to the way in which altering the molecular structure of a drug or other compound alters its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

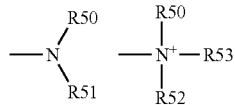

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

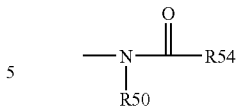

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

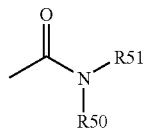

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

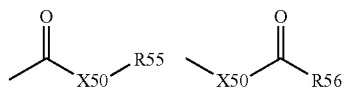

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

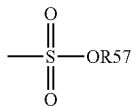

in which R57 is an electron pair, hydrogen, alkyl, cycloalkyl, or aryl.

The term "sulfate" is art recognized and includes a moiety that may be represented by the general formula:

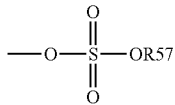

in which R57 is as defined above.

The term "sulfonamido" is art recognized and includes a moiety that may be represented by the general formula:

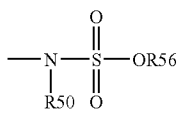

in which R50 and R56 are as defined above.

The term "sulfamoyl" is art-recognized and refers to a moiety that may be represented by the general formula:

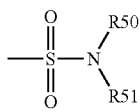

in which R50 and R51 are as defined above.

The term "sulfonyl" is art-recognized and refers to a moiety that may be represented by the general formula:

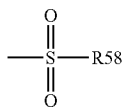

in which R58 is one of the following: hydrogen, allyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

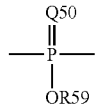

wherein Q50 represents S or O, and R59 represents hydrogen, a lower alkyl or an aryl. When used to substitute, e.g., an alkyl, the phosphoryl group of the phosphorylalkyl may be represented by the general formulas:

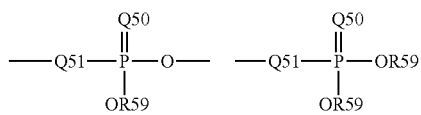

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

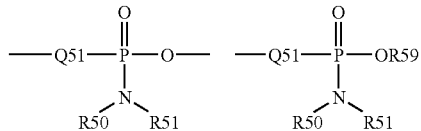

wherein Q51, R50, R51 and R59 are as defined above.

The term "phosphonamidite" is art-recognized and may be represented in the general formulas:

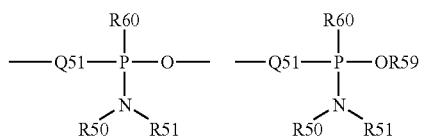

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67$^{th}$ Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenyl-ethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-ethoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59 (McGraw Hill Book Company: New York, 1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives. The terms "amino acid residue" and "peptide residue" are art-recognized and refer to an amino acid or peptide molecule without the —OH of its carboxyl group. The term "amino acid residue" further includes analogs, derivatives and congeners of any specific amino acid referred to herein, as well as C-terminal or N-terminal protected amino acid derivatives (e.g. modified with an N-terminal or C-terminal protecting group). The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "nucleic acid" is art-recognized and refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The terms "gene" or "recombinant gene" are art-recognized and refer to a nucleic acid comprising an open reading frame encoding a polypeptide, including both exonic and (optionally) intronic sequences.

The term "gene construct" is art-recognized and refers to a vector, plasmid, viral genome or the like which includes an "coding sequence" for a polypeptide or which is otherwise transcribable to a biologically active RNA (e.g., antisense, decoy, ribozyme, etc), can transfect cells, in certain embodiments mammalian cells, and may cause expression of the coding sequence in cells transfected with the construct.

The term "homology" is art-recognized and refers to sequence similarity between two peptides or between two nucleic acid molecules.

The term "operably linked" is art-recognized and refers to the relationship between two nucleic acid regions, means that they are functionally related to each other.

The term "host cell" is art-recognized and refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques.

The terms "recombinant protein," "heterologous protein" and "exogenous protein" are art-recognized and are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "regulatory element" is art-recognized and refers to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel; *Methods in Enzymology* 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g., renal cells, or cells of a neural origin, e.g., neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

The term "transfection" is art-recognized and refers to the introduction of a nucleic acid, e.g., an expression vector, into a recipient cell, which in certain embodiments may be by nucleic acid-mediated gene transfer. "Transformation," as used with respect to transfected nucleic acid, is an art-recognized term and refers to a process in which a cell's genotype is changed as a result of the cellular uptake of exogenous nucleic acid.

The term "transfer vector" is art-recognized and refers to a first nucleic acid molecule to which a second nucleic acid has been linked, and includes for example plasmids, cosmids or phages (as discussed in grater detail below). In certain embodiments of the present invention, the therapeutic agent is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. In certain embodiments, the therapeutic agent is the DNA sequence. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

The term "transgenic animal" is art-recognized and refers to any animal, often a non-human mammal, a bird or an amphibian, in which one or more of the cells of the animal contain nucleic acid introduced by way of human intervention, such as by transgenic techniques well known in the art. Such nucleic acid may be referred to as a "transgene." The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other therapeutic agent may be a "gene therapy construct," which is an expression vector which may alter the phenotype of a cell when taken up by the cell, or a gene construct. In certain embodiments, the gene therapy construct may be a "recombinant coding sequence" which encodes a polypeptide, or is transcribable to an antisense nucleic acid, a ribozyme, or any other RNA product which alters the phenotype of the cell in which it is produced. "Recombinant gene" refers to a genetic construct including a "recombinant coding sequence."

The term "antibody" is art-recognized and refers to whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compositions described herein include compositions which otherwise correspond thereto, and which have the same general properties thereof (such as other compositions comprising FabI/Fab K inhibitors), wherein one or more simple variations of substituents or components are made which do not adversely affect the characteristics of the compositions of interest. In general, the components of the compositions of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

FabI Inhibitors

The FabI inhibitor compounds of the present invention include those depicted by formula I:

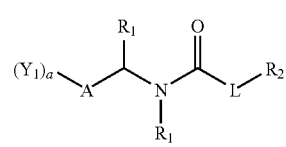

wherein, independently for each occurrence,

L is a bond, or L is alkyl, alkenyl, or cycloalkyl which may be substituted with one or more $R_1$;

A is a monocyclic ring of 4-7 atoms containing 0-2 heteroatoms, a bicyclic ring of 8-12 atoms containing 0-4 heteroatoms or a tricyclic ring of 8-12 atoms containing 0-6 heteroatoms wherein the rings are independently aliphatic, aromatic, heteroaryl or heterocyclic in nature, the heteroatoms are selected from N, S or O and the rings are optionally substituted with one or more groups selected from $C_{1-4}$ alkyl, $CH_2OH$, $OR"$, $SR"$, $CN$, $N(R")_2$, $CH_2N(R")_2$, $NO_2$, $CF_3$, $CO_2R"$, $CON(R")_2$, $COR"$, $NR"C(O)R"$, F, Cl, Br, I and $-S(O)_rCF_3$; wherein R" is H, alkyl or alkaryl;

$R_1$ is, independently for each occurrence, H, alkyl, cycloalkyl, aryl, or aralkyl;

$R_2$ is

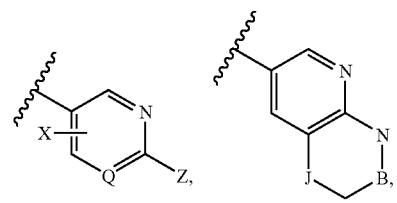

-continued

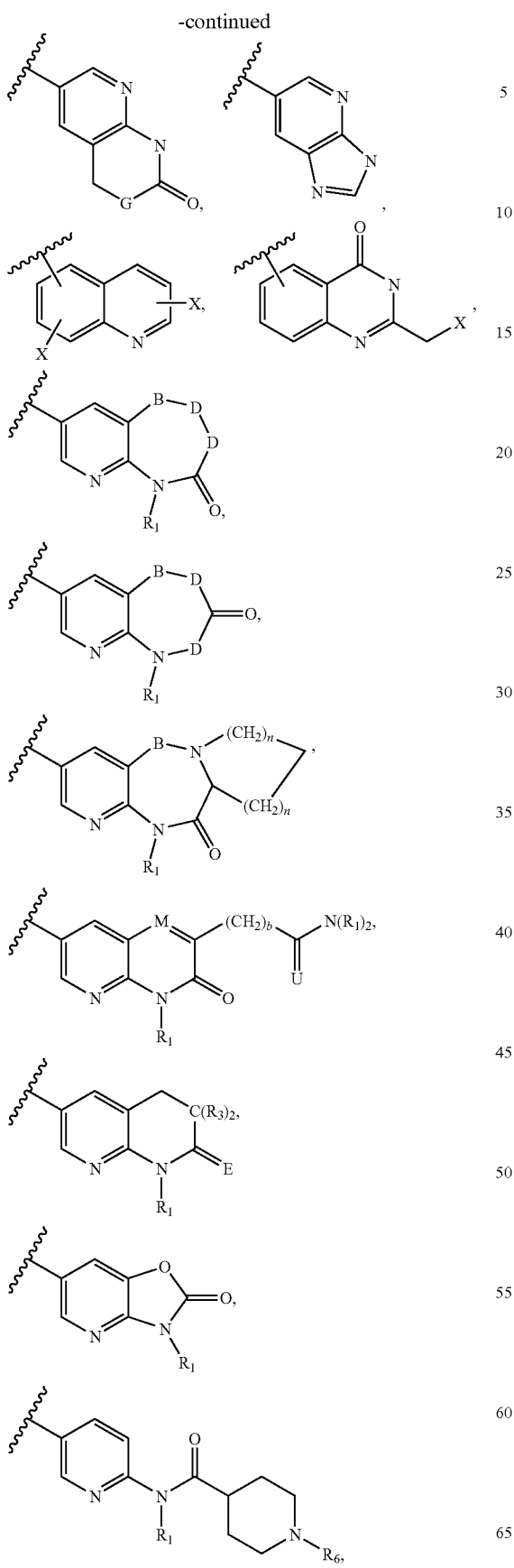

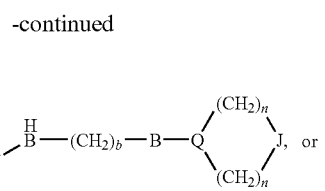

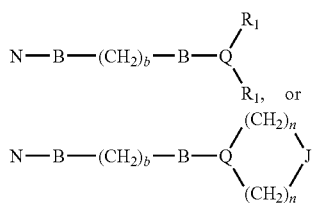

wherein, independently for each occurrence,
B is a bond, $C(R_1)_2$ or C=O;
E is O or S;
D is $C(R_1)_2$, $NR_1$, C=O,

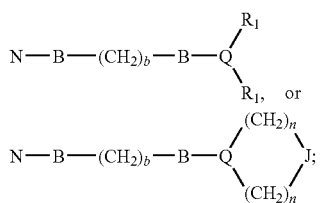

providing that the two Ds are different;
G is O, $NR_1$,

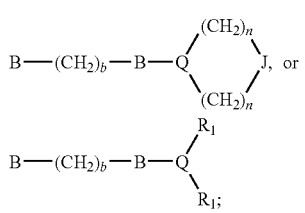

J is $NR_1$, $CH_2$, $CH_2CH_2$, or O;
M is $CR_1$ or N;
Q is N or CH;
U is O, $H_2$, or $CH_2$;
X is H, $C_{1-4}$ alkyl, $CH_2OH$, $OR_1$, $SR_1$, CN, $N(R_1)_2$, $CH_2N(R_1)_2$, $NO_2$, $CF_3$, $CO_2R_1$, $CON(R_1)_2$, $COR_1$, $NR_1C(O)R_1$, F, Cl, Br, I, —S(O)$_r$CF$_3$, Z is H, $C_{1-4}$ alkyl, $N(R_1)_2$, $NHC(O)R_1$, $NHCH_2C(O)R_1$ or NHC(O)CH=CHR$_1$;
r is 0, 1, or 2;

$R_6$ is $C(O)OR_1$;

$R_1$ is as previously defined; and b is an integer from 0-4;

$R_3$ is alkyl or cycloalkyl;

a is an integer from 0-4; and $Y_1$ is

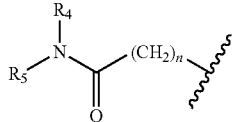

wherein, $R_4$ is a water solubilizing group;

$R_5$ is H, alkyl, or cycloalkyl; and n is an integer from 0 to 4.

In a further embodiment, the present invention includes compounds of formula I and the attendant definitions, wherein L is a $C_2$ alkenyl.

In a further embodiment, the present invention includes compounds of formula I and the attendant definitions, wherein L is a $C_2$ alkenyl and $R_2$ is

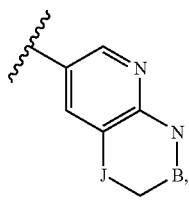

wherein B is C=O.

In a further embodiment, the present invention includes compounds of formula I and the attendant definitions, wherein L is a $C_2$ alkenyl and $R_2$ is

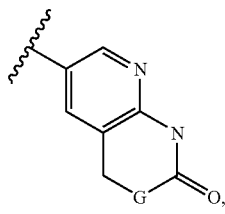

wherein G is

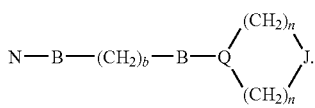

In a further embodiment, the present invention includes compounds of formula I and the attendant definitions, wherein L is a $C_2$ alkenyl and $R_2$ is

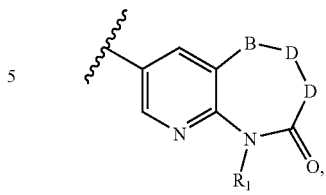

wherein $R_1$ is H.

In a further embodiment, the present invention includes compounds of formula I and the attendant definitions, wherein L is a $C_2$ alkenyl and $R_2$ is

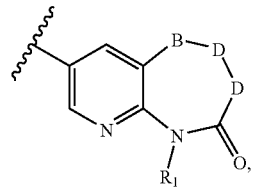

wherein $R_1$ is H and the D adjacent to B is $NR_1$.

In a further embodiment, the present invention includes compounds of formula I and the attendant definitions, wherein L is a $C_2$ alkenyl and $R_2$ is

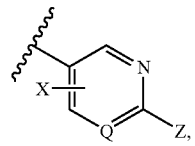

wherein Z is $N(R_1)_2$.

In a further embodiment, the present invention includes compounds of formula I and the attendant definitions, wherein L is a $C_2$ alkenyl and $R_2$ is

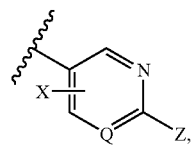

wherein Z is $N(R_1)_2$ and Q is

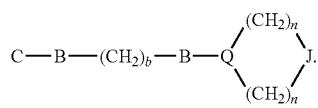

In a further embodiment, the present invention includes compounds of formula I and the attendant definitions, wherein A is a 6 membered monocyclic aryl.

In a further embodiment, the present invention includes compounds of formula I and the attendant definitions, wherein A is a 10 membered bicyclic aryl.

In a further embodiment, the present invention includes compounds of formula I and the attendant definitions, wherein A is a 12 membered tricyclic aryl.

In a further embodiment, the present invention includes compounds of formula I and the attendant definitions, wherein A is an 8 membered bicyclic heteroaryl.

In a further embodiment, the present invention includes compounds of formula I and the attendant definitions, wherein A is a 9 membered bicyclic heteroaryl.

In a further embodiment, the present invention includes compounds of formula I and the attendant definitions, wherein A comprises at least 1 heteroatom.

In a further embodiment, the present invention includes compounds of formula I and the attendant definitions, wherein A comprises at least 2 heteroatoms.

In a further embodiment, the present invention includes compounds of formula I and the attendant definitions, wherein A comprises at least 1 nitrogen atom.

In a further embodiment, the present invention includes compounds of formula I and the attendant definitions, wherein A comprises at least 1 oxygen atom.

In a further embodiment, the present invention includes compounds of formula I and the attendant definitions, wherein A comprises at least 1 sulfur atom.

In a further embodiment, the present invention includes compounds of formula I and the attendant definitions, wherein A comprises at least 2 sulfur atoms.

The present invention relates to, but is not limited to, the compounds of formula I wherein the compound is selected from the following representative list:

(E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide hydrochloride;

(E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide hydrochloride;

(E)-N-Methyl-3-(4-methyl-2-oxo-2,3,4,5-tetrahydro-1H-pyrido[2,3-e][1,4]diazepin-7-yl)-N-naphthalen-2-ylmethyl-acrylamide hydrochloide;

(E)-N-Methyl-3-(4-methyl-2-oxo-2,3,4,5-tetrahydro-1H-pyrido[2,3-e][1,4]diazepin-7-yl)-N-naphthalen-1-ylmethyl-acrylamide hydrochloride;

(E)-N-(4-Acetylamino-benzyl)-N-methyl-3-(7-oxo-5,6,7,8-tetrahydro-[1,8]naphthyridin-3-yl)acrylamide;

(E)-N-(4-Methanesulfonyl-benzyl)-N-methyl-3-(7-oxo-5,6,7,8-tetrahydro-[1,8]naphthyridin-3-yl)acrylamide;

(E)-N-(2-Methoxy-naphthalen-1-ylmethyl)-N-methyl-3-(7-oxo-5,6,7,8-tetrahydro-[1,8]naphthyridin-3-yl)acrylamide;

(E)-N-Methyl-N-(4-methyl-naphthalen-1-ylmethyl)-3-(7-oxo-5,6,7,8-tetrahydro-[1,8]naphthyridin-3-yl)acrylamide;

(E)-N-(2,3-Dimethyl-benzyl)-N-methyl-3-(7-oxo-5,6,7,8-tetrahydro-[1,8]naphthyridin-3-yl)acrylamide;

(E)-N-(4-Isopropyl-benzyl)-N-methyl-3-(7-oxo-5,6,7,8-tetrahydro-[1,8]naphthyridin-3-yl)acrylamide;

(E)-N-Indan-5ylmethyl-N-methyl-3-(7-oxo-5,6,7,8-tetrahydro-[1,8]naphthyridin-3-yl)acrylamide;

(E)-N-Indan-5ylmethyl-N-methyl-3-(4-methyl-2-oxo-2,3,4,5-tetrahydro-1H-pyrido[2,3-e][1,4]diazepin-7-yl)acrylamide hydrochloide;

(E)-N-Methyl-N-(3-methyl-benzo[b]thiophen-2-ylmethyl)-3-(4-methyl-2-oxo-2,3,4,5-tetrahydro-1H-pyrido[2,3-e][1,4]diazepin-7-yl)acrylamide hydrochloride;

(E)-N-(3,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-[2-(1H-Indol-3-yl)-ethyl]-N-methyl-3-(4-methyl-2-oxo-2,3,4,5-tetrahydro-1H-pyrido[2,3-e][1,4]diazepin-7-yl)acrylamide hydrochloride;

(E)-N-Methyl-3-(4-methyl-2-oxo-2,3,4,5-tetrahydro-1H-pyrido[2,3-e][1,4]diazepin-7-yl)-N-(2,4,5-trimethoxy-benzyl)acrylamide hydrochloride;

(E)-N-Methyl-3-(4-methyl-2-oxo-2,3,4,5-tetrahydro-1H-pyrido[2,3-e][1,4]diazepin-7-yl)-N-phenanthren-9-ylmethyl-acrylamide hydrochloride;

(E)-N-Acenaphthen-5-ylmethyl-N-methyl-3-(4-methyl-2-oxo-2,3,4,5-tetrahydro-1H-pyrido[2,3-e][1,4]diazepin-7-yl)acrylamide hydrochloride;

(E)-N-(4-Methoxy-naphthalen-1ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-Benzo[1,3]dioxol-5-ylmethyl-N-methyl-3-(4-methyl-2-oxo-2,3,4,5-tetrahydro-1H-pyrido[2,3-e][1,4]diazepin-7-yl)acrylamide hydrochloride;

(E)-N-(2,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-3-(4-methyl-2-oxo-2,3,4,5-tetrahydro-1H-pyrido[2,3-e][1,4]diazepin-7-yl)-N-quinolin-4-ylmethyl-acrylamide hydrochloride;

(E)-N-(4-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(2-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(3,4-Dimethyl-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-3-(4-methyl-2-oxo-2,3,4,5-tetrahydro-1H-pyrido[2,3-e][1,4]diazepin-7-yl)-N-(2,4,6-trimethyl-benzyl)acrylamide hydrochloride;

(E)-N-Methyl-3-(4-methyl-2-oxo-2,3,4,5-tetrahydro-1H-pyrido[2,3-e][1,4]diazepin-7-yl)-N-(2,4,5-trimethyl-benzyl)acrylamide hydrochloride;

(E)-N-Methyl-3-(4-methyl-2-oxo-2,3,4,5-tetrahydro-1H-pyrido[2,3-e][1,4]diazepin-7-yl)-N-quinolin-3-ylmethyl-acrylamide hydrochloride;

(E)-N-(3,4-Dimethoxy-benzyl)-N-methyl-3-(4-methyl-2-oxo-2,3,4,5-tetrahydro-NH-pyrido[2,3-e][1,4]diazepin-7-yl)acrylamide hydrochloride;

(E)-N-Benzofuran-2-ylmethyl-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(2-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride;

(E)-N-Biphenyl-2-ylmethyl-methyl-N-methyl-3-(4-methyl-2-oxo-2,3,4,5-tetrahydro-1H-pyrido[2,3-e][1,4]diazepin-7-yl)acrylamide hydrochloride;

(E)-N-Biphenyl-3-ylmethyl-N-methyl-3-(4-methyl-2-oxo-2,3,4,5-tetrahydro-1H-pyrido[2,3-e][1,4]diazepin-7-yl)acrylamide hydrochloride;

(E)-N-2-Ethoxy-napthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(2-Ethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-3-(4-methyl-2-oxo-2,3,4,5-tetrahydro-1H-pyrido[2,3-e][1,4]diazepin-7N-(2,3,4-trimethoxy-benzyl)acrylamide hydrochloride;

(E)-N-(2,3-Dihydro-benzo[1,4]dioxin-6ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(2,3-Diethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(3-Ethoxy-2-methoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(2-Ethoxy-3-methyl-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-methyl-3-(4-methyl-2-oxo-2,3,4,5-tetrahydro-1H-pyrido[2,3-e][1,4]diazepin-7-yl)-N-quinolin-5ylmethyl-acrylamide hydrochloride;

(E)-N-(3-Methoxy-2-propoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(3-Methoxy-2-isopropoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-methyl-N-(3-methyl-benzofuran-2-ylmethyl)-3-(4-methyl-2-oxo-2,3,4,5-tetrahydro-1H-pyrido[2,3-e][1,4]diazepin-7-yl)acrylamide hydrochloride;

(E)-N-(3-Chloro-2-methoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(3-Chloro-2-ethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-(2,3-Dihydro-benzo[1,4]dioxin-5-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(4,5-Dimethyl-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(2-methyl-benzofuran-3-ylmethyl)-3-(4-methyl-2-oxo-2,3,4,5-tetrahydro-1H-pyrido[2,3-e][1,4]diazepin-7-yl)acrylamide hydrochloride;

(E)-N-Methyl-3-(7-oxo-5,6,7,8-tetrahydro-[1,8]naphthyridin-3-yl)-N-quinolin-5-ylmethyl-acrylamide hydrochloride;

(E)-N-benzyl-N-methyl-3-(7-oxo-5,6,7,8-tetrahydro-[1,8]naphthyridin-3-yl)acrylamide;

(E)-N-methyl-N-(1-methyl-1H-indol-2-ylmethyl)-3-(4-methyl-2-oxo-2,3,4,5-tetrahydro-1H-pyrido[2,3-e][1,4]diazepin-7-yl)acrylamide hydrochloride;

(E)-7-{2-[Methyl-(1-methyl-1H-indol-2-ylmethyl)carbamoyl]vinyl}-2-oxo-1,2,3,5-tetrahydro-pyrido[2,3-e][1,4]diazepin-4-yl)acetic acid ethyl ester hydrochloride;

(E)-N-(2,3-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(4-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride;

(E)-N-(2-Methoxy-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

l-(+)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride;

(S)-(−)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride;

(E)-N-Benzo[b]thiophen-2-ylmethyl-N-methyl-3-(4-methyl-2-oxo-2,3,4,5-tetrahydro-1H-pyrido[2,3-e][1,4]diazepin-7-yl)acrylamide hydrochloride;

(E)-N-methyl-3-(4-methyl-2-oxo-2,3,4,5-tetrahydro-1H-pyrido[2,3-e][1,4]diazepin-7-yl)-N-(3-trifluoromethyl-benzyl)acrylamide hydrochloride;

(E)-N-(2-Chloro-benzyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(4-methyl-benzyl)-3-(4-methyl-2-oxo-2,3,4,5-tetrahydro-1H-pyrido[2,3-e][1,4]diazepin-7-yl)acrylamide hydrochloride;

(R)-(−)-(E)-N-Methyl-N-(1-methyl-1H-indol-2-ylmethyl)-3-(10-oxo-2,3,4,9,10,10$^a$-hexahydro-1H-3$^a$,8,9-triaza-benzo[f]azulen-6-yl)acrylamide hydrochloride;

(S)-(+)-(E)-N-Methyl-N-(1-methyl-1H-indol-2-ylmethyl)-3-(10-oxo-2,3,4,9,10,10$^a$-hexahydro-1H-3$^a$,8,9-triaza-benzo[f]azulen-6-yl)acrylamide hydrochloride;

(E)-3-[4-(4-Methoxy-benzyl)-2-oxo-2,3,4,5-tetrahydro-1H-pyrido[2,3-e][1,4]diazepin-7-yl]-N-methyl-N-(1-methyl-1H-indol-2-ylmethyl)acrylamide hydrochloride;

(E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide hydrochloride;

(E)-N-Methyl-N-(3-methyl-benzo[b]thiophen-2-ylmethyl)-3-[4-(2-morpholin-4-yl-ethyl)-2-oxo-2,3,4,5-tetrahydro-1H-pyrido[2,3-e][1,4]diazepin-7-yl]acrylamide hydrochloride;

(E)-N-Methyl-N-(3-methyl-benzo[b]thiophen-2-ylmethyl)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride;

(E)-N-Methyl-N-(3-methyl-benzo[b]thiophen-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-(2-Ethoxy-3-methoxy-benzyl)-N-methyl-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride;

(S)-(+)-(E)-N-Methyl-N-(3-methyl-benzo[b]thiophen-2-ylmethyl)-3-(10-oxo-2,3,4,9,10,10$^a$-hexahydro-1H-3$^a$,8,9-triaza-benzo azulen-6-yl)acrylamide hydrochloride;

(R)-(−)-(E)-N-Methyl-N-(3-methyl-benzo[b]thiophen-2-ylmethyl)-3-(10-oxo-2,3,4,9,10,10$^a$-hexahydro-1H-3$^a$,8,9-triaza-benzo[f]azulen-6-yl)acrylamide hydrochloride;

(E)-N-(4-Fluoro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(4-Chloro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-Methyl-N-(3-methyl-benzofuran-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-(2-Isopropoxy-3-methoxy-benzyl)-N-methyl-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-Methyl-N-(3-methyl-benzo[b]thiophen-2-ylmethyl)-3-{4-[3-(4-methyl-piperazin-1-yl)propyl]-2-oxo-2,3,4,5-tetrahydro-1H-pyrido[2,3-e][1,4]diazepin-7-yl}acrylamide hydrochloride;

(E)-N-Methyl-N-(2-methyl-benzofuran-3-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride;

(E)-N-(3-Chloro-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(5-Chloro-1-methyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(1,7-Dimethyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(5-Fluoro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-N-(5-Chloro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride;

(E)-3-(6-Amino-5-morpholin-4-ylmethyl-pyridin-3-yl)-N-(1,7-dimethyl-1H-indol-2-ylmethyl)-N-methyl-acrylamide hydrochloride;

(E)-3-(6-Amino-5-morpholin-4-ylmethyl-pyridin-3-yl)-N-(2-ethoxy-3-methoxy-benzyl)-N-methyl-acrylamide hydrochloride;

(E)-N-Methyl-N-(1-methyl-1H-indol-3-ylmethyl)-3-(4-methyl-2-oxo-2,3,4,5-tetrahydro-1H-pyrido[2,3-e][1,4]diazepin-7-yl)acrylamide;

(E)-7-{2-[Methyl-(1-methyl-1H-indol-3-ylmethyl)-carbamoyl]-vinyl}-2-oxo-1,2,3,5-tetrahydro-pyrido[2,3-e][1,4]diazepine-4-carboxylic acid benzyl ester;

(E)-3-(2,4-Dioxo-1,2,3,4-tetrahydro-pyrido[2,3-d]pyrimidin-6-yl)-N-methyl-N-(1-methyl-1H-indol-3-ylmethyl)acrylamide;

(E)-N-Methyl-N-(1-methyl-1H-indol-2-ylmethyl)-3-(2-oxo-2,3-dihydro-oxazolo[4,5-b]pyridin-6-yl)acrylamide;

(E)-N-Methyl-N-(1-methyl-1H-indol-3-ylmethyl)-3-(2-oxo-2,3-dihydro-oxazolo[4,5-b]pyridin-6-yl)acrylamide;

(E)-3-(6-Amino-5-{2-[methyl-(1-methyl-1H-indol-2-ylmethyl)carbamoyl]ethyl}pyridin-3-yl)-N-methyl-N-(1-methyl-1H-indol-2-ylmethyl)acrylamide;

(E)-3-(6-Amino-5-piperidin-1-ylmethyl-pyridin-3-yl)-N-methyl-N-(1-methyl-1H-indol-2-ylmethyl)acrylamide;

(E)-3-(6-Amino-5-pyrrolidin-1-ylmethyl-pyridin-3-yl)-N-methyl-N-(1-methyl-1H-indol-2-ylmethyl)acrylamide hydrochloride;

(E)-3-[6-Amino-5-(4-methyl-piperazin-1-ylmethyl)pyridin-3-yl]-N-methyl-N-(1-methyl-1H-indol-2-ylmethyl)acrylamide hydrochloride;

(E)-3-[6-Amino-5-(4-benzyl-piperidin-1-ylmethyl)pyridin-3-yl]-N-methyl-N-(1-methyl-1H-indol-2-ylmethyl)acrylamide hydrochloride;

(E)-3-(6-Amino-5-pyrrolidin-1-ylmethyl-pyridin-3-yl)-N-methyl-N-naphthalen-2-ylmethyl-acrylamide hydrochloride;

(E)-3-[6-Amino-5-(4-methyl-piperazin-1-ylmethyl)pyridin-3-yl]-N-methyl-N-(3-methyl-benzo[b]thiophen-2-ylmethyl)acrylamide hydrochloride;

(E)-3-(6-Amino-5-morpholin-4-ylmethyl-pyridin-3-yl)-N-methyl-N-(4-methyl-naphthalen-1-ylmethyl)acrylamide hydrochloride;

(E)-3-(6-Amino-5-morpholin-4-ylmethyl-pyridin-3-yl)-N-methyl-N-(3-methyl-benzo[b]thiophen-2-ylmethyl)acrylamide hydrochloride;

(E)-3-(6-Amino-5-morpholin-4-ylmethyl-pyridin-3-yl)-N-(3,4-dimethyl-thieno[2,3-b]thiophen-2-ylmethyl)-N-methyl-acrylamide hydrochloride;

(E)-3-[6-Amino-5-(4-methyl-piperazin-1-ylmethyl)pyridin-3-yl]-N-(2-ethoxy-3-methoxy-benzyl)-N-methyl-acrylamide hydrochloride;

(E)-3-[6-Amino-5-(4-methyl-piperazin-1-ylmethyl)pyridin-3-yl]-N-methyl-N-(4-methyl-naphthalen-1-ylmethyl)acrylamide hydrochloride;

(E)-3-[6-Amino-5-(4-methyl-piperazin-1-ylmethyl)pyridin-3-yl]-N-benzofuran-2-ylmethyl-N-methyl-acrylamide hydrochloride;

(E)-3-[6-Amino-5-(4-methyl-piperazin-1-ylmethyl)pyridin-3-yl]-N-(3-methoxy-2-propoxy-benzyl)-N-methyl-acrylamide hydrochloride;

(E)-3-[6-Amino-5-(4-methyl-piperazin-1-ylmethyl)pyridin-3-yl]-N-(2-ethoxy-3-methyl-benzyl)-N-methyl-acrylamide hydrochloride;

(E)-N-(3-Methoxy-2-propoxy-benzyl)-N-methyl-3-(7-oxo-5,6,7,8-tetrahydro-[1,8]naphthyridin-3-yl)acrylamide hydrochloride;

(E)-N-(2-Isopropoxy-3-methoxy-benzyl)-N-methyl-3-(7-oxo-5,6,7,8-tetrahydro-[1,8]naphthyridin-3-yl)acrylamide hydrochloride;

(E)-N-(2-Ethoxy-3-methoxy-benzyl)-N-methyl-3-(7-oxo-5,6,7,8-tetrahydro-[1,8]naphthyridin-3-yl)acrylamide hydrochloride;

(E)-3-[6-(2,5-Dioxo-pyrrolidin-1-yl)pyridin-3-yl]-N-methyl-N-(1-methyl-1H-indol-2-ylmethyl)acrylamide;

(E)-N-(5-{2-[Methyl-(1-methyl-1H-indol-2-ylmethyl)carbamoyl]vinyl}pyridin-2-yl)succinamide;

(E)-N-(5-{2-[Methyl-(1-methyl-1H-indol-2-ylmethyl)carbamoyl]vinyl}pyridin-2-yl)-4-(4-methyl-piperazin-1-yl)-4-oxo-butyramide;

(E)-N-(5-{2-[Methyl-(1-methyl-1H-indol-2-ylmethyl)carbamoyl]vinyl}pyridin-2-yl)-4-morpholin-4-yl-4-oxo-butyramide;

(E)-1-Methyl-piperidine-4-carboxylic acid (5-{2-[methyl-(1-methyl-1H-indol-2-ylmethyl)carbamoyl]vinyl}pyridin-2-yl)amide;

(E)-N-Methyl-N-(1-methyl-1H-indol-2-ylmethyl)-3-[6-(2-pyridin-4-yl-acetylamino)pyridin-3-yl]acrylamide;

(E)-1-Acetyl-piperidine-4-carboxylic acid (5-{2-[methyl-(1-methyl-1H-indol-2-ylmethyl)carbamoyl]vinyl}pyridin-2-yl)amide;

(E)-3-(6-Amino-pyridin-3-yl)-N-(2,3-dimethoxy-benzyl)-N-methyl-acrylamide;

(E)-N-(4-Acetylamino-benzyl)-3-(6-amino-pyridin-3-yl)-N-methyl-acrylamide;

(E)-3-[3-(2-Dimethylamino-ethyl)-2-oxo-1,2,3,4-tetrahydro-pyrido[2,3-d]pyrimidin-6-yl]-N-methyl-N-(1-methyl-1H-indol-2-ylmethyl)acrylamide;

(E)-N-Methyl-N-(1-methyl-1H-indol-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(4-methyl-naphthalen-1-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-Acenaphthen-5-ylmethyl-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(2-Ethoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(3-methyl-benzo[b]thiophen-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid;

Sodium (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetate;

Sodium (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetate;

(E)-N-Methyl-N-(1-methyl-1H-indol-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride;

(E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride;

(E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride;

(E)-2-Amino-5-{2-[methyl-(1-methyl-1H-indol-2-ylmethyl)carbamoyl]vinyl}-N-(2-morpholin-4-yl-ethyl)nicotinamide hydrochloride;

(E)-N-3-Methyl-benzo[b]thiophen-2-ylmethyl)-3-[3-(3-morpholin-4-yl-propyl)-2-oxo-1,2,3,4-tetrahydro-pyrido[2,3-d]pyrimidin-6-yl]acrylamide hydrochloride;

(E)-N-(2-Ethoxy-3-methoxy-benzyl)-N-methyl-3-[3-(3-morpholin-4-yl-propyl)-2-oxo-1,2,3,4-tetrahydro-pyrido[2,3-d]pyrimidin-6-yl]acrylamide hydrochloride;

(E)-N-(5-{2-[Methyl-(3-methyl-benzo[b]thiophen-2-ylmethyl)carbamoyl]vinyl}pyridin-2-yl)-4-(4-methyl-piperazin-1-yl)-4-oxo-butyramide;

(E)-N-(2,3-Diethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(2-Isopropoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(3-Methoxy-2-propoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(3-methyl-benzofuran-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride;

(E)-N-Methyl-N-(2-methyl-benzofuran-3-ylmethyl)-3-[3-(2-morpholin-4-ylethyl)-2-oxo-1,2,3,4-tetrahydro-pyrido[2,3-d]pyrimidin-6-yl]acrylamide hydrochloride;

(E)-N-(3-Chloro-2-ethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(4-Fluoro-naphthalen-1-ylmethyl)-N-methyl-3-[3-(2-morpholin-4-yl-ethyl)-2-oxo-1,2,3,4-tetrahydro-pyrido[2,3-d]pyrimidin-6-yl]acrylamide hydrochloride;

(E)-N-(2,3-Dimethoxy-benzyl)-N-methyl-3-(7-oxo-5,6,7,8-tetrahydro-[1,8]naphthyridin-3-yl)acrylamide;

(E)-3-(6-Amino-5-morpholin-4-ylmethyl-pyridin-3-yl)-N-methyl-N-(1-methyl-1H-indol-3-ylmethyl)acrylamide;

(E)-3-(6-Amino-pyridin-3-yl)-N-methyl-N-thieno[3,2-c]pyridin-2-ylmethyl-acrylamide;

(E)-N-Methyl-3-(4-methyl-2-oxo-2,3,4,5-tetrahydro-1H-pyrido[2,3-e][1,4]diazepin-7-yl)-N-thieno[3,2-c]pyridin-2-ylmethyl-acrylamide;

(E)-N-Methyl-3-(7-oxo-5,6,7,8-tetrahydro-[1,8]naphthyridin-3-yl)-N-thieno[3,2-c]pyridin-2-ylmethyl-acrylamide;

(E)-3-(6-Amino-pyridin-3-yl)-N-(2-ethoxy-3-methoxy-benzyl)-N-methyl-acrylamide hydrochloride;

(E)-3-(6-Amino-pyridin-3-yl)-N-(2-propoxy-3-methoxy-benzyl)-N-methyl-acrylamide hydrochloride;

(E)-3-(6-amino-pyridin-3-yl)-N-(2-isopropoxy-3-methoxy-benzyl)-N-methyl-acrylamide hydrochloride;

(E)-N-Acenaphthen-5-ylmethyl-3-(6-amino-pyridin-3-yl)-N-methyl-acrylamide hydrochloride;

(E)-N-(1H-Indol-5-ylmethyl)-N-methyl-3-(4-methyl-2-oxo-2,3,4,5-tetrahydro-1H-pyrido[2,3-e][1,4]diazepin-7-yl)-acrylamide;

(E)-N-Methyl-N-(1-methylindol-5-ylmethyl)-3-(4-methyl-2-oxo-2,3,4,5-tetrahydro-1H-pyrido[2,3-e][1,4]diazepin-7-yl)-acrylamide;

(E)-N-(1H-Indol-7-ylmethyl)-N-methyl-3-(4-methyl-2-oxo-2,3,4,5-tetrahydro-1H-pyrido[2,3-e][1,4]diazepin-7-yl)-acrylamide;

(E)-N-Methyl-N-(1-methylindol-7-ylmethyl)-3-(4-methyl-2-oxo-2,3,4,5-tetrahydro-1H-pyrido[2,3-e][1,4]diazepin-7-yl)-acrylamide;

(E)-N-(1H-Indol-6-ylmethyl)-N-methyl-3-(4-methyl-2-oxo-2,3,4,5-tetrahydro-1H-pyrido[2,3-e][1,4]diazepin-7-yl)-acrylamide;

(E)-N-3-(6-Amino-pyridin-3-yl)-N-methyl-N-(2-methyl-benzofuran-3-ylmethyl)-acrylamide hydrochloride;

(E)-3-(3,3-Dimethyl-2-oxo-2,3,4,5-tetrahydro-1H-pyrido[2,3-e][1,4]diazepin-7-yl)-N-methyl-N-(3-methyl-benzofuran-2-ylmethyl)acrylamide hydrochloride;

(E)-N-Methyl-N-(3-methyl-1H-inden-2-ylmethyl)-3-(4-methyl-2-oxo-2,3,4,5-tetrahydro-1H-pyrido[2,3-e][1,4]diazepin-7-yl)acrylamide hydrochloride;

(E)-3-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)propionic acid ethyl ester;

(E)-3-(6-amino-5-cyano-pyridin-3-yl)-N-methyl-N-(1-methyl-1H-indol-2-ylmethyl)-acrylamide hydrochloroide; or (E)-N-methyl-N-(1-methyl-1H-indol-2-ylmethyl)-3-(2-oxo-1,2,3,4-tetrahydro-pyrido-[2,3-b]pyrazin-7-yl)-acrylamide.

Also included in the antibacterial compositions of the present invention are pharmaceutically acceptable addition salts and complexes of the FabI inhibitors. In cases wherein the inhibitors may have one or more chiral centers, unless specified, the present invention comprises each unique racemic compound, as well as each unique nonracemic compound.

In cases in which the inhibitors have unsaturated carbon-carbon double bonds, both the cis (Z) and trans (E) isomers are within the scope of this invention. In cases wherein inhibitors may exist in tautomeric forms, such as keto-enol tautomers, such as

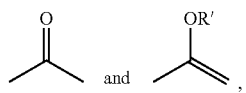

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in the antibiotic compounds of the present invention are prodrugs of the FabI inhibitors.

A variety of subject compounds and intermediates of them may be made by a person of ordinary skill in the art using conventional reaction techniques. Non-limiting examples of compounds and methods of making them may be found in U.S. patent application Ser. Nos. 08/790,043, 10/009,219, 10/089,019, 09/968,129, 09/968,123, 09/968,236, 09/959,172, 09/979,560, 09/980,369, 10/089,755, 10/089,739, 10/089,740, and PCT Application Nos. WO 0027628 and WO 0210332.

Synthetic Routes to Compounds of Formula I

A generalized chemical approach to assembling compounds of formula I is based on viewing the analogs as consisting of a central ene-amide flanked left-hand side (LHS) and right-hand side (RHS) moieties. Schematically, this is depicted in FIG. 2. Two possible bond disconnections envisioned in a retrosynthetic sense are shown with dashed lines. Schemes I to XXXV illustrate some of the general methods that can be used in the synthesis of compounds of formula I. It will be recognized by one skilled in the art that other disconections are possible resulting in alternative modes of assembly of the compounds of the invention.

Schemes I to VIII disclose the basic chemistry involved in the synthesis of the left hand side moieties of formula I wherein the requisite LHS coupling partners are amines and the late stage chemistry involves formation of the amide linkage. The amines are typically arylalky-amines which are most conveniently prepared from comercially available arylcarbaldehydes by the action of a reducing agent such as sodium borohydride in the presence of an alkyl amine such as methyl amine (Scheme I).

Scheme 1

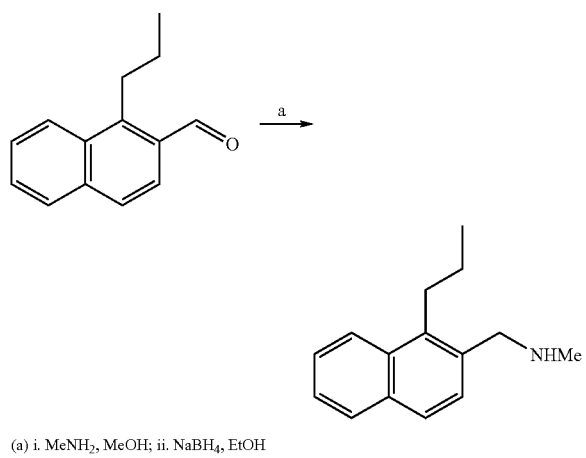

(a) i. MeNH$_2$, MeOH; ii. NaBH$_4$, EtOH

When the arylcarbaldehydes are not comercially available their synthesis can be effected by a number of general methods including the action of dimethylformamide on the lithium salt of aryl anions (Scheme IIb and IIIa).

Scheme II

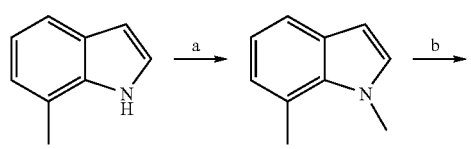

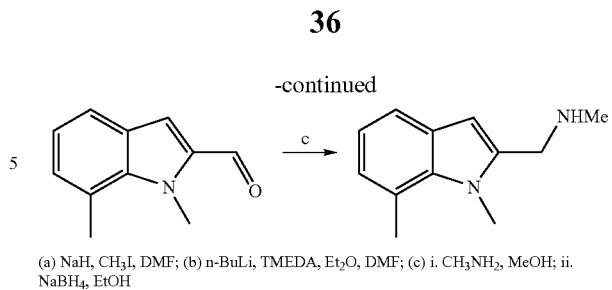

(a) NaH, CH$_3$I, DMF; (b) n-BuLi, TMEDA, Et$_2$O, DMF; (c) i. CH$_3$NH$_2$, MeOH; ii. NaBH$_4$, EtOH

Scheme III

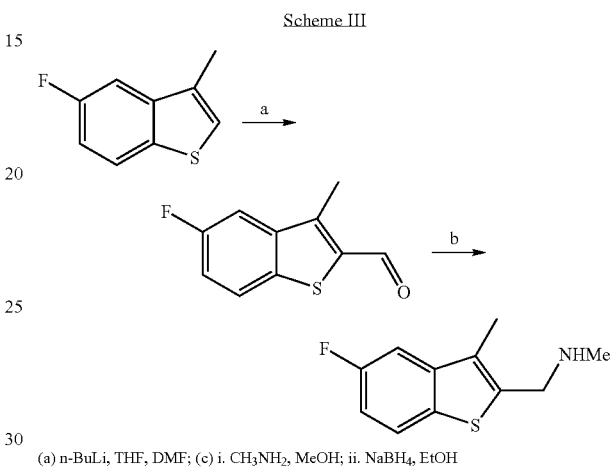

(a) n-BuLi, THF, DMF; (c) i. CH$_3$NH$_2$, MeOH; ii. NaBH$_4$, EtOH

Other methods of obtaining the desired arylcarbaldehydes include the widely employed oxidation of alcohols (Scheme Ivb) and a variety of miscellaneous methods (Scheme Va and Via).

Scheme IV

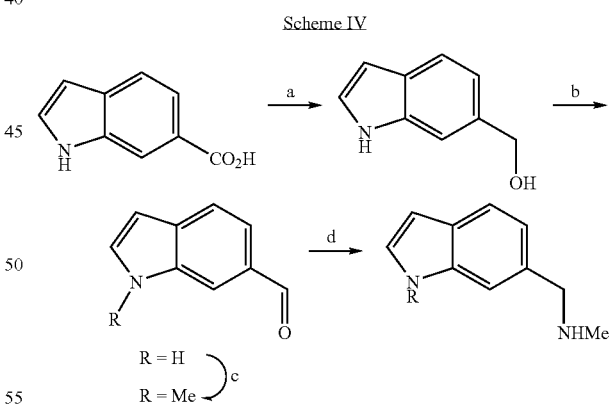

(a) LAH, THF; (b) Dess-Martine periodinane, CH$_2$Cl$_2$, DMF; (c) NaH, CH$_3$I, DMF
(d) i. CH$_3$NH$_2$, MeOH; ii. NaBH$_4$, EtOH Scheme V

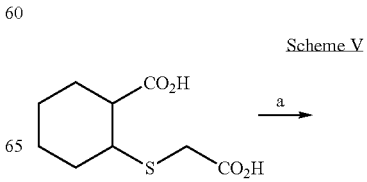

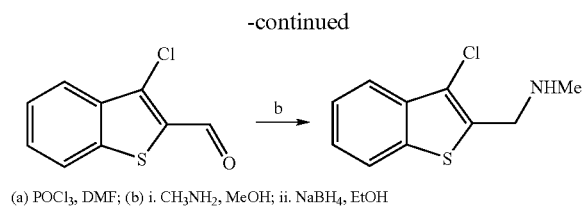

(a) POCl₃, DMF; (b) i. CH₃NH₂, MeOH; ii. NaBH₄, EtOH

Scheme VI

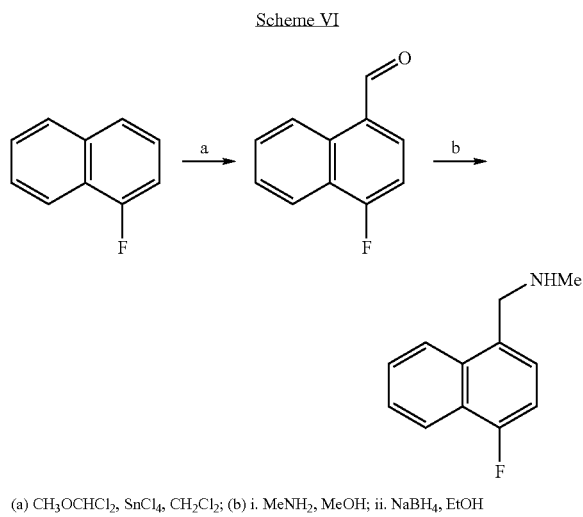

(a) CH₃OCHCl₂, SnCl₄, CH₂Cl₂; (b) i. MeNH₂, MeOH; ii. NaBH₄, EtOH

During the course of these syntheses it may be desirable to alkylate indole-like nitrogens This can be accomplished either prior to (Scheme IIa) or after formation of said carbaldehydes (Scheme Ivc) by the action of strong bases such as sodium hydride and the addition of alkylating agents such as alkyl halides. Likewise oxygen atoms appended to the aromatic systems (e.g. phenols) can be alkylated by the action of base (potassium carbonate) and an alkylhalide (Scheme VIIa).

Scheme VII

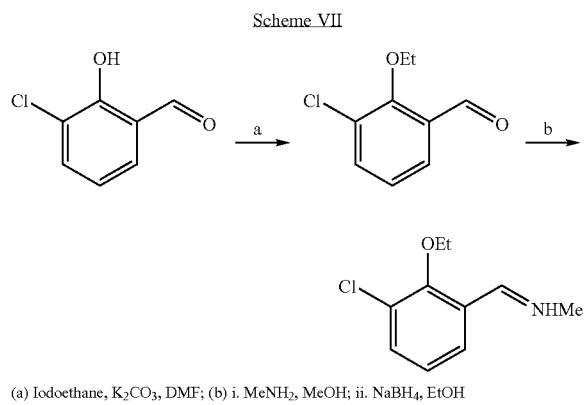

(a) Iodoethane, K₂CO₃, DMF; (b) i. MeNH₂, MeOH; ii. NaBH₄, EtOH

Yet another appraoch to the formation of the desired amines can be from the reduction of precursor amides (Scheme VIII)

Scheme VIII

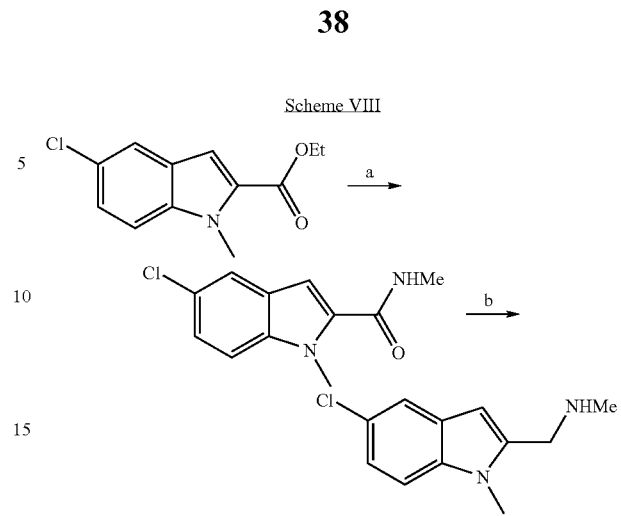

(a) CH₃Al(Cl)NHCH₃, toluene; (b) LiAlH₄, THF

Scheme IX describes the basic chemistry involved in the synthesis of the left hand side moieties of formula I wherein the requisite LHS coupling partners are ene-amides and the late stage chemistry involves formation of a carbon-carbon bond. The carbon-carbon bond formation is usually accomplished by Heck type chemistry which will be described subsequently. The ene-amide is prepared by activation of acylic acid to undergo coupling reaction (with an amine) by any one of the known methods for amide bond formation. One typically used procedure is to treat acrylic acid with a solution of a tertiary amine in DMF followed by the addition of 1-hydroxybenzotriazole hydrate and a carbodiimde such as 1-(3-dimethylaminopropyl)-3-ethyl-carbodiimide hydrochloride. The reaction mixture is then teated with the desired arylalkylamine such as methyl-(1-methyl-1H-indol-3-ylmethyl)-amine (Scheme IX).

Scheme IX

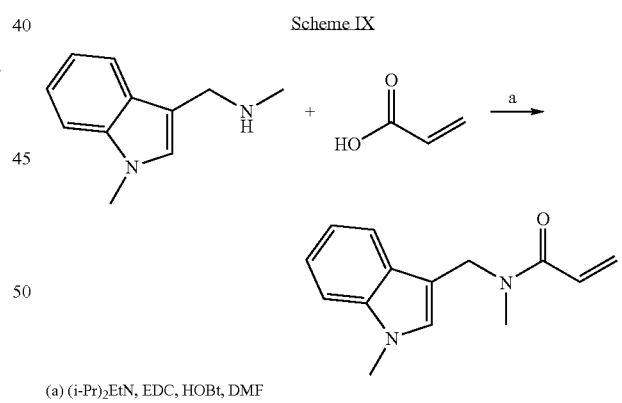

(a) (i-Pr)₂EtN, EDC, HOBt, DMF

Schemes X to XXIV disclose the basic chemistry involved in the synthesis of the right hand side moieties of formula I wherein the requisite RHS coupling partners are carboxylic acids and the late stage chemistry involves formation of the amide linkage. The carboxylic acids are typically arylalkenyl carboxylic acids whose preparation is illustrated by the schemes described below. A common starting material, 5-bromo-3-bromomethyl-pyridin-2-ylamine hydrobromide, is used in the construction of the right hand side moieties described in Schemes X-XVII. In some embodiments of the invention, this material is reacted with a commercial secondary amine (Schemes X-XII) or reacted with a secondary amine which is prepared in the manner illustrated (Schemes XIII-XIV). In either case, a tertiary base is employed. A common feature of the resultant products are compounds incorporating a pendent alkyl ester and an aminopyridine moiety which react in the presence of a base like sodium hydride to form the pyridodiazepinone bicyclic unit.

The pyridodiazepinones prepared in this manner have in common a bromine substitution in the pyridine ring. As will be seen from inspection of the Schemes X-XIV synthesis of arylalkenyl acids proceeds from intermediary bromo-pyridodiazepinones via Heck chemistry (e.g. Scheme Xc). Heck chemistry is carried out by admixture of an arylbromide with an alkylacrylate, such as tert-butylacrylate, in the presence of a palladium catalyst (Pd(OAc)$_2$, P(o-tol)$_3$) and a tertiary base such as di-isopropyl)ethylamine in an appropriate solvent or solvents (e.g. DMF and EtCN). The desired carboxylic acid is obtained by acid-catalysed hydrolysis of the tert-butyl ester (e.g. Scheme Xd).

Scheme X

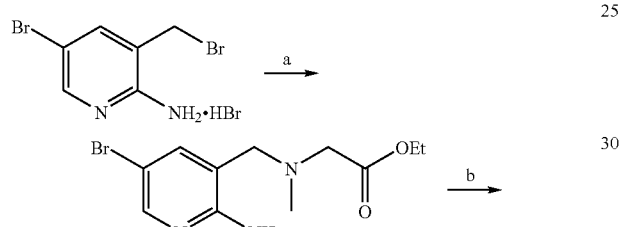

(a) sarcosine ethyl ester hydrochloride, Et$_3$N, DMF; (b) NaH, DMSO; (c) tert-butyl acrylate, Pd(OAc)$_2$, P(o-tol)$_3$, (I-Pr)$_2$EtN, EtCN, DMF; (d) i. TFA, CH$_2$Cl$_2$; ii. 4N HCl/dioxane Scheme XI

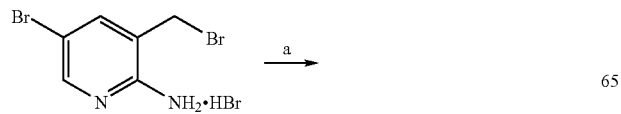

-continued

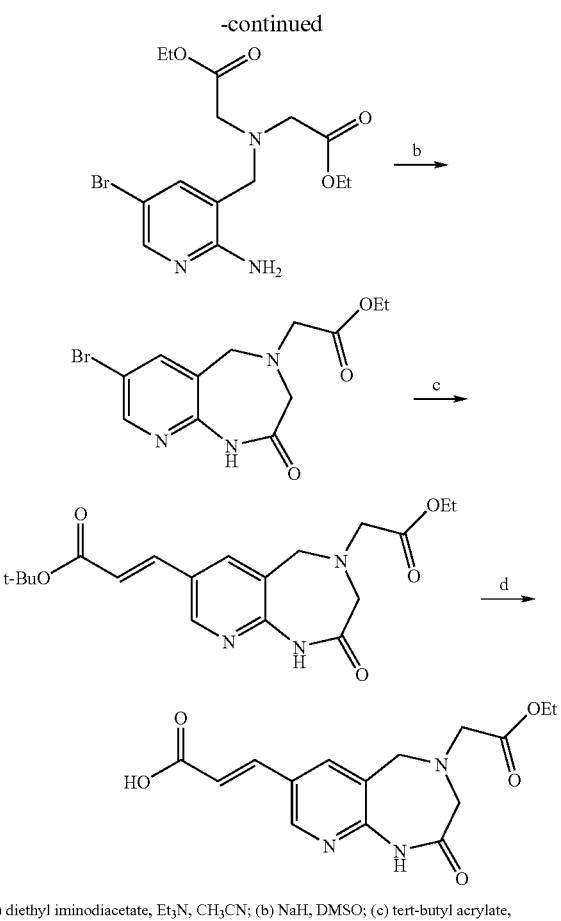

(a) diethyl iminodiacetate, Et$_3$N, CH$_3$CN; (b) NaH, DMSO; (c) tert-butyl acrylate, Pd(OAc)$_2$, P(o-tol)$_3$, (I-Pr)$_2$EtN, EtCN, DMF; (d) i. TFA, CH$_2$Cl$_2$; ii. 4N HCl/dioxane Scheme XII

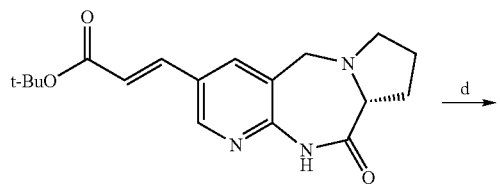

41

-continued

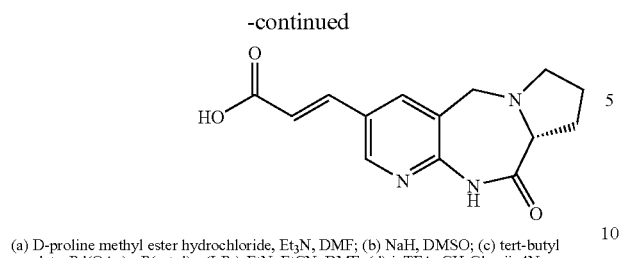

(a) D-proline methyl ester hydrochloride, Et$_3$N, DMF; (b) NaH, DMSO; (c) tert-butyl acrylate, Pd(OAc)$_2$, P(o-tol)$_3$, (I-Pr)$_2$EtN, EtCN, DMF; (d) i. TFA, CH$_2$Cl$_2$; ii. 4N HCl/dioxane Scheme XIII

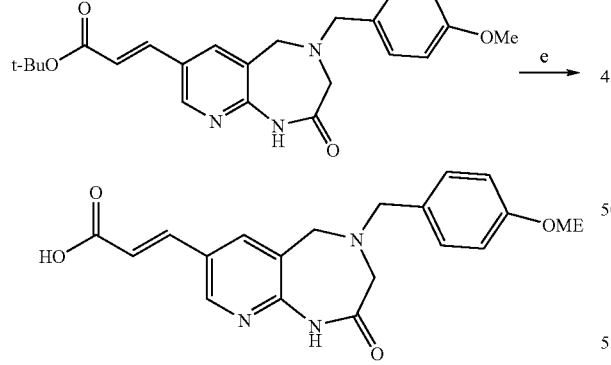

(a) p-anisaldehyde, NaBH$_3$CN, MeOH; (b) 5-bromo-3-bromomethyl-pyridin-2-ylamine hydrobromide, Et$_3$N, DMF; (c) NaH, DMSO; (d) tert-butyl acrylate, Pd(OAc)$_2$, P(o-tol)$_3$, (I-Pr)$_2$EtN, EtCN, DMF; (e) i. TFA, CH$_2$Cl$_2$; ii. 4N HCl/dioxane Scheme XIV

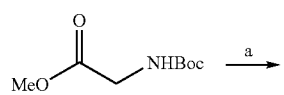

42

-continued

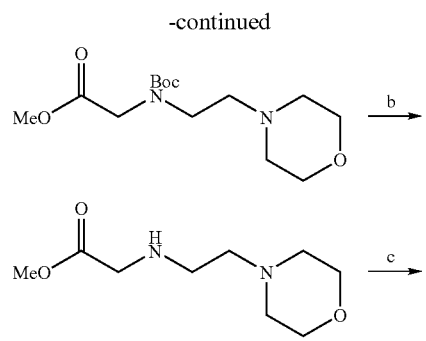

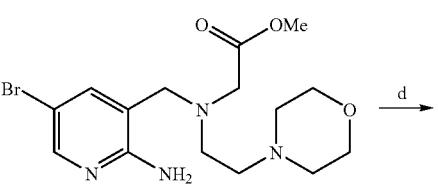

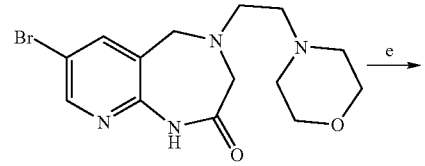

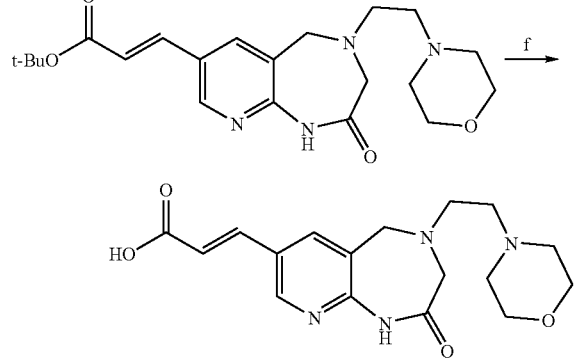

(a) N-(2-chloroethyl)morpholine, NaH, DMF; (b) TFA, CH$_2$CL$_2$; (c) 5-bromo-3-bromomethyl-pyridin-2-ylamine hydrobromide, Et$_3$N, DMF; (d) NaH, DMSO; (e) tert-butyl acrylate, Pd(OAc)$_2$, P(o-tol)$_3$, (I-Pr)$_2$EtN, EtCN, DMF; (f) i. TFA, CH$_2$Cl$_2$; ii. 4N HCl/dioxane Scheme XV

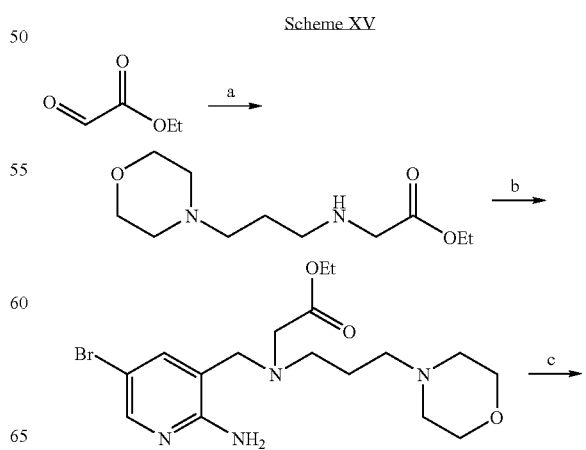
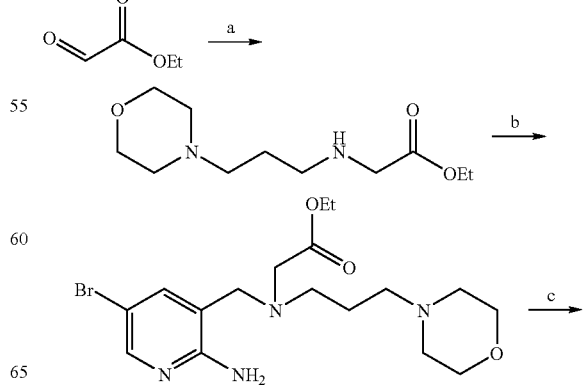

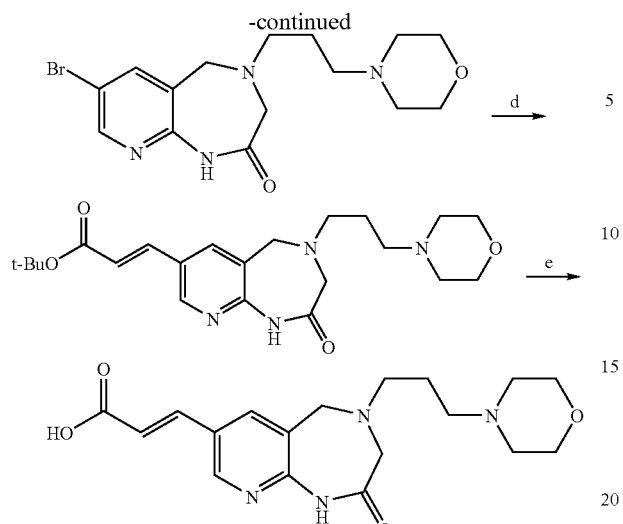

(a) 4-(3-aminopropyl)morpholine, NaBH₃CN, AcOH, MeOH; (b) 5-bromo-3-bromomethyl-pyridin-2-ylamine, Et₃N, DMF; (c) NaH, DMSO; (d) tert-butyl acrylate, Pd(OAc)₂, P(o-tol)₃, (I-Pr)₂EtN, EtCN, DMF; (e) i. TFA, CH₂Cl₂; ii. 4N HCl/dioxane In an analogous way to the chemistry described above, 5-bromo-3-bromomethyl-pyridin-2-ylamine hydrobromide, may be reacted with primary amines (Scheme XVI, XVII, XVI); subsequent cyclization with sodium hydride yields a pyridodiazepinone in which the nitrogen at the four position is unsubstituted. In Scheme XVI the final product represents a right hand side moiety of formula I wherein the requisite RHS coupling partners is an aryl bromide and the late stage chemistry involves formation of a carbon-carbon bond via Heck chemistry. One skilled in the art will recognize that the intermediate aryl bromides described in Schemes X-XX may also be used in late stage carbon-carbon bond forming chemistry.

Alternatively, the nitrogen at position four may be derivatized by reaction with alkylating (Scheme XVIIc) or acylating agents (Scheme XVIIIc). In the former case, further elaboration (Scheme XVIId,e) yields a derivatized bromopyridodiazepinone which is subjected to standard Heck coupling/deprotection sequence to give the desired acid. In the latter case, the CBz-protected pyridodiazepinone is similarly treated (Scheme XVIII).

Scheme XVI

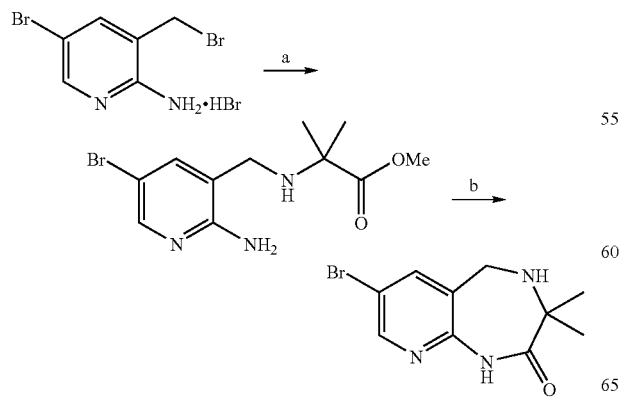

Scheme XVII

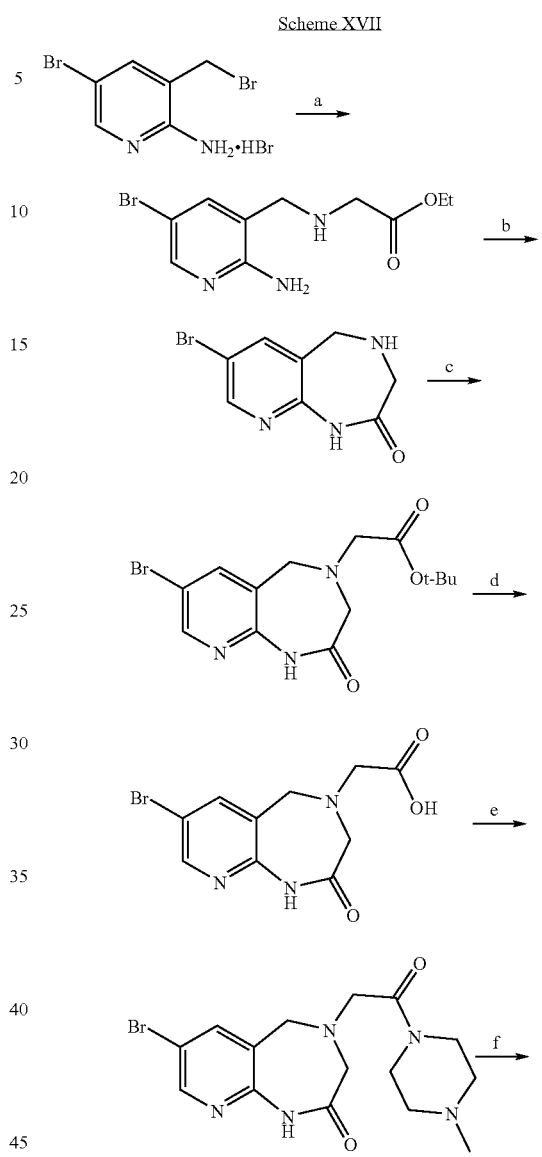

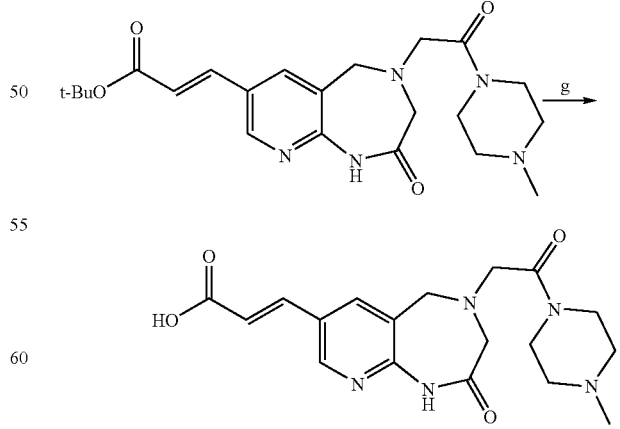

(a) glycine ethyl ester hydrochloride, Et₃N, DMF; (b) NaH, DMSO; (c) tert-butyl bromoacetate, Et₃N, DMF; (d) i. TFA, CH₂Cl₂; ii. 4N HCl/dioxane; (e) 1-methylpiperazine, (I-Pr)₂EtN, EDC, HOBt, CH₂Cl₂; (f) tert-butyl acrylate, Pd(OAc)₂, P(o-tol)₃, (I-Pr)₂EtN, EtCN, DMF; (g) i. TFA, CH₂Cl₂; ii. 4N HCl/dioxane

Scheme XVIII

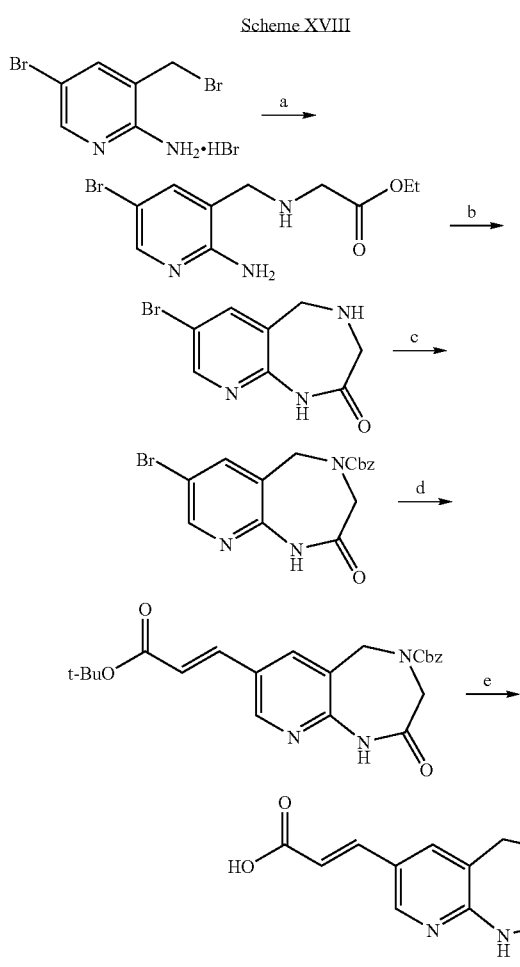

(a) glycine ethyl ester hydrochloride, Et₃N, DMF; (b) NaH, DMSO; (c) CbzCl, Et₃N, CH₂Cl₂; (d) tert-butyl acrylate, Pd(OAc)₂, P(o-tol)₃, (I-Pr)₂EtN, EtCN, DMF; (e) i. TFA, CH₂Cl₂; ii. 4N HCl/dioxane 5-Bromo-3-bromomethyl-pyridin-2-ylamine hydrobromide, may also be reacted with cyclic secondary amines (Scheme XIX); the desired acid is obtained in the usual way.

Scheme XIX

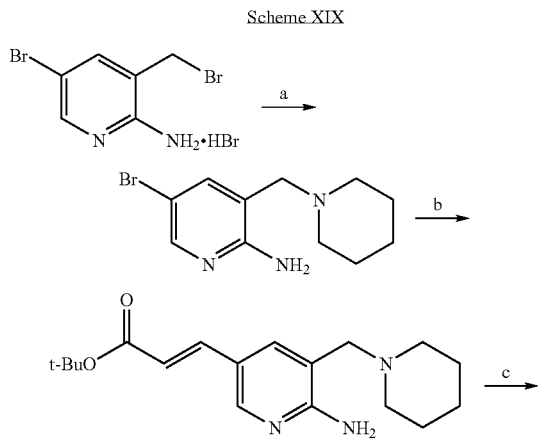

Right hand sides in which an aminopyridine ring is derivatized via an amide linkage may be realized by reaction of 2-amino-5-bromonicotinic acid hydrobromide with primary, amines. Heck coupling and hyrolysis gives the desired acid (Scheme XX)

Scheme XX

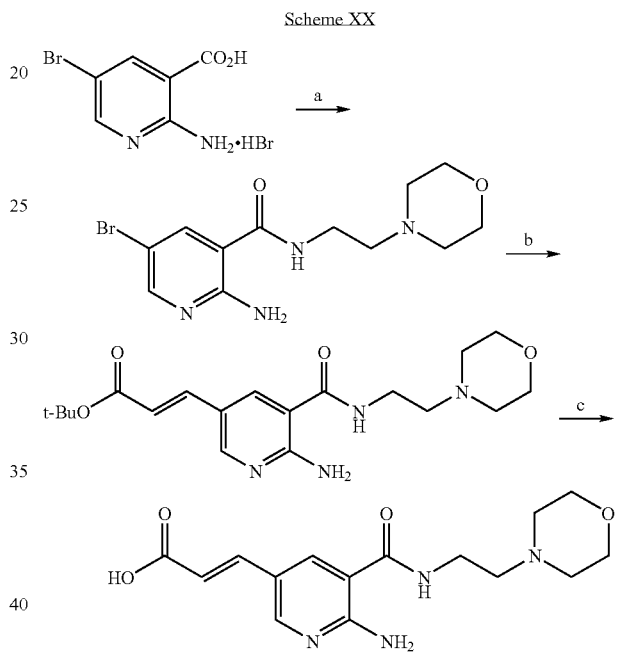

(a) 4-(2-aminoethyl)morpholine, EDC, HOBt, Et₃N, CH₂Cl₂; (b) tert-butylacrylate, DIEA, Pd(OAc)₂, P(o-tol)₃, EtCN, DMF; (c) i. TFA, CH₂Cl₂; ii. 4N HCl/1,4-dioxane Schemes XXI-XXIV are illustrative of methods use for preparing RHS moieties wherein 3,4-dihydro-1H-pyrido[2,3-d]pyrimidin-2-ones are incorporated as RHS moieties. Schemes XXI-XXIII show preparations wherein carboxylic acids are prepared and end stage chemistry involves amide bond formation, scheme V shows preparation of an aryl bromide employed in carbon-carbon bond forming end stage chemistry.

In each case an intermediate aminomethyl aminopyridine is prepared by amide bond reduction (Scheme XXI), reductive amination of aldehydes (Scheme XXII and Scheme XXIV) or, as described above in Scheme XVII, by displacement of an benzylic bromide with the desired primary amine. The latter method yields the starting material for Scheme XXIII. The subsequent step, common to all cases, is cyclization using carbonyl diimidazole to form the 3,4-dihydro-1H-pyrimidin-2-one ring. Other activated carbonyl equivalents are expected to affect a similar cyclization. In Schemes XXI-XXIII further elaboration using Heck coupling and hydrolysis gives the desired carboxylic acid RHS moieties.

Scheme XXI

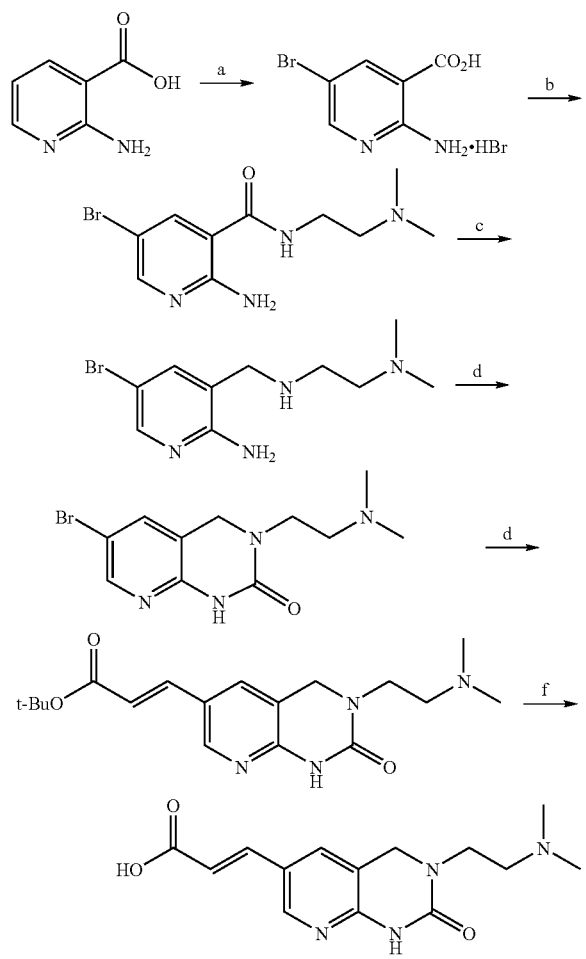

(a) Br$_2$, HOAc; (b) N,N-dimethylethylenediamine, EDC, HOBt, Et$_3$N, CH$_2$Cl$_2$; (c) i. BH$_3$; ii. HCl, MeOH; (d) CDI, 1,4-dioxane; (e) tert-butylacrylate, DIEA, Pd(OAc)$_2$, P(o-tol)$_3$, EtCN, DMF; (f) i. TFA, CH$_2$Cl$_2$; ii. 4N HCl/dioxane

Scheme XXII

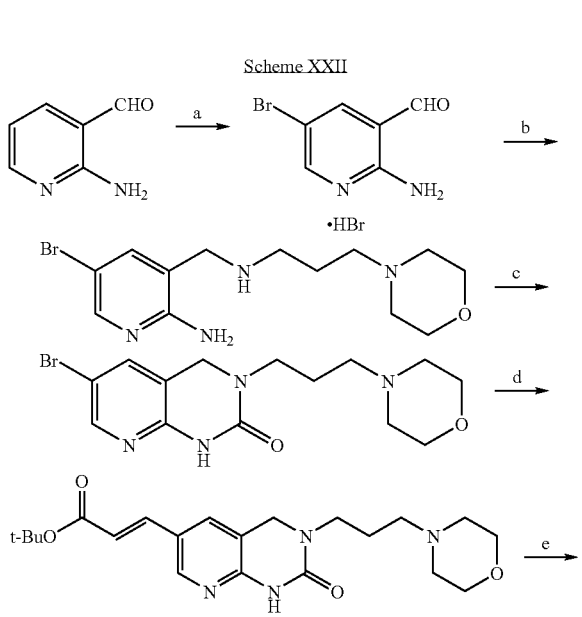

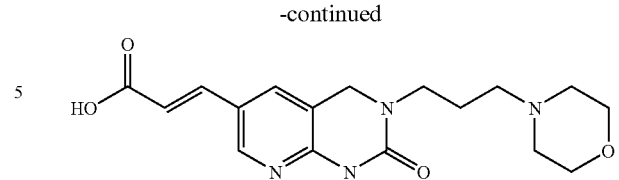

(a) Br$_2$, HOAc; (b) i. 4-(3-aminopropyl)morpholine, Et$_3$N, MeOH; ii NaBH$_4$; (c) CDI, 1,4-dioxane; (d) tert-butylacrylate, DIEA, Pd(OAc)$_2$, P(o-tol)$_3$, EtCN, DMF; (f) i. TFA, CH$_2$Cl$_2$; ii. 4N HCl/dioxane

Scheme XXIII

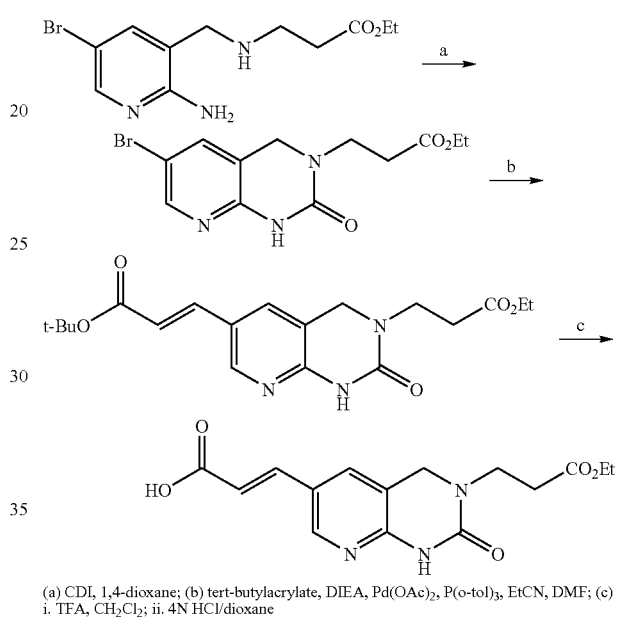

(a) CDI, 1,4-dioxane; (b) tert-butylacrylate, DIEA, Pd(OAc)$_2$, P(o-tol)$_3$, EtCN, DMF; (c) i. TFA, CH$_2$Cl$_2$; ii. 4N HCl/dioxane

Scheme XXIV

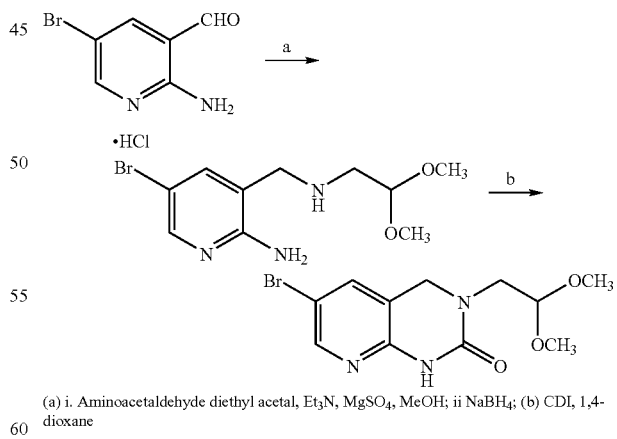

(a) i. Aminoacetaldehyde diethyl acetal, Et$_3$N, MgSO$_4$, MeOH; ii NaBH$_4$; (b) CDI, 1,4-dioxane Schemes XXV and XXVI are illustrative of the methods used for preparing (E)-3-(2,4-dioxo-1,2,3,4-tetrahydro-pyrido[2,3-d]pyrimidin-6-yl)-acrylic acid and (E)-3-(2-oxo-2,3-dihydro-oxazolo[4,5-b]pyridin-6-yl)-acrylic acid right hand sides respectivley.

Scheme XXV

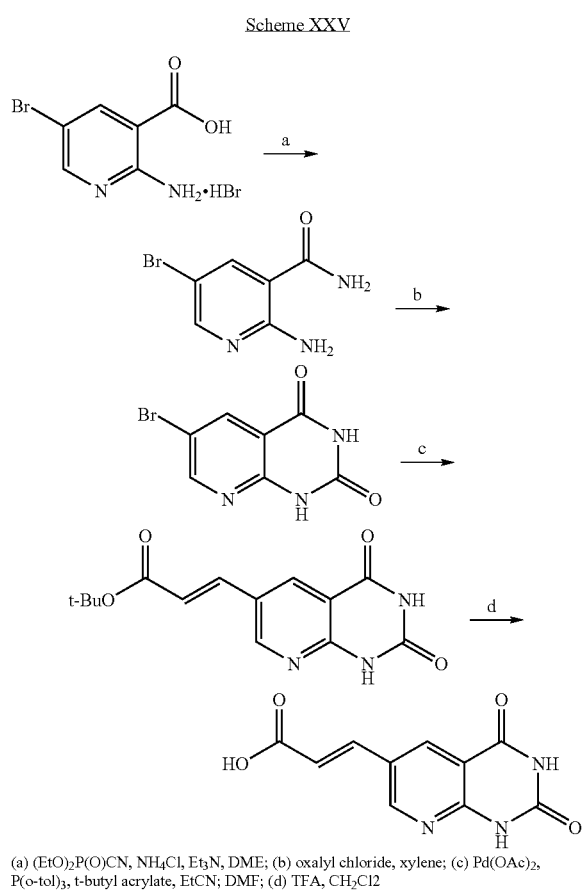

(a) (EtO)$_2$P(O)CN, NH$_4$Cl, Et$_3$N, DME; (b) oxalyl chloride, xylene; (c) Pd(OAc)$_2$, P(o-tol)$_3$, t-butyl acrylate, EtCN; DMF; (d) TFA, CH$_2$Cl2

Scheme XXVI

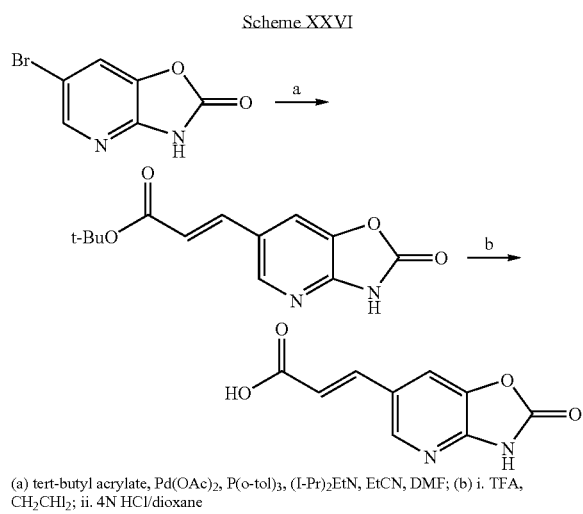

(a) tert-butyl acrylate, Pd(OAc)$_2$, P(o-tol)$_3$, (I-Pr)$_2$EtN, EtCN, DMF; (b) i. TFA, CH$_2$CHl$_2$; ii. 4N HCl/dioxane Schemes XXVII describes a specific example of a general method for assembly of compounds of formula I wherein the LHS coupling partners are amines, the RHS coupling partners are acids and the late stage chemistry involves formation of the amide linkage. There are many common methods for formation of amide linkages. In the example depicted in Scheme XXVII an acid ((E)-3-(4-methyl-2-oxo-2,3,4,5-tetrahydro-1H-pyrido[2,3-e][1,4]diazepin-7-yl)-acrylic acid) is activated by treatment with a carbodiimide (EDC) and hydroxybenzotriazole (HOBt) in the presence of a polar aprotic solvent (DMF) and reacted with a suitable amine (N-methyl-N-(1-methyl-1H-indol-3-ylmethyl)amine) in the presence of a tertiary amine base like diisopropylethylamine.

Scheme XXVII

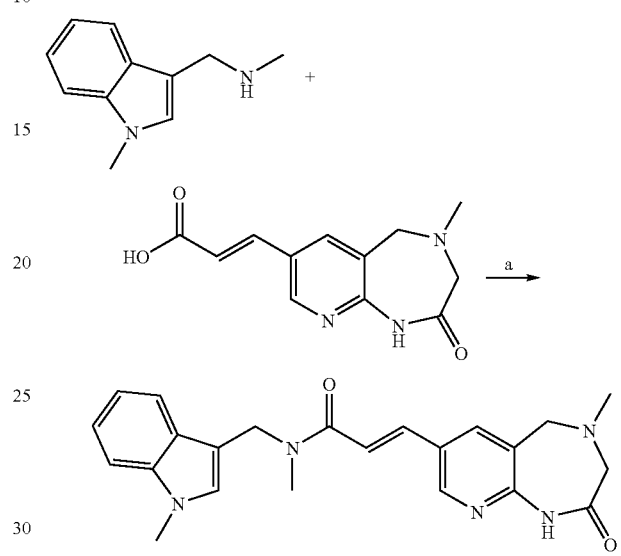

(a) N-methyl-N-(1-methyl-1H-indol-3-ylmethyl)amine, (i-Pr)$_2$EtN, EDC, HOBt, DMF An alternative method for assembling compounds of formula 1, generally referred to as Heck coupling, is depicted in Scheme XVIII. An acrylic amide such as N-methyl-N-(3-methyl-benzo[b]thiophen-2-ylmethyl)-acrylamide is treated with an aryl bromide such as 7-bromo-3,3-dimethyl-1,3,4,5-tetrahydro-pyrido[2,3-e][1,4]diazepin-2-one in the presence of a palladium catalyst (Pd(OAc)$_2$, P(o-tol)$_3$), a tertiary amine ((I—Pr)$_2$EtN) and an aprotic solvent or solvents (EtCN, DMF).

Scheme XXVIII

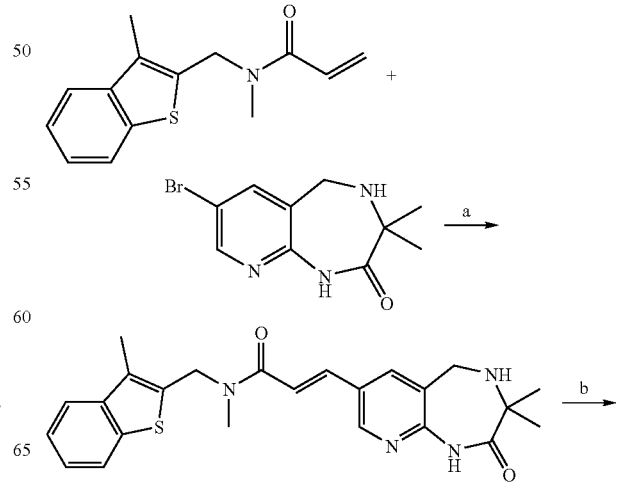

-continued

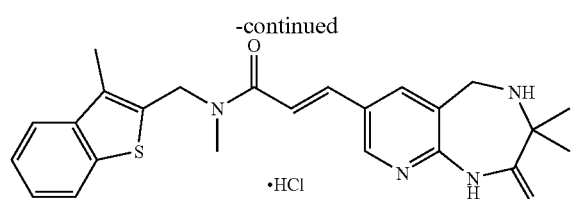

(a) a, a-dimethylglycine methyl ester hydrochloride, Et₃N, DMF; (b) NaH, DMSO; (c) N-methyl-N-(3-methyl-benzo[b]thiophen-2-ylmethyl)acrylamide, Pd(OAc)₂, P(o-tol)₃, (I-Pr)₂EtN, EtCN, DMF; (d) 1N HCl/Et₂O, CH₂Cl₂

To access certain compounds of the invention it may be necessary to perform synthetic manipulations after the right hand side and left hand side units have been assembled. Scheme XXIX for example outlines the conversion of an aminopyridine moiety to a cyclic imide followed by ring opening with ammonia.

Scheme XXIX

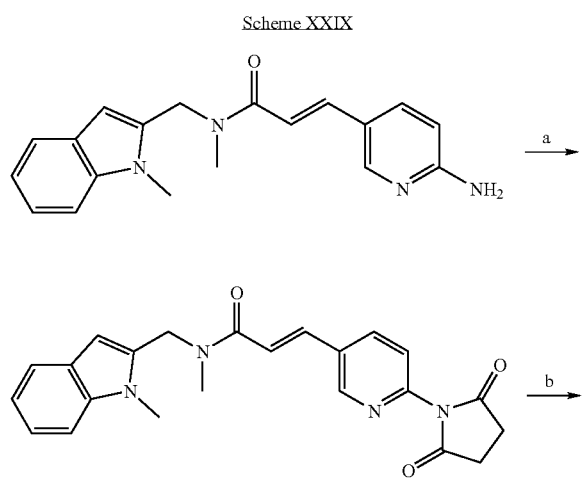

-continued

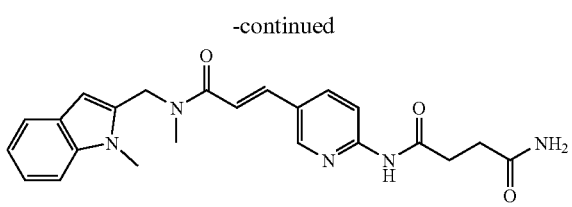

(a) succinic anhydride, 1,4-dioxane; (b) NH₃, 1,4-dioxane.

Additional examples of aminopyridine derivatization are given in Schemes XXX and XXXI which describe the acylation of the amine moeity to form amide linkages.

Scheme XXX

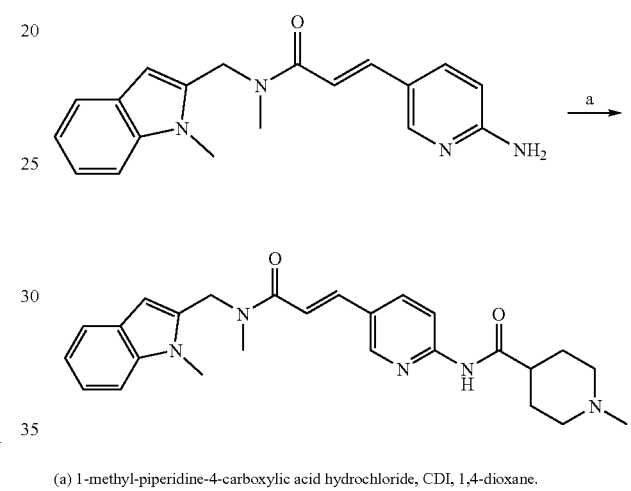

(a) 1-methyl-piperidine-4-carboxylic acid hydrochloride, CDI, 1,4-dioxane.

Scheme XXXI

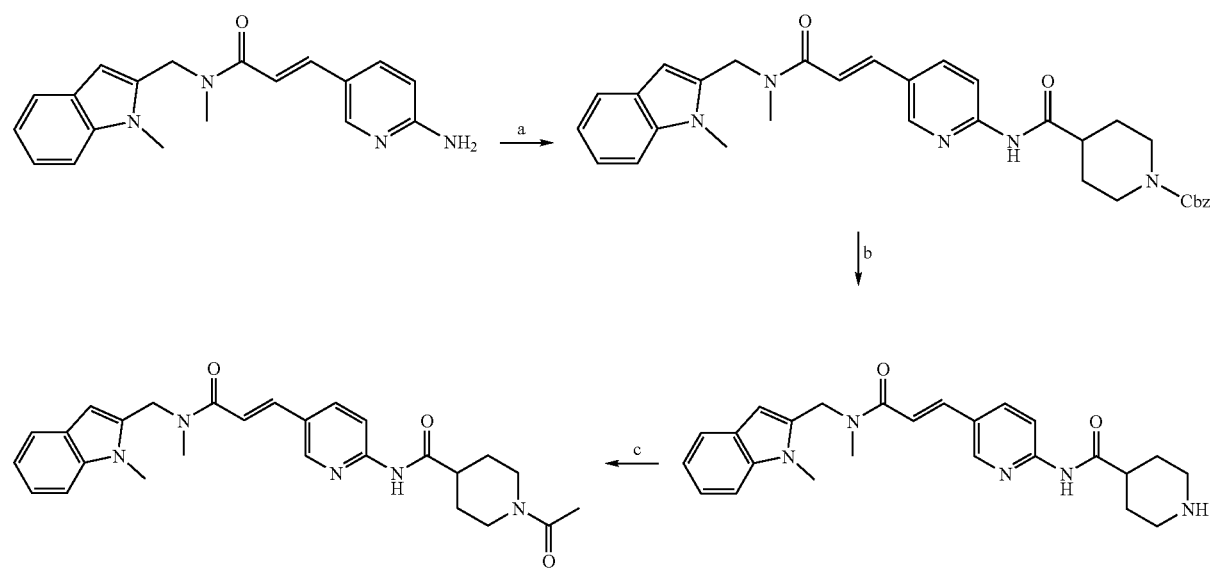

(a) [1-(carbobenzoxy)-4-piperidine]carboxylic acid, CDI, 1,4-dioxane; (b) TMSI, CH₂Cl₂; (c) Ac₂O, Et₃N, CH₂Cl₂.

In certain aspects of the invention it is desirable to have pyridodiazepinones in place on the right hand side with unsubstituted 4-position nitrogen. In these instances a suitable protecting group such as methoxybenzyl can temporarily mask the nitrogen. This protecting group may be removed in a two-step procedure by treatment with 1-chloroethyl chloroformate followed by hydrolysis of the intermediate carbamate. The hydrochloride salt may be prepared, if desired, through treatment with dilute acid (HCl) in an aprotic solvent such as ether (Scheme XXXII).

-continued

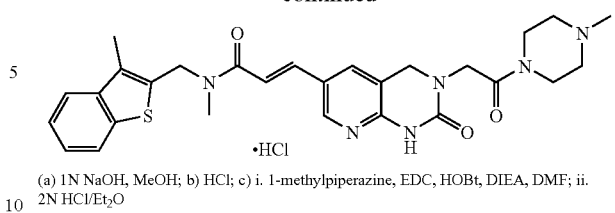

(a) 1N NaOH, MeOH; b) HCl; c) i. 1-methylpiperazine, EDC, HOBt, DIEA, DMF; ii. 2N HCl/Et₂O

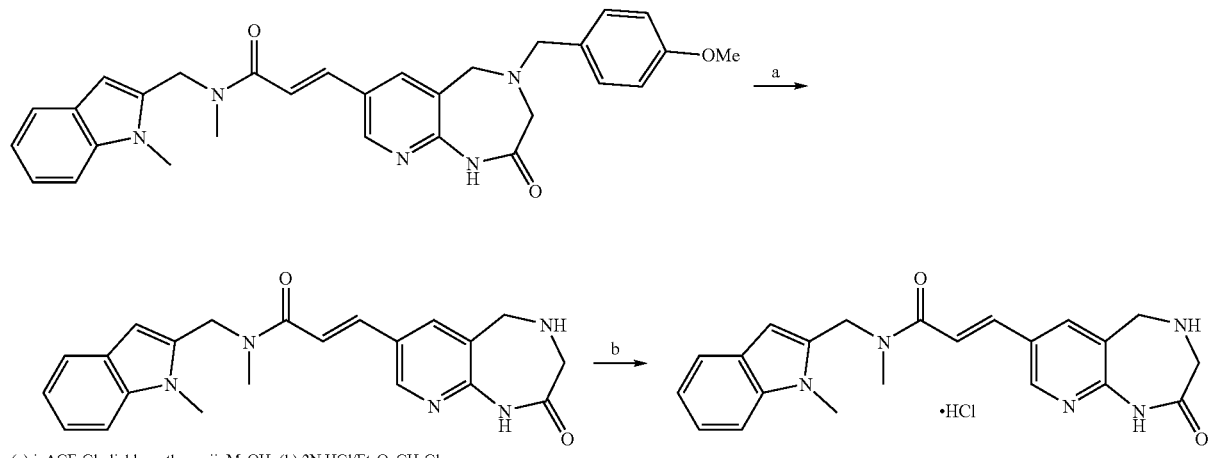

(a) i. ACE-Cl, dichloroethane; ii. MeOH; (b) 2N HCl/Et₂O, CH₂Cl₂.

Schemes XXIII and XXXIV respectively show methods for conversion of ester and dimethylether ether groups pendent on a 3,4-dihydro-1H-pyrido[2,3-d]pyrimidin-2-one right hand side to piperidine-containing tethers. These chemical manipulations are caried out after the standard coupling reactions described above are applied (e.g. Scheme XXVII or XXVIII).

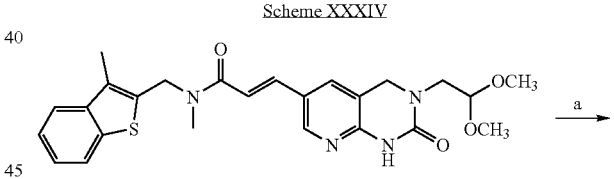

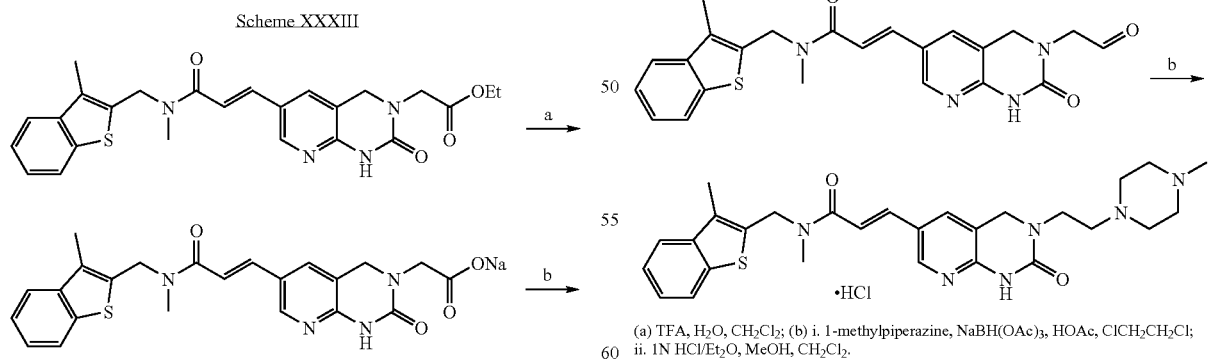

(a) TFA, H₂O, CH₂Cl₂; (b) i. 1-methylpiperazine, NaBH(OAc)₃, HOAc, ClCH₂CH₂Cl; ii. 1N HCl/Et₂O, MeOH, CH₂Cl₂.

Scheme XXXV illustrates a method of compound construction falling outside the general methods described above in that a dicarboxylic acid, prepared as in Scheme XXXIVa, is reacted with two equivalents of arylmethylamine using the standard amide couping conditions.

Scheme XXXV

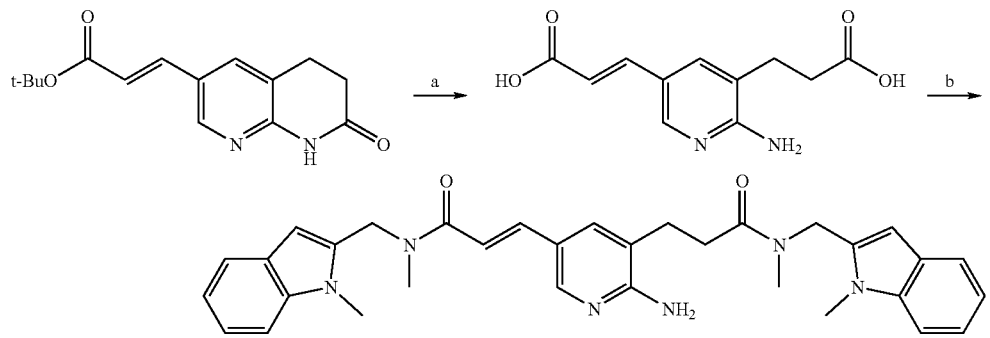

(a) i. Aq. NaOH, methanol, dioxane; (b) EDC, HOBt, DIEA, DMF, methyl-(1-methyl-1H-indol-2-ylmethyl)amine.

It will be recognized by one skilled in the art that other methods of LHS and RHS synthesis can be employed in the preparation of said intermediates. Likewise other methods of amide and/or carbon-carbon bond formation may be used to assemble the compounds of the inverntion. It is also apparent that combinations of LHS and RHS other than those described above can be envisioned to prepare compounds falling within the scope of the invention as represented by formula I. These possibilities are further detailed in the prepartations and examples section to follow.

Acid addition salts of the compounds of formula I can be prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts may be prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are some non-limiting examples of cations present in pharmaceutically acceptable salts.

Toxicology of Compounds

Acute toxicity can be assessed using increasing doses in mice and rodents. Exploratory acute toxicity in mice and/or rats after single dose may be undertaken to begin estimation of the therapeutic window of inhibitors and to identify the potential target organ is of toxicity. As candidate selection nears, these studies may provide guidance for the selection of proper doses in multi-dose studies, as well as establish any species specific differences in toxicities. These studies may be combined with routine PK measurements to assure proper dosages were achieved. Generally 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

Resistance Frequencies and Mechanisms of Compounds

In vitro resistance frequencies in bacteria of interest can be estimated for compounds of formula I. Experiments can determine whether resistant isolates arise when challenged to grow on solid media at 1×, 2× and 4×MIC concentrations. For example with respect to S. aureus or E. Coli, the experiments may use several recent clinical isolates of methicillin-sensitive and methicillin-resistant S. aureus and a laboratory strain of E. coli with acrA efflux pump defect In addition, experiments may use several characterized reclosing-resistant. S. aureus strains. The MICs of resistant strains isolated in this manner can then be determined. Subsequent experiments can determine whether resistant strains arise after serial passage of the strains in 0.5×MIC concentrations of each lead compound.

Mechanism of resistance may be determined in S. aureus laboratory strain, RN450 and in an E. coli laboratory strain carrying an acrA efflux pump mutation. Both high dose challenge (4×MIC) and sub-MIC serial passage may be used to obtain spontaneously arising resistant isolates. If no isolates are obtained with reasonable frequencies, chemical and physical mutagenesis methods can be used to obtain resistant isolates. The fabI gene from the chromosome of resistant isolates may be PCR amplified, then may be sequenced to determine whether changes in the FabI protein caused resistance. Triplicate PCR amplifications and sequences may be performed to assure that the observed sequence changes are correct, and did not arise from PCR errors during amplification. Strains carrying resistance mutations outside of the gene of interest may be documented and saved, characterized for their effects on susceptibilities of other antibiotics as evidence of possible efflux-mediated resistance mechanisms, characterized for their ability to alter compounds characterized for their effects on the expression of the specific mRNA and FabI protein.

Assays

Many different assay methods can be used to determine the activity of the compounds of the present invention. These assay methods include, for example, the following but also include other methods known to one of ordinary skill in the art.

S. aureus FabI Enzyme Inhibition Assay (NADH)

Assays are carried out in half-area, 96-well microtitre plates. Compounds are evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI. Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Reclosing, a commercial antibacterial agent and inhibitor of FabI, may be included in an assay as a positive control. Compounds of this invention may have $IC_{50}$'s from about 5.0 micromolar to about 0.05 micromolar.

S. aureus FabI Enzyme Inhibition Assay (NADPH)(Modified)

Assays are carried out in half-area, 96-well microtitre plates. Compounds are evaluated in 150-uL assay mixtures containing 100 mM NaADA, pH 6.5 (ADA=N-[2acetamido]-2-iminodiacetic acid), 4% glycerol, 0.25 mM crotonoyl CoA, 50 uM NADPH, and an appropriate dilution of S. aureus FabI. Inhibitors are typically varied over the range of 0.01-10 uM. The consumption of NADPH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Reclosing, a commercial antibacterial agent and inhibitor of FabI, is currently included in all assays as a positive control.

H. influenzae FabI Enzyme Inhibition Assay

Assays are carried out in half-area, 96-well microtiter plates. Compounds are evaluated in 150-uL assay mixtures containing 100 mM MES, 51 mM diethanolamine, 51 mM triethanolamine, pH 6.5 (MES=2-(N-morpholino)ethanesulfonic acid), 4% glycerol, 25 uM crotonoyl-ACP, 50 uM NADH, and an appropriate dilution of H. influenzae FabI (approximately 20 nM). Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves. $IC_{50}$'s are estimated from a fit of the initial velocities to a standard, 4-parameter model, and are typically reported as the mean±S.D. of duplicate determinations. The apparent Ki is calculated assuming the inhibition is competitive with crotonoyl-ACP. A proprietary lead compound is currently included in all assays as a positive control.

E. coli FabI Enzyme Inhibition Assay

Assays are carried out in half-area, 96-well microtitre plates. Compounds are evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors are typically varied over the range of 0.01-10 uM. The consumption of NADH is monitored for 20 minutes at 30° C. by following the change in absorbance at 340 nm. Initial velocities are estimated from an exponential fit of the non-linear progress curves represented by the slope of the tangent at t=0 min. $IC_{50}$'s are estimated from a fit of the initial velocities to a standard, 4-parameter model and are typically reported as the mean±S.D. of duplicate determinations. Reclosing, a commercial antibacterial agent and inhibitor of FabI, is currently included in all assays as a positive control. Compounds of this invention have $IC_{50}$'s from about 100.0 micromolar to about 0.05 micromolar.

Preparation and Purification of Crotonoyl-ACP

Reactions contain 5 mg/mL E. coli apo-ACP, 0.8 mM crotonoyl-CoA (Fluka), 10 mM $MgCl_2$, and 30 uM S. pneumoniae ACP synthase in 50 mM NaHEPES, pH 7.5. The mixture is gently mixed on a magnetic stirrer at 23° C. for 2 hr, and the reaction is terminated by the addition of 15 mM EDTA and cooling on ice. The reaction mixture is filtered through a 0.2 micron filter (Millipore) and applied to a MonoQ column (Pharmacia) equilibrated with 20 mM Tris-Cl, pH 7.5. The column is washed with buffer until all non-adherent material is removed (as observed by UV detection), and the crotonoyl-ACP is eluted with a linear gradient of 0 to 400 mM NaCl.

S. aureus FabI Enzyme Inhibition Assay Using crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of S. aureus Fab I (approximately 20 nM). Inhibitors are typically varied over the range of 0.01-30 uM. The consumption of NADPH is monitored for 30 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent Ki is calculated from Equation 2 assuming the inhibition is competitve with crotonoyl-ACP. More specifically, measured $IC_{50}$ values for 24 compounds of the present invention, as provided in the representative list above, ranged from less than about 0.02 µM to about 25 µM with 11 of these compounds having an $IC_{50}$ of less than 1.

H. pylori FabI Enzyme Inhibition Assay Using Crotonoyl-ACP

Assays are carried out in half-area, 96-well microtitre plates. Compounds are evaluated in 100 uL assay mixtures containing 100 mM NaADA, pH 6.5 (ADA=N-(2-acetamido)-2-iminodiacetic acid), 4% glycerol, 10 uM crotonoyl-ACP, 50 uM NADH, 100 mM ammonium acetate, and an appropriate dilution of H. pylori-Fab I (approximately 15 nM). Inhibitors are typically varied over the range of 0.025-30 uM. The consumption of NADH is monitored for 30 minutes at 25° C. by following the change in absorbance at 340 nm. Initial velocities are estimated from a linear fit of the progress curves. IC50's are estimated from a fit of the initial velocities to a standard, 4-parameter model (Equation 1) and are typically reported as the mean±S.D. of duplicate determinations. Compounds of this invention in this assay have $IC_{50}$'s from about 60.0 micromolar to about 0.01 micromolar. The apparent K; is calculated from Equation 2 assuming the inhibition is competitve with crotonoyl-ACP.

$$v = Range/(1+[I]/IC50)s + Background \qquad \text{Equation 1:}$$

$$Ki(app) = IC50/(1+[S]/Ks) \qquad \text{Equation 2:}$$

S. pneumoniae FabK Enzyme Inhibition Assay Using Crotonoyl-ACP

Assays are carried out in half-area, 96-well microtitre plates. Compounds are evaluated in 100 uL assay mixtures containing 100 mM MES, 51 mM diethanolamine, 51 mM triethanolamine, pH 6.5 [MES=2-(N-morpholino)ethanesulfonic acid], 4% glycerol buffer, 100 mM $NH_4Cl$, 25 µM crotonoyl-ACP, 50 µM NADH, and 15 nM S. pneumoniae FabK. Inhibitors are typically varied over the range of 0.025-30 uM. The consumption of NADH is monitored for 30 minutes at 30° C. by following the change in absorbance at 340 nm. Initial velocities are estimated from a linear fit of the progress curves. IC$_{50}$'s are estimated from a fit of the initial velocities to a standard, 4-parameter model (Equation 1) and are typically reported as the mean±S.D. of duplicate determinations. Compounds of this invention in this assay have IC$_{50}$'s from about 60.0 micromolar to about 0.01 micromolar. The apparent K$_i$ is calculated from Equation 2 assuming the inhibition is competitve with crotonoyl-ACP.

Antimicrobial Activity Assay

Whole-cell antimicrobial activity is determined by broth microdilution using the National Committee for Clinical Laboratory Standards (NCCLS) recommended procedure, Document M7-A5, "Methods for Dilution Susceptibility Tests for Bacteria that Grow Aerobically". The compound is tested in serial two-fold dilutions ranging from 0.06 to 64 mcg/mL. A panel of 12 strains are evaluated in the assay. This panel consists of the following laboratory strains: *Enterococcus faecalis* 29212, *Staphylococcus aureus* 29213, *Staphylococcus aureus* 43300, *Moraxella catarrhalis* 49143, *Haemophilus influenzae* 49247, *Streptococcus pneumoniae* 49619, *Staphylococcus epidermidis* 1024939, *Staphylococcus epidermidis* 1024961, *Escherichia coli* AG100 (AcrAB$^+$), *Escherichia coli* A100A (AcrAB$^-$), *Pseudomonas aeruginosa* K767 (MexAB$^+$, OprM$^+$), *Pseudomonas aeruginosa* K1119 (MexAB$^-$, OprM$^-$). The minimum inhibitory concentration (MIC) is determined as the lowest concentration of compound that inhibited visible growth. A spectrophotometer is used to assist in determining the MIC endpoint.

MIC assays may be performed using the microdilution method in a 96 well format. The assays may be performed in 96 well plates with a final volume of 100 μl cation-adjusted Mueller Hinton broth containing 2 fold serial dilutions of compounds ranging from 32 to 0.06 μg/ml. Bacterial growth may be measured at 600 nm using a Molecular Devices SpectraMax 340PC spectrophotometer. MICs can then be determined by an absorbance threshold algorithm and confirmed in some cases by inspecting the plates over a light box.

Minimum Bactericidal Concentration (MBC) may be determined by plating aliquots of MIC dilution series that did not show bacterial growth onto Petri plates containing appropriate semi-solid growth media. The lowest compound concentration that resulted in >99% killing of bacterial cells (relative to initial bacterial inocula in MIC test) is defined as the MBC.

Several strain panels may be used at various points in the compound progression scheme. The primary panel may include single prototype strains of both community- and hospital-acquired pathogens for determining initial activities and spectra of activity. Secondary panel compositions will depend on the results of the primary panels, and will include 10-20 strains of relevant species that will include community acquired and antibiotic-resistant hospital acquired strains of *Staphylococcus aureus* and coagulase negative *Staphylococci* together with other strains that are sensitive to the new compounds, and negative control strains. The secondary panels will be used during optimization of lead chemical series. Tertiary panels will include 100-200 clinical strains of *S. aureus* and coagulase negative *Staphylococci* together with other relevant strains as for the secondary panels. The tertiary panels will be utilized during the compound candidate selection stage and preclinical studies to generate bacterial population efficacy parameters such as MIC$_{50}$ and MIC$_{90}$.

Using the assay described above, measured MIC values against *Staphylococcus aureus* 29213 for 24 compounds of the present invention, as provided in the representative list above, ranged from less than about 0.06 μg/ml to greater than about 30 μg/ml with 9 of these compounds having an MIC of less than 1.

*Franciscella tularensis* In Vitro Efficacy Studies

Routine MIC testing of *F. tularensis* may be undertaken on compounds that have demonstrated enzymatic activity inhibition against the *F. tularensis* FabI protein. The MIC testing of *F. tularensis* may be outsourced to a facility with BL3 capabilities, and with experience in handling *F. tularensis* cultures in the laboratory. The studies may be undertaken with the recommended methods for antimicrobial susceptibility testing of *F. tularensis*.

*Helicobacter pylori* In Vitro Efficacy Studies

Routine MIC testing of *H. pylori* may be undertaken on compounds that have demonstrated enzymatic activity inhibition against the *H. pylori* FabI protein. The studies may be undertaken with the recommended methods for antimicrobial susceptibility testing of *H. pylori*.

Cytotoxicity Assays

Cytotoxicity of the new compounds may be evaluated by the Alamar Blue assay according the manufacturers instructions. Human cell lines (e.g. Jurkat) grown in 96 well plates may be exposed to serial dilutions of the tested compounds. After adding Alamar Blue, cell viability may be determined by measuring the absorbance of the reduced and oxidized forms of Alamar Blue at 570 nm and 600 nm. Cytotoxicity may be reported as LD$_{50}$, the concentration that causes a 50% reduction in cell viability.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the FabI inhibitor) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulation

The antibacterial compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In certain embodiments, the subject compounds may be formulated as a tablet, pill capsule or other appropriate ingestible formulation (collectively hereinafter "tablet"), to provide a therapeutic dose in 10 tablets or fewer. In another example, a therapeutic dose is provided in 50, 40, 30, 20, 15, 10, 5 or 3 tablets.

In a certain embodiment, the antibacterial agent is formulated for oral administration as a tablet or an aqueous solution or suspension. In another embodiment of the tablet form of the antibacterial agent, the tablets are formulated such that the amount of antibacterial agent (or antibacterial agents) provided in 20 tablets, if taken together, would provide a dose of at least the median effective dose ($ED_{50}$), e.g., the dose at which at least 50% of individuals exhibited the quantal effect of inhibition of bacterial cell growth or protection (e.g., a statistically significant reduction in infection). In a further embodiment, the tablets are formulated such that the total amount of antibacterial agent (or antibacterial agents) provided in 10, 5, 2 or 1 tablets would provide at least an $ED_{50}$ dose to a patient (human or non-human mammal). In other embodiments, the amount of antibacterial agent (or antibacterial agents) provided in 20, 10, 5 or 2 tablets taken in a 24 hour time period would provide a dosage regimen providing, on average, a mean plasma level of the antibacterial agent(s) of at least the $ED_{50}$ concentration (the concentration for 50% of maximal effect of, e.g., inhibiting bacterial cell growth). In other embodiments less than 100 times, 10 times, or 5 times the $ED_{50}$ is provided. In other embodiments, a single dose of tablets (1-20 tablets) provides about 0.25 mg to 1250 mg of an antibacterial agent(s).

Likewise, the antibacterial agents can be formulated for parenteral administration, as for example, for subcutaneous, intramuscular or intravenous injection, e.g., the antibacterial agent can be provided in a sterile solution or suspension (collectively hereinafter "injectable solution"). The injectable solution is formulated such that the amount of antibacterial agent (or antibacterial agents) provided in a 200 cc bolus injection would provide a dose of at least the median effective dose, or less than 100 times the $ED_{50}$, or less than 10 or 5 times the $ED_{50}$. The injectable solution may be formulated such that the total amount of antibacterial agent (or antibacterial agents) provided in 100, 50, 25, 10, 5, 2.5, or 1 cc injections would provide an $ED_{50}$ dose to a patient, or less than 100 times the $ED_{50}$, or less than 10 or 5 times the $ED_{50}$. In other embodiments, the amount of antibacterial agent (or antibacterial agents) provided in a total volume of 100 cc, 50, 25, 5 or 2 cc to be injected at least twice in a 24 hour time period would provide a dosage regimen providing, on average, a mean plasma level of the antibacterial agent(s) of at least the $ED_{50}$ concentration, or less than 100 times the $ED_{50}$, or less than 10 or 5 times the $ED_{50}$. In other embodiments, a single dose injection provides about 0.25 mg to 1250 mg of antibacterial agent.

Efficacy of Treatment

The efficacy of treatment with the subject compositions may be determined in a number of fashions known to those of skill in the art.

In one exemplary method, the median survival rate of the bacteria or bacteria median survival time or life span for treatment with a subject composition may be compared to other forms of treatment with the particular FabI inhibitor, or with other antibiotic agents. The decrease in median bacteria survival rate or time or life span for treatment with a subject composition as compared to treatment with another method may be 10, 25, 50, 75, 100, 150, 200, 300, 400% even more. The period of time for observing any such decrease may be about 3, 5, 10, 15, 390, 60 or 90 or more days. The comparison may be made against treatment with the particular FabI inhibitor contained in the subject composition, or with other antibiotic agents, or administration of the same or different agents by a different method, or administration as part of a different drug delivery device than a subject composition. The comparison may be made against the same or a different effective dosage of the various agents. The different regiments compared may use measurements of bacterial levels to assess efficacy.

Alternatively, a comparison of the different treatment regimens described above may be based on the effectiveness of the treatment, using standard indicies for bacterial infections known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different FabI inhibitor.

As a non-limiting example, to determine if compounds are bactericidal or bacteriostatic at relevant concentrations, and to examine the kinetics of bacterial killing the following experiment may be performed with $S.$ $aureus,$ $S.$ $epidermidis$ and appropriate control strains and antibiotics. To fresh logarithmic cultures at $10^7$ viable cells/ml, compound may be added to reach concentrations of X1, X2 or X4 the MIC. Control cultures will receive no compound. At 1 hour intervals, aliquots will be diluted and plated for determining viable counts. Plots of viable cells vs. time for up to 24 hours will reveal bactericidal/bacteriostatic properties of the compounds, and also show the kill kinetics. These experiments are important to determine whether these inhibitors have time-dependent or concentration-dependent effects, and will be used to help set appropriate dosages in vivo in combination with pharmacokinetic and pharmacodynamic measurements.

In the practice of the instant methods, the antibacterial compositions of the present invention inhibit bacterial FabI with a $K_i$ of 5 µM or less, 1 µM or less, 100 nM or less, 10 nM or less or even 1 nM or less. In treatment of humans or other animals, the subject method may employ FabI inhibitors which are selective for the bacterial enzyme relative to the host animals' enoyl CoA hydratase, e.g., the $K_i$ for inhibition of the bacterial enzyme is at least one order, two orders, three orders, or even four or more orders of magnitude less than the $K_i$ for inhibition of enoyl CoA hydratase from the human (or other animal). That is, the practice of the subject method in vivo in animals utilizes FabI inhibitors with therapeutic indexes of at least 10, 100 or 1000.

Similarly, in the practice of the instant method, the antibacterial compounds of the present invention inhibit FabI with an $IC_{50}$ of 30 µM or less, 10 µM or less, 100 nM or less, or even 10 nM or less. In treatment of humans or other animals, the subject method may employ FabI inhibitors which are selective for the bacterial enzyme relative to the host animals' enoyl CoA hydratase, e.g., the $IC_{50}$ for inhibition of the bacterial enzyme is at least one order, two orders, three orders, or even four orders of magnitude less than the $IC_{50}$ for inhibition of enoyl CoA hydratase from the human (or other animal). That is, in preferred embodiments, the practice of the subject method in vivo in animals utilizes FabI inhibitors with therapeutic indexes of at least 10, 100 or 1000.

Alternatively, bacterial inhibition by an antibacterial compound of the present invention may also be characterized in terms of the minimum inhibitory concentration (MIC), which is the highest concentration of compound required to achieve complete inhibition of bacterial cell growth. Such values are well known to those in the art as representative of the effectiveness of a particular antibacterial agent against a particular organism or group of organisms. In the practice of the instant methods, the antibacterial compositions of the present invention inhibit bacterial growth with MIC values of about 32 µg/mL, less than about 16 µg/mL, less than about 8 µg/mL, less than about 4 µg/mL, less than about 2 µg/mL, less than about 1 µg/mL, less than about 0.5 µg/mL, less than about 0.25 µg/mL, or even less than about 0.125 µg/mL. The value of MIC90, defined as the concentration of a compound required to inhibit the growth of 90% of bacterial strains within a given bacterial strain population, can also be used. In certain embodiments, the compounds of the present invention are selected for use based, inter alia, on having MIC90 values of less than about 32 µg/mL, less than about 16 µg/mL, less than about 8 µg/mL, less than about 4 µg/mL, less than about 2 µg/mL, less than about 1 µg/mL, less than about 0.5 µg/mL, less than about 0.25 µg/mL, or even less than about 0.125 µg/mL.

In other embodiments, the subject compounds are selected for use in animals, or animal cell/tissue culture based at least in part on having $LD_{50}$'s at least one order, or two orders, or three orders, or even four orders or more of magnitude greater than the $ED_{50}$. That is, in certain embodiments where the subject compounds are to be administered to an animal, a suitable therapeutic index is preferably greater than 10, 100, 1000 or even 10,000.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

The examples which follow are intended in no way to limit the scope of this invention but are provided to illustrate how to prepare and use compounds of the present invention. Many other embodiments of this invention will be apparent to one skilled in the art.

EXAMPLES

General

Proton nuclear magnetic resonance ($^1$H NMR) spectra were recorded at either 200, 300 or 500 MHz, and chemical shifts are reported in parts per million (δ) downfield from the internal standard tetramethylsilane (TMS) or from deuterated solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, CD$_3$OD is tetradeuteriomethanol and D$_2$O is deuterated oxide. Mass spectra were obtained using electrospray (ESI) ionization techniques. Flash chromatography was carried out on E. Merck Kieselgel 60 (230-400 mesh) silica gel. Analytical HPLC was performed on Varian chromatography systems. Celite® is a filter aid composed of acid-washed diatomaceous silica, and is a registered trademark of Manville Corp., Denver, Colo. General abbreviations are as follows: EDC=1-(3-dimethylaminopropyl)-3-ethylcarbodiimide hydrochloride, HOBt=1-hydroxybenzotriazole hydrate, (I—Pr)$_2$EtN=N,N-diisopropylethylamine, DMF=N,N-dimethylformamide, MeOH=methanol, EtOH=ethanol, THF=tetrahydrofuran, DMSO=dimethylsulfoxide, Et$_2$O=diethyl ether, Ar=argon, Pd(OAc)$_2$=palladium(II)acetate, P(o-tol)$_3$=tri-ortho-tolylphoshine, EtOAc=ethyl acetate, ACE-Cl=1-chloroethyl chloroformate, satd=saturated, Et$_3$N=triethylamine, TFA=trifluoroacetic acid, NaBH(OAc)$_3$=sodium triacetoxyborohydride, HOAc=acetic acid, EtCN=proprionitrile, CBzCl=benzyl chloroformate, MeCN=acetonitrile.

Preparation 1

Preparation of Methyl-(1-propyl-naphthalen-2-ylmethyl)amine

A solution of 2.0 M methylamine in methanol (20 mL) was added to 1-propyl-naphthalene-2-carbaldehyde (0.983 g, 4.95 mmol) under N$_2$ and allowed to stir for 18 h. The solution was concentrated under reduced pressure. Then the resulting dark yellow oil was solvated in EtOH (20 mL) under N$_2$. To the solution was added NaBH$_4$ (0.187 g, 4.95 mmol) and the mixture allowed to stir for 6.5 h. The reaction was concentrated under reduced pressure, then solvated in 1 N NaOH (20 mL) and extracted with Et$_2$O (3×50 mL). The organics were combined, washed with brine (2×100 mL), dried over Na$_2$SO$_4$, filtered and concentrated to yield the title compound (0.94 g, 89%) as a yellow oil: $^1$H NMR (300 MHz, DMSO-d$_6$) δ 7.87-7.73 (m, 4H), 7.51-7.43 (m, 3H), 3.53 (m, 1H), 2.09 (s, 3H), 1.70-1.52 (m, 2H), 1.26-1.12 (m, 2H), 0.87-0.79 (m, 3H).

Preparation 2

Preparation of (4-Fluoro-naphthalen-1yl-1 methyl)methylamine a) 4-Fluoro-naphthalene-1-carbaldehyde A solution of α,α-dichloromethyl methyl ether (5.9 mL, 65 mmol) in CH$_2$Cl$_2$ (30 mL) was cooled in an ice bath and then treated dropwise over 15 min with SnCl$_4$ (7.6 mL, 65 mmol). After stirring for 45 min, a solution of 1-fluoronaphthalene (5.5 mL, 50 mmol) in CH$_2$Cl$_2$ (30 mL) was added. The mixture was allowed to slowly warm to room temperature while stirring overnight. The mixture was poured in ice water (100 mL) and diluted with CH$_2$Cl$_2$ (50 mL). The layers were separated. The organic layer was diluted with CH$_2$Cl$_2$ (100 mL), washed with H$_2$O (3×50 mL), dried over Na$_2$SO$_4$, filtered, and the solvent was removed in vacuo to give the title compound (7.62 g, 87%) as a pale yellow solid: MS (ESI) m/e 175 (M+H)$^+$.

b)(4-Fluoro-naphthalen-1-ylmethyl)methylamine

According to the procedure of Preparation 1, except substituting 4-fluoro-naphthalene-1-carbaldehyde for the 1-propyl-naphthalene-2-carbaldehyde, the title compound (3.18 g, 98%) was prepared as a golden oil: MS (ESI) m/e 190 (M+H)$^+$.

Preparation 3

Preparation of (4-Chloro-naphthalen-1-ylmethyl)methylamine a) 4-Chloro-naphthalene-1-carbaldehyde According to the procedure of Preparation 2(a), except substituting 1-chloronaphthalene for 1-fluoronaphthalene, the title compound (5.36 g, 55%) was prepared as a pale yellow oil: MS (ESI) m/e 191 (M+H)$^+$.

b)(4-Chloro-naphthalen-1-ylmethyl)methylamine

According to the procedure of Preparation 1, except substituting 4-chloro-naphthalene-1-carbaldehyde for the 1-propyl-naphthalene-2-carbaldehyde, the title compound (1.06 g, 60%) was prepared as a pale yellow oil: MS (ESI) m/e 206 (M+H)$^+$.

Preparation 4

Preparation of (3-chlorobenzo[b]thiophen-2-ylmethyl methylamine a) 3-chloro-benzo[b]thiophene-2-carbaldehyde Vilsmeier reagent was prepared via the dropwise addition of POCl$_3$ (7.9 mL, 84 mmol) into ice-cold DMF (14 mL). A solution of 2-carboxymethylsulfanyl-benzoic acid (3.0 g, 14 mmol) in DMF (15 mL) was added dropwise to the Vilsmeier reagent. The resulting mixture was warmed to room temperature and then heated to 80° C. for 3.5 h. The reaction mixture was cooled to ambient temperature. Crushed ice was added until a bright yellow precipitate appeared. The solid was isolated by filtration. Purification by flash column chromatography (silica gel, hexanes/ethyl acetate 3:2) gave the title compound (1.87 g, 68%) as a yellow powder: $^1$H NMR (300 MHz, CDCl$_3$) δ 10.36 (s, 1H), 8.03 (m, 1H), 7.86 (m, 1H), 7.59-7.53 (m, 2H).

b)(3-chlorobenzo[b]thiophen-2-ylmethyl)methylamine

To 3-chloro-benzo[b]thiophene-2-carbaldehyde (1.9 g, 9.5 mmol) was added a solution of 2 M methylamine in methanol (32 mL) and the resulting mixture was stirred overnight at room temperature. The mixture was concentrated under reduced pressure and the residue taken up in ethanol (32 mL). The solution was cooled to 0° C., NaBH$_4$ (0.54 g, 14 mmol) was added in one portion and stirring continued overnight. The mixture was concentrated under reduced pressure and the residue solvated in 1 M NaOH (200 mL). The mixture was extracted with diethyl ether (3×150 mL) and the combined organics were washed with brine (100 mL), dried over Na$_2$SO$_4$, filtered and concentrated under reduced pressure to give a yellow oil. Purification by flash column chromatography (silica gel, hexanes/ethyl acetate 1:1) gave the title compound (1.62 g, 80%) as a pale yellow oil which crystallized under vacuum: $^1$H NMR (300 MHz, CDCl$_3$) δ 7.70 (m, 2H), 7.45 (m, 2H), 4.08 (s, 2H), 2.51 (s, 3H).

Preparation 5

Preparation of (5-Chloro-1-methyl-1H-indol-2-ylmethyl methylamine a) 5-Chloro-1-methyl-1H-indole-2-carboxylic acid methylamide To a solution of 5-chloro-1-methyl-1H-indole-2-carboxylic acid ethyl ester (1.27 g, 5.3 mmol) in toluene (10 mL) was added ON-dimethyl-hydroxylamine (9.6 mL of a 1 M solution in toluene, 9.6 mmol). The resulting mixture was heated to reflux overnight after which the reaction was cooled to room temperature and quenched by the addition of 10% aqueous K$_2$CO$_3$ (50 mL). The mixture was extracted with ethyl acetate (3×200 mL). The combined organic layers were washed with brine (100 mL), dried over Na$_2$SO$_4$, filtered and concentrated to give the title compound (2.12 g, 96%) as a yellow solid: $^1$H NMR (300 MHz, CDCl$_3$) δ 7.59 (s, 1H), 7.27 (m, 2H), 6.73 (s, 1H), 6.13 (s, 1H), 4.03 (s, 3H), 3.01 (d, J=4.9 Hz, 3H); MS (ESI) m/e 222 (M+H)$^+$.

b)(5-Chloro-1-methyl-1H-indol-2-ylmethyl)methylamine

To an ice-cold solution of 5-chloro-1-methyl-1H-indole-2-carboxylic acid methylamide (2.12 g, 9.5 mmol) in THF (15 mL) was added lithium aluminum hydride (19 mL of a 1 M solution in THF, 19.0 mmol). Once the addition was complete, the resulting slurry was heated to reflux overnight. The mixture was cooled in an ice bath and carefully quenched by the consecutive addition of water (0.90 mL), 15% aqueous NaOH (0.90 mL) and water (2.5 mL). The resulting mixture was filtered through diatomaceous earth and the filtrate concentrated to give the title (2.00 g, quantitative) compound as an orange oil: $^1$H NMR (300 MHz, CDCl$_3$) δ 7.51 (d, J=1.8 Hz, 1H), 7.25-1.14 (m, 2H), 6.32 (s, 1H), 3.86 (s, 2H), 3.73 (d, J=4.8 Hz, 3H), 2.49 (s, 3H).

Preparation 6

Preparation of (1,7-dimethyl-1H-indol-2-ylmethyl)methylamine a) 1,7-Dimethyl-1H-indole Sodium hydride (1.15 g, 28.7 mmol, 60% in mineral oil) was rinsed with hexanes and then suspended in DMF (20 mL). To this suspension was added 7-methylindole (2.5 g, 19 mmol) portionwise. Gas evolution was allowed to subside between additions. The resulting brown mixture was stirred at room temperature for 15 min and then CH$_3$I (2.71 g, 95.5 mmol) was added in one portion. The exothermic reaction was cooled to 30° C. and stirred for 1 h. Saturated aqueous NH$_4$Cl (10 mL) was added and the mixture was concentrated under reduced pressure. The residue was combined with water (100 mL) and the mixture was then extracted with diethyl ether (3×100 mL). The combined organics were washed with brine, dried over Na$_2$SO$_4$, filtered and concentrated under reduced pressure to give the title compound (2.85 g, quantitative) as a red-pink oil which crystallized upon vacuum drying: $^1$H NMR (300 MHz, CDCl$_3$) δ 7.43 (d, J=7.6 Hz, 1H), 6.97-6.87 (m, 3H), 6.41 (d, J=3.1 Hz, 1H), 4.04 (s, 3H), 2.7 (s, 3H).

b) 1,7-Dimethyl-1H-indole-2-carbaldehyde

To a solution of 1,7-dimethylindole (2.85 g, 19.6 mmol) and TMEDA (3.3 mL, 21.6 mmol) in diethyl ether (30 mL) at −30° C. under N$_2$ was added n-butyllithium (13.5 mL of a 1.6 M solution in hexanes, 21.6 mmol) dropwise. The resulting orange solution was heated to reflux for 1 h and then DMF (4.6 mL, 58.8 mmol) was added in one portion. The solution was stirred at room temperature overnight. Saturated aqueous NH$_4$Cl solution was added and the mixture was then extracted with ethyl acetate (3×150 mL). The combined organics were washed with water (100 mL) and brine (100 mL), dried over Na$_2$SO$_4$, filtered and concentrated under reduced pressure to provide an orange oil. Purification by flash column chromatography (silica gel, hexanes/ethyl acetate, 95:5) gave the title compound (1.57 g, 46%) as a yellow solid: $^1$H NMR (300 MHz, CDCl$_3$) δ 9.83 (s, 1H), 7.54 (d, J=7.8 Hz, 1H), 7.21 (s, 1H), 7.09-7.02 (m, 2H), 4.39 (s, 3H), 2.79 (s, 3H).

c)(1,7-Dimethyl-1H-indol-2-ylmethyl)methylamine

To 1,7-dimethyl-1H-indole-2-carbaldehyde (1.57 g, 9.06 mmol) was added a solution of 2 M solution of methylamine in methanol (30 mL) and the resulting mixture stirred overnight at room temperature. The mixture was concentrated under reduced pressure and the residue taken up in ethanol (30 mL). The solution was cooled to 0° C. and then NaBH$_4$ (0.34 g, 9.1 mmol) was added in one portion. The mixture was stirred overnight. Additional NaBH$_4$ (0.18 g, 4.5 mmol) was added and the mixture was again stirred overnight. The mixture was concentrated under reduced pressure and the residue combined with 1 M NaOH (200 mL). The mixture was extracted with diethyl ether (3×150 mL). The combined organics were washed with brine (100 mL), dried over Na$_2$SO$_4$, filtered and concentrated under reduced pressure to give the title compound as a pale yellow oil (1.60 g, 94%): $^1$H NMR (300 MHz, CDCl$_3$) δ 7.37 (d, J=7.8 Hz, 1H), 6.93-6.87 (m, 2H), 6.34 (s, 1H), 4.02 (s, 3H), 3.84 (s, 2H), 2.77 (s, 3H), 2.50 (s, 3H).

Preparation 7

Preparation of (5-Fluoro-3-methyl-benzo[b] thiophen-2-ylmethyl)methylamine a) 5-Fluoro-3-methyl-benzo[b]thiophene-2-carbaldehyde To a solution of 5-fluoro-3-methyl-benzo[b]thiophene (4.83 g, 29.1 mmol) in THF (50 mL) at −30° C. under N$_2$ was added n-butyllithium (20.0 mL of a 1.6 M solution in hexanes, 32.0 mmol) dropwise. The resulting orange solution was stirred for 1 h and then DMF (3.4 mL, 43.7 mmol) was added in one portion. The solution was warmed slowly to room temperature and stirred overnight. Saturated aqueous NH$_4$Cl was added and the mixture was extracted with ethyl acetate (3×200 mL). The combined organics were washed with water (100 mL) and brine (100 mL), dried over Na$_2$SO$_4$, filtered and concentrated under reduced pressure to give the title compound (5.55 g, 97%) as a yellow solid: $^1$H NMR (300 MHz, CDCl$_3$) δ 10.32 (s, 1H), 7.80 (dd, J=9.0, 4.8 Hz, 1H), 7.53 (d J=9.3, 2.6 Hz, 1H), 7.31-7.24 (m, 1H), 2.76 (s, 3H).

b)(5-Fluoro-3-methyl-benzo[b]thiophen-2-ylmethyl)methylamine

To 5-fluoro-3-methyl-benzo[b]thiophene-2-carbaldehyde (5.43 g, 28.0 mmol) was added a solution of 2 M methylamine in methanol (94 mL) and the resulting mixture was stirred overnight at room temperature. The mixture was concentrated under reduced pressure and the residue taken up in ethanol (90 mL). The solution was cooled to 0° C. and then NaBH$_4$ (1.06 g, 28.0 mmol) was added in one portion. The mixture was stirred 4 hr, after which time NaBH$_4$ (0.54 g, 14.0 mmol) was added and the mixture was stirred overnight. The mixture was concentrated under reduced pressure and the residue combined with 1 M NaOH (200 mL). The mixture was extracted with diethyl ether (3×150 mL) and the combined organics were washed with brine (100 mL), dried over Na$_2$SO$_4$, filtered and concentrated under reduced pressure to the title compound (5.26 g, 90%) as a pale yellow oil: $^1$H NMR (300 MHz, CDCl$_3$) δ 7.71 (dd, J=9.0, 4.8 Hz, 1H), 7.27 (dd, J=9.3, 2.6 Hz, 1H), 7.09-7.04 (m, 1H), 4.00 (s, 2H), 2.51 (s, 3H), 2.31 (s, 3H).

Preparation 8

Preparation of (5-Chloro-3-methyl-benzo[b]thiophen-2-ylmethyl)methylamine a) 5-Chloro-3-methyl-benzo[b]thiophene-2-carbaldehyde To a solution of 5-chloro-3-methyl-benzo[b]thiophene (4.98 g, 27.3 mmol) in THF (50 mL) at −40° C. was added n-butyllithium (18.7 mL of a 1.6 M solution in hexanes, 30.0 mmol) dropwise. The resulting yellow solution was stirred for 1 h and then DMF (6.3 mL, 81.9 mmol) was added in one portion. The solution was warmed slowly to room temperature and stirred overnight. Saturated aqueous NH$_4$Cl was added and the mixture was extracted with ethyl acetate (3×200 mL). The combined organics were washed with water (100 mL) and brine (100 mL), dried over Na$_2$SO$_4$, filtered and concentrated under reduced pressure to give the title compound (6.62 g, 89%) as a yellow solid: $^1$H NMR (300 MHz, CDCl$_3$) δ 10.32 (s, 1H), 7.85 (s, 1H), 7.79 (d, J=8.7 Hz, 1H), 7.46 (dd, J=8.7, 2.0 Hz, 1H), 2.74 (s, 3H).

b)(5-Chloro-3-methyl-benzo[b]thiophen-2-ylmethyl)methylamine

To 5-chloro-3-methyl-benzo[b]thiophene-2-carbaldehyde (5.10 g, 24.2 mmol) was added a solution of 2 M methylamine in methanol (81 mL) and the resulting mixture was stirred overnight at room temperature. The mixture was concentrated under reduced pressure and the residue taken up in ethanol (81 mL). The solution was cooled to 0° C., NaBH$_4$ (1.37 g, 36.3 mmol) was added in one portion, and stirring was continued overnight. The mixture was concentrated under reduced pressure and the residue was combined with 1 M NaOH (200 mL). The mixture was extracted with diethyl ether (3×150 mL). The combined organics were washed with brine (100 mL), dried over Na$_2$SO$_4$, filtered and concentrated under reduced pressure to the title compound (4.83 g, 88%) as a pale yellow oil which crystallized under vacuum: $^1$H NMR (300 MHz, CDCl$_3$) δ 7.69-7.59 (m, 2H), 7.25 (m, 1H), 3.96 (s, 2H), 2.50 (s, 3H), 2.31 (s, 3H).

Preparation 9

Preparation of (3-Methoxy-2-propoxy-benzyl)methylamine a) 3-Methoxy-2-propoxy-benzaldehyde A suspension of 2-hydroxy-3-methoxy-benzaldehyde (10.0 g, 65.6 mmol), 1-bromopropane (60 mL, 657 mmol) and K$_2$CO$_3$ (11.3 g, 82.1 mmol) in MeCN (250 mL) was heated to reflux for 12 h. The mixture was cooled to ambient temperature and the solution filtered. The filtrate was concentrated to give the title compound (12.9 g, quantitative) as light yellow oil: MS (ESI) m/e 195 (M+H)$^+$.

b)(3-Methoxy-2-propoxy-benzyl)methylamine

According to the procedure of Preparation 1, except substituting 3-methoxy-2-propoxy-benzaldehyde for 1-propyl-naphthalene-2-carbaldehyde, the title compound (13.2 g, 96%) was prepared as a light yellow oil: MS (ESI) m/e 210 (M+H)$^+$.

Preparation 10

Preparation of (2-Isopropoxy-3-methoxy-benzyl)methylamine a) 2-Isopropoxy-3-methoxy-benzaldehyde According to the procedure of Preparation 9(a), except substituting 2-iodopropane for 1-bromopropane, the title compound (6.35 g, quantitative) was prepared as light yellow oil: $^1$H NMR (300 MHz, CDCl$_3$) δ 10.5 (s, 1H), 7.42 (dd, J=6.6, 2.9 Hz, 1H), 7.16-7.08 (m, 2H), 4.63 (app septet, J=6.2 Hz, 1H), 3.89 (s, 3H), 1.33 (d, J=6.2 Hz, 6H).

b)(2-Isopropoxy-3-methoxy-benzyl)methylamine

According to the procedure of Preparation 1, except substituting 2-isopropoxy-3-methoxy-benzaldehyde for 1-propyl-naphthalene-2-carbaldehyde, the title compound (6.39 g, 93%) was prepared as a yellow oil: MS (ESI) m/e 210 (M+H)$^+$.

Preparation 11

Preparation of (2-Ethoxy-3-methyl-benzylmethylamine a) 2-Ethoxy-3-methyl-benzaldehyde According to the procedure of Preparation 9(a), except substituting 2-hydroxy-3-methyl-benzaldehyde for 2-hydroxy-3-methoxy-benzaldehyde, and substituting iodoethane for 1-bromopropane, the title compound (10.8 g, 99%) was prepared as a brown oil: $^1$H NMR (300 MHz, CDCl$_3$) δ 10.4 (s, 1H), 7.69 (dd, J=7.6, 1.4 Hz, 1H), 7.46-7.43 (m, 1H), 7.13 (dd, J=7.6, 7.6 Hz, 1H), 4.01 (q, J=7.0 Hz, 2H), 2.34 (s, 3H), 1.46 (t, J=7.0 Hz, 3H).

b)(2-Ethoxy-3-methyl-benzyl)methylamine

According to the procedure of Preparation 1, except substituting 2-ethoxy-3-methyl-benzaldehyde for 1-propyl-naphthalene-2-carbaldehyde, the title compound (11.2 g, 95%) was prepared as a yellow oil: MS (ESI) m/e 180 (M+H)$^+$.

Preparation 12

Preparation of Methyl-naphthalen-2yl-methylamine

According to the procedure of Preparation 1, except substituting naphthalene-2-carbaldehyde for 1-propyl-naphthalene-2-carbaldehyde, the title compound (2.00 g, 91%) was prepared as a clear oil: $^1$H NMR (300 MHz, CDCl$_3$) δ 7.84-7.80 (m, 3H), 7.75 (s, 1H), 7.47-7.44 (m, 3H), 3.92 (s, 2H), 2.50 (s, 3H), 1.52 (br s, 1H).

Preparation 13

Preparation of Methyl-naphthalen-1-yl-methylamine

According to the procedure of Preparation 1, except substituting naphthalene-1-carbaldehyde for 1-propyl-naphthalene-2-carbaldehyde, the title compound (2.44 g, 91%) was prepared as an orange oil: $^1$H NMR (300 MHz, CDCl$_3$) δ 8.12 (d, J=8.1 Hz, 1H), 7.86 (d, J=7.5 Hz, 1H), 7.77 (d, J=8.4 Hz, 1H), 7.54-7.40 (m, 4H), 4.20 (s, 2H), 2.55 (s, 3H), 1.50 (br s, 1H).

Preparation 14

Preparation of (4-Methanesulfonyl-benzyl)methylamine

According to the procedure of Preparation 1, except substituting 4-methanesulfonyl-benzaldehyde for 1-propyl-naphthalene-2-carbaldehyde, the title compound (1.35 g, 63%) was prepared as an off-white solid: MS (ESI) m/e 200 $(M+H)^+$.

Preparation 15

Preparation of Methyl-quinolin-5-yl-methylamine

According to the procedure of Preparation 1, except substituting quinoline-5-carbaldehyde for 1-propyl-naphthalene-2-carbaldehyde, the title compound (1.21 g, 84%) was prepared as an orange solid: $^1$H NMR (300 MHz, DMSO-$d_6$) δ 8.90 (d, J=6.0 Hz, 1H), 8.61 (d, J=9.3 Hz, 1H), 7.91 (d, J=8.4 Hz, 1H), 7.68 (t, J=10.2 Hz, 1H), 7.57-7.51 (m, 2H), 4.08 (s, 2H), 2.34 (s, 3H), 2.13 (br s, 1H).

Preparation 16

Preparation of (2,3-Dimethylbenzyl)methylamine

According to the procedure of Preparation 1, except substituting 2,3-dimethylbenzaldehyde for 1-propyl-naphthalene-2-carbaldehyde, the title compound (1.69 g, 72%) was prepared as a yellow oil: $^1$H NMR (300 MHz, DMSO-$d_6$) δ 7.09-7.08 (m, 1H), 7.01-6.99 (m, 2H), 3.59 (s, 2H), 3.45 (br s, 1H), 2.29 (s, 3H), 2.22 (s, 3H), 2.16 (s, 3H).

Preparation 17

Preparation of (2,4,5-Trimethoxy-benzyl)methylamine

According to the procedure of Preparation 1, except substituting 2,4,5-trimethoxy-benzaldehyde for 1-propyl-naphthalene-2-carbaldehyde, the title compound (1.90 g, 88%) was prepared as a light yellow oil: $^1$H NMR (300 MHz, CDCl$_3$) δ 7.11 (s, 1H), 6.84 (s, 1H), 3.94 (s, 6H), 3.86 (s, 3H), 3.71 (s, 2H), 3.53 (br s, 1H), 2.44 (s, 3H).

Preparation 18

Preparation of Benzo[1,3]dioxol-5-ylmethyl-methylamine

According to the procedure of Preparation 1, except substituting benzo[1,3]dioxole-5-carbaldehyde for 1-propyl-naphthalene-2-carbaldehyde, the title compound (3.23 g, 97%) was prepared as a yellow oil: $^1$H NMR (300 MHz, DMSO-$d_6$) δ 6.88-6.75 (m, 3H), 5.96 (s, 2H), 3.52 (s, 2H), 2.20 (s, 3H), 1.95 (br s, 1H).

Preparation 19

Preparation of Benzo[1,3]dioxol-4-ylmethyl-methylamine

According to the procedure of Preparation 1, except substituting benzo[1,3]dioxole-4-carbaldehyde for 1-propyl-naphthalene-2-carbaldehyde, the title compound (1.79 g, 81%) was prepared as a yellow oil: $^1$H NMR (300 MHz, DMSO-$d_6$) δ 6.84-6.82 (m, 1H), 6.79-6.77 (m, 2H), 5.97 (s, 2H), 3.58 (s, 2H), 2.24 (s, 3H), 1.96 (br s, 1H).

Preparation 20

Preparation of (4-Ethoxy-3-methoxy-benzyl)methylamine

According to the procedure of Preparation 1, except substituting 4-ethoxy-3-methoxy-benzaldehyde for 1-propyl-naphthalene-2-carbaldehyde, the title compound (1.93 g, 89%) was prepared as a yellow oil: $^1$H NMR (300 MHz, DMSO-$d_6$) δ 6.90-6.76 (m, 3H), 3.97 (q, J=6.9 Hz, 2H), 3.71 (s, 3H), 3.53 (s, 2H), 2.22 (s, 3H), 2.12 (br s, 1H), 1.33-1.29 (t, J=6.9 Hz, 3H).

Preparation 21

Preparation of (2-Ethoxy-3-methoxy-benzyl)methylamine

According to the procedure of Preparation 1, except substituting 2-ethoxy-3-methoxy-benzaldehyde for 1-propyl-naphthalene-2-carbaldehyde, the title compound (2.03 g, 93%) was prepared as a yellow oil: $^1$H NMR (300 MHz, DMSO-$d_6$) δ 6.99-6.88 (m, 3H), 3.92 (q, J=6.9 Hz, 2H), 3.77 (s, 3H), 3.61 (s, 2H), 2.25 (s, 3H), 1.87 (br s, 1H), 1.26 (t, J=6.3 Hz, 3H).

Preparation 22

Preparation of (3,4-Dimethyl-benzyl)methylamine

According to the procedure of Preparation 1, except substituting 3,4-dimethyl-benzaldehyde for 1-propyl-naphthalene-2-carbaldehyde, the title compound (1.96 g, 89%) was prepared as a yellow oil: $^1$H NMR (300 MHz, DMSO-$d_6$) δ 6.92-6.80 (m, 3H), 3.71 (s, 6H), 3.55 (s, 2H), 2.23 (s, 3H), 1.94 (br s, 1H).

Preparation 23

Preparation of (2,4,5-Trimethyl-benzyl)methylamine

According to the procedure of Preparation 1, except substituting 2,4,5-trimethyl-benzaldehyde for 1-propyl-naphthalene-2-carbaldehyde, the title compound (1.48 g, 67%) was prepared as a yellow oil: $^1$H NMR (300 MHz, DMSO-$d_6$) δ 7.00 (s, 1H), 6.87 (s, 1H), 3.51 (s, 2H), 2.27 (s, 3H), 2.19 (s, 3H), 2.14 (s, 6H), 1.76 (br s, 1H).

Preparation 24

Preparation of Methyl-quinolin-3-yl-methylamine

According to the procedure of Preparation 1, except substituting quinoline-3-carbaldehyde for 1-propyl-naphthalene-2-carbaldehyde, the title compound (1.73 g, 73%) was prepared as a yellow oil: $^1$H NMR (300 MHz, DMSO-$d_6$) δ 9.29 (s, 1H), 8.60-8.58 (s, 2H), 8.09-8.04 (m, 2H), 7.85-7.79 (m, 1H), 7.69-7.64 (m, 1H), 3.52 (s, 3H), 3.33 (s, 2H).

Preparation 25

Preparation of (3,4-Dimethoxy-benzyl)methylamine

According to the procedure of Preparation 1, except substituting 3,4-dimethoxy-benzaldehyde for 1-propyl-naphthalene-2-carbaldehyde, the title compound (2.10 g, 96%) was prepared as a light yellow oil: $^1$H NMR (300 MHz, DMSO-d$_6$) δ 6.92-6.80 (m, 3H), 3.72 (d, J=4.5 Hz, 6H), 3.54 (s, 2H), 2.71 (br s, 1H), 2.23 (s, 3H).

Preparation 26

Preparation of (3,4-Dimethyl-thieno[2,3-b]thiophen-2-ylmethyl)methylamine

According to the procedure of Preparation 1, except substituting 3,4-dimethyl-thieno[2,3-b]thiophene-2-carbaldehyde for 1-propyl-naphthalene-2-carbaldehyde, the title compound (3.13 g, 97%) was prepared as a yellow oil: $^1$H NMR (300 MHz, DMSO-d$_6$) δ 7.07 (s, 1H), 3.78 (s, 2H), 2.42 (s, 3H), 2.35 (s, 3H), 2.30 (s, 3H), 2.19 (br s, 1H).

Preparation 27

Preparation of Benzofuran-2ylmethyl-methylamine

According to the procedure of Preparation 1, except substituting benzofuran-2-carbaldehyde for 1-propyl-naphthalene-2-carbaldehyde, the title compound (4.98 g, 92%) was prepared as an orange oil: $^1$H NMR (300 MHz, DMSO-d$_6$) δ 7.58-7.49 (m, 2H), 7.24-7.19 (m, 2H), 6.70 (s, 1H), 3.77 (s, 2H), 2.17 (s, 3H).

Preparation 28

Preparation of Methyl-(2-methyl-naphthalen-1-ylmethyl)amine

According to the procedure of Preparation 1, except substituting 2-methyl-naphthalene-1-carbaldehyde for 1-propyl-naphthalene-2-carbaldehyde, the title compound (1.72 g, 79%) was prepared as a yellow oil: $^1$H NMR (300 MHz, DMSO-d$_6$) δ 8.14 (d, J=8.4 Hz, 1H), 7.83 (d, J=8.3 Hz, 1H), 7.72 (d, J=8.1 Hz, 1H), 7.50-7.39 (m, 2H), 7.33 (d, J=8.3 Hz, 1H), 4.02 (s, 2H), 2.51 (s, 3H), 2.41 (s, 3H), 1.74 (br s, 1H).

Preparation 29

Preparation of Biphenyl-3-ylmethyl-methylamine

According to the procedure of Preparation 1, except substituting biphenyl-3-carbaldehyde for 1-propyl-naphthalene-2-carbaldehyde, the title compound (0.78 g, 76%) was prepared as a white solid: $^1$H NMR (300 MHz, DMSO-d$_6$) δ 7.66-7.52 (m, 2H), 7.48-7.28 (m, 7H), 3.69 (s, 2H), 2.28 (s, 3H), 2.15 (br s, 1H).

Preparation 30

Preparation of (2-Ethoxy-naphthalen-1-ylmethyl)methylamine

According to the procedure of Preparation 1, except substituting 2-ethoxy-naphthalene-1-carbaldehyde for 1-propyl-naphthalene-2-carbaldehyde, the title compound (2.02 g, 94%) was prepared as a yellow-orange oil: $^1$H NMR (300 MHz, DMSO-d$_6$) δ 8.08 (d, J=8.4 Hz, 1H), 7.85-7.82 (d, J=8.8 Hz, 2H), 7.74-7.33 (m, 3H), 4.18 (q, J=6.9 Hz, 2H), 4.06 (s, 2H), 2.31 (s, 3H), 1.62 (br s, 1H), 1.37 (t, J=6.9 Hz, 3H).

Preparation 31

Preparation of (2,3,4-Trimethoxy-benzyl)methylamine

According to the procedure of Preparation 1, except substituting 2,3,4-trimethoxy-benzaldehyde for 1-propyl-naphthalene-2-carbaldehyde, the title compound (2.17 g, quantitative) was prepared as light yellow oil: $^1$H NMR (300 MHz, DMSO-d$_6$) δ 7.99 (d, J=8.5 Hz 1H), 6.74 (d, J=8.5 Hz, 1H), 3.76 (s, 6H), 3.72 (s, 3H), 2.53 (s, 2H), 2.25 (s, 3H), 1.92 (br s, 1H).

Preparation 32

Preparation of (2,3-Dihydro-benzo[1,4]dioxin-6-ylmethyl)methylamine

According to the procedure of Preparation 1, except substituting 2,3-dihydro-benzo[1,4]dioxine-6-carbaldehyde for 1-propyl-naphthalene-2-carbaldehyde, the title compound (1.28 g, 59%) was prepared as a pale yellow oil: $^1$H NMR (300 MHz, DMSO-d$_6$) δ 6.78-6.73 (m, 3H), 4.20 (s, 4H), 3.48 (s, 2H), 2.20 (s, 3H), 1.96 (br s, 1H).

Preparation 33

Preparation of (2,3-Dihydro-benzo[1,4]dioxin-5-ylmethyl)methylamine

According to the procedure of Preparation 1, except substituting 2,3-dihydro-benzo[1,4]dioxine-5-carbaldehyde for 1-propyl-naphthalene-2-carbaldehyde, the title compound (1.97 g, 91%) was prepared as a yellow oil: $^1$H NMR (300 MHz, DMSO-d$_6$) δ 6.85-6.82 (m, 1H), 6.77-6.70 (m, 2H), 4.25-4.20 (m, 4H), 3.56 (s, 2H), 2.25 (s, 3H), 1.76 (br s, 1H).

Preparation 34

Preparation (4,5-Dimethyl-naphthalen-1-ylmethyl)methylamine

According to the procedure of Preparation 1, except substituting 4,5-dimethyl-naphthalene-1-carbaldehyde for 1-propyl-naphthalene-2-carbaldehyde, the title compound (0.88 g, 88%) was prepared as an off-white solid: $^1$H NMR (500 MHz, DMSO-d$_6$) δ 8.00 (d, J=8 Hz, 1H), 7.33-7.28 (m, 3H), 7.21 (s, 1H), 3.98 (s, 2H), 2.87 (two s, 6H), 2.33 (s, 3H), 1.96 (br s, 1H).

Preparation 35

Preparation of (2,3-Diethoxy-benzyl)methylamine

According to the procedure of Preparation 1, except substituting 2,3-diethoxy-benzaldehyde for 1-propyl-naphthalene-2-carbaldehyde, the title compound (1.81 g, 84%) was prepared as a yellow oil: $^1$H NMR (300 MHz, DMSO-d$_6$) δ 6.96-6.83 (m, 3H), 4.01 (q, J=6.9 Hz, 2H), 3.95 (q, J=6.9 Hz, 2H), 3.61 (s, 2H), 2.25 (s, 3H), 1.81 (br s, 1H), 1.33 (t, J=6.9 Hz, 3H), 1.27 (t, J=6.9 Hz, 3H).

Preparation 36

Preparation of (3-Ethoxy-2-methoxy-benzyl methylamine

According to the procedure of Preparation 1, except substituting 3-ethoxy-2-methoxy-benzaldehyde for 1-propyl-naphthalene-2-carbaldehyde, the title compound (1.60 g, 74%) was prepared as a yellow oil: $^1$H NMR (300 MHz, DMSO-$d_6$) δ 6.95-6.88 (m, 3H), 4.04 (q, J=6.9 Hz, 2H), 3.72 (s, 3H), 3.60 (s, 2H), 2.25 (s, 3H), 1.80 (br s, 1H), 1.34 (t, J=6.9 Hz, 3H).

Preparation 37

Preparation of Methyl-(3-methyl-benzofuran-2-ylmethyl)amine

According to the procedure of Preparation 1, except substituting 3-methyl-benzofuran-2-carbaldehyde for 1-propyl-naphthalene-2-carbaldehyde, the title compound (2.05 g, quantitative) was prepared as a yellow oil: $^1$H NMR (300 MHz, DMSO-$d_6$) δ 7.52 (dd, J=6.7, 2.1 Hz, 1H), 7.46 (dd, J=6.5, 2.0 Hz, 1H), 7.25-7.21 (m, 2H), 3.74 (s, 2H), 2.25 (s, 3H), 2.19 (s, 3H), 2.07 (br s, 1H).

Preparation 38

Preparation of (3-Chloro-2-methoxy-benzyl)methylamine

According to the procedure of Preparation 1, except substituting 3-chloro-2-methoxy-benzaldehyde for 1-propyl-naphthalene-2-carbaldehyde, the title compound (1.15 g, 55%) was prepared as a yellow oil: $^1$H NMR (300 MHz, DMSO-$d_6$) δ 7.37-7.33 (m, 2H), 7.11 (t, J=7.5 Hz, 1H), 3.77 (s, 3H), 3.68 (s, 2H), 2.27 (s, 3H), 2.01 (br s, Preparation 39

Preparation of (3-Choro-2-ethoxy-benzyl)methylamine a) 3-Chloro-2-ethoxy-benzaldehyde Iodoethane (1.54 mL, 19.2 mmol) was added to a stirring solution of 3-chloro-2-hydroxy-benzaldehyde (2.01 g, 12.8 mmol) and $K_2CO_3$ (3.90 g, 28.2 mmol) in DMF (25 mL). The mixture was heated to 50° C. and stirred for 2.5 h. The heat was removed and reaction stirred at room temperature for 18 h. The reaction was quenched with $H_2O$ (70 mL). The mixture was extracted with EtOAc (3×50 mL). The combined organics were washed with brine (2×50 mL), dried over $Na_2SO_4$, filtered and concentrated to yield the title compound (2.16 g, 91%) as a yellow oil: $^1$H NMR (300 MHz, DMSO-$d_6$) δ 10.27 (s, 1H), 7.85 (dd, J=7.8, 1.5 Hz, 1H), 7.72 (dd, J=7.8, 1.8 Hz, 1H), 7.33 (t, J=7.8 Hz, 1H), 4.14 (q, J=7.2 Hz, 2H), 1.39 (t, J=6.9 Hz, 3H).

b)(3-Chloro-2-ethoxy-benzyl)methylamine

According to the procedure of Preparation 1, except substituting 3-chloro-2-ethoxy-benzaldehyde for 1-propyl-naphthalene-2-carbaldehyde, the title compound (1.36 g, 58%) was prepared as a yellow oil: $^1$H NMR (500 MHz, DMSO-$d_6$) δ 7.36-7.33 (m, 2H), 7.14-7.08 (m, 1H), 3.93 (q, J=7.0 Hz, 2H), 3.67 (s, 2H), 2.24 (s, 3H), 2.07 (br s, 1H), 1.32 (t, J=6.9 Hz, 3H).

Preparation 40

Preparation of Methyl-thieno[3,2-c]pyridin-2-ylmethyl-amine a) Thieno[3,2-c]pyridine-2-carbaldehyde A solution of thieno[3,2-c]pyridine (500 mg, 3.70 mmol) in anhydrous THF (10 mL) was stirred under argon and maintained at −78° C. while a solution of 1.6 M n-butyllithium in hexane (2.5 mL, 4.07 mmol) was added dropwise. The resulting wine red solution was stirred for 5 min. then DMF (573 μL, 7.4 mmol) was added. The cooling bath was removed and the reaction mixture was stirred at room temperature for 16 hr. The reaction mixture was treated with 10% aqueous HCl, made alkaline with saturated aqueous $NaHCO_3$ and extracted with $CH_2Cl_2$ (2×50 mL) The combined organic fractions were concentrated in vacuo to give an oily residue which was subjected to flash chromatography on silica gel (70% ethyl acetate:hexanes) to give the title compound as a white solid (41.5%): $^1$H-NMR (300 MHz, DMSO-$d_6$) δ 10.20 (s, 1H), 9.39 (s, 1H), 8.60 (s, 1H), 8.59 (d, J=5.5 Hz, 1H), 8.19 (d, J=5.6 Hz, 1H); MS (ES) m/e 164 (M+H)$^+$.

b) Methylthieno[3,2-c]pyridine-2-methylamine

A solution of thieno[3,2-c]pyridine-2-carbaldehyde (720 mg, 4.41 mmol) in a 2.0 M solution of methylamine in methanol (25 mL) was stirred at room temperature for S hours. After this time, the mixture was concentrated to dryness, dissolved in anhydrous methanol (10 mL) then cooled to 0° C. To this solution was added $NaBH_4$ (167 mg, 4.41 mmol) in one portion. The mixture was allowed to warm to room temperature and stirred at this temperature overnight. The mixture was concentrated, dissolved in $CH_2Cl_2$ (100 mL) and treated with 1.0 N NaOH (20 mL). The aqueous layer was extracted with $CH_2Cl_2$ (2×20 mL). The combined organic fractions were washed with brine, dried over $Na_2SO_4$ then concentrated to give a yellow residue which was subjected to flash chromatography on silica gel (10% 2M $NH_3$ in MeOH:$CH_2Cl_2$). The title compound was obtained as a white solid in 63.6% yield: $^1$H-NMR (300 MHz, CDCl$_3$) δ 9.01 (s, 1H), 8.45 (d, J=5.5 Hz, 1H), 7.76 (d, J=5.5 Hz, 1H), 7.29 (s, 1H), 4.10 (s, 2H), 2.54 (s, 3H); MS (ES) m/e 179 (M+H)$^+$.

Preparation 41

Preparation of (1H-Indol-5-ylmethyl)methylamine

Indole-5-carbaldehyde (1.0 g, 6.9 mmol) was dissolved in anhydrous methanol (15 mL). Methylamine (9.9 mL of 2M solution in methanol, 19.8 mmol) was added and the reaction was stirred for 3 hr. The solution was concentrated to a yellow oil and then dissolved into anhydrous methanol (20 mL). Sodium borohydride (262 mg, 6.9 mmol) was added and the mixture was stirred overnight. Water (1 mL) was added and the solution was concentrated. Sodium hydroxide (5 mL, 1N) was added and the product was extracted with ethyl acetate (3×20 mL), dried over $MgSO_4$ and concentrated to afford the title compound as a brown oil (980 mg, 91%). $^1$H NMR (200 MHz, CDCl$_3$) δ 8.60 (s, 1H), 7.56 (s, 1H), 7.35-7.15 (m, 3H), 6.55 (m, 1H), 3.85 (s, 2H), 2.49 (s, 3H).

Preparation 42

Preparation of Methyl-(1-methylindol-5-ylmethyl)amine a) 1-Methylindole-5-carbaldehyde To a solution of indole-5-carbaldehyde (1.0 g, 6.9 mmol) in DMF (15 mL) was added sodium hydride (303 mg of 60% dispersion in oil, 7.59 mmol) in 3 portions. The mixture was stirred for 30 mins. Methyl iodide (1.96 g, 13.8 mmol) was then added and the mixture was stirred overnight. Ethyl acetate (200 mL) was added and solution was washed with $H_2O$ (3×20 mL) and brine (25 mL) dried over $MgSO_4$ and concentrated to afford N-methylindole-5-carboxaldehyde as an orange oil (1.0 g, 91%). $^1H$ NMR (200 MHz, $CDCl_3$) δ 10.05 (s, 1H), 8.09 (s, 1H), 7.90-7.80 (m, 1H), 7.35-7.15 (m, 2H), 6.85-6.80 (m, 1H), 3.95 (s, 3H).

b) Methyl-(1-methylindol-5-ylmethyl)amine

N-Methylindole-5-carbaldehyde (800 mg, 5.1 mmol) was dissolved in anhydrous methanol (15 mL). Methylamine (7.15 mL of 2M solution in methanol, 15.3 mmol) was added and the reaction was stirred for 3 hr. The solution was concentrated to a yellow oil and then dissolved into anhydrous methanol (15 mL). Sodium borohydride (194 mg, 5.1 mmol) was added and the mixture was stirred overnight. Water (1 mL) was added and the solution was concentrated to an orange oil. Sodium hydroxide (5 mL, 1N) was added and the product was extracted with ethyl acetate (3×20 mL), dried over $MgSO_4$ and concentrated to afford the title compound as an orange oil (885 mg, 100%). $^1H$ NMR (200 MHz, $CDCl_3$) δ 7.57(s, 1H), 7.35-7.11(m, 3H), 6.51 (d, J=2.9 Hz, 1H), 3.85 (s, 2H), 3.79 (s, 3H), 2.48 (s, 3H).

Preparation 43

Preparation of (1H-Indol-7-ylmethyl)methylamine

Indole-7-carbaldehyde (500 mg, 3.4 mmol) was dissolved in anhydrous methanol (10 mL). Methylamine (5.1 mL of 2M solution in methanol, 9.55 mmol) was added and the reaction was stirred for 3 hr. The solution was concentrated to a yellow oil and then dissolved into anhydrous methanol (10 mL). Sodium borohydride (131 mg, 3.45 mmol) was added and the mixture was stirred overnight. Water (1 mL) was added and the solution was concentrated. Sodium hydroxide (5 mL, 1N) was added and the indole was extracted with ethyl acetate (3×20 mL), dried over $MgSO_4$ and concentrated to afford the title compound as a yellow oil (484 mg, 92%). $^1H$ NMR (300 MHz, $CDCl_3$) δ 7.54 (s, 1H), 7.29-7.17 (m, 2H), 7.04 (d, J=3.1 Hz, 1H), 6.44 (d, J=3.1 Hz, 1H), 3.84 (s, 2H), 2.46 (s, 3H).

Preparation 44

Preparation of Methyl-(1-methylindol-7-ylmethyl)amine

To a solution of indole-7-carboxaldehyde (500 mg, 3.45 mmol) in DMF (8 mL) was added sodium hydride (152 mg of 60% dispersion in oil, 3.8 mmol). The mixture was stirred for 30 mins. Methyl iodide (0.98 g, 6.9 mmol) was then added and the mixture was stirred for 2 hrs. Ethyl acetate (200 mL) was added and solution was washed with $H_2O$ (3×20 mL) and brine (25 mL) dried over $MgSO_4$ and concentrated to afford N-methylindole-7-carboxaldehyde as a brown oil which was used without further purification.

The crude oil was dissolved in anhydrous methanol (10 mL). Methylamine (5.1 mL of 2M solution in methanol, 9.55 mmol) was added and the mixture was stirred for 3 hours. The solution was concentrated to a yellow oil and then dissolved into anhydrous methanol (10 mL). Sodium borohydride (131 mg, 3.45 mmol) was added and the mixture was stirred overnight. Water (1 mL) was added and the solution was concentrated to an orange oil. Sodium hydroxide (5 mL, 1N) was added and the product was extracted with ethyl acetate (3×20 mL), dried over $MgSO_4$ and concentrated to afford the title compound as a brown oil (400 mg, 68%). $^1H$ NMR (200 MHz, $CDCl_3$) δ 7.52 (dd, J=7.0, 2.0 Hz, 1H), 7.23-6.94 (m, 3H), 6.44 (d, J=3.1 Hz, 1H), 4.10 (s, 3H), 4.04 (s, 2H), 2.51 (s, 3H

Preparation 45

Preparation of (1H-Indol-6-ylmethyl)methylamine a)(1H-Indol-6-yl)methanol

Indole-6-carboxylic acid (1.0 g, 6.2 mmol) was dissolved into anhydrous THF (20 mL) under argon. Lithium aluminum hydride (494 mg, 13 mmol) was added portionwise and the mixture was stirred overnight. The mixture was cooled to 0° C. and ethyl acetate (10 mL) was carefully added, followed by methanol (5 mL) and water (5 mL). The mixture was stirred for 30 min. and filtered through celite. The solution was concentrated and dissolved into ethyl acetate (200 mL) and washed with brine (2×20 mL), dried over $MgSO_4$ and concentrated to afford the title compound as a brown oil (880 mg, 96%). $^1H$ NMR (300 MHz, $CDCl_3$) δ 8.30 (s, 1H), 7.58 (d, J=8.1 Hz, 1H), 7.23 (d, J=1.1 Hz, 1H), 7.13-7.05 (m, 2H), 6.51-6.49 (m, 1H), 4.70 (s, 2H).

b) 1H-Indole-6-carbaldehyde

Dess-Martin periodinane (1.53 g, 2.6 mmol) was dissolved into methylene chloride (15 mL). Indol-6-yl-methanol (500 mg, 3.4 mmol) in methylene chloride (12 mL) was added and the mixture was stirred for 1 hr. Sodium hydroxide (5 mL of 1 N solution) was added and the reaction was stirred for 15 min. The organic layer was separated and washed with $H_2O$ (5 mL), brine (5 mL), dried over $MgSO_4$ and concentrated to afford the title compound as a brown solid (275 mg, 56%). $^1H$ NMR (300 MHz, DMSO-$d_6$) δ 11.7 (s, 1H), 9.98 (s, 1H), 7.97 (s, 1H), 7.70-7.65 (m, 2H), 7.52 (dd, J=8.2, 1.4 Hz, 1H), 6.57-6.5 (m, 1H).

c)(1H-Indol-6-ylmethyl)methylamine

Indole-6-carboxaldehyde (90 mg, 0.62 mmol) was dissolved in anhydrous methanol (3 mL). Methylamine (0.95 mL of 2M solution in methanol, 1.86 mmol) was added and the reaction was stirred for 3 hr. The solution was concentrated to a yellow oil and then dissolved into anhydrous methanol (3 mL). Sodium borohydride (24 mg, 0.62 mmol) was added and the mixture was stirred overnight. Water (1 mL) was added and the solution was concentrated. Sodium hydroxide (2 mL, 1N) was added and the indole was extracted with ethyl acetate (3×10 mL), dried over $MgSO_4$ and concentrated to afford the title compound as a yellow oil (98 mg, 100%). $^1H$ NMR (300 MHz, $CDCl_3$) δ 9.02 (s, 1H), 7.57(d, J=8.1 Hz, 1H), 7.29 (s, 1H), 7.12 (d, J=3.1 Hz, 1H), 7.04 (d, J=8.1 Hz, 1H), 6.49 (d, J=2.7 Hz, 1H), 3.81 (s, 2H), 2.50 (s, 3H).

Preparation 46

Preparation of N-Methyl-N-(1-methyl-1H-indol-3ylmethyl)acrylamide

According to the procedure of Example 1 (a), except substituting acrylic acid for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-3-ylmethyl)amine for the methyl-(1-propyl-napthalen-2-yl-methyl)anine, the title compound (1.51 g, 58%) was prepared as a white solid: $^1$H NMR (300 MHz, DMSO-$d_6$) δ 7.71-7.50 (s, 1H), 7.34-7.21 (m, 2H), 7.15-6.90 (m, 2H), 6.80-6.53 (m, 1H), 6.45-6.35 (s, 1H), 5.72-5.67 (m, 1H), 4.80-4.75 (m, 2H), 3.77 (s, 3H), 3.05-2.99 (m, 3H).

Preparation 47

Preparation of N-methyl-N-(3-methyl-benzo[b]thiophen-2-ylmethyl)acrylamide

A solution of methyl-(3-methyl-benzo[b]thiophen-2-ylmethyl)amine (1.95 g, 11.4 mmol) in $CH_2Cl_2$ (40 mL) was treated with acryloyl chloride (1.2 mL, 14 mmol) and triethylamine (3.2 mL, 22 mmol). The mixture was stirred at room temperature for 1 h. The reaction mixture was diluted with $CH_2Cl_2$ (100 mL). The solution was washed with water and brine, dried over $Na_2SO_4$, filtered and concentrated under reduced pressure. Purification by column chromatography (silica gel, EtOAc/hexanes, 40/60) gave the title compound (2.10 g, 75%) as a pale yellow solid: MS (ESI) m/e 246 $(M+H)^+$.

Preparation 48

Preparation of (E)-3-(4-methyl-2-oxo-2,3,4,5-tetrahydro-1H-pyrido[2,3-e][1,4]diazepin-7-yl)acrylic acid a) [2-Amino-5-bromo-pyridin-3-ylmethyl)methylamino]acetic acid ethyl ester A solution of 5-bromo-3-bromomethyl-pyridin-2-ylamine hydrobromide (1.98 g, 5.71 mmol) and sarcosine ethyl ester hydrochloride (0.90 g, 5.86 mmol) in DMF (60 mL) was treated with triethylamine (2.6 mL, 18.5 mmol). After stirring at room temperature under $N_2$ for 2 h, the cloudy mixture was diluted with $H_2O$ (100 mL) and extracted with EtOAc (3×100 mL). The combined organic layers were washed with $H_2O$ (3×50 mL) and brine (50 mL), dried over $Na_2SO_4$, filtered, and the solvent was removed in vacuo. Purification by flash column chromatography (silica gel, $CH_2Cl_2$/MeOH, 98:2) gave the title compound (1.37 g, 79%) as a white solid: $^1$H NMR (300 MHz, CDCl$_3$) δ 8.03 (d, J=2.3 Hz, 1H), 7.32 (d, J=2.3 Hz, 1H), 5.76 (s, 2H), 4.20 (q, J=7.1 Hz, 2H), 3.47 (s, 2H), 3.24 (s, 2H), 2.28 (s, 3H), 1.29 (t, J=7.1 Hz, 3H); MS (ESI) m/e 302 $(M+H)^+$.

b) 7-Bromo-4-methyl-1,3,4,5-tetrahydro-pyrido[2,3-e][1,4]diazepin-2-one

A solution of [2-amino-5-bromo-pyridin-3-ylmethyl)methylamino]acetic acid ethyl ester (1.37 g, 4.53 mmol) in DMSO (50 mL) was treated with NaH (0.18 g, 4.5 mmol). After stirring at room temperature under $N_2$ for 2 h, the mixture was stored in the freezer overnight. The mixture was allowed to warm to room temperature, diluted with $H_2O$ (200 mL), and extracted with EtOAc (3×150 mL). The combined organic layers were washed with $H_2O$ (2×50 mL) and brine (50 mL), dried over $Na_2SO_4$, filtered, and the solvent was removed in vacuo. Purification by flash column chromatography (silica gel, $CH_2Cl_2$/MeOH, 98:2) gave the title compound (0.88 g, 76%) as a white solid: $^1$H NMR (300 MHz, CDCl$_3$) δ 8.57 (s, 1H), 8.35 (d, J=2.2 Hz, 1H), 7.61 (d, J=2.1 Hz, 1H), 3.91 (s, 2H), 3.74 (s, 2H), 2.49 (s, 3H); MS (ESI) m/e 256 $(M+H)^+$.

c)(E)-3-(4-Methyl-2-oxo-2,3,4,5-tetrahydro-1H-pyrido[2,3-e][1,4]diazepin-7-yl)acrylic acid tert-butyl ester A suspension of 7-bromo-4-methyl-1,3,4,5-tetrahydro-pyrido[2,3-e][1,4]diazepin-2-one (0.63 g, 2.5 mmol) in propionitrile (10 mL) and DMF (3 mL) was de-oxygenated with Ar for 25 min. The mixture was treated with tert-butyl acrylate (1.5 mL, 10 mmol) and (i-Pr)$_2$EtN (0.9 mL, 5 mmol) and was de-oxygenated with Ar for 10 min. Pd(OAc)$_2$ (56 mg, 0.25 mmol) and P(o-tol)$_3$ (150 mg, 0.49 mmol) were added simultaneously, and the mixture was de-oxygenated a third time for 5 min. The mixture was heated to reflux for 18 h, then allowed to cool. The resulting precipitate was isolated by filtration, dissolved in $CH_2Cl_2$, filtered through Celite, and the solvent was removed in vacuo to give the title compound (0.60 g, 80%) as an off-white solid: $^1$H NMR (300 MHz, CDCl$_3$) δ 8.63 (s, 1H), 8.41 (d, J=2.0 Hz, 1H), 7.62 (d, J=1.7 Hz, 1H), 7.52 (d, J=16.0 Hz, 1H), 6.37 (d, J=16.0 Hz, 1H), 3.96 (s, 2H), 3.77 (s, 2H), 2.49 (s, 3H), 1.53 (s, 9H); MS (ESI) m/e 304 $(M+H)^+$.

d)(E)-3-(4-Methyl-2-oxo-2,3,4,5-tetrahydro-1H-pyrido[2,3-e][1,4]diazepin-7-yl)acrylic acid A suspension of (E)-3-(4-methyl-2-oxo-2,3,4,5-tetrahydro-1H-pyrido[2,3-e][1,4]diazepin-7-yl)acrylic acid tert-butyl ester (0.59 g, 1.9 mmol) in $CH_2Cl_2$ (7 mL) was treated with TFA (7 mL). After stirring at room temperature under $N_2$ for 45 min, the clear tan solution was concentrated in vacuo. The resulting oil was treated with anhydrous HCl in dioxane (10 mL, 4.0 M) and sonicated until the oil was converted to a fine off-white solid. After stirring under $N_2$ for 20 min, the solid was isolated by filtration, washed with Et$_2$O, and dried under vacuum for several hours to give the title compound (0.77 g, quantitative) as an off-white solid: $^1$H NMR (300 MHz, DMSO-$d_6$) δ 12.27 (bs, 1H), 11.28 (s, 1H), 8.78 (d, J=1.9 Hz, 1H), 8.32 (d, J=1.9 Hz, 1H), 7.65 (d, J=16.1 Hz, 1H), 6.63 (d, J=16.1 Hz, 1H), 4.32 (s, 2H), 3.82 (s, 2H), 2.89 (s, 3H); MS (ESI) m/e 248 $(M+H)^+$.

Preparation 49

Preparation of (E)-3-(4-Ethoxycarbonylmethyl-2-oxo-2,3,4,5-tetrahydro-1H-pyrido[2,3-e][1,4]diazepin-7-yl)acrylic acid hydrochloride a) [(2-Amino-5-bromo-pyridin-3-ylmethyl)ethoxycarbonylmethyl-amino]acetic acid ethyl ester A suspension of 5-bromo-3-bromomethyl-pyridin-2-ylamine hydrobromide (12.0 g, 34.6 mmol) and diethyl iminodiacetate (7.0 mL, 39.1 mmol) in $CH_3CN$ (350 mL) was treated with triethylamine (10.7 mL, 76.1 mmol). After stirring at room temperature under $N_2$ for 4 h, the solvent was removed in vacuo. The resulting yellow slurry was partitioned between $H_2O$ (400 mL) and EtOAc (400 mL), and the aqueous layer was extracted with EtOAc (200 mL). The combined organic layers were washed with brine (100 mL), dried over $Na_2SO_4$, filtered and the solvent was removed in vacuo. Purification by flash column chromatography (silica gel, $CH_2Cl_2$/MeOH, 99:1) gave the title compound (6.55 g, 51%) as a light tan oil: MS (ESI) m/e 374 $(M+H)^+$.

b)(7-Bromo-2-oxo-1,2,3,5-tetrahydro-pyrido[2,3-e][1,4]diazepin-4-yl)acetic acid ethyl ester A solution of [(2-amino-5-bromo-pyridin-3-ylmethyl) ethoxycarbonylmethyl-amino]-acetic acid ethyl ester (6.52 g, 17.4 mmol) in DMSO (170 mL) was treated with NaH (0.70 g, 17.5 mmol). After stirring at room temperature overnight, the mixture was diluted with $H_2O$ (300 mL) and extracted with EtOAc (4×200 mL). The combined organic layers were washed with $H_2O$ (3×100 mL) and brine (100 mL), dried over $Na_2SO_4$, filtered and the solvent was removed in vacuo to give the title compound (6.18 g, quantitative) as an off-white solid: MS (ESI) m/e 328 (M+H)$^+$.

c)(E)-3-(4-Ethoxycarbonylmethyl-2-oxo-2,3,4,5-tetrahydro-1H-pyrido[2,3-e][1,4]diazepin-7-yl)acrylic acid tert-butyl ester A suspension of (7-Bromo-2-oxo-1,2,3,5-tetrahydro-pyrido[2,3-e][1,4]diazepin-4-yl)acetic acid ethyl ester (6.18 g, 17.4 mmol) in propionitrile (70 mL) and DMF (17 mL) was de-oxygenated with Ar for 30 min. The mixture was treated with tert-butyl acrylate (10.2 mL, 69.6 mmol) and (i-Pr)$_2$EtN (6.4 mL, 37 mmol) and was then de-oxygenated with Ar for 10 min. Pd(OAc)$_2$ (0.39 g, 1.7 mmol) and P(o-tol)$_3$ (1.06 mg, 3.48 mmol) were added simultaneously, and the mixture was de-oxygenated a third time for 5 min. After heating to reflux for 14 h, the mixture was allowed to cool and then concentrated in vacuo. The resulting residue was diluted with $CH_2Cl_2$ and filtered through Celite. The orange filtrate was concentrated in vacuo. The resulting residue was diluted with EtOAc (200 mL) and washed with $H_2O$ (100 mL). The aqueous layer was extracted with EtOAc (2×100 mL). The combined organic layers were washed with $H_2O$ (2×100 mL) and brine (100 mL), dried over $Na_2SO_4$, filtered and the solvent was removed in vacuo. Purification by flash column chromatography (silica gel, $CH_2Cl_2$/MeOH, 97:3) and again by flash column chromatography (silica gel, $CH_2Cl_2$/MeOH, 99:1) gave the title compound (2.55 g, 39%) as an off-white solid: MS (ESI) m/e 376 (M+H)$^+$.

d)(E)-3-(4-Ethoxycarbonylmethyl-2-oxo-2,3,4,5-tetrahydro-1H-pyrido[2,3-e][1,4]diazepin-7-yl)acrylic acid hydrochloride A solution of (E)-3-(4-ethoxycarbonylmethyl-2-oxo-2,3,4,5-tetrahydro-1H-pyrido[2,3-e][1,4]diazepin-7-yl)acrylic acid tert-butyl ester (1.14 g, 3.04 mmol) in $CH_2Cl_2$ (8 mL) was treated with TFA (8 mL). After stirring at room temperature under $N_2$ for 45 min, the clear tan solution was concentrated in vacuo. The resulting oil was treated with anhydrous HCl in dioxane (10 mL, 4.0 M) and sonicated until the oil was converted to a fine off-white solid. The resulting mixture was diluted with $Et_2O$ (100 mL) and stirred under $N_2$ for 20 min. The solid was isolated by filtration, washed with $Et_2O$, and dried under vacuum at 50° C. overnight to give the title compound (1.05 g, 88%) as an off-white solid: $^1$H NMR (300 MHz, DMSO-d$_6$) δ 10.57 (s, 1H), 8.56-8.55 (m, 1H), 8.10 (s, 1H), 6.57 (d, J=16.0 Hz, 1H), 6.57 (d, J=16.0 Hz, 1H), 4.14-4.05 (m, 3H), 3.62-3.56 (m, 6H), 1.18 (t, J=7.1 Hz, 3H); MS (EST) m/e 320 (M+H)$^+$.

Preparation 50

Preparation of (R)-(E)-3-(10-Oxo-2,3,4,9,10,10a-hexahydro-1H-3a,8,9-triaza-benzo[f]azulen-6-yl) acylic acid hydrochloride a)(R)-1-(2-Amino-5-bromo-pyridin-3-ylmethyl)pyrrolidine-2-carboxylic acid methyl ester A suspension of 5-bromo-3-bromomethyl-pyridin-2-ylamine hydrobromide (8.00 g, 23.1 mmol) and D-proline methyl ester hydrochloride (4.53 g, 27.4 mmol) in $CH_3CN$ (100 mL) was treated with a solution of triethylamine (10.4 mL, 74.0 mmol) in $CH_3CN$ (100 mL). After stirring at room temperature for 5 h, the cloudy mixture was diluted with $H_2O$ (300 mL) and extracted with EtOAc (3×200 mL). The combined organic layers were washed with brine (100 mL), dried over $Na_2SO_4$, filtered and the solvent was removed in vacuo. Purification by flash column chromatography (silica gel, $CH_2Cl_2$/MeOH, 99:1 to 98:2) gave the title compound (6.55 g, 90%) as a colorless oil: MS (ESI) m/e 314 (M+H)$^+$.

b)(R)-6-Bromo-1,2,3,4,9,10a-hexahydro-3a,8,9-triaza-benzo[f]azulen-10-one

A solution of (R)-1-(2-amino-5-bromo-pyridin-3-ylmethyl)pyrrolidine-2-carboxylic acid methyl ester (6.52 g, 20.8 mmol) in DMSO (200 mL) was treated with NaH (60% dispersion in mineral oil, 0.83 g, 20.7 mmol). After stirring at room temperature for 3 h, the mixture was stored in the freezer for 3 d. The mixture was allowed to warm to room temperature, diluted with $H_2O$ (400 mL), and extracted with EtOAc (4×200 mL). The combined organic layers were washed with $H_2O$ (3×100 mL) and brine (100 mL), dried over $Na_2SO_4$, filtered and the solvent was removed in vacuo. Purification by flash column chromatography (silica gel, $CH_2Cl_2$/MeOH, 99:1) gave the title compound (3.94 g, 67%) as an off-white solid: MS (ESI) m/e 282 (M+H)$^+$.

c)(R)-(E)-3-(10-Oxo-2,3,4,9,10,10a-hexahydro-1H-3a,8,9-triaza-benzo[f]azulen-6-yl)acrylic acid tert-butyl ester A suspension of (R)-6-bromo-1,2,3,4,9,10a-hexahydro-3a,8,9-triaza-benzo[f]azulen-10-one (3.91 g, 13.8 mmol) in propionitrile (80 mL) and DMF (20 mL) was de-oxygenated with Ar for 25 min. The mixture was treated with tert-butyl acrylate (8.1 mL, 55 mmol) and (i-Pr)$_2$EtN (5.1 mL, 29 mmol) and was de-oxygenated with Ar for 15 min. Pd(OAc)$_2$ (0.31 g, 1.4 mmol) and P(o-tol)$_3$ (0.84 mg, 2.8 mmol) were added simultaneously, and the mixture was de-oxygenated a third time for 10 min. The mixture was heated to reflux overnight then allowed to cool. The resulting precipitate was isolated by filtration, dissolved in $CH_2Cl_2$, filtered through Celite, and the solvent was removed in vacuo to give the title compound (2.53 g, 56%) as an off-white solid: MS (ESI) m/e 330 (M+H)$^+$.

d)(R)-(E)-3-(10-Oxo-2,3,4,9,10,10a-hexahydro-1H-3a,8,9-triaza-benzo[f]azulen-6-yl)acrylic acid hydrochloride A solution of (R)-(E)-3-(10-oxo-2,3,4,9,10,10a-hexahydro-1H-3a,8,9-triaza-benzo[f]azulen-6-yl)acrylic acid tert-butyl ester (2.53 g, 7.68 mmol) in $CH_2Cl_2$ (15 mL) was treated with TFA (15 mL). After stirring at room temperature under $N_2$ for 45 min, the clear tan solution was concentrated in vacuo. The resulting oil was treated with anhydrous HCl (30 mL of a 4.0 M solution in dioxane, 120 mmol). The resulting mixture was sonicated for 10 min, stirred under $N_2$ for 20 min, diluted with $Et_2O$ (100 mL), sonicated for 20 min and stirred for 20 min. The solid was isolated by filtration, washed with $Et_2O$, and dried under vacuum at 50° C. overnight to give the title compound (2.66 g, quantitative) as an off-white solid: MS (ESI) m/e 274 (M+H)$^+$.

Preparation 51

Preparation of (S)-(E)-3-(10-Oxo-2,3,4,9,10,10a-hexahydro-1H-3a,8,9-triaza-benzo[f]azulen-6-yl) acrylic acid hydrochloride a)(S)-1-(2-Amino-5-bromo-pyridin-3-ylmethyl)pyrrolidine-2-carboxylic acid methyl ester A solution of 5-bromo-3-bromomethyl-pyridin-2-ylamine hydrobromide (6.00 g, 17.3 mmol) and L-proline methyl ester hydrochloride (2.88 g, 17.4 mmol) in DMF (125 mL) was treated with a solution of triethylamine (7.8 mL, 55.5 mmol) in DMF (75 mL). After stirring at room temperature under $N_2$ for 3 h, the cloudy mixture was diluted with $H_2O$ (300 mL) and extracted with EtOAc (2×300 mL). The combined organic layers were washed with $H_2O$ (2×100 mL) and brine (100 mL), dried over $Na_2SO_4$, filtered and the solvent was removed in vacuo. Purification by flash column chromatography (silica gel, $CH_2Cl_2$/MeOH, 99:1 to 98:2) gave the title compound (3.66 g, 67%) as a pale yellow oil: MS (ESI) m/e 314 (M+H)$^+$.

b)(S)-6-Bromo-1,2,3,4,9,10a-hexahydro-3a,8,9-triaza-benzo[f]azulen-10-one

A solution of (S)-1-(2-amino-5-bromo-pyridin-3-ylmethyl)pyrrolidine-2-carboxylic acid methyl ester (3.66 g, 11.6 mmol) in DMSO (120 mL) was treated with NaH (60% dispersion in mineral oil, 0.47 g, 11.7 mmol). After stirring at room temperature for 4 h, the mixture was diluted with $H_2O$ (2500 mL) and extracted with EtOAc (5×150 mL). The combined organic layers were washed with $H_2O$ (4×100 mL) and brine (100 mL), dried over $Na_2SO_4$, filtered and the solvent was removed in vacuo. Purification by flash column chromatography (silica gel, $CH_2Cl_2$/MeOH, 99:1) gave the title compound (2.75 g, 84%) as an off-white solid: MS (ESI) m/e 282 (M+H)$^+$.

c) (S)-(E)-3-(10-Oxo-2,3,4,9,10,10a-hexahydro-1H-3a,8,9-triaza-benzo[f]azulen-6-yl)acrylic acid tert-butyl ester A suspension of (S)-6-bromo-1,2,3,4,9,10a-hexahydro-3a,8,9-triaza-benzo[f]azulen-10-one (1.46 g, 5.17 mmol) in propionitrile (40 mL) and DMF (10 mL) was de-oxygenated with Ar for 30 min. The mixture was treated with tert-butyl acrylate (3.0 mL, 20 mmol) and (i-Pr)$_2$EtN (1.9 mL, 11 mmol) and was de-oxygenated with Ar for 10 min. Pd(OAc)$_2$ (0.12 g, 0.53 mmol) and P(o-tol)$_3$ (0.34 mg, 1.12 mmol) were added simultaneously, and the mixture was de-oxygenated a third time for 5 min. The mixture was heated to reflux overnight then allowed to cool. The resulting precipitate was isolated by filtration, dissolved in $CH_2Cl_2$, filtered through Celite and the solvent was removed in vacuo to give the title compound (0.68 g, 40%) as an off-white solid: MS (ESI) m/e 330 (M+H)$^+$.

d) (S)-(E)-3-(10-Oxo-2,3,4,9,10,10a-hexahydro-1H-3a,8,9-triaza-benzo[f]azulen-6-yl)acrylic acid hydrochloride A solution of (S)-(E)-3-(10-oxo-2,3,4,9,10,10a-hexahydro-1H-3a,8,9-triaza-benzo[f]azulen-6-yl)acrylic acid tert-butyl ester (0.65 g, 1.97 mmol) in $CH_2Cl_2$ (7 mL) was treated with TFA (7 mL). After stirring at room temperature for 30 min, the clear tan solution was concentrated in vacuo. The resulting oil was treated with anhydrous dioxane (20 mL of a 4.0 M solution in dioxane, 80 mmol). The resulting mixture was sonicated for 5 min, stirred under $N_2$ for 5 min and diluted with $Et_2O$. The solid was isolated by filtration, suspended in $Et_2O$, concentrated to dryness, and dried under vacuum overnight to give the title compound (0.60 g, 88%) as an off-white solid: MS (ESI) m/e 274 (M+H)$^+$.

Preparation 52

Preparation of (E)-3-[4-(4-Methoxy-benzyl)-2-oxo-2,3,4,5-tetrahydro-1H-pyrido[2,3-e][1,4]diazepin-7-yl]acrylic acid hydrochloride a) (4-Methoxy-benzylamino)acetic acid ethyl ester A suspension of glycine ethyl ester hydrochloride (10.0 g, 71.6 mmol) and NaBH$_3$CN (5.00 g, 79.6 mmol) in MeOH (60 mL) was treated dropwise over 15 min with p-anisaldehyde (11.0 mL, 90.4 mmol). After stirring at room temperature overnight, the solvent was removed in vacuo. The residue was partitioned between $CH_2Cl_2$ (200 mL) and saturated aqueous NaHCO$_3$ (300 mL). The aqueous layer was extracted with $CH_2Cl_2$ (2×200 mL) and the combined organic layers were washed with brine, dried over $Na_2SO_4$, filtered and the solvent was removed in vacuo. Purification by flash column chromatography (silica gel, hexanes/EtOAc, 90:10 to 50:50) gave the title compound (7.77 g, 49%) as a colorless liquid: MS (ESI) m/e 224 (M+H)$^+$.

b) [(2-Amino-5-bromo-pyridin-3-ylmethyl)-(4-methoxy-benzyl)amino]acetic acid ethyl ester A solution of 5-bromo-3-bromomethyl-pyridin-2-ylamine hydrobromide (11.9 g, 34.3 mmol) and (4-methoxy-benzylamino)acetic acid ethyl ester (7.70 g, 34.5 mmol) in DMF (200 mL) was treated with triethylamine (10.0 mL, 71.2 mmol). After stirring at room temperature overnight, the cloudy mixture was diluted with $H_2O$ (400 mL) and extracted with EtOAc (2×300 mL). The combined organic layers were washed with $H_2O$ (3×100 mL) and brine (100 mL), dried over $Na_2SO_4$, filtered and the solvent was removed in vacuo to give the title compound (13.0 g, 93%) as a yellow syrup: MS (ESI) n/e 408 (M+H)$^+$.

c) 7-Bromo-4-(4-methoxy-benzyl)-1,3,4,5-tetrahydro-pyrido[2,3-e][1,4]diazepin-2-one A solution of [(2-amino-5-bromo-pyridin-3-ylmethyl)-(4-methoxy-benzyl)amino]acetic acid ethyl ester (13.0 g, 31.9 mmol) in DMSO (200 mL) was treated with NaH (60% dispersion in mineral oil, 1.30 g, 32.5 mmol). After stirring at room temperature overnight, the mixture was diluted with $H_2O$ (500 mL) and a precipitate formed. The solid was isolated by filtration, washed with $H_2O$, and dried under vacuum at 50° C. for 6.5 h to give the title compound (7.16 g, 62%) as a tan powder: MS (ESI) m/e 362 (M+H)$^+$.

d) (E)-3-[4-(4-Methoxy-benzyl)-2-oxo-2,3,4,5-tetrahydro-1H-pyrido[2,3-e][1,4]diazepin-7-yl]acrylic acid tert-butyl ester A suspension of 7-bromo-4-(4-methoxy-benzyl)-1,3,4,5-tetrahydro-pyrido[2,3-e][1,4]diazepin-2-one (5.00 g, 13.8 mmol) in propionitrile (80 mL) and DMF (20 mL) was de-oxygenated with Ar for 25 min. The mixture was treated with tert-butyl acrylate (8.1 mL, 55 mmol) and (i-Pr)$_2$EtN (5.1 mL, 29 mmol) and was de-oxygenated with Ar for 15 min. Pd(OAc)$_2$ (0.32 g, 1.43 mmol) and P(o-tol)$_3$ (0.85 g, 2.79 mmol) were added simultaneously, and the mixture was de-oxygenated a third time for 5 min. The mixture was heated to reflux overnight, then allowed to cool. The resulting precipitate was isolated by filtration. Purification by flash column chromatography (silica gel, $CH_2Cl_2$/MeOH, 99:1) gave the title compound (3.54 g, 63%) as a white solid: MS (ESI) m/e 410 (M+H)$^+$.

e) (E)-3-[4-(4-Methoxy-benzyl)-2-oxo-2,3,4,5-tetrahydro-1H-pyrido[2,3-e][1,4]diazepin-7-yl]acrylic acid hydrochloride A suspension of (E)-3-[4-(4-methoxy-benzyl)-2-oxo-2,3,4,5-tetrahydro-1H-pyrido[2,3-e][1,4]diazepin-7-yl]acrylic acid tert-butyl ester (3.54 g, 8.65 mmol) in $CH_2Cl_2$ (20 mL) was treated with TFA (20 mL). After stirring at room temperature under $N_2$ for 25 min, the clear tan solution was concentrated in vacuo. The resulting residue was treated with anhydrous HCl (40 mL of a 4.0 M solution in dioxane, 160 mmol) and sonicated for 15 min. The solid was isolated by filtration, washed with $Et_2O$ and dried under vacuum at 50° C. for 3 d to give the title compound (3.40 g, 92%) as a white solid: $^1$H NMR (300 MHz, DMSO-d$_6$) δ 12.38 (br s, 1H), 11.32 (s, 1H), 8.77 (s, 1H), 8.28 (s, 1H), 7.66-7.58 (m, 3H), 7.02 (d, J=8.6 Hz, 2H), 6.63 (d, J=16.1 Hz, 1H), 4.41-4.27 (m, 5H), 3.79 (s, 3H), 3.68 (s, 2H); MS (ESI) m/e 354 (M+H)$^+$.

Preparation 53

Preparation of (E)-3-[4-(2-Morpholin-4-yl-ethyl)-2-oxo-2,3,4,5-tetrahydro-1H-pyrido[2,3-e][1,4]diazepin-7-yl]acrylic acid hydrochloride a) [tert-Butoxycarbonyl-(2-morpholin-4-yl-ethyl)amino]acetic acid methyl ester A solution of N-tert-butoxycarbonyl glycine methyl ester (9.4 mL, 63.6 mmol) in DMF (250 mL) was cooled in an ice bath and treated with NaH (60% dispersion in mineral oil, 2.85 g, 71.2 mmol). After stirring at 0° C. under $N_2$ for 30 min and then at room temperature for 30 min, the mixture was cooled in an ice bath and treated with a solution of 4-(2-chloroethyl)morpholine (10.5 g, 70 mmol) in DMF (50 mL). After stirring at 0° C. for 30 min, the mixture was stirred at room temperature overnight. The mixture was diluted with $H_2O$ (600 mL) and then extracted with EtOAc (5×300 mL). The combined organic layers were washed with $H_2O$ (4×100 mL) and brine (100 mL), dried over $Na_2SO_4$, filtered and the solvent was removed in vacuo. Purification by flash column chromatography (silica gel, $CH_2Cl_2$/MeOH, 98:2) gave the title compound (0.79 g, 4%) as a colorless oil: MS (ESI) m/e 303 (M+H)$^+$.

b) (2-Morpholin-4-yl-ethylamino)acetic acid methyl ester

A solution of [tert-butoxycarbonyl-(2-morpholin-yl-ethyl)amino]acetic acid methyl ester (0.79 g, 2.61 mmol) in $CH_2Cl_2$ (10 mL) was treated with TFA (10 mL). After stirring at room temperature for 1 h, the solution was concentrated in vacuo. The oil was dissolved in $CH_2Cl_2$ (50 mL) and the resulting solution was washed with saturated aqueous $NaHCO_3$ (50 mL). The aqueous layer was extracted with $CH_2Cl_2$ (10×50 mL). The combined organic layers were dried over $Na_2SO_4$, filtered and the solvent was removed in vacuo to give the title compound (0.40 g, 76%) as a yellow oil: $^1$H NMR (300 MHz, $CDCl_3$) δ 3.69-3.74 (m, 7H), 3.45 (s, 2H), 2.69-2.73 (m, 2H), 2.45-2.52 (m, 6H), 1.84 (s, 1H).

c) [(2-Amino-5-bromo-pyridin-3-ylmethyl)-(2-morpholin-4-yl-ethyl)amino]acetic acid methyl ester A solution of (2-Morpholin-4-yl-ethylamino)acetic acid methyl ester (0.40 g, 2.0 mmol) and triethylamine (1.0 mL, 7.11 mmol) in DMF (20 mL) was treated with 5-bromo-3-bromomethyl-pyridin-2-ylamine hydrobromide (0.70 g, 2.0 mmol). After stirring at room temperature under for 7 h, the cloudy mixture was diluted with $H_2O$ (50 mL) and then extracted with EtOAc (4×50 mL). The combined organic layers were washed with $H_2O$ (3×50 mL) and brine (50 mL), dried over $Na_2SO_4$, filtered and the solvent was removed in vacuo. Purification by flash column chromatography (silica gel, $CH_2Cl_2$/MeOH, 98:2 to 96:4) gave the title compound (0.46 g, 60%) as a colorless oil: MS (ESI) m/e 387 (M+H)$^+$.

d) 7-Bromo-4-(2-morpholin-4-yl-ethyl)-1,3,4,5-tetrahydro-pyrido[2,3-e][1,4]diazepin-2-one A solution of [(2-amino-5-bromo-pyridin-3-ylmethyl)-(2-morpholin-4-yl-ethyl)amino]acetic acid methyl ester (0.34 g, 0.88 mmol) in DMSO (10 mL) was treated with NaH (60% dispersion in mineral oil, 35 mg, 0.88 mmol). After stirring at room temperature overnight, the mixture was diluted with $H_2O$ (20 mL), and then extracted with EtOAc (4×50 mL). The combined organic layers were washed with $H_2O$ (3×50 mL) and brine (50 mL), dried over $Na_2SO_4$, filtered and the solvent was removed in vacuo. The resulting pale yellow oil was purified by flash column chromatography (silica gel, $CH_2Cl_2$/MeOH, 97:3 to 90:10) to give the title compound (0.24 g, 57%) as an off-white solid: MS (ESI) m/e 355 (M+H)$^+$.

e) (E)-3-[4-(2-Morpholin-4-yl-ethyl)-2-oxo-2,3,4,5-tetrahydro-1H-pyrido[2,3-e][1,4]diazepin-7-yl]acrylic acid tert-butyl ester A suspension of 7-bromo-4-(2-morpholin-4-yl-ethyl)-1,3,4,5-tetrahydro-pyrido[2,3-e][1,4]diazepin-2-one (0.18 g, 0.52 mmol) in propionitrile (4 mL) and DMF (1 mL) was de-oxygenated with Ar for 15 min. The mixture was treated with tert-butyl acrylate (0.3 mL, 2 mmol) and (i-Pr)$_2$EtN (0.2 mL, 1 mmol) and was de-oxygenated with Ar for 10 min. Pd(OAc)$_2$ (12 mg, 0.053 mmol) and P(o-tol)$_3$ (32 mg, 0.10 mmol) were added simultaneously, and the mixture was de-oxygenated a third time for 5 min. The mixture was heated to reflux overnight, then allowed to cool. The mixture was diluted with $Et_2O$ (50 mL) and the resulting solution washed with $H_2O$ (20 mL). The organic layer was dried over $Na_2SO_4$, filtered and the solvent was removed in vacuo. Purification by flash column chromatography (silica gel, $CH_2Cl_2$/MeOH, 97:3) gave the title compound (92 mg, 44%) as an off-white solid: $^1$H NMR (300 MHz, DMSO-d$_6$) 89.51 (s, H), 8.52 (s, 1H), 7.61-7.49 (m, 2H), 6.36 (d, J=16.0 Hz, 1H), 4.07 (s, 2H), 3.90 (s, 2H), 3.70-3.67 (m, 4H), 2.78-2.74 (m, 2H), 2.52-2.49 (m, 6H), 1.53 (s, 9H); MS (ESI) m/e 403 (M+H)$^+$.

f) (E)-3-[4-(2-Morpholin-4-yl-ethyl)-2-oxo-2,3,4,5-tetrahydro-1H-pyrido[2,3-e][1,4]diazepin-7-yl]acrylic acid hydrochloride A solution of (E)-3-[4-(2-morpholin-4-yl-ethyl)-2-oxo-2,3,4,5-tetrahydro-1H-pyrido[2,3-e][1,4]diazepin-7-yl]acrylic acid tert-butyl ester (92 mg, 0.23 mmol) in $CH_2Cl_2$ (2 mL) was treated with TFA (2 mL). After stirring at room temperature for 30 min, the clear tan solution was concentrated in vacuo. The resulting oil was treated with anhydrous HCl (4 mL of a 4.0 M solution in dioxane, 16 mmol) and then sonicated for 15 min. The mixture was diluted with $Et_2O$ and sonicated for 10 min. The solid was isolated by filtration, washed with $Et_2O$ and dried under vacuum at 50° C. for 4.5 hr to give the title compound (0.10 g, 96%) as an off-white solid: MS (ESI) m/e 347 (M+H)$^+$.

Preparation 54

Preparation of (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid hydrochloride a) [(2-Amino-5-bromo-pyridin-3-ylmethyl)amino]acetic acid ethyl ester A solution of 5-bromo-3-bromomethyl-pyridin-2-ylamine hydrobromide (6.00 g, 17.3 mmol) and glycine ethyl ester hydrochloride (2.41 g, 17.3 mmol) in DMF (200 mL) was treated with triethylamine (7.8 mL, 56 mmol). After stirring at room temperature for 3.5 h, the cloudy mixture was diluted with $H_2O$ (300 mL) and then extracted with EtOAc (2×300 mL). The combined organic layers were washed with $H_2O$ (3×100 mL) and brine (100 mL), dried over $Na_2SO_4$, filtered and the solvent was removed in vacuo. Purification by flash column chromatography (silica gel, $CH_2Cl_2$/MeOH, 98:2) gave the title compound (2.83 g, 57%) as a white solid: $^1$H NMR (300 MHz, $CDCl_3$) δ 8.04 (d, J=2.3 Hz, 1H), 7.36 (d, J=2.3 Hz, 1H), 5.56 (s, 2H), 4.22 (q, J=7.2 Hz, 2H), 3.71 (s, 2H), 3.38 (s, 2H), 1.73 (s, 1H), 1.30 (t, J=7.2 Hz, 3H); MS (ESI) m/e 288 (M+H)$^+$.

b) 7-Bromo-1,3,4,5-tetrahydro-pyrido[2,3-e][1,4]diazepin-2-one

A solution of [(2-amino-5-bromo-pyridin-3-ylmethyl)amino]acetic acid ethyl ester (1.79 g, 6.21 mmol) in DMSO (70 mL) was treated with NaH (60% dispersion in mineral oil, 0.25 g, 6.2 mmol). After stirring at room temperature for 27 h, the mixture was diluted with H₂O (300 mL), and extracted then with EtOAc (4×150 mL). The combined organic layers were washed with H₂O (3×50 mL) and brine (50 mL), dried over Na₂SO₄, filtered and the solvent was removed in vacuo to give the title compound (1.09 g, 72%) as an off-white solid: $^1$H NMR (300 MHz, CDCl₃) δ 8.26 (d, J=2.1 Hz, 1H), 8.17 (s, 1H), 7.54 (d, J=1.9 Hz, 1H), 4.03 (s, 2H), 3.93 (s, 2H), 1.85 (br s, 1H); MS (ESI) m/e 242 (M+H)⁺.

c) (7-Bromo-2-oxo-1,2,3,5-tetrahydro-pyrido[2,3-e][1,4]diazepin-4-yl)acetic acid tert-butyl ester A solution of 7-bromo-1,3,4,5-tetrahydro-pyrido[2,3-e][1,4]diazepin-2-one (2.29 g, 9.46 mmol) in DMF (100 mL) was treated with tert-butylbromoacetate (1.7 mL, 12 mmol) and triethylamine (1.5 mL, 11 mmol). After stirring at room temperature overnight, the mixture was diluted with H₂O (300 mL) and then extracted with EtOAc (3×200 mL). The combined organic layers were washed with H₂O (3×100 mL) and brine (100 mL), dried over Na₂SO₄, filtered and the solvent was removed in vacuo. Purification by flash column chromatography (silica gel, hexanes/EtOAc, 2:1) gave the title compound (1.61 g, 48%) as a white powder: MS (ESI) m/e 356 (M+H)⁺.

d) (7-Bromo-2-oxo-1,2,3,5-tetrahydro-pyrido[2,3-e][1,4]diazepin-4-yl)acetic acid hydrochloride A solution of (7-bromo-2-oxo-1,2,3,5-tetrahydro-pyrido[2,3-e][1,4]diazepin-4-yl)acetic acid tert-butyl ester (1.61 g, 4.52 mmol) in CH₂Cl₂ (20 mL) was treated with TFA (15 mL). After stirring at room temperature for 1 h, the solution was concentrated in vacuo. The resulting slurry was treated with anhydrous HCl (40 mL of a 4.0 M) and sonicated for 1.5 h, diluted with Et₂O and stirred for 1 h. The solid was isolated by filtration, washed with Et₂O, and dried under vacuum at 50° C. overnight to give the title compound (1.66 g, 98%) as a white solid: MS (ESI) m/e 300 (M+H)⁺.

e) 7-Bromo-4-[2-(4-methyl-piperazin-1-yl)-2-oxo-ethyl]-1,3,4,5-tetrahydro-pyrido[2,3-e][1,4]diazepin-2-one A suspension of (7-bromo-2-oxo-1,2,3,5-tetrahydro-pyrido[2,3-e][1,4]diazepin-4-yl)acetic acid hydrochloride (1.66 g, 4.45 mmol) in CH₂Cl₂ (50 mL) was treated sequentially with (i-Pr)₂EtN (3.1 mL, 18 mmol), N-methyl piperazine (0.54 mL, 4.87 mmol), HOBt (0.66 g, 4.88 mmol), and EDC (0.95 g, 4.96 mmol). After string overnight, the mixture was diluted with CH₂Cl₂ (100 mL) and then washed with H₂O (100 mL). The aqueous layer was extracted with CH₂Cl₂ (4×100 mL). The combined organic layers were dried over Na₂SO₄, filtered and the solvent was removed in vacuo. Purification by flash column chromatography (silica gel, CH₂Cl₂/MeOH, 97:3 to 95:5) gave the title compound (1.42 g, 83%) as an off-white solid: MS (ESI) m/e 382 (M+H)⁺.

f) (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid tert-butyl ester A suspension of 7-Bromo-4-[2-(4-methyl-piperazin-1-yl)-2-oxo-ethyl]-1,3,4,5-tetrahydro-pyrido[2,3-e][1,4]diazepin-2-one (1.39 g, 3.64 mmol) in propionitrile (32 mL) and DMF (8 mL) was de-oxygenated with Ar for 15 min. The mixture was treated with tert-butyl acrylate (2.1 mL, 14 mmol) and (i-Pr)₂EtN (1.3 mL, 7.4 mmol) and then was de-oxygenated with Ar for 10 min. Pd(OAc)₂ (83 mg, 0.37 mmol) and P(o-tol)₃ (0.22 g, 0.73 mmol) were added simultaneously, and the mixture was de-oxygenated a third time for 10 min. The mixture was heated to reflux overnight, then allowed to cool. The resulting precipitate was isolated by filtration and dissolved in CH₂Cl₂. The solution was filtered through Celite and the solvent was removed in vacuo to give the title compound (1.13 g, 72%) as an off-white solid: MS (ESI) m/e 430 (M+H)⁺.

g) (E)-3-{4-[2-(4-Methyl-piperazin-1-yl)-2-oxo-ethyl]-2-oxo-2,3,4,5-tetrahydro-1H-pyrido[2,3-e][1,4]diazepin-7-yl}acrylic acid hydrochloride A suspension of (E)-3-{4-[2-(4-Methyl-piperazin-1-yl)-2-oxo-ethyl]-2-oxo-2,3,4,5-tetrahydro-1H-pyrido[2,3-e][1,4] diazepin-7-yl}acrylic acid tert-butyl ester (1.12 g, 2.61 mmol) in CH₂Cl₂ (10 mL) was treated with TFA (10 mL). After stirring at room temperature for 35 min, the solution was concentrated in vacuo. The resulting oil was treated with anhydrous HCl (20 mL of a 4.0 M solution in dioxane, 80 mmol) and the resulting mixture was sonicated for 1 h. The mixture was diluted with Et₂O (50 mL) and sonicated for 10 min. The solid was isolated by filtration, washed with Et₂O and dried under vacuum at 50° C. for 4 h to give the title compound (1.72 g, quantitative) as an off-white solid: $^1$H NMR (500 MHz, DMSO-d₆) δ 11.60 (br s, 1H), 11.09 (br s, 1H), 8.82 (s, 1H), 8.47 (s, 1H), 7.66 (d, J=19.9 Hz, 1H), 6.65 (d, J=16.1 Hz, 1H), 4.43-4.40 (m, 2H), 4.31 (br s, 2H), 3.95-3.91 (m, 1H), 3.84 (br s, 2H), 3.56 (s, 4H), 3.42 (br s, 2H), 3.23-2.97 (m, 2H), 2.76 (d, J=4.1 Hz, 3H); MS (ESI) m/e 374 (M+H)⁺.

Preparation 55

Preparation of (E)-3-[4-(3-Morpholin-4-yl-propyl)-2-oxo-2,3,4,5-tetrahydro-1H-pyrido[2,3-e][1,4]diazepin-7-yl]acrylic acid hydrochloride a) (3-Morpholin-4-yl-propylamino)acetic acid ethyl ester A solution of 4-(3-aminopropyl)morpholine (10.0 mL, 68.4 mmol) in MeOH (180 mL) was cooled in an ice bath and treated with ethyl glyoxylate (~50% solution in toluene, 20.0 mL, 98.0 mmol) and HOAc (12 mL). After stirring for 15 min, NaBH₃CN (4.81 g, 76.5 mmol) was added and the mixture was allowed to stir at 0° C. for 2 h. The mixture was diluted with saturated aqueous NaHCO₃ (500 mL) and then extracted with EtOAc (5×300 mL) followed by CH₂Cl₂ (9×200 mL). The combined CH₂Cl₂ layers were dried over Na₂SO₄, filtered and the solvent was removed in vacuo to give the title compound (7.44 g, 47%) as a colorless oil: MS (ESI) m/e 231 (M+H)⁺.

b) [(2-Amino-5-bromo-pyridin-3-ylmethyl)-(3-morpholin-4-yl-propyl)amino]acetic acid ethyl ester A solution of 5-bromo-3-bromomethyl-pyridin-2-ylamine hydrobromide (11.2 g, 32.3 mmol) and (3-morpholin-4-yl-propylamino)acetic acid ethyl ester (7.44 g, 32.3 mmol) in DMF (200 mL) was treated with triethylamine (9.5 mL, 68 mmol). After stirring at room temperature overnight, the mixture was diluted with H₂O (400 mL) and then extracted with EtOAc (5×250 mL). The combined organic layers were washed with H₂O (2×200 mL) and brine (200 mL), dried over Na₂SO₄, filtered and the solvent was removed in vacuo to give the title compound (11.8 g, 87%) as a yellow oil: MS (ESI) m/e 415 (M+H)⁺.

c) 7-Bromo-4-(3-morpholin-4-yl-propyl)-1,3,4,5-tetrahydro-pyrido[2,3-e][1,4]diazepin-2-one A solution of [(2-amino-5-bromo-pyridin-3-ylmethyl)-(3-morpholin-4-yl-propyl)amino]acetic acid ethyl ester (11.8 g, 28.3 mmol) in DMSO (200 mL) was treated with NaH (60% dispersion in mineral oil, 1.13 g, 28.3 mmol). After stirring at room temperature overnight, the mixture was diluted with H₂O (400 mL) and then extracted with EtOAc (7×250 mL). The combined organic layers were washed with H₂O (2×200 mL) and brine (200 mL), dried over Na₂SO₄, filtered and the solvent was removed in vacuo. Purification by flash column chromatography (silica gel, CH₂Cl₂/MeOH, 97:3 to 96:4)

gave the title compound (5.76 g, 55%) as an off-white powder: MS (ESI) m/e 369 (M+H)⁺.

d) (E)-3-[4-(3-Morpholin-4-yl-propyl)-2-oxo-2,3,4,5-tetrahydro-1H-pyrido[2,3-e][1,4]diazepin-7-yl]acrylic acid tert-butyl ester A suspension of 7-bromo-4-(3-morpholin-4-yl-propyl)-1,3,4,5-tetrahydro-pyrido[2,3-e][1,4]diazepin-2-one (5.70 g, 15.4 mmol) in propionitrile (120 mL) and DMF (30 mL) was de-oxygenated with Ar for 15 min. The mixture was treated with tert-butyl acrylate (9.0 mL, 61 mmol) and (i-Pr)$_2$EtN (5.7 mL, 33 mmol) and was de-oxygenated with Ar for 10 min. Pd(OAc)$_2$ (0.35 g, 1.6 mmol) and P(o-tol)$_3$ (0.94 g, 3.1 mmol) were added simultaneously, and the mixture was de-oxygenated a third time for 5 min. The mixture was heated to reflux overnight, then allowed to cool. The mixture was diluted with Et$_2$O (200 mL). The organic solution was filtered through Celite, washed with H$_2$O (200 mL), dried over Na$_2$SO$_4$, filtered and then concentrated in vacuo. Purification by flash column chromatography (silica gel, CH$_2$Cl$_2$/MeOH, 97:3 to 96:4) gave the title compound (3.49 g, 55%) as a tan solid: MS (ESI) m/e 417 (M+H)⁺.

e) (E)-3-[4-(3-Morpholin-4-yl-propyl)-2-oxo-2,3,4,5-tetrahydro-1H-pyrido[2,3-e][1,4]diazepin-7-yl]acrylic acid hydrochloride A solution of (E)-3-[4-(3-Morpholin-4-yl-propyl)-2-oxo-2,3,4,5-tetrahydro-1H-pyrido[2,3-e][1,4]diazepin-7-yl] acrylic acid tert-butyl ester (2.21 g, 5.30 mmol) in CH$_2$Cl$_2$ (20 mL) was treated with TFA (20 mL). After stirring at room temperature for 30 min, the solution was concentrated in vacuo. The resulting oil was treated with anhydrous HCl (50 mL of a 4.0 M solution in dioxane, 200 mmol) and the mixture was sonicated for 1.5 h. The mixture was diluted with Et$_2$O (200 mL) and sonicated for 15 min. The solid was isolated by filtration, washed with Et$_2$O, and dried under vacuum at 50° C. for 5 h to give the title compound (3.08 g, quantitative) as an off-white solid: ¹H NMR (500 MHz, DMSO-d$_6$) δ 11.23 (br s, 2H), 8.74 (s, 1H), 8.36 (s, 1H), 7.63 (d, J=15.9, 1H), 6.63 (d, J=16.0 Hz, 1H), 4.33 (br s, 2H), 3.90 (br s, 6H), 3.24 (m, 8H), 2.22 (br s, 2H); MS 361 (M+H)⁺.

Preparation 56

Preparation of (E)-7-(2-carboxy-vinyl)-2-oxo-1,2,3,5-tetrahydro-pyrido[2,3-e][1,4]diazepine-4-carboxylic acid benzyl ester hydrochloride a) 7-Bromo-2-oxo-1,2,3,5-tetrahydro-pyrido[2,3-e][1,4]diazepine-4-carboxylic acid benzyl ester A suspension of 7-bromo-1,3,4,5-tetrahydro-pyrido[2,3-e][1,4]diazepin-2-one (1.08 g, 4.46 mmol) in CH$_2$Cl$_2$ (60 mL) was treated with Et$_3$N (0.80 mL, 5.7 mmol) and then cooled in an ice bath. The chilled suspension was treated dropwise with CbzCl (4.5 mmol) to give a clear solution. The ice bath was removed and the solution was allowed to stir overnight. The mixture was diluted with CH$_2$Cl$_2$ (90 mL), washed with H$_2$O (50 mL) and brine (50 mL), dried over Na$_2$SO$_4$, filtered and the solvent was removed in vacuo. Purification by flash column chromatography (silica gel, CH$_2$Cl$_2$/MeOH, 99.5:0.5 to 99:1) gave the title compound (0.52 g, 31%) as a white solid: ¹H NMR (300 MHz, CDCl$_3$) δ 8.31-8.36 (m, 2H), 7.49-7.71 (m, 1H), 7.34-7.40 (m, 4H), 7.19-7.21 (m, 1H), 5.08-5.12 (m, 2H), 4.43-4.65 (m, 4H); MS (ESI) m/e 376 (M+H)⁺.

b) (E)-7-(2-tert-Butoxycarbonyl-vinyl)-2-oxo-1,2,3,5-tetrahydro-pyrido[2,3-e][1,4]diazepine-4-carboxylic acid benzyl ester A suspension of 7-bromo-2-oxo-1,2,3,5-tetrahydro-pyrido[2,3-e][1,4]diazepine-4-carboxylic acid benzyl ester (0.52 g, 1.4 mmol) in propionitrile (10 mL) and DMF (3 mL) was de-oxygenated with Ar for 20 min. The mixture was treated with tert-butyl acrylate (0.83 mL, 10 mmol) and (i-Pr)$_2$EtN (0.50 mL, 2.9 mmol) and was de-oxygenated with Ar for 10 min. Pd(OAc)$_2$ (34 mg, 0.15 mmol) and P(o-tol)$_3$ (84 mg, 0.27 mmol) were added simultaneously, and the mixture was de-oxygenated a third time for 5 min. The mixture was heated to reflux overnight, then allowed to cool. The resulting precipitate was isolated by filtration, washed with EtOAc and dissolved in CH$_2$Cl$_2$. The solution was filtered through Celite and the solvent was removed in vacuo to give the title compound (0.31 g, 53%) as an off-white solid: ¹H NMR (300 MHz, CDCl$_3$) δ 8.49-8.57 (m, 1H), 8.30 (s, 1H), 7.43-7.73 (m, 2H), 7.33 (s, 4H), 7.17-7.18 (m, 1H), 6.21-6.40 (m, 1H), 5.05-5.11 (m, 2H), 4.46-4.68 (m, 4H), 1.54-1.57 (m, 9H); MS (ESI) m/e 424 (M+H)⁺.

c) (E)-7-(2-Carboxy-vinyl)-2-oxo-1,2,3,5-tetrahydro-pyrido[2,3-e][1,4]diazepine-4-carboxylic acid benzyl ester hydrochloride A solution of (E)-7-(2-tert-butoxycarbonyl-vinyl)-2-oxo-1,2,3,5-tetrahydro-pyrido[2,3-e][1,4]diazepine-4-carboxylic acid benzyl ester (0.31 g, 0.73 mmol) in CH$_2$Cl$_2$ (5 mL) was treated with TFA (5 mL). After stirring at room temperature for 30 min, the clear tan solution was concentrated in vacuo. The resulting oil was treated with anhydrous HCl (10 mL of a 4.0 M solution in dioxane, 40 mmol) to give a cloudy mixture. The mixture was diluted with Et$_2$O (200 mL) to give an off-white precipitate. After stirring for 15 min, the solid was isolated by filtration, washed with Et$_2$O, and dried under vacuum for 1.5 h to give the title compound (0.27 g, 91%) as an off-white solid: ¹H NMR (300 MHz, DMSO-d$_6$) δ 10.50-10.47 (m, 1H), 8.49 (s, 1H), 8.09-8.15 (m, 1H), 7.53-7.59 (m, 1H), 7.15-7.33 (m, 5H), 6.51-6.65 (m, 1H), 5.42 (bs, 2H), 5.05-5.08 (m, 2H), 4.63 (s, 2H), 4.43 (s, 2H); MS (ESI) m/e 368 (M+H)⁺.

Preparation 57

Preparation of (E)-3-(2-Oxo-2,3-dihydro-oxazolo[4,5-b]pyridine-6-yl)acrylic acid hydrochloride a) (E)-3-(2-Oxo-2,3-dihydro-oxazolo[4,5-b]pyridin-6-yl) acrylic acid tert-butyl ester A stirred solution of 6-bromo-3H-oxazolo[4,5-b]pyridin-2-one (1.00 g, 4.65 mmol), tert-butyl acrylate (2.7 mL, 18 mmol), palladium(II) acetate (104 mg, 0.465 mmol), tri-o-tolylphosphine (283 mg, 0.930 mmol), and N,N-diisopropylethylamine (1.7 mL, 9.7 mmol) in N,N-dimethylformamide (4 mL) and propionitrile (16 mL) was deoxygenated by bubbling argon through the solution for 20 min. The mixture was heated to reflux for 21 h, then allowed to cool. The mixture was concentrated in vacuo. The residue was dissolved in dichloromethane (100 mL). The solution was washed with water (2×200 mL), dried over sodium sulfate, filtered, and the solvent removed in vacuo to give a dark brown oil. Purification by flash column chromatography (silica gel, gradient from 98:2 to 94:6 CHCl$_3$/MeOH) gave the title compound (283 mg, 23%) as a brown solid: ¹H NMR (300 MHz, CDCl$_3$) δ 8.24 (d, J=1.4 Hz, 1H), 7.64-7.55 (m, 2H), 6.37 (d, J=16.0 Hz, 1H), 1.55 (s, 9H).

b) (E)-3-(2-Oxo-2,3-dihydro-oxazolo[4,5-b]pyridin-6-yl)acrylic acid hydrochloride A solution of (E)-3-(2-oxo-2,3-dihydro-oxazolo[4,5-b]pyridine-6-yl)acrylic acid tert-butyl ester (274 mg, 1.04 mmol) in dichloromethane (5 mL) and trifluoroacetic acid (5 mL) was stirred for 30 min, then the solvents were removed in vacuo. The residue was suspended in anhydrous HCl (5 mL of a 4 M solution in 1,4-dioxane, 20 mmol) and the mixture was sonicated for 1 min. The resulting solid was collected by filtration, washed with diethyl ether and then dried in vacuo to give the title compound (194 mg, 77%) as a light brown solid: $^1$H NMR (300 MHz, DMSO-$d_6$) δ 8.31 (s, 1H), 8.13 (s, 1H), 7.63 (d, J=16.0 Hz, 1H), 6.60 (d, J=16.0 Hz, 1H).

Preparation 58

Preparation of (E)-3-[6-Amino-5-(2-carboxy-ethyl)pyridin-3-yl]acrylic acid

A solution of (E)-3-(7-oxo-5,6,7,8-tetrahydro-[1,8]naphthyridin-3-yl)acrylic acid tert-butyl ester (0.86 g, 3.0 mmol) was stirred in methanol (10 mL), dioxane (10 mL) and aq. NaOH (15 mL of a 1 N solution, 15 mmol) for 4 days. The clear solution was neutralized with aq. HCl (15 mL of a 1 N solution, 15 mmol) and stirred for 20 min. The white precipitate was collected by filtration to give (E)-3-[6-amino-5-(2-carboxy-ethyl)pyridin-3-yl]acrylic acid (0.57 g, 78%): MS (ESI) m/e 237 (M+H)$^+$.

Preparation 59

Preparation of (E)-3-(6-Amino-5-piperidin-1-ylmethyl-pyridin-3-yl)acrylic acid hydrochloride a) 5-Bromo-3-piperidin-1-ylmethyl-pyridin-2-ylamine An ice-cold suspension of 5-bromo-3-bromomethyl-pyridin-2-ylamine hydrobromide (10.0 g, 28.8 mmol) in MeCN (100 mL) was treated with piperidine (6.4 mL, 64.8 mmol). After stirring at room temperature for 3.5 h, the mixture was diluted with Et$_2$O (500 mL). The solution was filtered and then concentrated to give the title compound (4.16 g, 53%) as a pale, yellow solid: MS (ESI) m/e 270 (M+H)$^+$.

b) (E)-3-(6-Amino-5-piperidin-1-ylmethyl-pyridin-3-yl)acrylic acid tert-butyl ester A solution of 5-bromo-3-piperidin-1-ylmethyl-pyridin-2-ylamine (500 mg, 1.85 mmol), tert-butyl acrylate (0.3 mL, 2.0 mmol), (i-Pr)$_2$EtN (0.5 mL, 2.8 mmol) and P(o-tol)$_3$ (114 mg, 0.37 mmol) in EtCN (10 mL) was de-oxygenated with argon for 30 min. Pd(OAc)$_2$ (43 mg, 0.19 mmol) was added, and the mixture was de-oxygenated for 15 min. The mixture was heated to reflux for 18 h and then allowed to cool. The solvent was removed in vacuo. The residue was partitioned between EtOAc and H$_2$O. The organic layer was washed with H$_2$O and satd NaCl, dried over Na$_2$SO$_4$ and concentrated. Purification by column chromatography (silica gel, CH$_2$Cl$_2$ to 96:4 CH$_2$Cl$_2$/CH$_3$OH) gave the title compound (350 mg, 60%) as a yellow solid: MS (ESI) nm/e 318 (M+H)$^+$.

c) (E)-3-(6-Amino-5-piperidin-1-ylmethyl-pyridin-3-yl)acrylic acid hydrochloride A suspension of 3-(6-amino-5-piperidin-1-ylmethyl-pyridin-3-yl)acrylic acid tert-butyl ester (250 mg, 0.79 mmol) in CH$_2$Cl$_2$ (3 mL) was treated with TFA (2 mL). After stirring at room temperature under N$_2$ for 45 min, the solution was concentrated. The resulting oil was treated with anhydrous HCl in dioxane (10 mL, 4.0 M) and then sonicated until the oil was converted to a fine off-white solid. After stirring under N$_2$ for 20 min, the solid was isolated by filtration, washed with Et$_2$O, and dried under vacuum for several hours to give the title compound (282 mg, quantitative) as an off-white solid: $^1$H NMR (300 MHz, DMSO-$d_6$) δ 10.6 (br s, 1H), 8.53 (d, J=2.1 Hz, 1H), 8.39-8.28 (m, 3H), 7.53 (d, J=15.0 Hz, 1H), 6.46 (d, J=15.0 Hz, 1H), 4.33 (s, 2H), 3.43-3.35 (m, 2H), 2.97 (s, 2H), 1.79-1.69 (m, 5H), 1.35 (s, 1H).

Preparation 60

Preparation of (E)-3-(6-Amino-5-pyrrolidin-1-ylmethyl-pyridin-3-yl)acrylic acid hydrochloride a) 5-Bromo-3-pyrrolidin-1-ylmethyl-pyridin-2-ylamine According to the procedure of Preparation 59(a), except substituting pyrrolidine for piperidine, the title compound (2.40 g, 34%) was prepared as an off-white solid: $^1$H NMR (300 MHz, CDCl$_3$) 67 8.01 (d, J=2.3 Hz, 1H), 7.34 (d, J=2.3 Hz, 1H), 5.67 (s, 2H), 3.51 (s, 2H), 2.48-2.44 (m, 4H), 1.80-1.60 (m, 4H).

b) (E)-3-(6-Amino-5-pyrrolidin-1-ylmethyl-pyridin-3-yl)acrylic acid tert-butyl ester According to the procedure of Preparation 59(b), except substituting 5-bromo-3-pyrrolidin-1-ylmethyl-pyridin-2-ylamine for 5-bromo-3-piperidin-1-ylmethyl-pyridin-2-ylamine, the title compound (1.60 g, 61%) was prepared as a light yellow solid: $^1$H NMR (300 MHz, CDCl$_3$) δ 8.08 (d, J=2.1 Hz, 1H), 7.50-7.44 (m, 2H), 6.17 (d 1H), 6.00 (s, 2H), 3.56 (s, 2H), 2.49-2.45 (m, 4H), 1.81-1.76 (m, 4H), 1.52 (s, 9H).

c) (E)-3-(6-Amino-5-pyrrolidin-1-ylmethyl-pyridin-3-yl)acrylic acid hydrochloride According to the procedure of Preparation 59(c), except substituting (E)-3-(6-amino-5-pyrrolidin-1-ylmethyl-pyridin-3-yl)acrylic acid tert-butyl ester for (E)-3-(6-amino-5-piperidin-1-ylmethyl-pyridin-3-yl)acrylic acid tert-butyl ester, the title compound (1.68 g, quantitative) was prepared as an off-white solid: $^1$H NMR (300 MHz, DMSO-$d_6$) δ 11.9 (br s, 1H), 8.66-8.38 (m, 4H), 7.56 (d, J=15.9 Hz, 1H), 6.49 (d, J=15.9 Hz, 1H), 4.46 (s, 2H), 3.57-3.50 (m, 2H), 3.19-3.01 (m, 2H), 1.91-1.88 (m, 4H).

Preparation 61

Preparation of (E)-3-[6-Amino-5-(4-methyl-piperazin-1-ylmethyl)-pyridin-3-yl]acrylic acid hydrochloride a) 5-Bromo-3-(4-methyl-piperazin-1-ylmethyl)pyridin-2-ylamine According to the procedure of Preparation 59(a), except substituting 1-methylpiperizine for piperidine, the title compound (2.32 g, 30%) was prepared as a light, yellow solid: $^1$H NMR (300 MHz, CDCl$_3$) δ 8.03 (d, J=2.3 Hz, 1H), 7.32 (d, J=2.3 Hz, 1H), 5.63 (s, 2H), 3.42 (s, 2H), 2.46-2.36 (m, 8H), 2.30 (s, 3H).

b) (E)-3-[6-Amino-5-(4-methyl-piperazin-1-ylmethyl)pyridin-3-yl]acrylic acid tert-butyl ester According to the procedure of Preparation 59(b), except substituting 5-bromo-3-(4-methyl-piperazin-1-ylmethyl)pyridin-2-ylamine for 5-bromo-3-piperidin-1-ylmethyl-pyridin-2-ylamine, the title compound (1.18 g, 45%) was prepared as a yellow solid: $^1$H NMR (300 MHz, CDCl$_3$) δ 8.09 (d, J=2.2 Hz, 1H), 7.49-7.44 (m, 2H), 6.18 (d, J=15.9 Hz, 1H), 5.95 (br s, 2H), 3.47 (s, 2H), 2.38-2.59 (m, 7H), 2.96 (s, 4H), 1.52 (s, 9H).

c) (E)-3-[6-Amino-5-(4-methyl-piperazin-1-ylmethyl)pyridin-3-yl]acrylic acid hydrochloride According to the procedure of Preparation 59(c), except substituting (E)-3-[6-amino-5-(4-methyl-piperazin-1-ylmethyl)-pyridin-3-yl]acrylic acid tert-butyl ester (1.18 g, 3.55 mmol) for (E)-3-(6-amino-5-piperidin-1-ylmethyl-pyridin-3-yl)acrylic acid tert-butyl ester, the title compound (1.72 g, quantitative) was prepared as an off-white solid: $^1$H NMR (300 MHz, DMSO-d$_6$) δ 10.98 (br s, 1H), 8.61-8.34 (m, 4H), 7.53 (d, J=16.0 Hz, 1H), 6.53 (d, J=15.9 Hz, 1H), 3.81 (br s, 2H), 3.56 (s, 3H), 3.45-3.37 (m, 2H), 3.20-3.08 (m, 2H), 2.76 (s, 4H); MS (ESI) m/e 277 (M+H)$^+$.

Preparation 62

Preparation of (E)-3-[6-Amino-5-(4-benzyl-piperidin-1ylmethyl)pyridin-3yl]acrylic acid hydrochloride a) 3-(4-Benzyl-piperidin-1-ylmethyl)-5-bromo-pyridin-2-ylamine According to the procedure of Preparation 59(a), except substituting 4-benzylpiperidine (5.6 mL, 31.7 mmol) for piperidine and adding K$_2$CO$_3$ (19.9 g, 144 mmol) as base, the title compound (9.81 g, 95%) was prepared as a light, yellow solid: MS (ESI) m/e 36 (M+H)$^+$.

b) (E)-3-[6-Amino-5-(4-benzyl-piperidin-1-ylmethyl)pyridin-3-yl]acrylic acid tert-butyl ester According to the procedure of Preparation 59(b), except substituting 3-(4-Benzyl-piperidin-1-ylmethyl)-5-bromo-pyridin-2-ylamine for 5-bromo-3-piperidin-1-ylmethyl-pyridin-2-ylamine, the title compound (4.48 g, 80%) was prepared as a yellow solid: MS (ESI) m/e 408 (M+H)$^+$.

c) (E)-3-[6-Amino-5-(4-benzyl-piperidin-1-ylmethyl)pyridin-3-yl]acrylic acid hydrochloride According to the procedure of Preparation 59(c), except substituting (E)-3-[6-amino-5-(4-benzyl-piperidin-1-ylmethyl)pyridin-3-yl]acrylic acid tert-butyl ester for 3-(6-amino-5-piperidin-1-ylmethyl-pyridin-3-yl)acrylic acid tert-butyl ester, the title compound (5.24 g, quantitative) was prepared as an off-white solid: $^1$H NMR (300 MHz, DMSO-d$_6$) δ 10.56 (br s, 1H), 8.61-8.37 (m, 3H), 7.51 (d, J=15.9, 1H), 7.32-7.17 (m, 6H), 6.50-6.42 (m, 1H), 4.35 (br s, 2H), 3.45-3.37 (m, 2H), 3.11-2.92 (m, 2H), 1.75-1.51 (m, 6H), MS (ESI) m/e 352 (M+H)$^+$.

Preparation 63

Preparation of (E)-3-(2,4-dioxo-1,2,3,4-tetrahydro-pyrido[2,3-d]pyrimidin-6-yl)acrylic acid a) 2-Amino-5-bromo-nicotinic acid hydrobromide Bromine (7.5 mL, 146 mmol) was added dropwise over 10 min to a suspension of 2-amino-nicotinic acid (20.0 g, 145 mmol) in glacial acetic acid (250 mL) cooled in an ice bath. After the bromine addition was complete, the mixture was stirred at ambient temperature for 2 d. The resulting light yellow solid was isolated by filtration, washed with Et$_2$O, and dried under high vacuum (40° C.) for several hours to give the title compound (40.0 g, 93%): $^1$H NMR (300 MHz, DMSO-d$_6$) δ 8.33 (d, J=2.5 Hz, 1H), 8.20 (d, J=2.5 Hz, 1H), 8.02 (bs, 3H); ESI MS m/e 217 (M+H)$^+$.

b) 2-Amino-5-bromo-nicotinamide

To an ice-cold suspension of 2-amino-5-bromo-nicotinic acid hydrobromide (5.11 g, 17.1 mmol) and ammonium chloride (9.15 g, 171 mmol) in dimethoxyethane (170 mL) was added Et$_3$N (4.8 mL, 34.2 mmol). After 10 min, diethylphosphoryl cyanide was added dropwise and the cold bath removed. After 4 h, the solution was filtered and the filtrate concentrated. The resulting residue was partitioned between EtOAc and water. The organic layer was washed with satd NaHCO$_3$ (2×) and satd NaCl, dried (Na$_2$SO$_4$) and concentrated under reduced pressure. The yellow solid was dissolved in EtOAc and then hexanes were added until precipitation occurred. The solid was collected by filtration and then triturated with EtOAc to give the title compound (1.62 g, 44%) as a yellow solid: $^1$H NMR (300 MHz, DMSO-d$_6$) δ 8.13 (s, 2H), 8.04 (bs, 1H), 7.46 (bs, 1H), 7.37 (bs, 2H).

c) 6-Bromo-1H-pyrido[2,3-d]pyrimidine-2,4-dione

Oxalyl chloride (100 mL, 1.16 mmol) was added dropwise to a suspension of 2-amino-5-bromo-nicotinamide (500 mg, 2.31 mmol) in toluene (5 mL) and the resulting mixture was heated to reflux for 4 h. The reaction mixture was cooled and the mustard-colored solid which had formed was collected by filtration. The solid was washed with a small amount of water, MeOH, and then dried under high vacuum (40° C.) overnight to give the title compound (435 mg, 77%): $^1$H NMR (300 MHz, DMSO-d$_6$) δ 11.86 (s, 1H), 11.60 (s, 1H), 8.72 (d, J=2.5 Hz, 1H), 8.35 (d, J=2.5 Hz, 1H); $^{13}$C NMR (126 MHz, DMSO-d$_6$) δ 161.4, 154.8, 151.2, 150.17, 137.8, 112.6, 111.6.

d) (E)-3-(2,4-Dioxo-1,2,3,4-tetrahydro-pyrido[2,3-d]pyrimidin-6-yl)acrylic acid tert-butyl ester A suspension of 6-bromo-1H-pyrido[2,3-d]pyrimidine-2,4-dione (430 mg, 1.59 mmol) in propionitrile (8 mL) and DMF (2 mL) was treated with tert-butyl acrylate (0.93 mL, 6.4 mmol), (i-Pr)$_2$EtN (0.6 mL, 3.3 mmol) and P(o-tol)$_3$ (100 mg, 0.32 mmol). The solution was deoxygenated with Ar for 20 min. Pd(OAc)$_2$ (36 mg, 0.16 mmol) was added and the mixture was deoxygenated with a stream of Ar for 10 min. The mixture was heated to reflux for 17 h, then allowed to cool. The resulting precipitate was isolated by filtration to give the title compound (384 mg, 83%) as a gray solid: $^1$H NMR (300 MHz, DMSO-d$_6$) δ 11.88 (s, 1H), 11.54 (s, 1H), 8.96 (d, J=2.2 Hz, 1H), 8.53 (d, J=2.2 Hz, 1H), 7.65 (d, J=16.1 Hz, 1H), 6.72 (d, J=16.1 Hz, 1H), 1.49 (s, 9H); ESI MS m/e 290 (M+H)$^+$.

e) (E)-3-(2,4-Dioxo-1,2,3,4-tetrahydro-pyrido[2,3-d]pyrimidin-6-yl)acrylic acid

To a suspension of (E)-3-(2,4-dioxo-1,2,3,4-tetrahydro-pyrido[2,3-d]pyrimidin-6-yl)acrylic acid tert-butyl ester (379 mg, 1.19 mmol) in CH$_2$Cl$_2$ (10 mL) was added trifluoroacetic acid (2 mL). After 6 h, the solvent was concentrated, the resulting solid was treated with anhydrous HCl (10 mL of a 4 M solution in dioxane, 40 mmol) and the mixture was sonicated for 10 min. The mixture was diluted with Et$_2$O and the solution was filtered. The olive solid was dried under high vacuum at 45° C. overnight to give the title compound (323 mg, 91%) as the TFA salt: $^1$H NMR (300 MHz, DMSO-d$_6$) δ 11.89 (s, 1H), 11.56 (s, 1H), 8.94 (d, J=1.8 Hz, 1H), 8.53 (d, J=1.8 Hz, 1H), 7.69 (d, J=16.1 Hz, 1H), 6.72 (d, J=16.1 Hz, 1H), 4.40 (bs, 1H); ESI MS m/e 234 (C$_{10}$H$_7$N$_3$O$_4$+H)$^+$.

Preparation 64

Preparation of (E)-3-[3-(2-dimethylamino-ethyl)-2-oxo-1,2,3,4-tetrahydro-pyrido[2,3-d]-pyrimidin-6-yl]acrylic acid hydrochloride a) 2-Amino-5-bromo-N-(2-dimethylamino-ethyl)nicotinamide To a suspension of 2-amino-5-bromo-nicotinic acid hydrobromide (4.00 g, 13.4 mmol) in CH$_2$Cl$_2$ (150 mL) was added Et$_3$N (2.79 mL, 20.1 mmol), EDC (2.70 g, 14.1 mmol), and HOBt (1.91 g, 14.1 mmol) at 0° C., and the mixture was stirred for 10 min. N,N-dimethylethylenediamine was then added, and the mixture was allowed to stir overnight at room temperature. The organic solution was washed with 2 N NaOH (2×20 mL), H$_2$O (2×20 mL) and brine, dried over Na$_2$SO$_4$ and filtered. The solvent was concentrated to give the title compound (2.70 g, 70%) as a yellow solid: MS (ESI) m/e 287 (M+H)$^+$.

b) 5-Bromo-3-[(2-dimethylamino-ethylamino)methyl]pyridin-2-ylamine

2-Amino-5-bromo-N-(2-dimethylamino-ethyl)nicotinamide (2.15 g, 7.48 mmol) was added to a BH$_3$ solution (37.5 mL of a 1 M solution in THF, 37.5 mmol), and the mixture was heated to reflux for 6 h. After cooling, the solvent was removed in vacuo. The residue was dissolved in MeOH (20 mL). Concentrated HCl (3 mL) and H$_2$O (3 mL) were added and the mixture was heated to reflux for 2 h. The solvent was then concentrated and the aqueous residue was basified to pH 12 with aqueous NaOH (6 N). The resulting aqueous suspension was extracted with CH$_2$Cl$_2$ (3×60 mL). The combined organics were washed with brine, dried over Na$_2$SO$_4$, filtered and concentrated under reduced pressure to give the title compound (0.50 g, 25%) as a colorless oil: MS (ESI) m/e 273 (M+H)$^+$.

c) 6-Bromo-3-(2-dimethylamino-ethyl)-3,4-dihydro-1H-pyrido[2,3-d]pyrimidin-2-one A solution of 5-bromo-3-[(2-dimethylamino-ethyl)methyl]pyridin-2-ylamine (490 mg, 1.79 mmol) and 1,1'-carbonyldiimidazole (349 mg, 2.15 mmol) in 1,4-dioxane (15 mL) was heated to 80° C. for 14 h. TLC analysis indicated remaining starting material. After cooling, additional 1,1'-carbonyldiimidazole (349 mg, 2.15 mmol) and 1,4-dioxane (10 mL) were added, and the solution was heated to reflux overnight. The solvent was removed in vacuo. The residue was dissolved in CH$_2$Cl$_2$ (80 mL). The solution was washed with satd NaHCO$_3$, water and brine, dried over Na$_2$SO$_4$ and concentrated. Purification by column chromatography (silica gel, CH$_2$Cl$_2$/MeOH/Et$_3$N, 92:7:1) gave the title compound (270 mg, 50%) as a tan solid: $^1$H NMR (300 MHz, DMSO-d$_6$) δ 9.83 (s, 1H), 8.16 (d, J=2.1 Hz, 1H), 7.76 (s, 1H), 4.48 (s, 2H), 3.37 (t, J=6.5 Hz, 2H), 2.40 (t, J=6.5 Hz, 2H), 2.16 (s, 6H).

d) (E)-3-[3-(2-Dimethylamino-ethyl)-2-oxo-1,2,3,4-tetrahydro-pyrido[2,3-d]pyrimidin-6-yl]acrylic acid tert-butyl ester To a solution of 6-bromo-3-(2-dimethylamino-ethyl)-3,4-dihydro-1H-pyrido[2,3-d]pyrimidin-2-one (240 mg, 0.802 mmol) in propionitrile (16 mL) and DMF (4 mL) was added tert-butyl acrylate (0.46 mL, 3.2 mmol) and (i-Pr)$_2$EtN (0.28 mL, 1.6 mmol), Pd(OAc)$_2$ (18 mg, 0.080 mmol) and P(o-tol)$_3$ (49 mg, 0.16 mmol). The mixture was degassed with Ar for 15 min. The mixture was heated to reflux overnight, and then allowed to cool. The dark solution was filtered through a pad of Celite. The filtrate was concentrated. Purification by column chromatography (silica gel, CH$_2$Cl$_2$/MeOH/Et$_3$N, 94/5.5/0.5) gave the title compound (150 mg, 54%) as a pale-yellow solid: MS (ESI) m/e 347 (M+H)$^+$.

e) (E)-3-[3-(2-Dimethylamino-ethyl)-2-oxo-1,2,3,4-tetrahydro-pyrido[2,3-d]-pyrimidin-6-yl]acrylic acid hydrochloride A solution of (E)-3-[3-(2-dimethylamino-ethyl)-2-oxo-1,2,3,4-tetrahydro-pyrido[2,3-d]pyrimidin-6-yl]acrylic acid tert-butyl ester (145 mg, 0.419 mmol) in CH$_2$Cl$_2$ (4 mL) was treated with TFA (2 mL). After stirring at room temperature for 30 min, the clear tan solution was concentrated in vacuo. The resulting oil was treated with anhydrous HCl (4.0 mL of 4 M solution in dioxane, 16 mmol) and stirred until the oil was converted to a solid. The solid was isolated by filtration, washed with Et$_2$O and dried under vacuum over night to give the title compound (155 mg, quantitative) as a pale yellow solid: $^1$H NMR (300 MHz, DMSO-d$_6$) δ 10.18 (s, 1H), 9.70 (br s, 1H), 8.36 (d, J=1.4 Hz, 1H), 7.92 (s, 1H), 7.55 (d, J=16.0 Hz, 1H), 6.48 (d, J=16.0 Hz, 1H), 4.53 (s, 2H), 4.50 (br s, 2H), 3.71 (t, J=5.6 Hz, 2H), 3.31 (t, J=5.6 Hz, 2H), 2.84 (s, 3H), 2.82 (s, 3H).

Preparation 65

Preparation of (E)-3-[3-(2-Morpholin-4-yl-ethyl)-2-oxo-1,2,3,4-tetrahydro-pyrido[2,3-d]pyrimidin-6-yl] acylic acid hydrochloride a) 2-Amino-5-bromo-N-(2-morpholin-4-yl-ethyl)nicotinamide According to the procedure of Preparation 64(a), except substituting 4-(2-aminoethyl)morpholine for the N,N-dimethylethylenediamine, the title compound (18 g, 82%) was prepared as a pale yellow solid: MS (ESI) m/e 329 (M+H)$^+$.

b) 5-Bromo-3-[(2-morpholin-4-yl-ethylamino)methyl]pyridin-2-ylamine

According to the procedure of Preparation 64(b), except substituting 2-amino-5-bromo-N-(2-morpholin-4-yl-ethyl)nicotinamide for 2-amino-5-bromo-N-(2-dimethylaminoethyl)nicotinamide, the title compound (5.0 g, 35%) was prepared as a colorless oil: MS (ESI) m/e 315 (M+H)$^+$.

c) 6-Bromo-3-(2-morpholin-4-yl-ethyl)-3,4-dihydro-1H-pyrido[2,3-d]pyrimidin-2-one According to the procedure of Preparation 64(c), except substituting 5-bromo-3-[(2-morpholin-4-yl-ethylamino)methyl]pyridin-2-ylamine for 5-bromo-3-[(2-dimethylaminoethyl)methyl]pyridin-2-ylamine, the title compound (1.1 g, 20%) was prepared as pale yellow solid: MS (ESI) m/e 341 (M+H)$^+$.

d) (E)-3-[3-(2-Morpholin-4-yl-ethyl)-2-oxo-1,2,3,4-tetrahydro-pyrido[2,3-d]pyrimidin-6-yl]acrylic acid tert-butyl ester According to the procedure of Preparation 64(d), except substituting 6-bromo-3-(2-morpholin-4-yl-ethyl)-3,4-dihydro-1H-pyrido[2,3-d]pyrimidin-2-one for 6-bromo-3-(2-dimethylamino-ethyl)-3,4-dihydro-1H-pyrido[2,3-d]pyrimidin-2-one, the title compound (0.67 g, 54%) was prepared as a white solid: MS (ES) m/e 389 (M+H)$^+$.

e) (E)-3-[3-(2-Morpholin-4-yl-ethyl)-2-oxo-1,2,3,4-tetrahydro-pyrido[2,3-d]pyrimidin-6-yl]acrylic acid hydrochloride According to the procedure of Preparation 64(e), except substituting (E)-3-[3-(2-morpholin-4-yl-ethyl)-2-oxo-1,2,3,4-tetrahydro-pyrido[2,3-d]pyrimidin-6-yl]acrylic acid tert-butyl ester for the (E)-3-[3-(2-dimethylamino-ethyl)-2-oxo-1,2,3,4-tetrahydro-pyrido[2,3-d]pyrimidin-6-yl]acrylic acid tert-butyl ester, the title compound (0.71 g, quantitative) was prepared as a white solid: $^1$H NMR (300 MHz, DMSO-d$_6$) δ 10.64 (br s, 1H), 10.17 (br s, 1H), 8.36 (s, 1H), 7.93 (s, 1H), 7.54 (d, J=15.9 Hz, 1H), 6.49 (d, J=16.0 Hz, 1H), 5.95 (br s, 2H), 4.56 (s, 2H), 3.98-3.94 (m, 2H), 3.79-3.72 (m, 4H), 3.56-3.53 (m, 2H), 3.37-3.35 (m, 2H), 3.15-3.05 (m, 2H); MS (ESI) m/e 333 (M+H)$^+$.

Preparation 66

Preparation of (E)-3-[3-(3-Morpholin-4-yl-propyl)-2-oxo-1,2,3,4-tetrahydro-pyrido[2,3-d]pyrimidin-6-yl]acrylic acid hydrochloride a) 2-Amino-5-bromo-pyridine-3-carbaldehyde hydrobromide Bromine (1.1 mL, 20 mmol) in HOAc (20 mL) was added dropwise to a solution of 2-amino-pyridine-3-carbaldehyde (2.5 g, 20 mmol) in HOAc (50 mL) while stirring. After the addition, the mixture was allowed to stir for 2 h at room temperature. The precipitate was collected by filtration and washed with diethyl ether to afford the title compound (4.4 g, 77%) as a pale yellow solid: MS (ESI) m/e 201 (M+H)$^+$.

b) 5-Bromo-3-[(3-morpholin-4-yl-propylamino)methyl]pyridin-2-ylamine

To a solution of 2-amino-5-bromo-pyridine-3-carbaldehyde hydrobromide (4.30 g, 15.3 mmol) in MeOH (100 mL) was added triethylamine (4.3 mL, 31 mmol) and the mixture was stirred at room temperature for 10 min. The resulting suspension was treated with 4-(3-aminopropyl)morpholine (2.5 mL, 17 mmol) and the mixture was stirred for 7 h. TLC analysis indicated remaining starting material. Additional 4-(3-aminopropyl)morpholine (1.0 mL, 6.8 mmol) was added, and the mixture was allowed to stir overnight at room temperature. The mixture was cooled and then NaBH$_4$ (0.87 g, 23.0 mmol) was added in two portions. The mixture was stirred at room temperature for 4 h. The solvent was removed in vacuo. Purification by column chromatography (silica gel, CH$_2$Cl$_2$/MeOH/Et$_3$N, 97/2.5/0.5 to 85/14.5/0.5) gave the title compound (2.70 g, 54%) as a brown oil: MS (ESI) m/e 329 (M+H)$^+$.

c) 6-Bromo-3-(3-morpholin-4-yl-propyl)-3,4-dihydro-1H-pyrido[2,3-d]pyrimidin-2-one According to the procedure of Preparation 64(c), except substituting 5-bromo-3-[(3-morpholin-4-yl-propylamino)methyl]pyridin-2-ylamine for 5-bromo-3-[(2-dimethylamino-ethyl)methyl]pyridin-2-ylamine, the title compound (2.00 g, 69%) was prepared as pale yellow solid: MS (ESI) m/e 355 (M+H)$^+$.

d) (E)-3-[3-(2-Morpholin-4-yl-propyl)-2-oxo-1,2,3,4-tetrahydro-pyrido[2,3-d]pyrimidin-6-yl]acrylic acid tert-butyl ester According to the procedure of Preparation 64(d), except substituting 6-bromo-3-(3-morpholin-4-yl-propyl)-3,4-dihydro-1H-pyrido[2,3-d]pyrimidin-2-one for 6-bromo-3-(2-dimethylamino-ethyl)-3,4-dihydro-1H-pyrido[2,3-d]pyrimidin-2-one, the title compound (1.5 g, 66%) was prepared as a pale yellow solid: MS (ESI) m/e 403 (M+H)$^+$.

e) (E)-3-[3-(3-Morpholin-4-yl-propyl)-2-oxo-1,2,3,4-tetrahydro-pyrido[2,3-d]pyrimidin-6-yl]acrylic acid hydrochloride According to the procedure of Preparation 64(e), except substituting (E)-3-[3-(2-morpholin-4-yl-propyl)-2-oxo-1,2,3,4-tetrahydro-pyrido[2,3-d]pyrimidin-6-yl]acrylic acid tert-butyl ester for (E)-3-[3-(2-dimethylamino-ethyl)-2-oxo-1,2,3,4-tetrahydro-pyrido[2,3-d]pyrimidin-6-yl]acrylic acid tert-butyl ester, the title compound (1.5 g, 99%) was prepared as a yellow solid: $^1$H NMR (300 MHz, DMSO-d$_6$) δ 10.08 (s, 1H), 8.36 (d, J=1.5 Hz, 1H), 7.96 (s, 1H), 7.59-7.49 (m, 1H), 6.53-6.45 (m, 1H), 4.55-4.48 (m, 2H), 4.00-3.75 (m, 4H), 3.48-3.36 (m, 4H), 3.20-2.95 (m, 4H), 2.10-1.96 (m, 2H); MS (ESI) m/e 347 (M+H)$^+$.

Preparation 67

Preparation of (E)-3-(3-Ethoxycarbonylmethyl-2-oxo-1,2,3,4-tetrahydro-pyrido[2,3-d]pyrimidin-6-yl) acrylic acid hydrochloride a) (6-Bromo-2-oxo-1,4-dihydro-2H-pyrido[2,3-d]pyrimidin-3-yl)acetic acid ethyl ester According to the procedure of Preparation 64(c), except substituting [(2-amino-5-bromo-pyridin-3-ylmethyl)amino] acetic acid ethyl ester for 5-bromo-3-[(2-dimethylaminoethyl)methyl]pyridin-2-ylamine, the title compound (6.70 g, 67%) was prepared as a white solid: MS (ESI) m/e 314 (M+H)$^+$.

b) (E)-3-(3-Ethoxycarbonylmethyl-2-oxo-1,2,3,4-tetrahydro-pyrido[2,3-d]pyrimidin-6-yl)acrylic acid tert-butyl ester According to the procedure of Preparation 64(d), except substituting (6-bromo-2-oxo-1,4-dihydro-2H-pyrido[2,3-d]pyrimidin-3-yl)acetic acid ethyl ester for 6-bromo-3-(2-dimethylamino-ethyl)-3,4-dihydro-1H-pyrido[2,3-a]pyrimidin-2-one, the title compound (2.10 g, 76%) was prepared as a white solid: MS (ESI) m/e 362 (M+H)$^+$.

c) (E)-3-(3-Ethoxycarbonylmethyl-2-oxo-1,2,3,4-tetrahydro-pyrido[2,3-d]pyrimidin-6-yl)acrylic acid hydrochloride According to the procedure of Preparation 64(e), except substituting (E)-3-(3-ethoxycarbonylmethyl-2-oxo-1,2,3,4-tetrahydro-pyrido[2,3-d]pyrimidin-6-yl)acrylic acid tert-butyl ester for the (E)-3-[3-(2-dimethylamino-ethyl)-2-oxo-1,2,3,4-tetrahydro-pyrido[2,3-d]pyrimidin-6-yl]acrylic acid tert-butyl ester, the title compound (1.80 g, 96%) was prepared as a white solid: $^1$H NMR (300 MHz, DMSO-d$_6$) δ 10.90-9.51 (m, 2H), 8.37 (s, 1H), 7.95 (s, 1H), 7.57-7.51 (m, 1H), 6.48 (d, J=16.0 Hz, 1H), 4.53 (s, 2H), 4.18-4.11 (m, 4H), 1.21 (t, J=7.0 Hz, 3H); MS (ESI) m/e 306 (M+H)$^+$.

Preparation 68

Preparation of (E)-3-[3-(2-Ethoxycarbonyl-ethyl)-2-oxo-1,2,3,4-tetrahydro-pyrido[2,3-d]pyrimidin-6-yl] acrylic acid hydrochloride a) 3-[(2-Amino-5-bromo-pyridin-3-ylmethyl)amino]propionic acid ethyl ester A mixture of 5-bromo-3-bromomethyl-pyridin-2-ylamine hydrobromide (9.41 g, 27.1 mmol) and β-alanine ethyl ester hydrochloride (5.00 g, 32.5 mmol) in DMF (75 mL) was treated with N,N-diisopropylethylamine (16.5 mL, 94.9 mmol). After stirring at room temperature for 4 h, the cloudy mixture was diluted with CH$_2$Cl$_2$ (100 mL) and H$_2$O. The aqueous layer was extracted with CH$_2$Cl$_2$ (2×150 mL). The combined organic layers were washed with brine, dried over Na$_2$SO$_4$, filtered and the solvent removed in vacuo. Purification by column chromatography (silica gel, CH$_2$Cl$_2$/MeOH/Et$_3$N, 95/4.5/0.5 to 80/19.5/0.5) gave the title compound (1.90 g, 23%) as a tan oil: MS (ESI) m/e 302 (M+H)$^+$.

b) 3-(6-Bromo-2-oxo-1,4-dihydro-2H-pyrido[2,3-d]pyrimidin-3-yl)propionic acid ethyl ester According to the procedure of Preparation 64(c), except substituting 3-[(2-amino-5-bromo-pyridin-3-ylmethyl)amino]propionic acid ethyl ester for 5-bromo-3-[(2-dimethylamino-ethyl)methyl]pyridin-2-ylamine, the title compound (1.7 g, 83%) was prepared as a white solid: MS (ESI) m/e 328 (M+H)+.

c) (E)-3-[3-(2-Ethoxycarbonyl-ethyl)-2-oxo-1,2,3,4-tetrahydro-pyrido[2,3-d]pyrimidin-6-yl]acrylic acid tert-butyl ester According to the procedure of Preparation 64(d), except substituting 3-(6-bromo-2-oxo-1,4-dihydro-2H-pyrido[2,3-d]pyrimidin-3-yl)propionic acid ethyl ester for the 6-bromo-3-(2-dimethylamino-ethyl)-3,4-dihydro-1H-pyrido[2,3-d]pyrimidin-2-one, the title compound (0.39 g, 21%) was prepared as a white solid: MS (ESI) m/e 376 (M+H)+.

d) (E)-3-[3-(2-Ethoxycarbonyl-ethyl)-2-oxo-1,2,3,4-tetrahydro-pyrido[2,3-d]pyrimidin-6-yl]acrylic acid According to the procedure of Preparation 64(e), except substituting (E)-3-[3-(2-ethoxycarbonyl-ethyl)-2-oxo-1,2,3,4-tetrahydro-pyrido[2,3-d]pyrimidin-6-yl]acrylic acid tert-butyl ester for the (E)-3-[3-(2-dimethylamino-ethyl)-2-oxo-1,2,3,4-tetrahydro-pyrido[2,3-d]pyrimidin-6-yl]acrylic acid tert-butyl ester, the title compound (0.16 g, 44%) was prepared as a yellow solid: $^1$H NMR (500 MHz, DMSO-$d_6$) δ 8.30 (d, J=1.5 Hz, 1H), 8.16 (s, 1H), 7.70-7.60 (m, 1H), 6.60-6.50 (m, 1H), 4.70 (s, 2H), 4.13 (q, J=7.0 Hz, 2H), 3.74-3.68 (t, J=6.5 Hz, 2H), 2.74-2.66 (t, J=6.5 Hz, 2H), 1.25 (t, J=5.5 Hz, 3H); MS (ESI) m/e 320 (M+H)+.

Preparation 69

Preparation of 6-Bromo-3-(2,2-dimethoxy-ethyl)-3,4-dihydro-1H-pyrido[2,3-d]pyrimidin-2-one a) 5-Bromo-3-[(2,2-dimethoxy-ethylamino)methyl]pyridin-2-ylamine According to the procedure of Preparation 66(b), except substituting aminoacetaldehyde diethyl acetal for the 4-(3-aminopropyl)morpholine, the title compound (1.30 g, 45%) was prepared as a yellow solid: MS (ESI) m/e 290 (M+H)+.

b) 6-Bromo-3-(2,2-dimethoxy-ethyl)-3,4-dihydro-1H-pyrido[2,3-d]pyrimidin-2-one

According to the procedure of Preparation 64(c), except substituting 5-bromo-3-[(2,2-dimethoxy-ethylamino)methyl]pyridin-2-ylamine for 5-bromo-3-[(2-dimethylamino-ethyl)methyl]pyridin-2-ylamine, the title compound (6.40 g, 73%) was prepared as a white solid: MS (ESI) m/e 316 (M+H)+.

Preparation 70

Preparation of (E)-3-{6-Amino-5-[(2-morpholin-4-yl-ethylamino)methyl]pyridin-3-yl}acrylic acid hydrochloride a) (E)-3-[6-Amino-5-(2-morpholin-4-yl-ethylcarbamoyl)pyridin-3-yl]acrylic acid tert-butyl ester According to the procedure of Preparation 64(d), except substituting 2-amino-5-bromo-N-(2-morpholin-4-yl-ethyl)nicotinamide for 6-bromo-3-(2-dimethylamino-ethyl)-3,4-dihydro-1H-pyrido[2,3-d]pyrimidin-2-one, the title compound (2.48 g, 99%) was prepared as a yellow solid: $^1$H NMR (300 MHz, CDCl$_3$) δ 8.30 (d, J=2.4 Hz, 1H), 7.75 (d, J=2.1 Hz, 1H), 7.46 (d, J=15.9 Hz, 1H), 7.02-6.83 (m, 1H), 6.65 (br s, 2H), 6.22 (d, J=15.9, 1H), 3.77-3.69 (m, 4H), 3.56-3.50 (m, 2H), 2.62 (t, J=6.0 Hz, 2H), 2.53 (t, J=4.5 Hz, 4H), 1.53 (s, 9H); MS (ESI) m/e 377 (M+H)+.

b) (E)-3-[6-Amino-5-(2-morpholin-4-yl-ethylcarbamoyl)-pyridin-3-yl]acrylic acid hydrochloride According to the procedure of Preparation 64(e), except substituting (E)-3-[6-amino-5-(2-morpholin-4-yl-ethylcarbamoyl)pyridin-3-yl]acrylic acid tert-butyl ester for (E)-3-[3-(2-methylamino-ethyl)-2-oxo-1,2,3,4-tetrahydro-pyrido[2,3-d]pyrimidin-6-yl]acrylic acid tert-butyl ester, the title compound (2.34 g, 91%) was prepared as a white solid: MS (ESI) m/e 321 (M+H)+.

Preparation 71

Preparation of (E)-3-(6-Amino-5-morpholin-4-ylmethyl-pyridin-3-yl)acrylic acid hydrochloride a) 5-Bromo-3-morpholin-4-ylmethyl-pyridin-2-ylamine According to the procedure of Preparation 59(a), except substituting morpholine for piperidine, the title compound (11.5 g, 97%) was prepared as yellow foam: $^1$H NMR (300 MHz, CDCl$_3$) δ 8.04 (d, J=2.4 Hz, 1H), 7.35 (d, J=2.3 Hz, 1H), 5.61 (s, 2H), 3.72-3.69 (m, 4H), 3.42 (s, 2H), 2.44-2.41 (m, 4H).

b) (E)-3-(6-Amino-5-morpholin-4-ylmethyl-pyridin-3-yl) acrylic acid tert-butyl ester According to the procedure of Preparation 59(b), except substituting 5-bromo-3-morpholin-4-ylmethyl-pyridin-2-ylamine for 5-bromo-3-piperidin-1-ylmethyl-pyridin-2-ylamine, the title compound (11.3 g, 84%) was prepared as a yellow solid: $^1$H NMR (300 MHz, CDCl$_3$) δ 8.11 (d, J=2.2 Hz, 1H), 7.49-7.44 (m, 2H), 6.19 (d, J=15.9 Hz, 1H), 5.89 (s, 2H), 3.72-3.69 (m, 4H), 3.47 (s, 2H), 2.45-2.42 (m, 4H), 1.53 (s, 9H).

c) (E)-3-(6-Amino-5-morpholin-4-ylmethyl-pyridin-3-yl) acrylic acid hydrochloride According to the procedure of Preparation 59(c), except substituting (E)-3-(6-amino-5-morpholin-4-ylmethyl-pyridin-3-yl)acrylic acid tert-butyl ester for (E)-3-(6-amino-5-piperidin-1-ylmethyl-pyridin-3-yl)acrylic acid tert-butyl ester, the title compound (12.9 g, quantitative) was prepared as an off-white solid: MS (ESI) m/z 264 [M+H]+.

Preparation 72

Preparation of 7-Bromo-4-[3-(4-methyl-piperazin-1-yl)-propyl]-1,3,4,5-tetrahydro-pyrido[2,3-e][1,4]diazepin-2-one a) [3-(4-Methyl-piperazin-1-yl)propylamino]acetic acid ethyl ester A solution of 4-(3-aminopropyl)-1-methylpiperazine (3.1 mL, 20 mmol) in MeOH (50 mL) was cooled in an ice bath and treated with ethyl glyoxylate (~50% solution in toluene, 5.6 mL, 27 mmol) and AcOH (3 mL). After stirring for 15 min, NaBH$_3$CN (1.37 g, 21.8 mmol) was added and the mixture was allowed to stir for 7 h while slowly warming to room temperature. The mixture was diluted with saturated aqueous NaHCO$_3$ (150 mL) and then extracted with EtOAc (3×100 mL) followed by CH$_2$Cl$_2$ (3×100 mL). The combined CH$_2$Cl$_2$ layers were dried over Na$_2$SO$_4$, filtered and the solvent was removed in vacuo to give the title compound (1.81 g, 38%) as a colorless oil: MS (ESI) m/e 244 (M+H)+.

b) {(2-Amino-5-bromo-pyridin-3-ylmethyl)-[3-(4-methyl-piperazin-1-yl)propyl]amino}acetic acid ethyl ester A solution of [3-(4-methyl-piperazin-1-yl)propylamino] acetic acid ethyl ester (1.80 g, 7.41 mmol) and triethylamine (2.3 mL, 16.4 mmol) in DMF (50 mL) was treated with 5-bromo-3-bromomethyl-pyridin-2-ylamine hydrobromide (2.57 g, 7.41 mmol). After stirring at room temperature for 3 d, the mixture was diluted with H$_2$O (100 mL) and then extracted with EtOAc (4×100 mL). The combined organic layers were dried over Na$_2$SO$_4$, filtered and the solvent was removed in vacuo. Purification by flash column chromatography (silica gel, CH$_2$Cl$_2$/MeOH, 97:3 to 90:10) gave the title compound (0.50 g, 16%) as a colorless oil: MS (ESI) m/e 428 (M+H)$^+$.

c) 7-Bromo-4-[3-(4-methyl-piperazin-1-yl)propyl]-1,3,4,5-tetrahydro-pyrido[2,3-e][1,4]diazepin-2-one A solution of {(2-amino-5-bromo-pyridin-3-ylmethyl)-[3-(4-methyl-piperazin-1-yl)propyl]amino}acetic acid ethyl ester (0.50 g, 1.17 mmol) in DMSO (10 mL) was treated with NaH (60% dispersion in mineral oil, 47 mg, 1.17 mmol). After stirring at room temperature for 3 d, the mixture was diluted with H$_2$O (30 mL) and then extracted with EtOAc (4×50 mL). The combined organic layers were dried over Na$_2$SO$_4$, filtered and the solvent was removed in vacuo. Purification by flash column chromatography (silica gel, CH$_2$Cl$_2$, MeOH, 92:8 to 87:13) gave the title compound (0.23 g, 51%) as a white solid: MS (ESI) m/e 382 (M+H)$^+$.

Preparation 73

Preparation of 7-Bromo-3,3-dimethyl-1,3,4,5-tetrahydro-pyrido[2,3-e][1,4]diazepin-2-one a) 2-[(2-Amino-5-bromo-pyridin-3-ylmethyl)amino]-2-methylpropionic acid methyl ester A solution of 5-bromo-3-bromomethyl-pyridin-2-ylamine hydrobromide (11.0 g, 31.7 mmol) and 2-amino-2-methylpropionic acid methyl ester (5.80 g, 49.5 mmol) in DMF (220 mL) was treated with triethylamine (9.0 mL, 18.5 mmol). After stirring at room temperature for 3 d, the mixture was diluted with H$_2$O (400 mL) and then extracted with EtOAc (4×200 mL). The combined organic layers were washed with H$_2$O (3×100 mL) and brine (100 mL), dried over Na$_2$SO$_4$, filtered and the solvent was removed in vacuo. Purification by flash column chromatography (silica gel, CH$_2$Cl$_2$/MeOH, 99:1) gave the title compound (3.87 g, 40%) as a light yellow solid: MS (ESI) m/e 302 (M+H)$^+$.

b) 7-Bromo-3,3-dimethyl-1,3,4,5-tetrahydro-pyrido[2,3-e][1,4]diazepin-2-one

A solution of 2-[(2-amino-5-bromo-pyridin-3-ylmethyl)amino]-2-methylpropionic acid methyl ester (2.63 g, 8.71 mmol) in DMSO (100 mL) was treated with NaH (60% dispersion in mineral oil, 0.35 g, 8.7 mmol). After stirring at room temperature overnight, the mixture was diluted with H$_2$O (200 mL) and then extracted with EtOAc (5×150 mL). The combined organic layers were washed with H$_2$O (3×100 mL) and brine (100 mL), dried over Na$_2$SO$_4$, filtered and the solvent was removed in vacuo. Purification by flash column chromatography (silica gel, CH$_2$Cl$_2$/MeOH, 99:1 to 98:2) gave (0.79 g, 33%) as an off-white solid: MS (ESI) m/z 270 (M+H)$^+$.

The following examples illustrate methods for preparing the biologically active compounds of this invention from intermediate compounds such as those described in the foregoing Preparations.

Example 1

Preparation of (E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide hydrochloride a) (E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide (E)-3-(4-Methyl-2-oxo-2,3,4,5-tetrahydro-1H-pyrido[2,3-e][1,4]diazepin-7-yl)acrylic acid hydrochloride (1.40 g, 1.25 mmol) was added to a solution of methyl-(1-propyl-naphthalen-2-ylmethyl)amine (0.292 g, 1.37 mmol) and diisopropylethylamine (0.65 mL, 3.75 mmol) in DMF (25 mL) followed by the addition of 1-hydroxybenzotriazole hydrate (0.185 g, 1.37 mmol) and 1-(3-dimethylaminopropyl)-3-ethylcarbodiimide hydrochloride (0.263 g, 1.37 mmol). The reaction was allowed to stir at room temperature for 18 h. The reaction was quenched with H$_2$O (70 mL) then concentrated to a yellow oil. Purification by column chromatography (silica gel, CH$_2$Cl$_2$/MeOH, 99:1 to 95:5) gave the title compound (0.229 g, 41%) as a glassy orange solid and as a mixture of amide rotamers: $^1$H NMR (500 MHz, DMSO-d$_6$) δ 10.35 (s, 1H), 8.55-8.54 (m, 1H), 8.24-8.14 (m, 1H), 7.98-7.86 (m, 5H), 7.72-7.24 (m, 3), 3.75 (s, 2H), 3.42 (s, 2H), 3.86 (s, 2H), 2.54-2.36 (m, 6H), 2.11-2.02 (m, 2H), 1.40-1.34 (m, 2H), 1.01-0.98 (m, 3H).

b) (E)-N-Methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide hydrochloride A 2 M solution of hydrogen chloride in Et$_2$O (0.25 ml, 0.518 mmol) was added to (E)-N-methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide (0.229 g, 0.518 mmol) in CH$_2$Cl$_2$ (5 mL) via syringe. The solution was allowed to stir for 18 h during time which a precipitate fell out of the solution. The product was collected by filtration and was washed with Et$_2$O (100 mL). The product was dried to give the title compound (0.182 g, 73%) as an orange solid and as a mixture of amide rotamers: $^1$H NMR (300 MHz, DMSO-d$_6$) δ 12.00 (br s, 1H), 11.22 (s, 1H), 8.86-8.82 (m, 1H), 8.38-8.32 (m, 1H), 7.94-7.87 (m, 4H), 7.74-7.29 (m, 5H), 6.06-5.64 (m, 1H), 4.40-4.30 (m, 2H), 3.94-3.91 (br s, 2H), 2.93-2.57 (m, 6H), 2.10-2.05 (m, 2H), 1.37-1.32 (m, 2H), 1.02-0.97 (m, 3H); MS (ESI) m/e 443 (M+H)$^+$.

Example 2

Preparation of (E)-3-(3,3-Dimethyl-2-oxo-2,3,4,5-tetrahydro-1H-pyrido[2,3-e][1,4]diazepin-7-yl)-N-methyl-N-(3-methyl-benzor[b]thiophen-2-ylmethl)acrylamide hydrochloride a) (E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide A suspension of 7-bromo-3,3-dimethyl-1,3,4,5-tetrahydro-pyrido[2,3-e][1,4]diazepin-2-one (0.17 g, 0.63 mmol) in propionitrile (4 mL) and DMF (1 mL) was de-oxygenated with Ar for 10 min. The mixture was treated with N-methyl-N-(3-methyl-benzo[b]thiophen-2-ylmethyl)acrylamide (0.20 g, 0.81 mmol) and (i-Pr)$_2$EtN (0.24 mL, 1.3 mmol) and was de-oxygenated with Ar for 5 min. Pd(OAc)$_2$ (14 mg, 0.062 mmol) and P(o-tol)$_3$ (38 mg, 0.12 mmol) were added simultaneously, and the mixture was de-oxygenated a third time for 5 min. The mixture was heated to reflux for 4 h, then allowed to cool. The resulting precipitate was isolated by filtration, washed with EtOAc, dissolved in $CH_2Cl_2$, and the solvent was removed in vacuo. Purification by flash column chromatography (silica gel, $CH_2Cl_2$/MeOH, 98:2) gave the title compound (0.15 g, 56%) as a white solid: $^1H$ NMR (300 MHz, $CDCl_3$) δ 8.97 (s, 1H), 8.45 (s, 1H), 7.77-7.65 (m, 3H), 7.53 (s, 1H), 7.40-7.29 (m, 2H), 6.98-6.84 (m, 1H), 4.94-4.89 (m, 2H), 4.02 (s, 2H), 3.15-3.10 (m, 3H), 2.43 (s, 3H), 1.70 (s, 1H), 1.49 (s, 6H); MS (ESI) nm/e 435 $(M+H)^+$.

b) (E)-3-(3,3-Dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide hydrochloride A suspension of (E)-3-(3,3-dimethyl-2-oxo-2,3,4,5-tetrahydro-1H-pyrido[2,3-e][1,4]diazepin-7-yl)-N-methyl-N-(3-methyl-benzo[b]thiophen-2-ylmethyl)acrylamide (0.15 g, 0.35 mmol) in $CH_2Cl_2$ (10 mL) was treated with anhydrous HCl in $Et_2O$ (0.35 mL, 1.0 M). After stirring for 5 min, the mixture was diluted with $Et_2O$ (50 mL) and allowed to stir for 1 h. The solid was isolated by filtration, washed with $Et_2O$, and dried under vacuum at 60° C. for 4 d to give the title compound (0.16 g, 96%) as a light yellow powder and as a mixture of amide rotamers: $^1H$ NMR (300 MHz, DMSO-$d_6$) δ 10.92 (s, 1H), 10.56 (br s, 2H), 8.66-8.67 (m, 1H), 8.40 (s, 1H), 7.86-7.89 (m, 1H), 7.73-7.75 (m, 1H), 7.58-7.63 (m, 1H), 7.30-7.40 (m, 3H), 4.90-5.13 (m, 2H), 4.39-4.41 (m, 2H), 2.94-3.17 (m, 3H), 2.43 (s, 3H), 1.63 (s, 6H); MS (ESI) m/e 435 $(M+H)^+$.

Example 3

Preparation of (E)-N-Methyl-3-(4-methyl-2-oxo-2,3,4,5-tetrahydro-1H-pyrido[2,3-e][1,4]diazepin-7-yl)-N-naphthalen-2-ylmethyl-acrylamide hydrochloride According to the procedure of Example 1, except substituting methyl-naphthalen-2-ylmethyl-amine for the methyl-(1-propyl-naphthalen-2-ylmethyl)amine, the title compound (0.397 g, quantitative) was prepared as an off-white solid and as a mixture of amide rotamers: $^1H$ NMR (300 MHz, DMSO-$d_6$) δ 11.00-10.86 (br s, 1H), 11.28-11.24 (m, 1H), 8.85-8.81 (m, 1H), 8.35-8.29 (m, 1H), 7.95-7.75 (m, 4H), 7.67-7.62 (m, 1H), 7.54-7.38 (m, 4H), 5.01-4.81 (m, 2H), 4.31 (br s, 2H), 3.73 (br s, 2H), 3.17-2.97 (m, 3H), 2.91-2.87 (m, 3H); MS (ESI) m/e 401 $(M+H)^+$.

Example 4

Preparation of (E)-N-Methyl-3-(4-methyl-2-oxo-2,3,4,5-tetrahydro-1H-pyrido[2,3-e][1,4]diazepin-7-yl)-N-naphthalen-1-ylmethyl-acrylamide hydrochloride According to the procedure of Example 1, except substituting methyl-naphthalen-1-ylmethyl-amine for the methyl-(1-propyl-naphthalen-2-ylmethyl)amine, the title compound (0.382 g, quantitative) was prepared as an off white solid and as a mixture of amide rotamers: $^1H$ NMR (300 MHz, DMSO-$d_6$) δ 12.24-12.15 (br s, 1H), 11.27-11.21 (m, 1H), 8.85-8.76 (m, 1H), 8.36-8.30 (m, 1H), 8.20-7.02 (m, 9H), 5.36-5.12 (m, 2H), 4.29 (br s, 2H), 3.86-3.77 (br s, 2H), 3.17-3.10 (m, 3H), 2.90-2.84 (m, 3H); MS (ESI) m/e 401 $(M+H)^+$.

Example 5

Preparation of (E)-N-(4-Acetylamino-benzyl)-N-methyl-3-(7-oxo-5,6,7,8-tetrahydro-[1,8]naphthyridin-3-yl)acrylamide According to the procedure of Example 1 (a), except substituting 4-acetamidobenzyl methyl amine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for (E)-3-(4-methyl-2-oxo-2,3,4,5-tetrahydro-1H-pyrido[2,3-e][1,4]diazepin-7-yl)acrylic acid hydrochloride, the title compound (0.283 g, 53%) was prepared as an off-white solid and as a mixture of amide rotamers: $^1H$ NMR (300 MHz, DMSO-$d_6$) δ 10.66-10.64 (m, 1H), 9.94-9.92 (m, 1H), 8.36-8.33 (m, 1H), 8.07-8.06 (m, 1H), 7.56-7.48 (m, 3H), 7.33-7.13 (m, 3H), 4.74-4.54 (m, 2H), 3.07-2.86 (m, 5H), 2.53-2.49 (m 2H), 2.01 (s, 3H); MS (ESI) m/e 379 $(M+H)^+$.

Example 6

Preparation of (E)-N-(4-Methanesulfonyl-benzyl)-N-methyl-3-(7-oxo-5,6,7,8-tetrahydro-[1,8]naphthyridin-3-yl)acrylamide According to the procedure of Example 1 (a), except substituting (4-methanesulfonyl-benzyl)methylamine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.400 g, 71%) was prepared as an off-white solid and as a mixture of amide rotamers: $^1H$ NMR (300 MHz, DMSO-$d_6$) δ 10.6-10.65 (m, 1H), 8.38-8.34 (m, 1H), 8.10-8.04 (m, 1H), 7.95-7.89 (m, 2H), 7.57-7.46 (m, 3H), 7.28-7.23 (m, 1H), 4.96-4.72 (m, 2H), 3.20-3.16 (m, 5H), 2.94-2.84 (m, 3H) 2.56-2.49 (m, 2H); MS (APCI) m/e 400 $(M+H)^+$.

Example 7

Preparation of (E)-N-(2-Methoxy-naphthalen-1-ylmethyl)-N-methyl-3-(7-oxo-5,6,7,8-tetrahydro-[1,8]naphthyridin-3-yl)acrylamide According to the procedure of Example 1 (a), except substituting (2-methoxy-naphthalen-1-ylmethyl)methylamine for the methyl-(1-propyl-naphthalen-2ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.403 g, 71%) was prepared as an orange-brown solid and as a mixture of amide rotamers: $^1H$ NMR (300 MHz, DMSO-$d_6$) δ 10.66 (s, 1H), 8.37 (s, 1H), 8.08-7.81 (m, 4H), 7.70-7.11 (m, 5H), 5.22-5.09 (m, 2H), 3.98-3.90 (m, 3H), 2.91-2.87 (m, 5H), 2.63-2.49 (m, 2H); MS (ESI) m/e 402 $(M+H)^+$.

Example 8

Preparation of (E)-N-Methyl-N-(4-methyl-naphthalen-1-ylmethyl)-3-(7-oxo-5,6,7,8-tetrahydro-[1,8]naphthyridin-3-yl)acrylamide According to the procedure of Example 1 (a), except substituting methyl-(4-methyl-naphthalen-1ylmethyl)amine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.410 g, 76%) was prepared as an off-white solid and as a mixture of amide rotamers: $^1$H NMR (300 MHz, DMSO-$d_6$) δ 10.67-10.62 (m, 1H), 8.38-8.29 (m, 1H), 8.15-7.94 (m, 3H), 7.60-3H), 7.36-7.02 (m, 3H), 5.30-5.06 (m, 2H), 3.04-2.73 (m, 5H), 2.65-2.45 (m, 5H); MS (ESI) m/e 386 (M+H)$^+$.

Example 9

Preparation of (E)-N-(2,3-Dimethyl-benzyl)-N-methyl-3-(7-oxo-5,6,7,8-tetrahydro-[1,8]naphthyridin-3-yl)acrylamide According to the procedure of Example 1 (a), except substituting 2,3-dimethylbenzylmethyl amine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.368 g, 75%) was prepared as an off-white solid and as a mixture of amide rotamers: $^1$H NMR (300 MHz, DMSO-$d_6$) δ 10.68-10.64 (m, 1H), 8.38-8.32 (m, 1H), 8.10-7.99 (m, 1H), 7.57-1H), 7.29-7.04 (m, 3H), 6.94-6.77 (m, 1H), 4.82-4.65 (m, 2H), 3.06-2.85 (m, 5H), 2.57-2.48 (m 2H), 2.28-2.14 (m, 6H); MS (APCI) m/e 350 (M+H)$^+$.

Example 10

Preparation of (E)-N-(4-Isopropyl-benzyl)-N-methyl-3-(7-oxo-5,6,7,8-tetrahydro-[1,8]naphthyridin-3-yl)acrylamide According to the procedure of Example 1 (a), except substituting (4-isopropyl-benzyl)methylamine for the methyl-(1-propyl-naphthalen-2-ylmethyl)amine, and substituting (E)-3-(7-oxo-5,6,7,8-tetrahydro-[1,8]naphthyridin-3yl) acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.223 g, 61%) was prepared as a light orange solid and as a mixture of amide rotamers: $^1$H NMR (300 MHz, DMSO-$d_6$) δ 10.66-10.64 (m, 1H), 8.36-8.33 (m, 1H), 8.07 (s, 1H), 7.55-7.48 (m, 1H), 7.33-7.11 (m, 5H), 4.77-4.56 (m, 2H), 3.09-2.81 (m, 6H), 2.56-2.49 (m 2H), 1.19-1.16 (m, 6H); MS (APCI) m/e 364 (M+H)$^+$.

Example 11

Preparation of (E)-N-Indan-5ylmethyl-N-methyl-3-(7-oxo-5,6,7,8-tetrahydro-[1,8]naphthyridin-3-yl)acrylamide According to the procedure of Example 1 (a), except substituting indan-5-ylmethyl-methylamine for the methyl-(1-propyl-naphthalen-2-ylmethyl)amine, and substituting (E)-3-(7-oxo-5,6,7,8-tetrahydro-[1,8]naphthyridin-3yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.232 g, 45%) was prepared as an off-white solid and as a mixture of amide rotamers: $^1$H NMR (300 MHz, DMSO-$d_6$) δ 10.66-10.64 (m, 1H), 8.36-8.33 (m, 1H), 8.07-8.06 (m, 1H), 7.54-7.49 (m, 1H), 7.33-6.89 (m, 4H), 4.75-4.56 (m, 2H), 3.07-2.72 (m, 9H), 2.53-2.49 (m, 2H), 2.04-1.94 (m 2H); MS (APCI) m/e 362 (M+H)$^+$.

Example 12

Preparation of (E)-N-Indan-5ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting indan-5-ylmethyl-methylamine for the methyl-(1-propyl-naphthalen-2-ylmethyl)amine, the title compound (0.060 g, 88%) was prepared as a white solid and as a mixture of amide rotamers: $^1$H NMR (300 MHz, DMSO-$d_6$) δ 12.02 (br s, 1H), 11.20 (s, 1H), 8.82-8.79 (m, 1H), 8.32-8.29 (m, 1H), 7.64-7.57 (m, 1H), 7.45-7.32 (m, 1H), 7.22-6.85 (m, 3H), 4.77-4.58 (m, 2H), 4.42 (br s, 2H), 3.80 (br s, 2H), 3.09-2.73 (m, 10H), 2.04-1.94 (m, 2H); MS (ESI) m/e 391 (M+H)$^+$.

Example 13

Preparation of (M-N-Methyl-N-(3-methyl-benzo[b]thiophen-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, the title compound (0.295 g, 98%) was prepared as a white solid and as a mixture of amide rotamers: $^1$H NMR (300 MHz, DMSO-$d_6$) δ 12.20 (br s, 1H), 11.22 (s, 1H), 8.83 (s, 1H), 8.34-8.31 (m, 1H), 7.89-7.86 (m, 1H), 7.75-7.72 (m 4H), 5.13-4.90 (m, 2H), 4.29 (br s, 2H), 3.80 (br s, 2H), 3.17-2.95 (m, 3H), 2.87 (s, 3H), 2.42 (s, 3H); MS (APCI) m/e 421 (M+H)$^+$.

Example 14

Preparation of (E)-N-(3,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3,5-dimethoxy-benzyl)methylamine for the methyl-(1-propyl-naphthalen-2-ylmethyl)amine, the title compound (0.307 g, quantitative) was prepared as an off-white solid and as a mixture of amide rotamers: $^1$H NMR (300 MHz, DMSO-$d_6$) δ 11.7 (br s, 11H), 10.88 (s, 11H), 8.71-8.68 (m, 1H), 8.25-8.22 (m, 1H), 7.61-7.56 (m, 1H), 7.39-7.31 (m, 1H), 6.42-6.35 (m, 3H), 4.75-4.55 (m, 2H), 4.09 (br s, 2H), 3.72-3.71 (m, 6H), 3.37 (br s, 2H), 3.11-2.89 (m, 3H), 2.73 (br s, 3H); MS (ESI) m/e 411 (M+H)$^+$.

Example 15

Preparation of (E)-N-[2-(1H-Indol-3-yl)-ethyl]-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting [2-(1H-indole-3yl)-ethyl]methylamine for the methyl-(1-propyl-naphthalen-2-ylmethyl)amine, the title compound (0.027 g, 72%) was prepared as a yellow solid and as a mixture of amide rotamers: $^1$H NMR (300 MHz, DMSO-d$_6$) δ 12.25 (br s, 1H), 11.26-11.22 (m, 1H), 10.85 (s, 1H), 8.82-8.41 (m, 1H), 8.33-7.82 (m, 1H), 7.64-6.73 (m, 7H), 4.59-4.31 (m, 4H), 3.78-3.64 (m, 3H), 3.17-2.91 (m, 7H); MS (APCI) m/e 404 (M+H)$^+$.

Example 16

Preparation of (E)-N-Methyl-3-(4-methyl-2-oxo-2,3,4,5-tetrahydro-1H-pyrido[2,3-e][1,4]diazepin-7-yl)-N-(2,4,5-trimethoxy-benzyl)acrylamide hydrochloride According to the procedure of Example 1, except substituting methyl-(2,4,5-trimethoxy-benzyl)amine for the methyl-(1-propyl-naphthalen-2-ylmethyl)amine, the title compound (0.220 g, 78%) was prepared as a light orange solid and as a mixture of amide rotamers: $^1$H NMR (300 MHz, DMSO-d$_6$) δ 11.75 (br s, 1H), 11.19 (s, 1H), 8.81-8.78 (m, 1H), 8.30-8.26 (m, 1H), 7.60-7.31 (m, 2H), 6.73-6.72 (m, 2H), 4.66-4.52 (m, 2H), 4.27 (br s, 2H), 3.79-3.64 (m, 11H), 3.09-2.86 (m, 6H); MS (ESI) m/e 441 (M+H)$^+$.

Example 17

Preparation of (E)-N-Methyl-3-(4-methyl-2-oxo-2,3,4,5-tetrahydro-1H-pyrido[2,3-e][1,4]diazepin-7-yl)-N-phenanthren-9-ylmethyl-acrylamide hydrochloride According to the procedure of Example 1, except substituting methyl-phenanthren-9-ylmethyl-amine for the methyl-(1-propyl-naphthalen-2-ylmethyl)amine, the title compound (0.511 g, 95%) was prepared as an off-white solid and as a mixture of amide rotamers: $^1$H NMR (300 MHz, DMSO-d$_6$) δ 11.99 (br s, 1H), 11.23-11.14 (m, 1H), 8.92-8.74 (m, 3H), 8.36-8.04 (m, 2H), 7.99-7.95 (m, 1H), 7.74-7.28 (m, 7H), 5.39-5.17 (m, 2H), 4.30-4.19 (m, 2H), 3.95-3.39 (m, 2H), 3.16-3.01 (m, 3H), 2.89-2.73 (m, 3H); MS (ESI) m/e 451 (M+H)$^+$.

Example 18

Preparation of (E)-N-Acenaphthen-5-ylmethyl-N-methyl-3-(4-methyl-2-oxo-2,3,4,5-tetrahydro-1H-pyrido[2,3-e][1,4]diazepin-7-yl acrylamide hydrochloride According to the procedure of Example 1, except substituting acenaphthen-5-ylmethyl-methylamine for the methyl-(1-propyl-naphthalen-2-ylmethyl)amine, the title compound (0.395 g, 91%) was prepared as a off-white solid and as a mixture of amide rotamers: $^1$H NMR (300 MHz, DMSO-d$_6$) δ 12.01 (br s, 1H), 11.19 (s, 1H), 8.82-8.76 (m, 1H), 8.32-8.22 (m, 1H), 7.81-7.63 (m, 2H), 7.55-7.14 (m, 5H), 5.25-5.03 (m, 2H), 4.28 (br s, 2H), 3.79 (m, 2H), 3.36 (br s, 4H), 3.04-2.73 (m, 6H); MS (ESI) m/e 427 (M+H)$^+$.

Example 19

Preparation of (E)-N-(4-Methoxy-naphthalen-1ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-methoxy-naphthalen-1-ylmethyl)methylamine for the methyl-(1-propyl-naphthalen-2ylmethyl)amine, the title compound (0.369 g, 87%) was prepared as an off-white solid and as a mixture of amide rotamers: $^1$H NMR (300 MHz, DMSO-d$_6$) δ 11.95 (br s, 1H), 11.22 (s, 1H), 8.83-8.76 (m, 1H), 8.32-8.02 (m, 2H), 8.10-8.00 (m, 1H), 7.69-7.32 (m, 5H), 7.11-6.95 (m, 1H), 5.25-5.03 (m, 2H), 4.29 (br s, 2H), 3.98-3.95 (m, 3H), 3.79 (m, 2H), 3.02-2.69 (m, 3H), 2.87-2.72 (m, 3H); MS (ESI) m/e 431 (M+H)$^+$.

Example 20

Preparation of (E)-N-Benzo[1,3]dioxol-5-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting benzo[1,3]dioxol-5-ylmethyl-methylamine for the methyl-(1-propyl-naphthalen-2-ylmethyl)amine, the title compound (0.374 g, 91%) was prepared as an off-white solid and as a mixture of amide rotamers: $^1$H NMR (300 MHz, DMSO-d$_6$) δ 12.25 (br s, 1H), 11.23 (s, 1H), 8.81 (s, 1H), 8.32 (s, 1H), 7.62-6.57 (m, 1H), 7.46-7.31 (m, 1H), 6.93-6.71 (m, 3H), 5.99 (s, 2H), 4.72-4.52 (m, 2H), 4.29 (br s, 2H), 3.81 (br s, 2H), 3.10-2.88 (m, 6H); MS (APCI) m/e 395 (M+H)$^+$.

Example 21

Preparation of (E)-N-(2,5-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,5-dimethoxy-benzyl)methylamine for the methyl-(1-propyl-naphthalen-2-ylmethyl)amine, the title compound (0.396 g, 93%) was prepared as an off-white solid and as a mixture of amide rotamers: $^1$H NMR (300 MHz, DMSO-d$_6$) δ 12.05 (br s, 1H), 11.20 (m, 1H), 8.82-8.77 (m, 1H), 8.33-8.27 (m, 1H), 7.61-7.56 (m, 1H), 7.41-7.34 (m, 1H), 6.98-6.93 (m, 1H), 6.86-6.82 (m, 1H), 6.60-6.59 (m, 1H), 4.73-4.55 (m, 2H), 4.28 (br s, 2H), 3.79-3.74 (m, 5H), 3.66-3.65 (m, 3H), 3.16-2.86 (m, 6H); MS (ESI) m/e 411 (M+H)$^+$.

Example 22

Preparation of (E)-N-Methyl-3-(4-methyl-2-oxo-2,3,4,5-tetrahydro-1H-pyrido[2,3-e][1,4]diazepin-7-yl)-N-quinolin-4-ylmethyl-acrylamide hydrochloride According to the procedure of Example 1, except substituting methyl-quinolin-4-ylmethyl-amine for the methyl-(1-propyl-naphthalen-2-ylmethyl)amine, the title compound (0.259 g, 92%) was prepared as an off-white solid and as a mixture of amide rotamers: $^1$H NMR (300 MHz, DMSO-d$_6$) δ 11.22-11.14 (m, 1H), 8.98-8.94 (m, 1H), 8.84-8.74 (m, 1H), 8.37-8.16 (m, 3H), 7.93-7.88 (m, 1H), 7.78-7.73 (m, 1H), 7.69-7.63 (m, 1H), 7.48-7.21 (m, 2H), 5.50-5.24 (m, 2H), 4.30-4.19 (m, 2H), 3.81-3.74 (m, 2H), 3.27 (s, 2H), 3.06 (s, 1H), 2.87-2.80 (m, 3H); MS (ESI) m/e 402 (M+H)$^+$.

Example 23

Preparation of (E)-N-(4-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-ethoxy-3-methoxy-benzyl)methylamine for the methyl-(1-propyl-naphthalen-2-ylmethyl)amine, the title compound (0.310 g, 95%) was prepared as an off-white solid and as a mixture of amide rotamers: $^1$H NMR (300 MHz, DMSO-$d_6$) δ 11.18 (m, 1H), 8.80-8.79 (m, 1H), 8.30-8.28 (m, 1H), 7.61-7.57 (m, 1H), 7.44-7.30 (m, 1H), 6.95-6.71 (m, 3H), 4.72-4.53 (m, 2H), 4.27 (br s, 2H), 3.99-3.92 (m, 2H), 3.79-3.72 (m, 5H), 3.08-2.72 (m, 6H), 1.33-1.26 (m, 3H); MS (EST) m/e 425 (M+H)$^+$.

Example 24

Preparation of (E)-N-(2-Ethoxy-3-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-ethoxy-3-methoxy-benzyl)methylamine for the methyl-(1-propyl-naphthalen-2-ylmethyl)amine, the title compound (0.381 g, 89%) was prepared as an off-white solid and as a mixture of amide rotamers: $^1$H NMR (300 MHz, DMSO-$d_6$) δ 12.01 (br s, 1H), 11.21 (s, 1H), 8.82-8.78 (m, 1H), 8.33-8.25 (m, 1H), 7.61-7.56 (m, 1H), 7.40-7.34 (m, 1H), 7.05-6.97 (m, 2H), 6.71-6.61 (m, 1H), 4.80-4.52 (m, 2H), 4.29 (br s, 2H), 4.0-3.94 (m, 2H), 3.79 (m, 5H), 3.11-2.87 (m, 6H), 1.31-1.25 (m, 3H); MS (ESI) m/e 425 (M+H)$^+$.

Example 25

Preparation of (E)-N-(3,4-Dimethyl-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3,4-dimethyl-benzyl)methylamine for the methyl-(1-propyl-naphthalen-2-ylmethyl)amine, the title compound (0.346 g, 91%) was prepared as an off-white solid and as a mixture of amide rotamers: $^1$H NMR (300 MHz, DMSO-$d_6$) δ 12.35 (br s, 1H), 11.23 (s, 1H), 8.82-8.79 (m, 1H), 8.34-8.30 (m, 1H), 7.62-7.57 (m, 1H), 7.44-7.32 (m, 1H), 7.14-7.08 (m, 1H), 7.02-6.92 (m, 2H), 4.74-4.55 (m, 2H), 4.28 (br s, 2H), 3.80 (m, 2H), 3.08-2.86 (m, 6H), 2.20-2.19 (m, 6H); MS (ESI) m/e 379 (M+H)$^+$.

Example 26

Preparation of (E)-N-Methyl-3-(4-methyl-2-oxo-2,3,4,5-tetrahydro-1H-pyrido[2,3-e][1,4]diazepin-7-yl)-N-(2,4,6-trimethyl-benzyl)acrylamide hydrochloride According to the procedure of Example 1, except substituting (2,4,6-trimethyl-benzyl)methylamine for the methyl-(1-propyl-naphthalen-2-ylmethyl)amine, the title compound (0.410 g, 94%) was prepared as an off-white solid and as a mixture of amide rotamers: $^1$H NMR (300 MHz, DMSO-$d_6$) δ 11.80 (br s, 1H), 11.20 (m, 1H), 8.84-8.80 (m, 1H), 8.37-8.31 (m, 1H), 7.61-7.56 (m, 1H), 7.32-7.27 (m, 1H), 6.87 (m, 2H), 4.83-4.68 (m, 2H), 4.28 (br s, 2H), 3.80 (m, 2H), 2.87-2.55 (m, 6H), 2.21-2.16 (m, 9H); MS (ESI) m/e 393 (M+H)$^+$.

Example 27

Preparation of (E)-N-Methyl-3-(4-methyl-2-oxo-2,3,4,5-tetrahydro-1H-pyrido[2,3-e][1,4]diazepin-7-yl)-N-(2,4,5-trimethyl-benzyl acrylamide hydrochloride According to the procedure of Example 1, except substituting (2,4,5-trimethyl-benzyl)methylamine for the methyl-(1-propyl-naphthalen-2-ylmethyl)amine, the title compound (0.344 g, 95%) was prepared as an off-white solid and as a mixture of amide rotamers: $^1$H NMR (300 MHz, DMSO-$d_6$) δ 11.91 (br s, 1H), 11.25-11.22 (m, 1H), 8.83-8.78 (m, 1H), 8.34-8.24 (m, 1H), 7.63-7.57 (m, 1H), 7.40-7.32 (m, 1H), 6.97-6.95 (m, 1H), 6.85-6.73 (m, 1H), 4.73-4.57 (m, 2H), 4.30 (br s, 2H), 3.96-3.82 (m, 2H), 3.04-2.87 (m, 6H), 2.21-2.15 (m, 9H); MS (ESI) m/e 393 (M+H)$^+$.

Example 28

Preparation of (E)-N-Methyl-3-(4-methyl-2-oxo-2,3,4,5-tetrahydro-1H-pyrido[2,3-e][1,4]diazepin-7-yl)-N-quinolin-3-ylmethyl-acrylamide hydrochloride According to the procedure of Example 1, except substituting methyl-quinolin-3-ylmethyl-amine for the methyl-(1-propyl-naphthalen-2-ylmethyl)amine, the title compound (0.360 g, 92%) was prepared as an off-white solid and as a mixture of amide rotamers: $^1$H NMR (300 MHz, DMSO-$d_6$) δ 12.00 (br s, 1H), 11.23-11.20 (m, 1H), 8.92-8.89 (m, 1H), 8.83-8.80 (m, 1H), 8.34-8.24 (m, 2H), 8.08-8.03 (m, 2H), 7.80-7.78 (m, 1H), 7.69-6.61 (m, 2H), 7.52-7.36 (m, 1H), 5.09-4.86 (m, 2H), 4.30-4.25 (m, 2H), 3.81 (br s, 2H), 3.25 (s, 2H), 3.01 (s, 1H), 2.88-2.85 (m, 3H); MS (ESI) m/e 402 (M+H)$^+$.

Example 29

Preparation of (E)-N-(3,4-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3,4-dimethoxy-benzyl)methylamine for the methyl-(1-propyl-naphthalen-2-ylmethyl)amine, the title compound (0.330 g, 92%) was prepared as a pale yellow solid and as a mixture of amide rotamers: $^1$H NMR (300 MHz, DMSO-$d_6$) δ 11.95 (br s, 1H), 11.23 (s, 1H), 8.82-8.81 (m, 1H), 8.32-8.30 (m, 1H), 7.63-7.57 (m, 1H), 7.45-7.32 (m, 1H), 6.95-6.86 (m, 2H), 6.81-6.71 (m, 1H), 4.74-41.55 (m, 2H), 4.28 (br s, 2H), 3.95-3.72 (m, 8H), 3.10-2.88 (m, 6H);
MS (ESI) m/e 411 (M+H)$^+$.

Example 30

Preparation of (E)-N-Benzofuran-2-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting benzofuran-2-ylmethyl-methylamine for the methyl-(1-propyl-naphthalen-2-ylmethyl)amine, the title compound (0.399 g, 93%) was prepared as an off white solid and as a mixture of amide rotamers: ¹H NMR (300 MHz, DMSO-d₆) δ 11.86 (br s, 1H), 11.22 (s, 1H), 8.83 (s, 1H), 8.32 (s, 1H), 7.63-7.20 (m, 6H), 6.86-6.82 (m, 1H), 5.02-4.81 (m, 2H), 4.28 (s, 2H), 3.80 (s, 2H), 3.24-3.02 (m, 3H), 2.87 (s, 3H); MS (ESI) m/e 391 (M+H)⁺.

Example 31

Preparation of (E)-N-Methyl-N-(2-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(2-methyl-naphthalen-1-ylmethyl)amine for the methyl-(1-propyl-naphthalen-2-ylmethyl)amine, the title compound (0.431 g, 95%) was prepared as a white solid and as a mixture of amide rotamers: ¹H NMR (300 MHz, DMSO-d₆) δ 12.01 (br s, 1H), 11.24 (s, 1H), 8.93-8.83 (m, 1H), 8.44-8.32 (m, 1H), 8.10-8.07 (m, 1H), 7.92-7.82 (m, 2H), 7.71-7.66 (m, 1H), 7.49-7.28 (m, 4H), 5.30-5.18 (m, 2H), 4.29 (br s, 2H), 3.79 (br s, 2H), 2.87-2.81 (m, 6H), 2.55-2.51 (s, 3H); MS (ESI) m/e 415 (M+H)⁺.

Example 32

Preparation of (E)-N-Biphenyl-2-ylmethyl-methyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting biphenyl-2-ylmethyl-methylamine for the methyl-(1-propyl-naphthalen-2-ylmethyl)amine, the title compound (0.255 g, 88%) was prepared as a white solid and as a mixture of amide rotamers: ¹H NMR (300 MHz, DMSO-d₆) δ 11.95 (br s, 1H), 11.22 (s, 1H), 8.80-8.76 (m, 1H), 8.31-8.19 (m, 1H), 7.57-7.17 (m, 11H), 4.76-4.59 (m, 2H), 4.29 (br s, 2H), 3.81 (br s, 2H), 2.99-2.73 (m, 6H); MS (ESI) m/e 427 (M+H)⁺.

Example 33

Preparation of (E)-N-Biphenyl-3-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting biphenyl-3-ylmethyl-methylamine for the methyl-(1-propyl-naphthalen-2-ylmethyl)amine, the title compound (0.404 g, 85%) was prepared as an off-white solid and as a mixture of amide rotamers: ¹H NMR (300 MHz, DMSO-d₆) δ 11.95 (br s, 1H), 11.22-11.21 (m, 1H), 8.82-8.81 (m, 1H), 8.32-8.30 (m, 11H), 7.65-7.21 (m, 11H), 7.92-7.82 (m, 2H), 4.92-4.71 (m, 2H), 4.28 (br s, 2H), 3.79 (br s, 2H), 2.17-2.96 (m, 3H), 2.88-2.84 (m, 3H); MS (ESI) m/e 427 (M+H)⁺.

Example 34

Preparation of (E)-N-(2-Ethoxy-napthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(2-ethoxy-naphthalen-1-ylmethyl)amine for the methyl-(1-propyl-naphthalen-2-ylmethyl)amine, the title compound (0.405 g, 90%) was prepared as a white solid and as a mixture of amide rotamers: ¹H NMR (300 MHz, DMSO-d₆) δ 12.35 (br s, 1H), 11.25 (s, 1H), 8.84-8.82 (m, 1H), 8.40-8.31 (m, 1H), 8.07-8.05 (m, 1H), 7.96-7.87 (m, 2H), 7.68-7.63 (m, 1H), 7.52-7.25 (m, 4H), 5.26-5.16 (m, 2H), 4.29-4.20 (m, 4H), 4.09 (br s, 2H), 2.91-2.63 (m, 6H), 1.43-1.29 (s, 3H); MS (ESI) m/e 445 (M+H)⁺.

Example 35

Preparation of (E)-N-(2-Ethoxy-benzyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-ethoxy-benzyl)methylamine for the methyl-(1-propyl-naphthalen-2-ylmethyl)amine, the title compound (0.409 g, 87%) was prepared as a white solid and as a mixture of amide rotamers: ¹H NMR (300 MHz, DMSO-d₆) δ 12.05 (br s, 1H), 11.20 (s, 1H), 8.82-8.77 (m, 1H), 8.32-8.27 (m, 1H), 7.61-7.55 (m, 1H), 7.44-7.35 (m, 1H), 7.27-7.20 (m, 1H), 7.09-6.90 (m, 3H), 4.76-4.59 (m, 2H), 4.28 (br s, 2H), 4.09-4.01 (m, 2H), 3.80 (br s, 2H), 3.16-2.85 (m, 6H), 1.37-1.27 (m, 3H); MS (ESI) m/e 395 (M+H)⁺.

Example 36

Preparation of (E)-N-Methyl-3-(4-methyl-2-oxo-2,3,4,5-tetrahydro-1H-pyrido[2,3-e][1,4]diazepin-7-yl)-N-(2,3,4-trimethoxy-benzyl)acrylamide hydrochloride According to the procedure of Example 1, except substituting (2,3,4-trimethoxy-benzyl)methylamine for the methyl-(1-propyl-naphthalen-2-ylmethyl)amine, the title compound (0.440 g, 92%) was prepared as a white solid and as a mixture of amide rotamers: ¹H NMR (300 MHz, DMSO-d₆) δ 12.25 (br s, 1H), 11.23 (s, 1H), 8.82-8.79 (m, 1H), 8.34-8.29 (m, 1H), 7.61-7.55 (m, 1H), 7.46-7.33 (m, 1H), 6.81-6.75 (m, 2H), 4.71-4.56 (m, 2H), 4.30 (br s, 2H), 3.81-3.74 (m, 11H), 3.11-2.85 (m, 6H); MS (ESI) m/e 441 (M+H)⁺.

Example 37

Preparation of (E)-N-(2,3-Dihydro-benzo[1,4]dioxin-6ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-dihydro-benzo[1,4]dioxin-6-ylmethyl)methylamine for the methyl-(1-propyl-naphthalen-2-ylmethyl)amine, the title compound (0.196 g, 93%) was prepared as a white solid and as a mixture of amide rotamers: ¹H NMR (300 MHz, DMSO-d₆) δ 12.25 (br s, 1H), 11.25 (s, 1H), 8.82 (s, 1H), 8.32 (s, 1H), 7.63-7.56 (m, 1H), 7.45-7.31 (m, 1H), 6.86-6.68 (m, 3H), 4.70-4.49 (m, 2H), 4.30 (br s, 2H), 4.21 (m, 4H), 3.82 (br s, 2H), 3.09-2.87 (m, 6H); MS (APCI) m/e 409 (M+H)⁺.

Example 38

Preparation of (E)-N-(2,3-Diethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-diethoxy-benzyl)methylamine for the methyl-(1-propyl-naphthalen-2-ylmethyl)amine, the title compound (0.331 g, 87%) was prepared as an off-white solid and as a mixture of amide rotamers: $^1$H NMR (300 MHz, DMSO-$d_6$) δ 12.49 (br s, 1H), 11.24-11.22 (m, 1H), 8.83-8.78 (m, 1H), 8.36-8.28 (m, 1H), 7.62-7.56 (m, 1H), 7.42-7.35 (m, 1H), 7.05-6.92 (m, 2H), 6.69-6.63 (m, 1H), 4.80-4.65 (m, 2H), 4.30(br s, 2H), 4.07-3.93 (m, 4H), 3.81 (br s, 2H), 3.12-2.80 (m, 6H), 1.37-1.25 (m, 6H); MS (APCI) m/e 439 (M+H)$^+$.

Example 39

Preparation of (E)-N-(3-Ethoxy-2-methoxy-benzyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-ethoxy-2-methoxy-benzyl)methylamine for the methyl-(1-propyl-naphthalen-2-ylmethyl)amine, the title compound (0.397 g, quantitative) was prepared as an off-white solid and as a mixture of amide rotamers: $^1$H NMR (300 MHz, DMSO-$d_6$) δ 12.25 (br s, 1H), 11.23-11.21 (m, 1H), 8.82-8.78 (m, 1H), 8.34-8.27 (m, 1H), 7.62-7.56 (m, 1H), 7.44-7.34 (m, 1H), 7.04-6.96 (m, 2H), 6.69-6.66 (m, 1H), 4.78-4.63 (m, 2H), 4.30 (br s, 2H), 4.09-4.02 (m, 2H), 3.82-3.76 (m, 5H), 3.12-2.86 (m, 6H), 1.38-1.32 (m, 3H); MS (ESI) m/e 425 (M+H)$^+$.

Example 40

Preparation of (B)-N-(2-Ethoxy-3-methyl-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-ethoxy-3-methyl-benzyl)methylamine for the methyl-(1-propyl-naphthalen-2-ylmethyl)amine, the title compound (0.358 g, 84%) was prepared as an off-white solid and as a mixture of amide rotamers: $^1$H NMR (300 MHz, DMSO-$d_6$) δ 12.21 (br s, 1H), 11.23-11.21 (m, 1H), 8.82-8.78 (m, 1H), 8.34-8.25 (m, 1H), 7.63-7.56 (m, 1H), 7.41-7.35 (m, 1H), 7.16-7.11 (m, 1H), 7.05-6.87 (m, 2H), 4.82-4.67 (m, 2H), 4.30 (br s, 2H), 3.90-3.80 (m, 4H), 3.18-2.86 (m, 6H), 2.24 (s, 3H), 1.42-1.28 (m, 3H); MS (ESI) m/e 409 (M+H)$^+$.

Example 41

Preparation of (E)-N-methyl-3-(4-methyl-2-oxo-2,3,4,5-tetrahydro-1H-pyrido[2,3-e][1,4]diazepin-7-yl)-N-quinolin-5ylmethyl-acrylamide hydrochloride According to the procedure of Example 1, except substituting methyl-quinolin-5-ylmethyl-amine for the methyl-(1-propyl-naphthalen-2-ylmethyl)amine, the title compound (0.399 g, quantitative) was prepared as an off-white solid and as a mixture of amide rotamers: $^1$H NMR (300 MHz, DMSO-$d_6$) δ 12.30 (br s, 1H), 11.19-11.13 (m, 1H), 8.90-8.98 (m, 1H), 8.82-8.62 (m, 2H), 8.34-8.18 (m, 1H), 8.06-7.99 (m, 1H), 7.83-7.87 (m, 1H), 7.72-7.27 (m, 4H), 5.41-5.15 (m, 2H), 4.28-4.19 (m, 2H), 3.79-3.74 (m, 2H), 3.12-3.01 (m, 3H), 2.85-2.79 (m, 3H); MS (ESI) m/e 402 (M+H)$^+$.

Example 42

Preparation of (E)-N-(3-Methoxy-2-propoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-methoxy-2-propoxy-benzyl)methylamine for the methyl-(1-propyl-naphthalen-2-ylmethyl)amine, the title compound (0.275 g, 87%) was prepared as an off-white solid and as a mixture of amide rotamers: $^1$H NMR (300 MHz, DMSO-$d_6$) δ 12.21 (m, 1H), 11.23-11.21 (m, 1H), 8.83-8.78 (m, 1H), 8.34-8.25 (m, 1H), 7.63-7.56 (m, 1H), 7.40-7.34 (m, 1H), 7.05-6.97 (m, 2H), 6.69-6.64 (m, 1H), 4.80-4.65 (m, 2H), 4.30 (m, 2H), 3.92-3.85 (m, 2H), 3.79 (s, 3H), 3.49 (br s, 2H), 3.12-2.86 (m, 6H), 1.75-1.68 (m, 2H), 1.01-0.94 (m, 3H); MS (ESI) m/e 439 (M+H)$^+$.

Example 43

Preparation of (E)-N-(3-Methoxy-2-isopropoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-methoxy-2-isopropoxy-benzyl)methylamine for the methyl-(1-propyl-naphthalen-2-ylmethyl)amine, the title compound (0.304 g, 85%) was prepared as an off-white solid and as a mixture of amide rotamers: $^1$H NMR (300 MHz, DMSO-$d_6$) δ 12.20 (br s, 1H), 11.24-11.21 (m, 1H), 8.82-8.77 (m, 1H), 8.35-8.23 (m, 1H), 7.61-7.56 (m, 1H), 7.40-7.30 (m, 1H), 7.04-6.93 (m, 2H), 6.67-6.61 (m, 1H), 4.79-4.65 (m, 2H), 4.59-4.48 (m, II), 4.30-4.28 (br s, 2H), 3.79 (s, 3H), 3.58-3.55 (m, 2H), 3.10-2.86 (m, 6H), 1.24-1.21 (m, 6H); MS (ESI) m/e 439 (M+H)$^+$.

Example 44

Preparation of (E)-N-methyl-N-(3-methyl-benzofuran-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(3-methyl-benzofuran-2-ylmethyl)amine for the methyl-(1-propyl-naphthalen-2-ylmethyl)amine, the title compound (0.376 g, 87%) was prepared as an off-white solid and as a mixture of amide rotamers: $^1$H NMR (300 MHz, DMSO-$d_6$) δ 12.16 (br s, 1H), 11.23 (s, 1H), 8.85-8.82 (m, 1H), 8.33 (s, 1H), 7.63-7.22 (m, 6H), 5.01-4.81 (m, 2H), 4.30 (m, 2H), 3.58 (br s, 2H), 3.20-2.88 (m, 6H), 2.27 (m, 3H); MS (ESI) m/e 405 (M+H)$^+$.

Example 45

Preparation of (E)-N-(3-Chloro-2-methoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-chloro-2-methoxy-benzyl)methylamine for the methyl-(1-propyl-naphthalen-2-ylmethyl)amine, the title compound (0.312 g, 92%) was prepared as an off-white solid and as a mixture of amide rotamers: $^1$H NMR (500 MHz, DMSO-d$_6$) δ 12.55 (br s, 1H), 11.21-11.19 (m, 1H), 8.82-8.79 (m, 1H), 8.35-8.28 (m, 1H), 7.61-7.57 (m, 1H), 7.45-7.31 (m, 2H), 7.19-7.11 (m, 2H), 4.87-4.70 (m, 2H), 4.30 (m, 2H), 3.82-3.77 (m, 51), 3.17-2.86 (m, 6H); MS (ESI) m/e 415 (M+)$^+$.

Example 46

Preparation of (E)-N-(3-Chloro-2-ethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-chloro-2-ethoxy-benzyl)methylamine for the methyl-(1-propyl-naphthalen-2-ylmethyl)amine, the title compound (0.169 g, 91%) was prepared as a white solid and as a mixture of amide rotamers: $^1$H NMR (500 MHz, DMSO-d$_6$) δ 12.44 (br s, 1H), 11.20-11.18 (m, 1H), 8.82-8.78 (m, 1H), 8.34-8.25 (m, 1H), 7.62-7.57 (m, 1H), 7.44-7.36 (m, 2H), 7.18-7.10 (m, 2H), 4.87-4.70 (m, 2H), 4.30 (m, 2H), 4.05-3.98 (m, 2H), 3.79-3.61 (m, 2H), 3.16-2.85 (m, 6H), 1.39-1.35 (m, 3H); MS (ESI) m/e 429 (M+H)$^+$.

Example 47

Preparation of (E)-N-(2,3-Dihydro-benzo[1,4]dioxin-5-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-dihydro-benzo[1,4]dioxin-5-ylmethyl)methylamine for the methyl-(1-propyl-naphthalen-2-ylmethyl)amine, the title compound (0.058 g, quantitative) was prepared as a white solid and as a mixture of amide rotamers: $^1$H NMR (300 MHz, DMSO-d$_6$) δ 12.15 (br s, 1H), 11.22-11.20 (m, 1H), 8.82-8.76 (m, 1H), 8.34-8.27 (m, 1H), 7.60-7.55 (m, 1H), 7.40-7.33 (m, 1H), 6.84-6.76 (m, 2H), 6.62-6.57 (m, 1H), 4.74-4.57 (m, 2H), 4.30-4.24 (m, 6H), 3.80 (br s, 2H), 3.16-2.87 (m, 6H); MS (ESI) m/e 409 (M+H)$^+$.

Example 48

Preparation of (E)-N-(4,5-Dimethyl-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4,5-dimethyl-naphthalen-1-ylmethyl)methylamine for the methyl-(1-propyl-naphthalen-2-ylmethyl)amine, the title compound (0.244 g, 66%) was prepared as a white solid and as a mixture of amide rotamers: $^1$H NMR (300 MHz, DMSO-d$_6$) δ 12.08 (br s, 1H), 11.22-11.17 (m, 1H), 8.83-8.73 (m, 1H), 8.33-8.17 (m, 1H), 7.94-7.87 (m, 1H), 7.68-7.62 (m, 1H), 7.45-7.22 (m, 51), 5.25-5.03 (m, 2H), 4.29-4.21 (m, 2H), 3.80 (br s, 2H), 3.11-3.04 (m, 3H), 2.97-2.81 (m, 9H); MS (ESI) m/e 429 (M+H)$^+$.

Example 49

Preparation of (E)-N-Methyl-N-(2-methyl-benzofuran-3-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(2-methyl-benzofuran-3-ylmethyl)amine for the methyl-(1-propyl-naphthalen-2-ylmethyl)amine, the title compound (0.213 g, 53%) was prepared as a white solid and as a mixture of amide rotamers: $^1$H NMR (300 MHz, DMSO-d$_6$) δ 12.24 (br s, 1H), 11.22 (s, 1H), 8.88-8.82 (m, 1H), 8.38-8.33 (m, 1H), 7.79-7.15 (m, 6H), 4.95-4.75 (m, 2H), 4.29 (br s, 2H), 3.80 (br s, 2H), 3.13-2.83 (m, 6H), 2.59-2.44 (m, 3H); MS (ESI) nm/e 405 (M+H)$^+$.

Example 50

Preparation of (E)-N-Methyl-3-(7-oxo-5,6,7,8-tetrahydro-[1,8]naphthyridin-3-yl)-N-quinolin-5-ylmethyl-acrylamide hydrochloride According to the procedure of Example 1, except substituting methyl-quinolin-5-ylmethyl-amine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.387 g, quantitative) was prepared as a tan solid and as a mixture of amide rotamers: $^1$H NMR (300 MHz, DMSO-d$_6$) δ 10.69-10.63 (m, 1H), 9.26-9.13 (m, 2H), 8.39-8.25 (m, 2H), 8.11-7.93 (m, 3H), 7.77-7.45 (m, 2H), 7.30-7.17 (m, 1H), 5.50-5.22 (m, 2H), 3.15-3.01 (m, 3H), 2.94-2.78 (m, 2H), 2.56-2.44 (m, 2H); MS (ESI) m/e 373 (M+H)$^+$.

Example 51

Preparation of (M)-N-benzyl-N-methyl-3-(7-oxo-5,6,7,8-tetrahydro-[1,8]naphthyridin-3-yl)acrylamide According to the procedure of Example 1 (a), except substituting benzyl-methylamine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.462 g, 93%) was prepared as an off-white solid and as a mixture of amide rotamers: $^1$H NMR (300 MHz, DMSO-d$_6$) δ 10.64 (s, 1H), 8.37-8.33 (m, 1H), 8.08-8.06 (m, 1H), 7.54-7.49 (m, 1H), 7.37-7.21 (m, 6H), 4.82-4.61 (m, 2H) 3.10-2.85 (m, 5H), 2.56-2.49 (m, 2H); MS (APCI) m/e 322 (M+H)$^+$.

Example 52

Preparation of (E)-N-methyl-N-(1-methyl-1H-indol-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(1-methyl-1H-indol-2-ylmethyl)amine for the methyl-(1-propyl-naphthalen-2-ylmethyl)amine, the title compound (0.27 g, 86%) was prepared as an off-white powder and as a mixture of amide rotamers: $^1$H NMR (300 MHz, DMSO-$d_6$) δ 11.96 (br s, 1H), 11.06-11.22 (m, 1H), 8.80-8.83 (m, 1H), 8.25-8.34 (m, 1H), 7.61-7.66 (m, 1H), 7.33-7.52 (m, 3H), 7.11-7.15 (m, 1H), 6.97-7.04 (m, 1H), 6.18-6.43 (m, 1H), 4.87-5.08 (m, 2H), 4.26-4.29 (m, 2H), 3.69-3.80 (m, 5H), 3.02-3.14 (m, 3I), 2.85-2.88 (m, 3H); MS (ESI) m/e 404 (M+H)$^+$.

Example 53

Preparation of (E)-(7-{2-[Methyl-(1-methyl-1H-indol-2-ylmethyl)carbamoyl]vinyl}-2-oxo-1,2,3,5-tetrahydro-pyrido[2,3-e][1,4]diazepin-4-yl)acetic acid ethyl ester hydrochloride According to the procedure of Example 1, except substituting methyl-(1-methyl-1H-indol-2-ylmethyl)amine for the methyl-(1-propyl-naphthalen-2-ylmethyl)amine, and substituting (E)-3-(4-ethoxycarbonylmethyl-2-oxo-2,3,4,5-tetrahydro-1H-pyrido[2,3-e][1,4]diazepin-7-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.22 g, 56%) was prepared as a yellow powder and as a mixture of amide rotamers: $^1$H NMR (300 MHz, DMSO-$d_6$) δ 10.53-10.54 (m, 1H), 8.56-8.59 (m, 1H), 8.09-8.16 (m, 1H), 7.28-7.61 (m, 4H), 7.10-7.15 (m, 1H), 6.99-7.04 (m, 1H), 6.19-6.42 (m, 1H), 4.86-5.06 (m, 2H), 4.00-4.14 (m, 5H), 3.62-3.72 (m, 7H), 2.99-3.12 (m, 3H), 1.12-1.20 (m, 3H); MS (ESI) m/e 476 (M+H)$^+$.

Example 54

Preparation of (E)-N-(2,3-Dimethoxy-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2,3-dimethoxy-benzyl)methylamine for the methyl-(1-propyl-naphthalen-2-ylmethyl)amine, the title compound (0.25 g, 58%) was prepared as an off-white powder and as a mixture of amide rotamers: $^1$H NMR (300 MHz, DMSO-$d_6$) δ 11.89 (br s, 1H), 11.21 (s, 1H), 8.78-8.82 (m, 1H), 8.26-8.33 (m, 1H), 7.56-7.61 (m, 1H), 7.34-7.44 (m, 1H), 6.96-7.07 (m, 2H), 6.67-6.71 (m, 1H), 4.64-4.79 (m, 2H), 4.28 (s, 2H), 3.74-3.81 (m, 8H), 2.87-3.13 (m, 6H); MS (ESI) m/e 411 (M+H)$^+$.

Example 55

Preparation of (E)-N-Methyl-N-(4-methyl-naphthalen-1-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(4-methyl-naphthalen-1-ylmethyl)amine for the methyl-(1-propyl-naphthalen-2-ylmethyl)amine, the title compound (0.41 g, 74%) was prepared as a tan powder and as a mixture of amide rotamers: $^1$H NMR (300 MHz, DMSO-$d_6$) δ 11.82 (br s, 1H), 11.16-11.20 (m, 1H), 8.74-8.83 (m, 1H), 8.06-8.33 (m, 3H), 7.56-7.69 (m, 3H), 7.33-7.39 (m, 3H), 5.09-5.32 (m, 2H), 4.20-4.28 (m, 2H), 3.80 (s, 2H), 2.99-3.06 (m, 3H), 2.81-2.86 (m, 3H), 2.64-2.66 (m, 3H); MS (ESI) m/e 415 (M+H)$^+$.

Example 56

Preparation of (M-N-(2-Methoxy-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-methoxy-naphthalen-1-ylmethyl)methylamine for the methyl-(1-propyl-naphthalen-2-ylmethyl)amine, the title compound (0.41 g, 71%) was prepared as an off-white powder and as a mixture of amide rotamers: $^1$H NMR (300 MHz, DMSO-$d_6$) δ 11.88 (br s, 1H), 11.20 (s, 1H), 8.81-8.85 (m, 1H), 8.30-8.36 (m, 1H), 7.88-8.08 (m, 3H), 7.24-7.69 (m, 5H), 5.15-5.24 (m, 2H), 4.28 (s, 2H), 3.80-3.99 (m, 5H), 2.64-2.90 (m, 6H); MS (ESI) m/e 431 (M+H)$^+$.

Example 57

Preparation of (R)-(+)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethyl)acrylamide hydrochloride According to the procedure of Example 1, except substituting (R)-(+)-N-methyl-1-(1-naphthyl)ethylamine for the methyl-(1-propyl-naphthalen-2-ylmethyl)amine, the title compound (0.26 g, 48%) was prepared as an off-white powder and as a mixture of amide rotamers: $[\alpha]^{25}_D$+92.6° (c 1.00, methanol); $^1$H NMR (300 MHz, DMSO-$d_6$) δ 12.11 (br s, 1H), 11.22 (s, 1H), 8.81-8.89 (m, 1H), 8.30-8.42 (m, 1H), 7.92-7.98 (m, 3H), 7.67-7.79 (m, 2H), 7.50-7.60 (m, 3H), 7.20-7.25 (m, 1H), 6.53-6.57 (m, 1H), 4.28 (s, 2H), 3.80 (s, 2H), 2.86-2.89 (m, 3H), 2.45-2.73 (m, 3H), 1.60-1.75 (m, 3H); MS (ESI) m/e 415 (M+H)$^+$.

Example 58

Preparation of (S)-(−)-(E)-N-Methyl-3-(4-methyl-2-oxo-2,3,4,5-tetrahydro-1H-pyrido[2,3-e][1,4]diazepin-7-yl)-N-(1-naphthalen-1-yl-ethylacrylamide hydrochloride According to the procedure of Example 1, except substituting (S)-(−)-N-methyl-1-(1-naphthyl)ethylamine for the methyl-(1-propyl-naphthalen-2-ylmethyl)amine, the title compound (0.34 g, 63%) was prepared as an off-white powder: $[\alpha]^{25}_D$−89.1° (c 1.00, methanol); $^1$H NMR (300 MHz, DMSO-$d_6$) δ 12.20 (br s, 1H), 11.21 (s, 1H), 8.88-8.81 (m, 1H), 8.41-8.30 (m, 1H), 7.98-7.92 (m, 3H), 7.72-7.67 (m, 2H), 7.59-7.50 (m, 3H), 7.25-7.19 (m, 1H), 6.57-6.51 (m, 1H), 4.28 (br s, 2H), 3.79 (br s, 2H), 2.89-2.85 (m, 3H), 2.73-2.67 (m, 3H), 1.75-1.59 (m, 3H); MS (ESI) m/e 415 (M+H)$^+$.

Example 59

Preparation of (E)-N-Benzo[b]thiophen-2-ylmethyl-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting benzo[b]thiophen-2-ylmethyl-methylamine for the methyl-(1-propyl-naphthalen-2-ylmethyl)amine, the title compound (0.40 g, 74%) was prepared as a tan powder: $^1$H NMR (300 MHz, DMSO-d$_6$) δ 11.94 (br s, 1H), 11.14 (s, 1H), 8.89-8.84 (m, 1H), 8.33-8.31 (m, 1H), 7.90-7.87 (m, 1H), 7.81-7.79 (m, 1H), 7.66-7.52 (m, 1H), 7.39-7.31 (m, 4H), 5.13-4.87 (m, 2H), 4.30 (br s, 2H), 3.81 (br s, 2H), 3.20-3.00 (m, 3H), 2.89 (s, 3H); MS (ESI) m/e 407 (M+H)$^+$.

Example 60

Preparation of (E)-N-methyl-3-(4-methyl-2-oxo-2,3,4,5-tetrahydro-1H-pyrido[2,3-e][1,4]diazepin-7-yl)-N-(3-trifluoromethyl-benzyl)acrylamide hydrochloride According to the procedure of Example 1, except substituting methyl-(3-trifluoromethyl-benzyl)amine for the methyl-(1-propyl-naphthalen-2-ylmethyl)amine, the title compound (0.39 g, 69%) was prepared as a tan powder: $^1$H NMR (300 MHz, DMSO-d$_6$) δ 12.08 (br s, 1H), 11.23 (s, 1H), 8.83-8.81 (m, 1H), 8.33-8.27 (m, 1H), 7.66-7.35 (m, 6H), 4.96-4.72 (m, 2H), 4.30 (br s, 2H), 3.80 (br s, 2H), 3.17-2.85 (m, 6H); MS (ESI) m/e 419 (M+H)$^+$.

Example 61

Preparation of (E)-N-(2-Chloro-benzyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (2-chlorobenzyl)methylamine for the methyl-(1-propyl-naphthalen-2-ylmethyl)amine, the title compound (0.38 g, 72%) was prepared as an off-white powder: $^1$H NMR (300 MHz, DMSO-d$_6$) δ 11.90 (br s, 1H), 11.23-11.91 (m, 1H), 8.83-8.78 (m, 1H), 8.34-8.24 (m, 1H), 7.63-7.32 (m, 5H), 7.20-7.16 (m, 1H), 4.92-4.71 (m, 2H), 4.30 (br s, 2H), 3.81 (br s, 2H), 3.20 (s, 2H), 2.91-2.86 (m, 4H); MS (ESI) m/e 385 (M+H)$^+$.

Example 62

Preparation of (E)-N-Methyl-N-(4-methyl-benzyl)-3-(4-methyl-2-oxo-2,3,4,5-tetrahydro-1H-pyrido[2,3-e][1,4]diazepin-7-yl)acrylamide hydrochloride According to the procedure of Example 1, except substituting N-methyl-N-(4-methylbenzyl)amine for the methyl-(1-propyl-naphthalen-2-ylmethyl)amine, the title compound (0.24 g, 48%) was prepared as tan powder: $^1$H NMR (300 MHz, DMSO-d$_6$) δ 12.25 (br s, 1H), 11.23-11.22 (m, 1H), 8.82-8.79 (m, 1H), 8.33-8.30 (m, 1H), 7.62-7.58 (m, 1H), 7.57-7.32 (m, 1H), 7.19-7.10 (m, 4H), 4.78-4.58 (m, 2H), 4.29 (br s 2H), 3.80 (br s, 2H), 3.09-2.87 (m, 6H), 2.28 (s, 3H); MS (ESI) m/e 365 (M+H)$^+$.

Example 63

Preparation of (R)-(−)-(E)-N-Methyl-N-(1-methyl-1H-indol-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(1-methyl-1H-indol-2-ylmethyl)amine for the methyl-(1-propyl-naphthalen-2-ylmethyl)amine, and substituting (R)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.19 g, 35%) was prepared as a tan powder: [α]$^{25}_D$ −173.9° (c 1.00, methanol); $^1$H NMR (300 MHz, DMSO-d$_6$) δ 12.50 (br s, 1H), 11.27 (s, 1H), 8.83-8.74 (m, 1H), 8.32-8.25 (m, 1H), 7.65-7.60 (m, 1H), 7.51-7.32 (m, 3H), 7.15-6.96 (m, 2H), 6.43-6.18 (m, 1H), 5.07-4.86 (m, 2H), 4.47-4.21 (m, 3H), 3.79-2.88 (m, 9H), 2.09-1.88 (m, 3H); MS (ESI) m/e 430 (M+H)$^+$.

Example 64

Preparation of (S)-(+)-(E)-N-Methyl-N-(1-methyl-1H-indol-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(1-methyl-1H-indol-2-ylmethyl)amine for the methyl-(1-propyl-naphthalen-2-ylmethyl)amine, and substituting (S)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (91 mg, 23%) was prepared as a tan powder: [α]$^{25}_D$ +197.7° (c 1.00, methanol); $^1$H NMR (300 MHz, DMSO-d$_6$) δ 12.51 (br s, 1H), 11.28 (s, 1H), 8.83-8.74 (m, 1H), 8.32-8.25 (m, 1H), 7.65-7.60 (m, 1H), 7.51-7.32 (m, 3H), 7.15-6.98 (m, 2H), 6.43-6.18 (m, 1H), 5.07-4.86 (m, 2H), 4.46-4.21 (m, 3H), 3.73-3.62 (m, 4H), 3.18-2.87 (m, 5H), 2.08-1.88 (m, 3H); MS (ESI) m/e 430 (M+H)$^+$.

Example 65

Preparation of (E)-3-[4-(4-Methoxy-benzyl)-2-oxo-2,3,4,5-tetrahydro-1H-pyrido[2,3-e][1,4]diazepin-7-yl]-N-methyl-N-(1-methyl-1H-indol-2-ylmethyl)acrylamide hydrochloride According to the procedure of Example 1, except substituting methyl-(1-methyl-1H-indol-2-ylmethyl)amine for the methyl-(1-propyl-naphthalen-2-ylmethyl)amine, and substituting (E)-3-[4-(4-methoxy-benzyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.20 g, 83%) was prepared as a tan powder: $^1$H NMR (300 MHz, DMSO-d$_6$) δ 12.07 (br s, 1H), 11.23-11.21 (m, 1H), 8.78 (s, 1H), 8.27-8.20 (m, 1H), 7.64-6.99 (m, 10H), 6.42-6.18 (m, 1H), 5.06-4.86 (m, 2H), 4.32-4.20 (m, 4H), 3.77-3.68 (m, 8H), 3.12-3.00 (m, 3H); MS (ESI) m/e 510 (M+H)$^+$.

Example 66

Preparation of (E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide hydrochloride [AP-501382]

a) (E)-N-Methyl-N-(1-methyl-1H-indol-2-ylmethyl)-3-(2-oxo-2,3,4,5-tetrahydro-1H-pyrido[2,3-e][1,4]diazepin-7-yl)acrylamide A solution of (E)-3-[4-(4-methoxy-benzyl)-2-oxo-2,3,4,5-tetrahydro-1H-pyrido[2,3-e][1,4]diazepin-7-yl]-N-methyl-N-(1-methyl-1H-indol-2-ylmethyl)acrylamide (2.00 g, 3.92 mmol), from Example 65, in dichloroethane (80 mL) was cooled in an ice bath and treated with 1-chloroethyl chloroformate (0.47 mL, 4.31 mmol). After stirring at 0° C. under $N_2$ for 30 min and then at room temperature for 30 min, the mixture was heated to reflux for 1.5 h. The mixture was allowed to cool and then concentrated to dryness. Purification by flash column chromatography (silica gel, $CH_2Cl_2$/MeOH, 97:3) gave a tan solid. The solid was suspended in methanol and heated to reflux for 2 h. The mixture was allowed to cool and the solid was isolated by filtration, dissolved in $CH_2Cl_2$, washed with 1 N NaOH, dried over $Na_2SO_4$, filtered and the solvent was removed in vacuo. Purification by flash column chromatography (silica gel, $CH_2Cl_2$/MeOH, 97:3 to 95:5) gave the title compound (0.70 g, 49%) as an off-white solid: $^1$H NMR (300 MHz, $CDCl_3$) δ 8.38-8.33 (m, 2H), 7.72-7.67 (m, 1H), 7.60-7.57 (m, 2H), 7.32-7.20 (m, 3H), 7.14-7.09 (m, 1H), 6.90-6.80 (m, 1H), 6.49-6.38 (m, 1H), 4.93-4.78 (m, 2H), 4.08 (s, 2H), 3.95 (s, 2H), 3.71 (s, 3H), 3.13-3.07 (m, 3H); MS (ESI) m/e 390 (M+H)$^+$.

b) (E)-N-Methyl-N-(1-methyl-1H-indol-2-ylmethyl)-3-(2-oxo-2,3,4,5-tetrahydro-1H-pyrido[[2,3-e][1,4]diazepin-7-yl)acrylamide hydrochloride According to the procedure of Example 1(b), except substituting (E)-N-methyl-N-(1-methyl-1H-indol-2-ylmethyl)-3-(2-oxo-2,3,4,5-tetrahydro-1H-pyrido[2,3-e][1,4]diazepin-7-yl)acrylamide for the (E)-N-methyl-3-(4-methyl-2-oxo-2,3,4,5-tetrahydro-1H-pyrido[2,3-e][1,4]diazepin-7-yl)-N-(1-propyl-naphthalen-2-ylmethyl)acrylamide, the title compound (0.14 g, 89%) was prepared as a tan solid: $^1$H NMR (300 MHz, DMSO-$d_6$) δ 11.09-11.06 (m, 1H), 9.90-9.89 (s, 2H), 8.76-8.73 (m, 1H), 8.31-8.23 (m, 1H), 7.64-7.59 (m, 1H), 7.51-7.31 (m, 3H), 7.15-7.10 (m, 1H), 7.03-6.96 (m, 1H), 6.43-6.16 (m, 1H), 5.07-4.86 (m, 2H), 4.26-4.20 (m, 2H), 3.85-3.80 (m, 2H), 3.73-3.69 (m, 3H), 3.13-3.01 (m, 3H); MS (ESI) m/e 390 (M+H)$^+$.

Example 67

Preparation of (E)-N-Methyl-N-(3-methyl-benzo[b]thiophen-2-ylmethyl)-3-[4-(2-morpholin-4-yl-ethyl)-2-oxo-2,3,4,5-tetrahydro-1H-pyrido[2,3-e][1,4]diazepin-7-yl]acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-[4-(2-morpholin-4-yl-ethyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (90 mg, 74%) was prepared as a tan solid: $^1$H NMR (300 MHz, DMSO-$d_6$) δ 10.58 (br s, 2H), 8.62 (s, 1H), 8.27-8.25 (m, 1H), 7.88-7.86 (m, 1H), 7.75-7.72 (m, 1H), 7.61-7.53 (m, 1H), 7.42-7.29 (m, 3H), 5.15-4.89 (m, 2H), 4.03-3.65 (m, 12H), 3.28-3.17 (m, 4H), 3.01-2.64 (m, 3H), 2.42 (s, 3H); MS (ESI) m/e 520 (M+H)$^+$.

Example 68

Preparation of (E)-N-Methyl-N-(3-methyl-benzo[b]thiophen-2-ylmethyl)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.18 g, 53%) was prepared as an off-white powder: $^1$H NMR (300 MHz, DMSO-$d_6$) δ 10.91 (br s, 1H), 10.55 (br s, 1H), 8.61 (s, 1H), 8.18 (s, 1H), 7.88-7.86 (m, 1H), 7.75-7.72 (m, 1H), 7.61-7.52 (m, 1H), 7.42-7.28 (m, 3H), 5.14-4.89 (m, 2H), 4.42-4.38 (m, 1H), 4.01 (br s, 3H), 3.65 (s, 4H), 3.39 (br s, 4H), 3.16 (s, 2H), 3.04-2.94 (m, 3H), 2.74 (br s, 3H), 2.42 (s, 3H); MS (ESI) m/e 547 (M+H)$^+$.

Example 69

Preparation of (E)-N-Methyl-N-(3-methyl-benzo[b]thiophen-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.20 g, 56%) was prepared as an off-white powder: $^1$H NMR (300 MHz, DMSO-$d_6$) δ 10.88 (br s, 1H), 10.48 (br s, 1H), 8.58 (s, 1H), 8.31 (s, 1H), 7.88-7.86 (m, 1H), 7.75-7.72 (m, 1H), 7.60-7.55 (m, 1H), 7.42-7.30 (m, 3H), 5.16-4.89 (m, 2H), 3.98 (br s, 2H), 3.92-3.79 (m, 4H), 3.63 (br s, 2H), 3.37-3.33 (m, 6H), 3.18-3.10 (m, 2H), 2.94 (s, 1H), 2.63 (br s, 2H), 2.42 (s, 3H), 1.92 (br s, 2H); MS (ESI) m/e 534 (M+H)$^+$.

Example 70

Preparation of (E)-N-(2-Ethoxy-3-methoxy-benzyl)-N-methyl-3-{4-[2-(4-methyl-piperazin-1-yl)-2-oxo-ethyl]-2-oxo-2,3,4,5-tetrahydro-1H-pyrido[2,3-e][1,4]diazepin-7-yl}acryl hydrochloride According to the procedure of Example 1, except substituting (2-ethoxy-3-methoxy-benzyl)methylamine for the methyl-(1-propyl-naphthalen-2-ylmethyl)amine, and substituting (E)-3-{4-[2-(4-methyl-piperazin-1-yl)-2-oxo-ethyl]-2-oxo-2,3,4,5-tetrahydro-1H-pyrido[2,3-e][1,4]diazepin-7-yl}acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (82 mg, 47%) was prepared as an off-white powder: $^1$H NMR (300 MHz, DMSO-d$_6$) δ 10.97 (br s, 1H), 10.67 (br s, 1H), 8.64-8.60 (m, 1H), 8.23-8.14 (m, 1H), 7.58-7.52 (m, 1H), 7.39-7.33 (m, 1H), 7.07-6.94 (m, 2H), 6.69-6.63 (m m, 2H), 4.42-4.38 (m, 1H), 4.09-3.93 (m, 3H), 3.79 (s, 3H), 3.68 (br s, 2H), 3.47-3.37 (m, 8H), 3.11-2.97 (m, 5H), 2.75 (br s, 3H), 1.31-1.24 (m, 3H); MS (ESI) m/e 551 (M+H)$^+$.

Example 71

Preparation of (S)-(+)-(E)-N-Methyl-N-(3-methyl-benzo[b]thiophen-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (S)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.15 g, 62%) was prepared as a tan powder: [α]$^{25}_D$+167.8° (c 1.05, methanol); $^1$H NMR (300 MHz, DMSO-d$_6$) δ 12.33 (br s, 1H), 11.30 (br s, 1H), 8.84 (s, 1H), 8.33 (s, 1H), 7.89-7.86 (m, 1H), 7.75-7.72 (m, 1H), 7.65-7.55 (m, 1H), 7.42-7.31 (m, 3H), 5.13-4.90 (m, 2H), 4.47-4.22 (m, 2H), 3.61 (br s, 1H), 3.42-3.39 (br s, 4H), 3.17-2.95 (m, 3H), 2.42 (s, 3H), 2.10-1.88 (2H); MS (ESI) m/e 447 (M+H)$^+$.

Example 72

Preparation of (R)-(−)-(E)-N-Methyl-N-(3-methyl-benzo[b]thiophen-2-ylmethyl)-3-(10-oxo-2,3,4,9,10,10a-hexahydro-1H-3a,8,9-triaza-benzo[f]azulen-6-yl)acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (R)-(E)-3-(10-oxo-2,3,4,9,10,10a-hexahydro-1H-3a,8,9-triaza-benzo[f]azulen-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (96 mg, 57%) was prepared as a tan powder: [α]$^{25}_D$ −154.3° (c 1.01, methanol); $^1$H NMR (300 MHz, DMSO-d$_6$) δ 12.47 (br s, 1H), 11.29 (br s, 1H), 8.84 (s, 1H), 8.33 (s 1H), 7.89-7.86 (m, 1H), 7.75-7.72 (m, 1H), 7.65-7.60 (m, 1H), 7.42-7.31 (m, 3H), 5.13-4.90 (m, 2H), 4.48-4.25 (m, 2H), 3.59-3.47 (m, 5H), 3.17-2.95 (m, 3H), 2.42 (s, 3H), 2.10-1.89 (m, 2H); MS (ESI) m/e 447 (M+H)$^+$.

Example 73

Preparation of (E)-N-(4-Fluoro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-fluoro-naphthalen-1-ylmethyl)methylamine for the methyl-(1-propyl-naphthalen-2-ylmethyl)amine, the title compound (0.20 g, 72%) was prepared as a white powder: $^1$H NMR (500 MHz, DMSO-d$_6$) δ 12.22 (br s, 1H), 11.26-11.17 (m, 1H), 8.83-8.76 (m, 1H), 8.34-8.10 (m, 3H), 7.72-7.64 (m, 3H), 7.44-7.32 (m, 3H), 5.32-5.09 (m, 2H), 4.30 (br s, 2H), 3.85 (br s, 2H), 3.12-2.98 (m, 3H), 2.89-2.83 (m, 3H); MS (ESI) m/e 419 (M+H)$^+$.

Example 74

Preparation of (E)-N-(4-Chloro-naphthalen-1-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (4-chloro-naphthalen-1-ylmethyl)methylamine for the methyl-(1-propyl-naphthalen-2-ylmethyl)amine, the title compound (0.28 g, 48%) was prepared as a white powder: $^1$H NMR (500 MHz, DMSO-d$_6$) δ 12.29 (br s, 1H), 11.23-11.17 (m, 1H), 8.84-8.75 (m, 1H), 8.33-8.18 (m, 3H), 7.76-7.32 (m, 6H), 5.37-5.12 (m, 2H), 4.31 (br s, 2H), 3.80 (br s, 2H), 3.11-3.00 (m, 3H), 2.89-2.82 (m, 3H); MS (ESI) m/e 435 (M+H)$^+$.

Example 75

Preparation of (M-N-Methyl-N-(3-methyl-benzofuran-2-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting methyl-(3-methyl-benzofuran-2-ylmethyl)amine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.28 g, 78%) was prepared as an off-white powder: $^1$H NMR (300 MHz, DMSO-d$_6$) δ 10.74-10.54 (m, 2H), 8.61 (s, 1H), 8.29 (s, 1H), 7.63-7.47 (m, 3H), 7.34-7.23 (m, 3H), 5.03-4.80 (m, 2H), 4.02 (br s, 2H), 3.87-3.79 (m, 4H), 3.65 (br s, 2H), 3.48-3.38 (br s, 4H), 3.20-2.93 (m, 5H), 2.72-2.57 (br s, 2H), 2.26 (s, 3H), 1.95 (s, 2H); MS (ESI) m/e 518 (M+H)$^+$.

Example 76

Preparation of (E)-N-(2-Isopropoxy-3-methoxy-benzyl)-N-methyl-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting (2-isopropoxy-3-methoxy-benzyl)methylamine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.17 g, 44%) was prepared as an off-white powder: $^1$H NMR (300 MHz, DMSO-d$_6$) δ 11.01 (br s, 1H), 10.66 (br s, 1H), 8.62 (br s, 1H), 8.35-8.22 (m, 1H), 7.57-7.52 (m, 1H), 7.40-7.32 (m, 1H), 7.05-6.93 (m, 2H), 6.66-6.62 (m, 1H), 4.80-4.64 (m, 2H), 4.60-4.45 (m, 1H), 4.08 (br s, 2H), 3.87-3.81 (m, 6H), 3.79 (s, 3H), 3.68 (br s, 2H), 3.50-3.38 (m, 4H), 3.21 (br s, 2H), 3.10-2.72 (m, 3H), 2.01 (br s, 2H), 1.27-1.15 (m, 6H); MS (ESI) m/e 552 (M+H)$^+$.

Example 77

Preparation of (E)-N-Methyl-N-(3-methyl-benzo[b]thiophen-2-ylmethyl)-3-{4-[3-(4-methyl-piperazin-1-yl)propyl]-2-oxo-2,3,4,5-tetrahydro-1H-pyrido[2,3-e][1,4]diazepin-7-yl}acrylamide hydrochloride According to the procedure of Example 2, except substituting 7-bromo-4-[3-(4-methyl-piperazin-1-yl)propyl]-1,3,4,5-tetrahydro-pyrido[2,3-e][1,4]diazepin-2-one for the 7-bromo-3,3-dimethyl-1,3,4,5-tetrahydro-pyrido[2,3-e][1,4]diazepin-2-one, the title compound (0.15 g, 49/O) was prepared as a tan powder: $^1$H NMR (300 MHz, DMSO-d$_6$) δ 11.06 (br s, 1H), 10.64 (br s, 1H), 8.63 (s, 1H), 8.29-8.22 (m, 1H), 7.88-7.86 (m, 1H), 7.75-7.72 (m, 1H), 7.61-7.53 (m, 1H), 7.42-7.29 (m, 3H), 5.14-4.89 (m, 2H), 4.04 (br s, 2H), 3.65 (br s, 2H), 3.48-3.31 (m, 13H), 3.24-2.29 (m, 3H), 2.76 (br s, 2H), 2.42 (s, 3H), 1.89 (br s, 2H); MS (ESI) m/e 547 (M+H)$^+$.

Example 78

Preparation of (E)-N-Methyl-N-(2-methyl-benzofuran-3-ylmethyl)-3-[4-(3-morpholin-4-yl-propyl)-2-oxo-2,3,4,5-tetrahydro-1H-pyrido[2,3-e][1,4]diazepin-7-yl]acrylamide hydrochloride According to the procedure of Example 1, except substituting methyl-2-methyl-benzofuran-3-ylmethyl)amine for the methyl-(1-propyl-naphthalen-2-ylmethyl)amine, and substituting (E)-3-[4-(3-morpholin-4-yl-propyl)-2-oxo-2,3,4,5-tetrahydro-1H-pyrido[2,3-e][1,4]diazepin-7-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.24 g, 68%) was prepared as a white powder: $^1$H NMR (300 MHz, DMSO-d$_6$) δ 10.86 (br s, 1H), 10.47 (br s, 1H), 8.54 (br s, 1H), 8.38-8.29 (m, 1H), 7.78-7.46 (m, 3H), 7.32-7.15 (m, 3H), 4.97-4.74 (m, 2H), 4.02-3.91 (m, 5H), 3.87-3.79 (m, 4H), 3.63 (br s, 2H), 3.45-3.29 (m, 4H), 3.27-3.15 (m, 4H), 3.07-2.82 (m, 3H), 1.93 (br s, 2H); MS (ESI) m/e 518 (M+H)$^+$.

Example 79

Preparation of (E)-N-(3-Chloro-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (3-chlorobenzo[b]thiophen-2-ylmethyl)methylamine for the methyl-(1-propyl-naphthalen-2-ylmethyl)amine, the title compound (0.39 g, 88%) was prepared as an off-white powder: $^1$H NMR (300 MHz, DMSO-d$_6$) δ 12.40-11.21 (m, 2H), 8.84 (s, 1H), 8.35-8.30 (m, 1H), 8.04-8.00 (m, 1H), 7.79-7.77 (m, 1H), 7.55-7.34 (m, 4H), 5.21-4.94 (m, 2H), 4.29 (br s, 2H), 3.81 (br s, 2H), 3.24-3.00 (m, 3H), 2.88 (s, 3H); MS (ESI) m/e 441 (M+H)$^+$.

Example 80

Preparation of (E)-N-(5-Chloro-1-methyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (5-chloro-1-methyl-1H-indol-2-ylmethyl)methylamine for the methyl-(1-propyl-naphthalen-2-ylmethyl)amine, the title compound (0.32 g, 43%) was prepared as an off-white powder: $^1$H NMR (300 MHz, DMSO-d$_6$) δ 12.50-11.20 (m, 2H), 8.83-8.80 (m, 1H), 8.35-8.27 (m, 1H), 7.66-7.34 (m, 4H), 7.14-7.11 (m, 1H), 6.41-6.18 (m, 1H), 5.08-4.86 (m, 2H), 4.45-4.15 (m, 2H), 3.80-3.45 (m, 5H), 3.02-2.88 (m, 3H), 2.73 (s, 3H); MS (ESI) m/e 438 (M+H)$^+$.

Example 81

Preparation of (E)-N-(1,7-Dimethyl-1H-indol-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (1,7-dimethyl-1H-indol-2-ylmethyl)methylamine for the methyl-(1-propyl-naphthalen-2-ylmethyl)amine, the title compound (0.25 g, 43%) was prepared as an off-white powder: $^1$H NMR (300 MHz, DMSO-d$_6$) δ 11.85-11.12 (m, 2H), 8.78 (s, 1H), 8.31-8.21 (m, 1H), 7.65-7.60 (m, 1H), 7.38-7.27 (m, 2H), 6.88-6.82 (m, 2H), 6.39-6.11 (m, 1H), 5.03-4.83 (m, 2H), 4.24 (br s, 2H), 3.95-3.44 (m, 5H), 3.17-3.01 (m, 6H), 2.82-2.72 (m, 3H); MS (ESI) m/e 418 (M+H)$^+$.

Example 82

Preparation of (E)-N-(5-Fluoro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (5-fluoro-3-methyl-benzo[b]thiophen-2-ylmethyl)methylamine for the methyl-(1-propyl-naphthalen-2-ylmethyl)amine, the title compound (0.33 g, 75%) was prepared as a white powder: $^1$H NMR (300 MHz, DMSO-d$_6$) δ 12.15-11.20 (m, 2H), 8.82 (s, 1H), 8.33-8.29 (m, 1H), 7.93-7.89 (m, 1H), 7.65-7.19 (m, 4H), 5.14-4.89 (m, 2H), 4.27 (br s, 2H), 3.80 (br s, 2H), 3.18-2.96 (m, 3H), 2.86 (s, 3H), 2.40 (s, 3H); MS (ESI) m/e 439 (M+H)$^+$.

Example 83

Preparation of (E)-N-(5-Chloro-3-methyl-benzo[b]thiophen-2-ylmethyl)-N-methyl-3-(4-methyl-2-oxo-2,3,4,5-tetrahydro-1H-pyrido[2,3-e][1,4]diazepin-7-yl)acrylamide hydrochloride According to the procedure of Example 1, except substituting (5-chloro-3-methyl-benzo[b]thiophen-2-ylmethyl)methylamine for the methyl-(1-propyl-naphthalen-2-ylmethyl)amine, the title compound (0.39 g, 75%) was prepared as an off-white powder: $^1$H NMR (300 MHz, DMSO-d$_6$) δ 11.90-11.25 (m, 2H), 8.85 (s, 1H), 8.34-8.31 (m, 1H), 7.94-7.32 (m, 5H), 5.15-4.90 (m, 2H), 4.31 (br s, 2H), 3.83 (br s, 2H), 3.18-2.89 (m, 6H), 2.38 (s, 3H); MS (ESI) m/e 455 (M+H)$^+$.

Example 84

Preparation of (E)-3-(6-Amino-5-morpholin-4-ylmethyl-pyridin-3-yl)-N-(1,7-dimethyl-1H-indol-2-ylmethyl)-N-methyl-acrylamide hydrochloride According to the procedure of Example 1, except substituting (1,7-dimethyl-1H-indol-2-ylmethyl)methylamine for the methyl-(1-propyl-naphthalen-2-ylmethyl)amine, and substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.31 g, 80%) was prepared as pale yellow powder: $^1$H NMR (300 MHz, DMSO-$d_6$) δ 8.49 (s, 1H), 8.38-8.35 (m, 1H), 7.54-7.49 (m, 1H), 7.31-7.14 (m, 2H), 6.85-6.81 (m, 2H), 6.37-6.08 (m, 1H), 5.03-4.81 (m, 2H), 4.31 (br s, 2H), 3.96-3.72 (m, 7H), 3.42-2.99 (m, 10H), 2.72 (s, 3H);
MS (ESI) m/e 434 (M+H)$^+$.

Example 85

Preparation of (E)-3-(6-Amino-5-morpholin-4-ylmethyl-pyridin-3-yl)-N-(2-ethoxy-3-methoxy-benzyl)-N-methyl-acrylamide hydrochloride According to the procedure of Example 1, except substituting (2-ethoxy-3-methoxy-benzyl)methylamine for the methyl-(1-propyl-naphthalen-2-ylmethyl)amine, and substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.27 g, 70%) was prepared as pale yellow powder: $^1$H NMR (300 MHz, DMSO-$d_6$) δ 8.83-8.65 (m, 1H), 8.40 (s, 1H), 7.52-7.45 (m, 1H), 7.29-7.24 (m, 1H), 7.04-6.96 (m, 2H), 6.65-6.64 (m, 1H), 4.80-4.64 (m, 2H), 4.35 (br s, 2H), 4.02-3.79 (m, 10H), 3.39-2.83 (m, 8H), 1.31-1.25 (m, 3H); MS (ESI) m/e 441 (M+H)$^+$.

Example 86

Preparation of (E)-N-Methyl-N-(1-methyl-1H-indol-3-ylmethyl)-3-(4-methyl-2-oxo-2,3,4,5-tetrahydro-1H-pyrido[2,3-e][1,4]diazepin-7-yl)acrylamide According to the procedure of Example 1 (a), except substituting methyl-(1-methyl-1H-indol-3-ylmethyl)amine for the methyl-(1-propyl-naphthalen-2-ylmethyl)amine, the title compound (0.70 g, 75%) was prepared as an off-white powder and as a mixture of amide rotamers: $^1$H NMR (300 MHz, CDCl$_3$) δ 8.39-8.26 (m, 2H), 7.72-7.53 (m, 3H), 7.36-7.09 (m, 3H), 7.02-6.84 (m, 1H), 4.86-4.84 (m, 2H), 3.95-3.90 (m, 2H), 3.78-3.76 (m, 5H), 3.13-3.08 (m, 3H), 2.49-2.46 (m, 3H); MS (ESI) m/e 404 (M+H)$^+$.

Example 87

Preparation of (E)-7-{2-[Methyl-(1-methyl-1H-indol-3-ylmethyl)-carbamoyl]-vinyl}-2-oxo-1,2,3,5-tetrahydro-pyrido[2,3-e][1,4]diazepine-4-carboxylic acid benzyl ester According to the procedure of Example 1 (a), except substituting methyl-(1-methyl-1H-indol-3-ylmethyl)amine for the methyl-(1-propyl-naphthalen-2-ylmethyl)amine, and substituting (E)-7-(2-carboxy-vinyl)-2-oxo-1,2,3,5-tetrahydro-pyrido[2,3-e][1,4]diazepine-4-carboxylic acid benzyl ester hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.29 g, 73%) was prepared as an off-white powder and as a mixture of amide rotamers: $^1$H NMR (300 MHz, DMSO-$d_6$) δ 10.43 (s, 1H), 8.51 (s, 1H), 8.11-8.25 (m, 1H), 7.53-7.64 (m, 2H), 7.30-7.42 (m, 5H), 7.12-7.20 (m, 4H), 6.98-7.03 (m, 1H), 5.03-5.08 (m, 2H), 4.75-4.93 (m, 2H), 4.62 (s, 2H), 4.41 (s, 2H), 3.73-3.77 (m, 3H), 2.91-3.06 (m, 3H); MS (ESI) m/e 524 (M+H)$^+$.

Example 88

Preparation of (E)-3-(2,4-Dioxo-1,2,3,4-tetrahydro-pyrido[2,3-d]pyridin-6-yl)-N-methyl-N-(1-methyl-1H-indol-3-ylmethyl)acrylamide According to the procedure of Example 1 (a), except substituting methyl-(1-methyl-1H-indol-3-ylmethyl)amine for the methyl-(1-propyl-naphthalen-2-ylmethyl)amine, and substituting (E)-3-(2,4-dioxo-1,2,3,4-tetrahydro-pyrido[2,3-d]pyrimidin-6-yl)acrylic acid for the (E)-3-(4-methyl-2-oxo-2,3,4,5-tetrahydro-1H-pyrido[2,3-e][1,4]diazepin-7-yl) acrylic acid hydrochloride, the title compound (0.16 g, 34%) was prepared as a tan solid and as a mixture of amide rotamers; $^1$H NMR (300 MHz, DMSO-$d_6$) δ 11.84 (s, 1H), 11.53 (s, 1H), 8.91 (s, 1H), 8.73-8.66 (m, 1H), 7.78-7.30 (m, 5H), 7.17-7.12 (m, 1H), 7.03-6.98 (m, 1H), 4.96-4.73 (m, 2H), 3.76 (s, 3H), 3.07-2.90 (m, 3H); MS (ESI) m/e 390 (M+H)$^+$.

Example 89

Preparation of (E)-N-Methyl-N-(1-methyl-1H-indol-2-ylmethyl)-3-(2-oxo-2,3-dihydro-oxazolo[4,5-b]pyridin-6-yl)acrylamide According to the procedure of Example 1 (a), except substituting methyl-(1-methyl-1H-indol-2-ylmethyl)amine for the methyl-(1-propyl-naphthalen-2-ylmethyl)amine, and substituting (E)-3-(2-oxo-2,3-dihydro-oxazolo[4,5-b]pyridine-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.23 g, 34%) was prepared as an off-white solid and as a mixture of amide rotamers: $^1$H NMR (300 MHz, DMSO-$d_6$) δ 12.64 (br s, 1H), 8.37-8.12 (m, 2H), 7.64 (d, J=15.3 Hz, 1H), 7.51-7.26 (m, 3H), 7.17-7.07 (m, 1H), 7.04-6.94 (m, 1H), 6.42-6.17 (m, 1H), 5.06-4.85 (m, 2H), 3.73-3.68 (m, 3H), 3.12-2.99 (m, 3H); MS (ESI) m/e 363 (M+H)$^+$.

Example 90

Preparation of (E)-N-Methyl-N-(1-methyl-1H-indol-3-ylmethyl)-3-(2-oxo-2,3-dihydro-oxazolo[4,5-b]pyridin-6-yl)acrylamide According to the procedure of Example 1 (a), except substituting methyl-(1-methyl-1H-indol-3-ylmethyl)amine for the methyl-(1-propyl-naphthalen-2-ylmethyl)amine, and substituting (E)-3-(2-oxo-2,3-dihydro-oxazolo[4,5-b]pyridine-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, the title compound (0.075 g, 23%) was prepared as a light brown solid: $^1$H NMR (300 MHz, CDCl$_3$) δ 8.28-8.24 (m, 1H), 7.82 (d, J=15.4 Hz, 1H), 7.71-7.49 (m, 2H), 7.37-6.87 (m, 5H), 4.88-4.86 (m, 2H), 3.78 (s, 3H), 3.16-3.12 (m, 3H); MS (ESI) m/e 363 (M+H)$^+$.

Example 91

Preparation of (E)-3-(6-Amino-5-{2-[methyl-(1-methyl-1H-indol-2-ylmethyl)carbamoyl]ethyl}pyridin-3-yl)-N-methyl-N-(1-methyl-1H-indol-2-ylmethyl acrylamide According to the procedure of Example 1 (a), except substituting methyl-(1-methyl-1H-indol-2-ylmethyl)amine for the methyl-(1-propyl-naphthalen-2-ylmethyl)amine, and substituting (E)-3-[6-amino-5-(2-carboxy-ethyl)pyridin-3-yl]acrylic acid for the (E)-3-(4-methyl-2-oxo-2,3,4,5-tetrahydro-1H-pyrido[2,3-e][1,4]diazepin-7-yl)acrylic acid hydrochloride, the title compound (0.37 g, 28%) was prepared as an off-white powder and as a mixture of amide rotamers: $^1$H NMR (300 MHz, DMSO-$d_6$) δ 8.07 (m, 1H), 7.75-7.68 (m, 1H), 7.49-7.34 (m, 5H), 7.11-6.98 (m, 5H), 6.39-6.12 (m, 4H), 4.95-4.68 (m, 4H), 3.69 (s, 3H), 3.61 (s, 3H), 3.02-2.71 (m, 10H); MS (ESI) m/e 549 (M+H)$^+$.

Example 92

Preparation of (E)-3-(6-Amino-5-piperidin-1-ylmethyl-pyridin-3-yl)-N-methyl-N-(1-methyl-1H-indol-2-ylmethyl)acrylamide According to the procedure of Example 1 (a), except substituting (E)-3-(6-amino-5-piperidin-1-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, and substituting methyl-(1-methyl-1H-indol-2-ylmethyl)amine for the methyl-(1-propyl-naphthalen-2-ylmethyl)amine, the title compound (294 mg, 54%) was prepared as an off-white powder and as a mixture of amide rotamers: $^1$H NMR (300 MHz, DMSO-$d_6$) δ 8.12 (s, 1H), 7.78-7.68 (m, 1H), 7.49-7.38 (m, 3H), 7.14-6.97 (m, 3H), 6.63 (s, 2H), 6.41-6.18 (m, 1H), 5.02-4.83 (m, 21), 3.72-3.67 (m, 3H), 3.39-3.34 (m, 3H), 3.09-2.96 (m, 3H), 2.29 (br s, 3H), 1.49-1.40 (m, 6H); MS (ESI) m/e 418 (M+H)$^+$.

Example 93

Preparation of (E)-3-(6-Amino-5-pyrrolidin-1-ylmethyl-pyridin-3-yl)-N-methyl-N-(1-methyl-1H-indol-2-ylmethyl)acrylamide hydrochloride According to the procedure of Example 1, except substituting (E)-3-(6-amino-5-pyrrolidin-1-ylmethyl-pyridin-3-yl) acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (223 mg, 82%) was prepared as a light, yellow powder and as a mixture of amide rotamers: $^1$H NMR (300 MHz, DMSO-$d_6$) δ 10.2 (br s, 1H), 8.35 (s, 1H), 8.21 (s, 1H), 7.52-7.39 (m, 3H), 7.24-7.01 (m, 4H), 6.41-6.16 (m, 1H), 5.05-4.85 (m, 2H), 4.29 (s, 2H), 3.74-3.68 (m, 3H), 3.10-3.00 (m, 6H), 2.10-1.82 (m, 5H); MS (ESI) m/e 404 (M+H)$^+$.

Example 94

Preparation of (E)-3-[6-Amino-5-(4-methyl-piperazin-1-ylmethyl)pyridin-3-yl]-N-methyl-N-(1-methyl-1H-indol-2-ylmethyl)acrylamide hydrochloride According to the procedure of Example 1, except substituting (E)-3-[6-amino-5-(4-methyl-piperazin-1-ylmethyl)-pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (136 mg, 14%) was prepared as an off-white powder and as a mixture of amide rotamers: $^1$H NMR (300 MHz, DMSO-$d_6$) δ 10.7 (br s, 1H), 8.39 (s, 1H), 8.33 (s, 1H), 8.07 (br s, 2H), 7.55-7.01 (m, 6H), 6.41-6.17 (m, 1H), 5.07-4.85 (m, 2H), 3.73-3.62 (m, 7H), 3.11-2.98 (m, 8H), 2.73 (s, 3H); MS (ESI) m/e 433 (M+H)$^+$.

Example 95

Preparation of (E)-3-[6-Amino-5-(4-benzyl-piperidin-1-ylmethyl)pyridin-3-yl]-N-methyl-N-(1-methyl-1H-indol-2-ylmethyl)acrylamide hydrochloride According to the procedure of Example 1, except substituting (E)-3-[6-amino-5-(4-benzyl-piperidin-1-ylmethyl)-pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (156 mg, 30%) was prepared as an off-white powder and as a mixture of amide rotamers: $^1$H NMR (300 MHz, DMSO-$d_6$) δ 8.36-8.25 (m, 2H), 7.52-6.98 (m, 14H), 6.40-6.15 (m, 1H), 5.05-4.84 (m, 2H), 4.20 (s, 2H), 3.74-3.67 (m, 3H), 3.58-5.30 (m, 8H), 3.10-2.73 (m, 6H); MS (ESI) m/e 508 (M+H)$^+$.

Example 96

Preparation of (E)-3-(6-Amino-5-pyrrolidin-1-ylmethyl-pyridin-3-yl)-N-methyl-N-naphthalen-2-ylmethyl-acrylamide hydrochloride According to the procedure of Example 1, except substituting (E)-3-(6-amino-5-pyrrolidin-1-ylmethyl-pyridin-3-yl) acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-naphthalen-2-ylmethyl-amine for the methyl-(1-propyl-naphthalen-2-ylmethyl)amine, the title compound (51 mg, 57%) was prepared as a light, yellow solid and as a mixture of amide rotamers: $^1$H NMR (300 MHz, DMSO-$d_6$) δ 8.36-8.25 (m, 2H), 7.52-6.98 (m, 4H), 6.40-6.15 (m, 1H), 5.05-4.84 (m, 2H), 4.20 (s, 2H), 3.74-3.67 (m, 3H), 3.58-5.30 (m, 8H), 3.10-2.73 (m, 6H); MS (ESI) m/e 401 (M+H)$^+$.

Example 97

Preparation of (E)-3-[6-Amino-5-(4-methyl-piperazin-1-ylmethyl)pyridin-3-yl]-N-methyl-N-(3-methyl-benzo[b]thiophen-2-ylmethyl)acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(3-methyl-benzo[b]thiophen-2-ylmethyl)amine for the methyl-(1-propyl-naphthalen-2-ylmethyl)amine, the title compound (101 mg, 46%) was prepared as a light, yellow powder and as a mixture of amide rotamers: $^1$H NMR (300 MHz, DMSO-$d_6$) δ 10.6 (br s, 1H), 8.27 (s, 1H), 8.16 (s, 1H), 7.87 (d, J=7.6 Hz, 1H), 7.73 (d, J=7.1 Hz, 1H), 7.52-7.28 (m, 5H), 7.11 (d, J=15.3 Hz, 1H), 5.11-4.89 (m, 2H), 3.55 (br s, 2H), 3.37-3.23 (m, 4H), 3.14 (s, 2H), 3.10-2.92 (m, 5H), 2.72 (s, 3H), 2.42 (s, 3H);
MS (ESI) m/e 450 (M+H)$^+$.

Example 98

Preparation of (E)-3-(6-Amino-5-morpholin-4-ylmethyl-pyridin-3-yl)-N-methyl-N-(4-methyl-naphthalen-1-ylmethyl)acrylamide hydrochloride According to the procedure of Example 1, except substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-N-(4-methyl-naphthalen-1-ylmethyl)amine for the methyl-(1-propyl-naphthalen-2-ylmethyl)amine, the title compound (66 mg, 62%) was prepared as a pale, yellow powder and as a mixture of amide rotamers: $^1$H NMR (300 MHz, DMSO-$d_6$) δ 8.61-8.35 (m, 2H), 8.14-8.05 (m, 2H), 7.61-7.52 (m, 3H), 7.36-7.03 (m, 3H), 5.30-5.07 (m, 2H), 4.45-4.23 (m, 2H), 3.94-3.65 (m, 6H), 3.45-3.17 (m, 4H), 3.04-2.94 (m, 4H), 2.65 (s, 3H); MS (ESI) m/e 431 (M+H)$^+$.

Example 99

Preparation of (E)-3-(6-Amino-5-morpholin-4-ylmethyl-pyridin-3-yl)-N-methyl-N-(3-methyl-benzo[b]thiophen-2-ylmethyl)acrylamide hydrochloride According to the procedure of Example 1, except substituting (E)-3-(6-amino-5-morpholin-4-ylmethyl-pyridin-3-yl)acrylic acid for the (E)-3-(4-methyl-2-oxo-2,3,4,5-tetrahydro-1H-pyrido[2,3-e][1,4]diazepin-7-yl)acrylic acid hydrochloride, and substituting methyl-N-(3-methyl-benzo[b]thiophen-2-ylmethyl)amine for the methyl-(1-propyl-naphthalen-2-ylmethyl)amine, the title compound (111 mg, 67%) was prepared as a pale, yellow solid and as a mixture of amide rotamers: $^1$H NMR (300 MHz, DMSO-$d_6$) δ 8.60 (br s, 1H), 8.40 (s, 1H), 7.87 (d, J=7.4 Hz, 1H), 7.73 (d, J=6.9 Hz, 1H), 7.51 (d, J=15.3 Hz, 1H), 7.42-7.15 (m, 3H), 5.12-4.88 (m, 2H), 3.91-3.35 (m, 12H), 3.15 (s, 3H), 2.93 (s, 1H), 2.41 (s, 3H); MS (ESI) m/e 437 (M+H)$^+$;

Example 100

Preparation of (E)-3-(6-Amino-5-morpholin-4-ylmethyl-pyridin-3-yl)-N-(3,4-dimethyl-thieno[2,3-b]thiophen-2-ylmethyl)-N-methyl-acrylamide hydrochloride According the procedure of Example 1, except substituting (E)-3-(6-amino-5-morpholin-4-ylmethyl-pyridin-3-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3,4-dimethyl-thieno[2,3-b]thiophen-2-ylmethyl)methylamine for the methyl-(1-propyl-naphthalen-2-ylmethyl)amine, the title compound was prepared (70 mg, 13%) as a light, yellow powder and as a mixture of amide rotamers: $^1$H NMR (300 MHz, DMSO-$d_6$) δ 8.63 (s, 1H), 8.40 (s, 1H), 7.51 (d, J=15.1 Hz, 1H), 7.20-7.12 (m 2H), 5.00-4.77 (m, 2H), 4.40-4.32 (m, 2H), 3.95-3.15 (m, 10H), 3.13 (s, 3H), 2.90 (s, 1H), 2.46 (s, 3H), 2.45 (s, 3H); MS (ESI) m/e 457 (M+H)$^+$.

Example 101

Preparation of (E)-3-[6-Amino-5-(4-methyl-piperazin-1-ylmethyl)pyridin-3-yl]-N-(2-ethoxy-3-methoxy-benzyl)-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (2-ethoxy-3-methoxy-benzyl)methylamine for the methyl-(1-propyl-naphthalen-2-ylmethyl)amine, the title compound (177 mg, 25%) was prepared as a pale, yellow solid and as a mixture of amide rotamers: $^1$H NMR (300 MHz, DMSO-$d_6$) δ 10.4 (s, 1H), 8.28-8.19 (m, 2H), 7.73 (s, 1H), 7.47 (d, J=15.3 Hz, 1H), 7.21 (dd, J=14.9, 5.4 Hz, 1H), 7.05-6.94 (m, 2H), 6.64 (dd, J=7.2, 7.2 Hz, 1H), 4.78-4.63 (m, 2H), 4.03-3.93 (m, 2H), 3.79 (s, 3H), 3.55-3.33 (m, 7H), 3.09-2.85 (m, 7H), 2.74 (s, 3H), 1.31-1.25 (m, 3H); MS (ESI) m/e 454 (M+H)$^+$.

Example 102

Preparation of (E)-3-[6-Amino-5-(4-methyl-piperazin-1-ylmethyl)pyridin-3-yl]-N-methyl-N-(4-methyl-naphthalen-1-ylmethyl)acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(4-methyl-naphthalen-1-ylmethyl)amine for the methyl-(1-propyl-naphthalen-2-ylmethyl)amine, the title compound (143 mg, 20%) was prepared as a pale, yellow solid and as a mixture of amide rotamers: $^1$H NMR (300 MHz, DMSO-$d_6$) δ 10.9 (s, 1H), 8.35-8.29 (m, 2H), 8.18-8.05 (m, 4H), 7.65-7.52 (m, 3H), 7.41-7.03 (m, 3H), 5.30-5.07 (m, 2H), 3.63-3.33 (m, 6H), 3.04-2.95 (m, 7H), 2.72-2.65 (m, 6H); MS (ESI) nm/e 444 (M+H)$^+$.

Example 103

Preparation of (E)-3-[6-Amino-5-(4-methyl-piperazin-1-ylmethyl)pyridin-3-yl]-N-benzofuran-2-ylmethyl-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting benzofuran-2-ylmethyl-methylamine for the methyl-(1-propyl-naphthalen-2-ylmethyl)amine, the title compound (158 mg, 20%) was prepared as an off-white solid and as a mixture of amide rotamers: $^1$H NMR (300 MHz, DMSO-$d_6$) δ 10.7 (s, 1H), 8.35-8.33 (m, 2H), 7.99 (br s, 2H), 7.62-7.19 (m, 6H), 6.82 (d, J=12.2 Hz, 1H), 5.01-4.80 (m, 2H), 3.62-3.25 (m, 6H), 3.22 (s, 2H), 3.10-2.92 (m, 5H), 2.73 (s, 3H);

MS (ESI) m/e 420 (M+H)$^+$.

Example 104

Preparation of (E)-3-[6-Amino-5-(4-methyl-piperazin-1-ylmethyl) pyridin-3-yl]-N-(3-methoxy-2-propoxy-benzyl)-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3-methoxy-2-propoxy-benzyl)methylamine for the methyl-(1-propyl-naphthalen-2-ylmethyl)amine, the title compound (50 mg, 6%) was prepared as an off-white solid and as a mixture of amide rotamers: $^1$H NMR (300 MHz, DMSO-$d_6$) δ 10.6 (br s, 1H), 8.16 (d, J=9.2 Hz, 1H), 7.86 (s, 1H), 7.43 (d, J=15.2 Hz, 1H), 7.08-6.93 (m, 3H), 6.70-6.63 (m, 3H), 4.77-4.63 (m, 2H), 3.87 (q, J=6.8 Hz, 2H), 3.79 (s, 3H), 3.48-3.31 (m, 5H), 3.09-2.86 (m, 6H), 2.72 (s, 3H), 2.44-2.35 (m, 2H), 1.71 (app sextet, J=7.0 Hz, 2H), 0.98 (t, J=7.3 Hz, 3H); MS (ESI) m/e 468 (M+H)$^+$.

Example 105

Preparation of (E)-3-[6-Amino-5-(4-methyl-piperazin-1-ylmethyl)pyridin-3-yl]-N-(2-ethoxy-3-methyl-benzyl)-N-methyl-acrylamide hydrochloride According to the procedure of Example 1, except substituting (E)-3-[6-amino-5-(4-methyl-piperazin-1-ylmethyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (3-methyl-2-ethoxy-benzyl)methylamine for the methyl-(1-propyl-naphthalen-2-ylmethyl)amine, the title compound (114 mg, 17%) was prepared as an off-white solid: $^1$H NMR (300 MHz, DMSO-$d_6$) δ 8.42 (s, 1H), 8.33 (d, J=6.0 Hz, 1H), 8.13 (br s, 2H), 7.48 (dd, J=10.0, 5.1 Hz, 1H), 7.27 (d, J=9.3 Hz, 1H), 7.13 (dd, J=10.6, 4.4 Hz, 1H), 7.04-6.97 (m, 1H), 6.90-6.87 (m, 1H), 4.81-4.66 (m, 2H), 3.87-3.81 (m, 2H), 3.63-3.36 (m, 7H), 3.10-2.85 (m, 7H), 2.72 (s, 3H), 2.24 (s, 3H), 1.35 (t, J=4.2 Hz, 3H);

MS (ESI) m/e 438 (M+H)$^+$.

Example 106

Preparation of (E)-N-(3-Methoxy-2-propoxy-benzyl)-N-methyl-3-(7-oxo-5,6,7,8-tetrahydro-[1,8]naphthyridin-3-yl)acrylamide hydrochloride According to the procedure of Example 1, except substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, and substituting (3-methoxy-2-propoxy-benzyl)methylamine for the methyl-(1-propyl-naphthalen-2-ylmethyl)amine, the title compound (193 mg, 22%) was prepared as a white solid and as a mixture of amide rotamers: $^1$H NMR (300 MHz, DMSO-$d_6$) δ 10.6 (s, 1H), 8.35 (d, J=14.1 Hz, 1H), 8.09-8.01 (m, 1H), 7.50 (dd, J=15.2, 2.5 Hz, 1H), 7.24 (d, J=15.3 Hz, 1H), 7.07-6.94 (m, 2H), 6.67-6.62 (m, 1H), 5.43 (br s, 1H), 4.79-4.64 (m, 2H), 3.87 (q, J=6.9 Hz, 2H), 3.79 (s, 3H), 3.10-2.86 (m, 5H), 2.56-2.45 (m, 2H), 1.71 (app sextet, J=7.1 Hz, 2H), 0.97 (q, J=7.3 Hz, 3H); MS (ESI) nm/e 410 (M+H)$^+$.

Example 107

Preparation of (E)-N-(2-Isopropoxy-3-methoxy-benzyl)-N-methyl-3-(7-oxo-5,6,7,8-tetrahydro-[1,8]naphthyridin-3-yl)acrylamide hydrochloride According to the procedure of Example 1, except substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, and substituting (2-isopropoxy-3-methoxy-benzyl)methylamine for the methyl-(1-propyl-naphthalen-2-ylmethyl)amine, the title compound (326 mg, 83%) was prepared as a white solid and as a mixture of amide rotamers: $^1$H NMR (300 MHz, DMSO-$d_6$) δ 10.6 (s, 1H), 8.36 (d, J=17.3 Hz, 1H), 8.10-7.98 (m, 1H), 7.50 (d, J=15.3 Hz, 1H), 7.28-7.17 (m, 1H), 7.05-6.93 (m, 2H), 6.63 (dd, J=7.3, 7.3 Hz, 1H), 5.77 (br s, 1H), 4.77-4.63 (m, 2H), 4.59-4.45 (m, 1H), 3.79 (s, 3H), 3.08-2.81 (m, 5H), 2.56-2.44 (m, 2H), 1.23 (t, J=5.7 Hz, 6H);

MS (ESI) m/e 410 (M+H)$^+$.

Example 108

Preparation of (E)-N-(2-Ethoxy-3-methoxy-benzyl)-N-methyl-3-(7-oxo-5,6,7,8-tetrahydro-[1,8]naphthyridin-3-yl)acrylamide hydrochloride According to the procedure of Example 1, except substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, and substituting (2-ethoxy-3-methoxy-benzyl)methylamine for the methyl-(1-propyl-naphthalen-2-ylmethyl)amine, the title compound (429 mg, 88%) was prepared as an off-white solid and as a mixture of amide rotamers: $^1$H NMR (300 MHz, DMSO-$d_6$) δ 10.6 (s, 1H), 8.34 (d, J=13.2 Hz, 1H), 8.08-8.01 (m, 1H), 7.50 (dd, J=9.2, 2.0 Hz, 1H), 7.25 (dd, J=9.3, 5.5 Hz, 1H), 7.06-6.94 (m, 2H), 6.67 (dd, J=11.4, 4.7 Hz, 1H), 4.91 (br s, 1H), 4.78-4.64 (m, 2H), 4.02-3.95 (m, 2H), 3.79 (s, 3H), 3.09-2.86 (m, 5H), 2.55-2.49 (m, 2H), 1.30-1.26 (m, 3H); MS (ESI) m/e 396 (M+H)$^+$.

Example 109

Preparation of (E)-3-[6-(2,5-Dioxo-pyrrolidin-1-yl) pyridin-3-yl]-N-methyl-N-(1-methyl-1H-indol-2-ylmethyl)acrylamide A solution of 3-(6-aminopyridin-3-yl)-N-methyl-N-(1-methyl-1H-indol-2-ylmethyl)acrylamide (1.40 g, 4.37 mol) and succinic anhydride (520 mg, 5.24 mmol) in 1,4-dioxane (50 mL) was heated to reflux for 5 h. Another portion of succinic anhydride (520 mg, 5.24 mmol) was then added, and the solution was maintained at reflux overnight. The solvent was removed in vacuo. The residue was dissolved in $CH_2Cl_2$, and the solution was washed with satd $NaHCO_3$, water and brine, dried over $Na_2SO_4$, and concentrated. Purification by column chromatography (silica gel, $CH_2Cl_2$/MeOH, 98:2 to 97:3) gave the title compound (1.40 g, 76%) as an off-white solid and as a mixture of amide rotamers: mp 185-187° C.; $^1$H NMR (300 MHz, DMSO-$d_6$) δ 8.92-8.88 (m, 1H), 8.41-8.32 (m, 1H 7.69-7.64 (m, 1H), 7.52-7.34 (m, 4H), 7.15-7.09 (m, 1H), 7.04-6.99 (m, 1H), 6.44-6.21 (m, 1H), 5.08-4.87 (m, 2H), 3.73-3.70 (m, 3H), 3.14-3.00 (m, 3H), 2.83-2.81 (m, 4H); MS (ESI) m/e 403 (M+H)$^+$.

Example 110

Preparation of (E)-N-(5-{2-[Methyl-(1-methyl-1H-indol-2-ylmethyl)carbamoyl]vinyl}pyridin-2-yl)succinamide A mixture of (E)-3-[6-(2,5-dioxo-pyrrolidin-1-yl)pyridin-3-yl]-N-methyl-N-(1-methyl-1H-indol-2-ylmethyl)acrylamide (260 mg, 0.645 mmol) and ammonia (12 mL of 0.5M solution in 1,4-dioxane, 6.0 mmol) in a sealed tube was heated to 60° C. overnight. After cooling to ambient temperature, the resulting white precipitate was collected by filtration. The resulting solid was triturated with MeOH, washed with $Et_2O$, and dried under high vacuum at 50° C. for 2 d to give the title compound (140 mg, 52%) as a white solid and as a mixture of amide rotamers: mp 225-227° C.; $^1$H NMR (300 MHz, DMSO-$d_6$) δ 10.67-10.63 (m, 1H), 8.62-8.58 (m, 1H), 8.21-8.07 (m, 2H), 7.60-7.25 (m, 5H), 7.12 (dd, J=7.7, 7.4 Hz, 1H), 7.00 (dd, J=7.3, 6.9 Hz, 1H), 6.77 (br s, 1H), 6.42-6.17 (m, 1H), 5.05-4.85 (m, 2H), 3.72-3.68 (m, 3H), 3.12-2.99 (m, 3H), 2.64-2.60 (m, 2H), 2.40-2.36 (m, 2H); MS (ESI) m/e 420 (M+H)$^+$.

Example 111

Preparation of (E)-N-(5-{2-[Methyl-(1-methyl-1H-indol-2-ylmethyl)carbamoyl]vinyl}pyridin-2-yl)-4-(4-methyl-piperazin-1-yl-4-oxo-butyramide According to the procedure of Example 110, except substituting 1-methylpiperazine for the ammonia, the title compound (250 mg, 77%) was prepared as a light yellow solid and as a mixture of amide rotamers, after silica gel chromatography: mp 145-147° C. dec; $^1$H NMR (300 MHz, DMSO-$d_6$) δ 10.70-10.66 (m, 1H), 8.62-8.58 (m, 1H), 8.21-8.07 (m, 2H), 7.60-7.25 (m, 4H), 7.12-7.10 (m, 1H), 7.03-6.98 (m, 1H), 6.42-6.17 (m, 1H), 5.06-4.85 (m, 2H), 3.72-3.68 (m, 3H), 3.48 (br s, 4H), 3.12-2.99 (m, 3H), 2.63-2.26 (m, 11H), MS (ESI) m/e 503 (M+H)$^+$.

Example 112

Preparation of (E)-N-(5-{2-[Methyl-(1-methyl-1H-indol-2-ylmethyl)carbamoyl]vinyl}pyridin-2-yl)-4-morpholin-4-yl-4-oxo-butyramide According to the procedure of Example 110, except substituting morpholine for the ammonia, the title compound (200 mg, 57%) was prepared as a light yellow solid and as a mixture of amide rotamers: mp 206-209° C. dec; $^1$H NMR (300 MHz, DMSO-$d_6$) δ 10.70-10.66 (m, 1H), 8.62-8.58 (m, 1H), 8.21-8.07 (m, 2H), 7.60-7.39 (m, 3H), 7.34-7.25 (m, 1H), 7.12 (dd, J=7.4, 7.2 Hz, 1H), 7.03 (dd, J=7.3, 7.2 Hz, 1H), 6.42-6.17 (m, 1H), 5.06-4.85 (m, 2H), 3.72-3.68 (m, 3H), 3.57-3.37 (m, 8H), 3.12-2.99 (m, 3H), 2.70-2.56 (m, 4H); MS (ESI) m/e 490 (M+H)$^+$.

Example 113

Preparation of (E)-1-Methyl-piperidine-4-carboxylic acid (5-{2-[methyl-(1-methyl-1H-indol-2-ylmethyl)carbamoyl]vinyl}pyridin-2-yl)amide A solution of 1-methylpiperidine-4-carboxylic acid hydrochloride (184 mg, 1.03 mmol), 1,1'-carbonyldiimidazole (167 mg, 1.03 mmol) and triethylamine (0.26 mL, 1.8 mol) in 1,4-dioxane (20 mL) was heated to reflux for 3 h. (E)-3-(6-Aminopyridin-3-yl)-N-methyl-N-(1-methyl-1H-indol-2-ylmethyl)acrylamide (300 mg, 0.936 mmol) was then added and the resulting solution was heated to reflux overnight. TLC analysis indicated remaining starting material. After cooling, additional 1-methylpiperidine-4-carboxylic acid (184 mg, 1.03 mmol) and 1,1'-carbonyldiimidazole (167 mg, 1.03 mmol) were added, and the solution was heated to reflux overnight. The solvent was removed in vacuo. The residue was dissolved in $CH_2Cl_2$ (100 mL), and the solution was washed with satd $NaHCO_3$, water and brine, dried over $Na_2SO_4$ and concentrated. Purification by column chromatography (silica gel, $CH_2Cl_2$/MeOH/$Et_3N$, 94:5:1 to 89:10:1) gave the title compound (330 mg, 79%) as a pale yellow solid and as a mixture of amide rotamers: mp 120-135° C. dec; $^1$H NMR (300 MHz, DMSO-$d_6$) δ 10.65-10.61 (m, 1H), 8.62-8.57 (m, 1H), 8.23-8.06 (m, 2H), 7.60-7.34 (m, 3H), 7.31-7.25 (m, 1H), 7.12 (dd, J=8.0, 7.2 Hz, 1H), 7.03-6.98 (m, 1H), 6.42-6.16 (m, 1H), 5.06-4.85 (m, 2H), 3.72-3.68 (m, 3H), 3.12-2.99 (m, 3H), 2.85-2.82 (m, 2H), 2.52-2.44 (m, 1H), 2.19 (s, 3H), 1.95-1.88 (m, 2H), 1.74-1.61 (m, 4H); MS (ESI) m/e 446 (M+H)$^+$.

Example 114

Preparation of (E)-N-Methyl-N-(1-methyl-1H-indol-2-ylmethyl)-3-[6-(2-pyridin-4-yl-acetylamino)pyridin-3-yl]acrylamide According to the procedure of Example 113, except substituting 4-pyridylacetic acid hydrochloride for the 1-methylpiperidine-4-carboxylic acid hydrochloride, the title compound (140 mg, 34%) was prepared as a light yellow solid: $^1$H NMR (300 MHz, DMSO-$d_6$) δ 11.04-10.99 (m, 1H), 8.66-8.62 (m, 1H), 8.53-8.52 (m, 2H), 8.23-8.02 (m, 2H), 7.61-7.27 (m, 6H), 7.15-7.10 (m, 1H), 7.04-6.99 (m, 1H), 6.42-6.17 (m, 1H), 5.06-4.86 (m, 2H), 3.83-3.68 (m, 5H), 3.12-3.00 (m, 3H); MS (ESI) m/e 440 (M+H)$^+$.

Example 115

Preparation of (E)-1-Acetyl-piperidine-4-carboxylic acid (5-{2-[methyl-(1-methyl-1H-indol-2-ylmethyl)carbamoyl]vinyl}pyridin-2-yl)amide a) (E)-4-(5-{2-[Methyl-(1-methyl-1H-indol-2-ylmethyl)carbamoyl]vinyl}pyridin-2-ylcarbamoyl)piperidine-1-carboxylic acid benzyl ester A solution of [1-(carbobenzoxy)-4-piperidine]carboxylic acid (250 mg, 0.950 mmol) and 1,1'-carbonyldiimidazole (162 mg, 1.00 mmol) in 1,4-dioxane (15 mL) was heated to reflux for 3 h. (E)-3-(6-Aminopyridin-3-yl)-N-methyl-N-(1-methyl-1H-indol-2-ylmethyl)acrylamide (304 mg, 0.950 mol) was then added and the resulting solution was heated to reflux overnight. TLC analysis indicated remaining starting material. After cooling, additional [1-(carbobenzoxy)-4-piperidine]carboxylic acid (250 mg, 0.950 mmol) and 1,1'-carbonyldiimidazole (162 mg, 1.00 mmol) were added, and the mixture was heated to reflux overnight. The solvent was removed in vacuo. The residue was dissolved in $CH_2Cl_2$ (100 mL), and the solution was washed with satd $NaHCO_3$, water and brine, dried over $Na_2SO_4$, and concentrated. Purification by column chromatography (silica gel, $CH_2Cl_2$/MeOH, 98:2 to 97:3) gave the title compound (420 mg, 78%) a white solid and as a mixture of amide rotamers: $^1$H NMR (300 MHz, $CDCl_3$) δ 8.40 (s, 1H), 8.24 (d, J=8.7 Hz, 1H), 7.97-7.88 (m, 2H), 7.72 (d, J=15.4 Hz, 1H), 7.59 (d, J=7.9 Hz, 1H), 7.36-7.20 (m, 7H), 7.11 (dd, J=7.7, 7.0 Hz, 1H), 6.89 (d, J=15.3 Hz, 1H), 6.50-6.40 (m, 1H), 5.14 (s, 2H), 4.93-4.82 (m, 2H), 4.40-4.10 (m, 2H), 3.72-3.69 (m, 3H), 3.12-3.07 (m, 3H), 2.93-2.88 (m, 2H), 2.50-2.42 (m, 1H), 2.00-1.70 (m, 4H); MS (ESI) m/e 566 (M+H)$^+$.

b) (E)-Piperidine-4-carboxylic acid (5-{2-[methyl-(1-methyl-1H-indol-2-ylmethyl) carbamoyl]vinyl}pyridin-2-yl)amide To a solution of (E)-4-(5-{2-[methyl-(1-methyl-1H-indol-2-ylmethyl)carbamoyl]vinyl}pyridin-2-ylcarbamoyl)piperidine-1-carboxylic acid benzyl ester (250 mg, 0.442 mmol) in $CH_2Cl_2$ (15 mL) was added trimethylsilyl iodide (0.25 mL, 1.8 mmol). The mixture was stirred at ambient temperature for 2 h, and then quenched by the addition of MeOH. The solvent was removed in vacuo. Purification by column chromatography (silica gel, $CH_2Cl_2$/MeOH/$Et_3N$, 94.5:5:0.5 to 89.5:10:0.5 to 74.5:35:0.5) gave the title compound (110 mg, 58%) as a white solid and as a mixture of amide rotamers: $^1$H NMR (300 MHz, DMSO-$d_6$) δ 10.59-10.55 (m, 1H), 8.62-8.57 (m, 1H), 8.19-8.09 (m, 2H), 7.60-7.25 (m, 4H), 7.18-7.09 (m, 1H), 7.12-6.98 (m, 1H), 6.42-6.17 (m, 1H), 5.06-4.85 (m, 2H), 3.72-3.68 (m, 3H), 2.99-2.94 (m, 3H), 2.60-2.42 (m, 5H), 1.70-1.65 (m, 2H), 1.50-1.45 (m, 2H).

c) (E)-1-Acetyl-piperidine-4-carboxylic acid (5-{2-[methyl-(1-methyl-1H-indol-2-ylmethyl)carbamoyl]vinyl}pyridin-2-yl)amide To a solution of (E)-piperidine-4-carboxylic acid (5-{2-[methyl-(1-methyl-1H-indol-2-ylmethyl)carbamoyl]vinyl}pyridin-2-yl)amide (80 mg, 0.18 mmol) in $CH_2Cl_2$ (5 mL) was added excess of triethylamine and acetic anhydride (58 mg, 0.56 mmol). The reaction mixture was stirred at ambient temperature overnight. The solvent was removed in vacuo. Purification by column chromatography (silica gel, $CH_2Cl_2$/MeOH/$Et_3N$, 96.5:3:0.5) gave the title compound (87 mg, 99%) as pale yellow solid and as a mixture of amide rotamers: mp=100-120° C. dec; $^1$H NMR (300 MHz, DMSO-$d_6$) δ 10.72-10.67 (m, 1H), 8.63-8.59 (m, 1H), 8.23-8.06 (m, 2H), 7.60-7.26 (m, 4H), 7.12 (dd, J=1H), 7.03-6.98 (m, 1H), 6.42-6.17 (m, 1H), 5.06-4.85 (m, 2H), 4.39 (d, J=3.86 (d, J=11.6 Hz, 1H), 3.72-3.68 (m, 3H), 3.12-2.99 (m, 4H), 2.76 (m, 1H), 2.00 (s, 3H), 1.81-1.77 (m, 2H), 1.68-1.32 (m, 2H), 1.12-0.95 (m, 1H); MS (ESI) m/e 474 (M+H)$^+$.

Example 116

Preparation of (E)-3-(6-Amino-pyridin-3-yl)-N-(2,3-dimethoxy-benzyl)-N-methyl-acrylamide According to the procedure of Example 1 (a), except substituting (2,3-dimethoxy-benzyl)methyl-amine for the methyl-1-propyl-naphthalen-2-ylmethyl)amine, and substituting (E)-3-(6-amino-pyridin-3-yl)acrylic acid for the (E)-3-(4-methyl-2-oxo-2,3,4,5-tetrahydro-1H-pyrido[2,3-e][1,4]diazepin-7-yl)acrylic acid hydrochloride, the title compound was prepared as a pale yellow solid (434 mg, 53%): $^1$H NMR (300 MHz, DMSO-$d_6$) δ 8.14 (d, J=11.3 Hz, 1H), 7.89-7.77 (m, 1H), 7.44-7.39 (m, 1H), 7.05-6.94 (m, 3H), 6.68-6.45 (m, 4H), 4.74-4.61 (m, 2H), 3.80 (s, 3H), 3.74 (s, 3H), 3.07-2.86 (m, 3H); MS (ESI) m/e 328 (M+H)$^+$.

Example 117

Preparation of (E)-N-(4-Acetylamino-benzyl)-3-(6-amino-pyridin-3-yl)-N-methyl-acrylamide According to the procedure of Example 1 (a), except substituting N-(4-methylaminomethyl-phenyl)acetamide for the methyl-(1-propyl-naphthalen-2-ylmethyl)amine, and substituting (E)-3-(6-amino-pyridin-3-yl)acrylic acid for the (E)-3-(4-methyl-2-oxo-2,3,4,5-tetrahydro-1H-pyrido[2,3-e][1,4]diazepin-7-yl)acrylic acid hydrochloride, the title compound was prepared as a pale yellow solid (200 mg, 25%): $^1$H NMR (300 MHz, DMSO-$d_6$) δ 9.93 (s, 1H), 8.15-8.13 (m, 1H), 7.86-7.79 (m, 1H), 7.54-7.39 (m, 3H), 7.15 (s, 2H), 7.03-6.93 (m, 1H), 6.46 (s, 3H), 4.70-4.53 (m, 2H), 3.04-2.87 (m, 3H), 2.02 (s, 3H); MS (ESI) m/e 325 (M+H)$^+$.

Example 118

Preparation of (E)-3-[3-(2-Dimethylamino-ethyl)-2-oxo-1,2,3,4-tetrahydro-pyrido[2,3-d]pyrimidin-6-yl]-N-methyl-N-(1-methyl-1H-indol-2-ylmethyl)acrylamide According to the procedure of Example 1 (a), except substituting (E)-3-[3-(2-dimethylamino-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (40 mg, 22%) was prepared as a pale yellow solid: $^1$H NMR (300 MHz, DMSO-$d_6$) δ 9.98 (br s, 1H), 8.38-8.33 (m, 1H), 8.00-7.91 (m, 1H), 7.57-7.42 (m, 3H), 7.22-7.01 (m, 3H), 6.42-6.16 (m, 1H), 5.04-4.85 (m, 2H), 4.53-4.47 (m, 2H), 3.72-3.68 (m, 3H), 3.51-3.31 (m, 4H), 3.11-2.99 (m, 4H), 2.72-2.39 (m, 5H); MS (ESI) m/e 447 (M+H)$^+$.

Example 119

Preparation of (E)-N-Methyl-N-(1-methyl-1H-indol-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (355 mg, 61%) was prepared as a pale yellow solid: $^1$H NMR (300 MHz, DMSO-d$_6$) δ 10.16-9.98 (m, 2H), 8.42-8.37 (m, 1H), 8.00-7.92 (m, 1H), 7.58-7.39 (m, 3H), 7.24-6.99 (m, 3H), 6.42-6.15 (m, 1H), 5.06-4.85 (m, 2H), 4.57-4.51 (m, 2H), 4.00-3.97 (m, 2H), 3.73-3.37 (m, 11H), 3.15-2.98 (m, 5H); MS (ESI) m/e 489 (M+H)$^+$.

Example 120

Preparation of (E)-N-Methyl-N-(4-methyl-naphthalen-1-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(4-methyl-naphthalen-1-ylmethyl)amine for the methyl-(1-propyl-naphthalen-2-ylmethyl)amine, the title compound (175 mg, 50%) was prepared as a white solid: $^1$H NMR (300 MHz, DMSO-d$_6$) δ 10.50 (br s, 1H), 10.14-10.09 (m, 1H), 8.41-8.30 (m, 1H), 8.16-7.85 (m, 3H), 7.69-7.53 (m, 3H), 7.40-7.01 (m, 3H), 5.37-4.85 (m, 4H), 4.65-4.46 (m, 2H), 3.99-3.93 (m, 2H), 3.78-3.31 (m, 6H), 3.20-2.98 (m, 5H), 2.65-2.63 (m, 3H); MS (ESI) m/e 500 (M+H)$^+$.

Example 121

Preparation of (E)-N-Acenaphthen-5-ylmethyl-N-methyl-3-[3-(2-morpholin-4-yl-ethyl)-2 oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting acenaphthen-5-ylmethyl-methylamine for the methyl-(1-propyl-naphthalen-2-ylmethyl)amine, the title compound (175 mg, 43%) was prepared as a pale yellow solid: $^1$H NMR (300 MHz, DMSO-d$_6$) δ 10.15-10.11 (m, 2H), 8.41-8.33 (m, 1H), 7.98-7.96 (m, 1H), 7.88-7.74 (m, 1H), 7.60-7.44 (m, 2H), 7.38-7.12 (m, 4H), 5.23-5.01 (m, 2H), 4.55-4.46 (m, 2H), 4.00-3.96 (m, 2H), 3.86-3.36 (m, 10H), 3.12-2.89 (m, 7H); MS (ESI) m/e 512 (M+H)$^+$.

Example 122

Preparation of (E)-N-(2-Ethoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting (2-ethoxy-3-methoxy-benzyl)methylamine for the methyl-(1-propyl-naphthalen-2-ylmethyl)amine, the title compound (155 mg, 37%) was prepared as a off-white solid: $^1$H NMR (300 MHz, DMSO-d$_6$) δ 10.15-10.13 (m, 2H), 8.40-8.35 (m, 1H), 8.00-7.92 (m, 1H), 7.54-7.42 (m, 1H), 7.25-7.20 (m, 1H), 7.13-6.68 (m, 2H), 6.66-6.61 (m, 1H), 5.11 (br s, 1H), 4.78-4.63 (m, 2H), 4.57-4.52 (m, 2H), 4.01-3.95 (m, 4H), 3.82-3.58 (m, 9H), 3.37-3.35 (m, 2H), 3.20-2.86 (m, 5H), 1.28-1.18 (m, 3H); MS (ESI) m/e 510 (M+H)$^+$.

Example 123

Preparation of (E)-N-Methyl-N-(3-methyl-benzo[b]thiophen-2-ylmethyl)-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(3-methyl-benzo[b]thiophen-2-ylmethyl)amine for the methyl-(1-propyl-naphthalen-2-ylmethyl)amine, the title compound (140 mg, 33%) was prepared as a off-white solid: $^1$H NMR (300 MHz, DMSO-d$_6$) δ 10.45 (br s, 1H), 10.14 (s, 1H), 8.41-8.39 (m, 1H), 8.01 (s, 1H), 7.88-7.86 (m, 1H), 7.74-7.73 (m, 1H), 7.56-7.53 (m, 1H), 7.41-7.18 (m, 3H), 6.31 (br s, 1H), 5.11-4.88 (m, 2H), 4.57-4.55 (m, 2H), 3.99-3.96 (m, 2H), 3.75-3.71 (m, 4H), 3.57-3.55 (m, 2H), 3.39-3.37 (m, 2H), 3.1.5-2.94 (m, 5H), 2.42 (s, 3H); MS (ESI) m/e 506 (M+H)$^+$.

Example 124

Preparation of (E-(6-{2-[Methyl-(1-methyl-1H-indol-2-ylmethyl carbamoyl]vinyl}-2-oxo-1,4-dihydro-2H-pyrido[2,3-d]pyrimidin-3-yl)acetic acid a) (E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester According to the procedure of Example 1 (a), except substituting (E)-3-(3-ethoxycarbonylmethyl-2-oxo-1,2,3,4-tetrahydro-pyrido[2,3-d]pyrimidin-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(1-methyl-1H-indol-2-ylmethyl)amine for the methyl-(1-propyl-naphthalen-2-ylmethyl)amine, the title compound (1.20 g, 89%) was prepared as a tan solid and as a mixture of amide rotomers: $^1$H NMR (300 MHz, CDCl$_3$) δ 8.34-8.28 (m, 1H), 7.66-7.34 (m, 2H), 7.60-7.53 (m, 2H), 7.33-7.21 (m, 2H), 7.11 (t, J=7.5 Hz, 1H), 6.83 (d, J=15.0 Hz, 1H), 6.50-6.40 (m, 1H), 4.93-4.30 (m, 2H), 4.59-4.52 (m, 2H), 4.27-4.19 (m, 4H), 3.71 (s, 3H), 3.13-3.06 (m, 3H), 1.30 (t, J=7.2 Hz, 3H); MS (ESI) m/e 462 (M+H)$^+$.

b) (E)-(6-{2-[Methyl-(1-methyl-1H-indol-2-ylmethyl)carbamoyl]vinyl}-2-oxo-1,4-dihydro-2H-pyrido[2,3-d]pyrimidin-3-yl)acetic acid A suspension of (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester (0.40 g, 0.87 mmol) in methanol (30 mL) was treated with 1N NaOH (10 mL, 10 mmol). The mixture was heated at reflux for 2 h. After cooling, the methanol was evaporated. The residue was diluted with H$_2$O (15 mL) and neutralized to pH 6 with 2N HCl. The solid was collected by filtration, and triturated subsequently with a mixture CH$_3$CN/H$_2$O (9:1, v/v), diethyl ether, and methanol to give the title compound (180 mg, 48%) as a tan solid: $^1$H NMR (300 MHz, DMSO-d$_6$) δ 12.78 (s, 1H), 10.09-10.06 (m, 1H), 8.39-8.36 (m, 1H), 8.01-7.92 (m, 1H), 7.57-7.39 (m, 3H), 7.26-6.69 (m, 3H), 6.42-6.18 (m, 1H), 5.04-4.85 (m, 2H), 4.53-4.48 (m, 2H), 4.05-4.01 (m, 2H), 3.72-3.68 (m, 3H), 3.11-2.99 (m, 3H); MS (ESI) m/e 434 (M+H)$^+$.

Example 125

Preparation of Sodium (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetate A suspension of (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester (0.19 g, 0.40 mmol) in methanol (20 mL) was treated with 1N NaOH (0.80 mL, 0.80 mmol). The mixture was heated at reflux for 2 h. After cooling, the solid was collected by filtration to give the title compound (140 mg, 77%) as an off-white solid: $^1$H NMR (300 MHz, DMSO-d$_6$+D$_2$O) δ 8.30-8.25 (m, 1H), 7.97-7.86 (m, 1H), 7.55-7.42 (m, 3H), 7.17-7.05 (m, 3H), 6.46-6.22 (m, 1H), 5.03-4.86 (m, 2H), 4.55 (s, 1H), 4.48 (s, 1H), 3.76-3.67 (m, 5H), 3.13-3.05 (m, 3H); MS (ESI) m/e 434 (M+H)$^+$.

Example 126

Preparation of Sodium (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetate a) (E)-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid ethyl ester According to the procedure of Example 1 (a), except substituting (E)-3-(3-ethoxycarbonylmethyl-2-oxo-1,2,3,4-tetrahydro-pyrido[2,3-d]pyrimidin-6-yl)acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and substituting methyl-(3-methyl-benzo[b]thiophen-2-ylmethyl)amine for the methyl-(1-propyl-naphthalen-2-ylmethyl)amine, the title compound (380 mg, 59%) was prepared as a tan solid and as a mixture of amide rotomers: $^1$H NMR (300 MHz, DMSO-d$_6$) δ 10.15 (s, 1H), 8.40 (s, 1H), 8.01 (s, 1H), 7.87 (d, J=7.5 Hz, 1H), 7.43 (d, J=7.8 Hz, 1H), 7.64 (d, J=15.3 Hz, 1H), 7.42-7.16 (m, 3H), 5.11-4.88 (m, 2H), 4.53 (s, 2H), 4.18-4.11 (m, 4H), 3.14-2.93 (m, 3H), 2.42 (s, 3H), 1.21 (t, J=6.9 Hz, 3H); MS (ESI) m/e 479 (M+H)$^+$.

b) Sodium (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetate According to the procedure of Example 125, except substituting (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid ethyl ester for the (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester, the title compound (300 mg, 85%) was prepared as a white solid: $^1$H NMR (300 MHz, DMSO-d$_6$+D$_2$O) δ 8.29-8.28 (m, 1H), 7.95-7.84 (m, 2H), 7.77 (d, J=4.8 Hz, 1H), 7.53-7.49 (m, 1H), 7.46-7.43 (m, 1H), 7.40-7.37 (m, 1H), 7.22-7.09 (m, 1H), 5.07-4.89 (m, 2H), 4.55-4.53 (m, 2H), 3.78-3.77 (m, 2H), 3.17-3.01 (m, 3H), 2.42 (s, 3H); MS (ESI) m/e 451 (M+H)$^+$.

Example 127

Preparation of (E)-N-Methyl-N-(1-methyl-1H-indol-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride According to the procedure of Example 1, except substituting (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid for the (E)-3-(4-methyl-2-oxo-2,3,4,5-tetrahydro-1H-pyrido[2,3-e][1,4]diazepin-7-yl)acrylic acid hydrochloride, and substituting 1-methylpiperazine for the methyl-(1-propyl-naphthalen-2-ylmethyl)amine, the title compound (173 mg, 43%) was prepared as a off-white solid: $^1$H NMR (300 MHz, DMSO-d$_6$) □ 10.78 (br s, 1H), 10.07-10.03 (m, 1H), 8.41-8.37 (m, 1H), 7.98-7.90 (m, 1H), 7.57-7.39 (m, 3H), 7.25-6.99 (m, 3H), 6.42-6.17 (m, 1H), 5.04-4.85 (m, 2H), 4.46-4.03 (m, 5H), 3.72-3.68 (m, 3H), 3.44-3.41 (m, 3H), 3.11-2.91 (m, 7H), 2.78 (s, 3H); MS (ESI) m/e 516 (M+H)$^+$.

Example 128

Preparation of (E)-N-Methyl-N-(3-methyl-benzo[b]thiophen-2-ylmethyl)-3-{3-[2-(4-methyl-piperazin-1yl)-2-oxo-ethyl]-2-oxo-1,2,3,4-tetrahydro-pyrido[2,3-d]pyrimidin-6-yl}acrylamide hydrochloride a) (E)-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid According to the procedure of Example 124 (b), except substituting (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid ethyl ester for the (E)-(6-{2-[methyl-(1-methyl-1H-indol-2-ylmethyl)carbamoyl]vinyl}-2-oxo-1,4-dihydro-2H-pyrido[2,3-d]pyrimidin-3-yl)acetic acid ethyl ester, the title compound (720 mg, 89%) was prepared as a light yellow solid and as a mixture of amide rotomers: $^1$H NMR (300 MHz, DMSO-d$_6$) δ 10.78 (br s, 1H), 10.08 (s, 1H), 8.39 (s, 1H), 8.01 (s, 1H), 7.88 (d, J=7.5 Hz, 1H), 7.74 (d, J=7.4 Hz, 1H), 7.56-7.16 (m, 4H), 5.11-4.88 (m, 2H), 4.52 (s, 2H), 4.04 (s, 2H), 3.14-2.93 (m, 3H), 2.42 (s, 3H); MS (ESI) m/e 451 (M+H)$^+$.

b) (E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride According to the procedure of Example 1, except substituting (E)-(6-{2-[methyl-(3-methyl-benzo[b]thiophen-2-ylmethyl)carbamoyl]vinyl}-2-oxo-1,4-dihydro-2H-pyrido[2,3-d]pyrimidin-3-yl)acetic acid for the (E)-3-(4-methyl-2-oxo-2,3,4,5-tetrahydro-1H-pyrido[2,3-e][1,4]diazepin-7-yl) acrylic acid, and substituting 1-methylpiperazine for the methyl-(1-propyl-naphthalen-2-ylmethyl)amine, the title compound (44 mg, 9%) was prepared as a pale-yellow solid, after purification by preparative HPLC: $^1$H NMR (300 MHz, DMSO-$d_6$) δ 10.60 (br s, 1H), 10.06 (s, 1H), 8.40 (s, 1H), 7.98 (s, 1H), 7.87 (d, J=7.5 Hz, 1H), 7.73 (d, J=8.0 Hz, 1H), 7.56-7.51 (m, 1H), 7.42-7.15 (m, 3H), 5.11-4.88 (m, 2H), 4.46-4.38 (m, 4H), 4.22-4.04 (m, 2H), 3.61-3.42 (m, 4H), 3.17-2.73 (m, 8H), 2.42 (s, 3H); MS (ESI) m/e 533 (M+H)$^+$.

Example 129

Preparation of (E)-N-Methyl-N-(3-methyl-benzo[b]thiophen-2-ylmethyl)-3-{3-[2-(4-methyl-piperazin-1-yl)-2-oxo-ethyl]-2-oxo-1,2,3,4-tetrahydro-pyrido[2,3-d]pyrimidin-6-yl}acrylamide hydrochloride a) (E)-3-[3-(2,2-Dimethoxy-ethyl)-2-oxo-1,2,3,4-tetrahydro-pyrido[2,3-d]pyrimidin-6-yl]-N-methyl-N-(3-methyl-benzo[b]thiophen-2-ylmethyl)acrylamide According to the procedure of Example 2, except substituting 6-bromo-3-(2,2-dimethoxy-ethyl)-3,4-dihydro-1H-pyrido[2,3-d]pyrimidin-2-one for the 7-bromo-3,3-dimethyl-1,3,4,5-tetrahydro-pyrido[2,3-e][1,4]diazepin-2-one, the title compound (490 mg, 60%) was prepared as a white solid and as a mixture of amide rotomers: $^1$H NMR (300 MHz, CDCl$_3$) δ 8.33 (br s, 1H), 8.07-8.02 (m, 1H), 7.78-7.76 (m, 1H), 7.71-7.67 (m, 2H), 7.52-7.48 (m, 1H), 7.38-7.22 (m, 2H), 6.89-6.80 (m, 1H), 4.95-4.88 (m, 2H), 4.61-4.58 (m, 3H), 3.52-3.51 (m, 2H), 3.44 (s, 6H), 3.15-3.11 (m, 3H), 2.44 (s, 3H); MS (ESI) m/e 481 (M+H)$^+$.

b) (E)-N-Methyl-N-(3-methyl-benzo[b]thiophen-2-ylmethyl)-3-[2-oxo-3-(2-oxo-ethyl)-1,2,3,4-tetrahydro-pyrido[2,3-d]pyrimidin-6-yl]acrylamide A suspension of (E)-3-[3-(2,2-dimethoxy-ethyl)-2-oxo-1,2,3,4-tetrahydro-pyrido[2,3-d]pyrimidin-6-yl]-N-methyl-N-(3-methyl-benzo[b]thiophen-2-ylmethyl)acrylamide (450 mg, 0.937 mmol) in CH$_2$Cl$_2$ (20 mL) was treated with TFA (1 mL) and H$_2$O (1 mL). The reaction was allowed to stir overnight at room temperature. The solution was washed with saturated NaHCO$_3$ (2×15 mL). The aqueous solutions were extracted with CH$_2$Cl$_2$ (40 mL). The combined CH$_2$Cl$_2$ solutions were washed with brine, dried over Na$_2$SO$_4$, and concentrated to give the title compound (440 mg, 99%) as a white solid and as amide rotomers: $^1$H NMR (300 MHz, DMSO-$d_6$) δ 10.15 (s, 1H), 9.54 (s, 1H), 8.40 (s, 1H), 8.02 (s, 1H), 7.87 (d, J=7.5 Hz, 1H), 7.73 (d, J=7.8 Hz, 1H), 7.53-7.31 (m, 4H), 5.11-4.88 (m, 2H), 4.51 (s, 2H), 4.18 (s, 2H), 3.15-2.93 (m, 3H), 2.42 (s, 3H); MS (ESI) m/e 435 (M+H)$^+$.

c) (E)-N-Methyl-N-(3-methyl-benzo[b]thiophen-2-ylmethyl)-3-{3-[2-(4-methyl-piperazin-1-yl)-ethyl]-2-oxo-1,2,3,4-tetrahydro-pyrido[2,3-d]pyrimidin-6-yl}acrylamide hydrochloride To a suspension of (E)-N-methyl-N-(3-methyl-benzo[b]thiophen-2-ylmethyl)-3-[2-oxo-3-(2-oxo-ethyl)-1,2,3,4-tetrahydro-pyrido[2,3-d]pyrimidin-6-yl]acrylamide (410 mg, 0.945 mmol) in dichloroethane (25 mL) was added 1-methylpiperazine (0.16 mL, 1.4 mmol) and a few drops of HOAc, followed by the addition of NaBH(OAc)$_3$ (320 mg, 1.51 mmol). The reaction mixture was allowed to stir over night at room temperature. The resulting precipitate was collected by filtration to give a white solid. Purification by column chromatography (silica gel, CH$_2$Cl$_2$/MeOH/Et$_3$N, 90/9.5/0.5 to 85/14.5/0.5) afforded the free base (400 mg, 82%) of the title compound. The free base was dissolved in a mixture of CH$_2$Cl$_2$/MeOH (8 mL/0.7 mL). To this was added 1N HCl in diethyl ether (0.48 mL, 0.48 mmol), and the mixture was stirred at room temperature for 30 min. The resulting precipitate was collected by filtration to give the title compound (190 mg, 72%) as a white solid: $^1$H NMR (300 MHz, DMSO-$d_6$) δ 11.95-10.90 (m, 1H), 10.07 (s, 1H), 8.40 (s, 1H), 7.99 (s, 1H), 7.87 (d, J=4.5 Hz, 1H), 7.73 (d, J=4.5 Hz, 1H), 7.54 (d, J=9.3 Hz, 1H), 7.41-7.17 (m, 3H), 5.11-4.88 (m, 2H), 4.58-4.56 (m, 2H), 3.93-3.29 (m, 1H), 3.17 (s, 3H), 2.94-2.80 (m, 4H), 2.42 (s, 3H); MS (ESI) m/e 519 (M+H)$^+$.

Example 130

Preparation of (E)-2-Amino-5-{2-[methyl-(1-methyl-1H-indol-2-ylmethyl)carbamoyl]vinyl}-N-(2-morpholin-4-yl-ethyl)nicotinamide hydrochloride According to the procedure of Example 1, except substituting 3-[6-amino-5-(2-morpholin-4-yl-ethylcarbamoyl)pyridin-3-yl]acrylic acid hydrochloride for the (E)-3-(4-methyl-2-oxo-2,3,4,5-tetrahydro-1H-pyrido[2,3-e][1,4]diazepin-7-yl)acrylic acid hydrochloride, and methyl-(1-methyl-1H-indol-2-ylmethyl)amine for the methyl-(1-propyl-naphthalen-2-ylmethyl)amine, the title compound (170 mg, 23%) was prepared as a pale yellow solid: $^1$H NMR (300 MHz, DMSO-$d_6$) δ 10.87-10.61 (m, 1H), 9.69-9.66 (m, 1H), 9.40-9.28 (m, 1H), 8.70-8.31 (m, 3H), 7.95-7.39 (m, 4H), 7.15-6.97 (m, 2H), 6.40-6.08 (m, 1H), 5.27-4.85 (m, 2H), 3.94-3.55 (m, 12H), 3.20-2.96 (m, 6H); MS (ESI) m/e 477 (M+H)$^+$.

Example 131

Preparation of (E)-N-(3-Methyl-benzo[b]thiophen-2-ylmethyl)-3-[3-(3-morpholin-4-yl-propyl)-2-oxo-1,2,3,4-tetrahydro-pyrido[2,3-d]pyrimidin-6-yl]acrylamide hydrochloride According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-[3-(3-morpholin-4-yl-propyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl) acrylic acid hydrochloride, the title compound (0.86 g, 86%) was prepared as an off-white solid: $^1$H NMR (500 MHz, DMSO-$d_6$) δ 10.96 (br s, 1H), 10.01 (br s, 1H), 8.39 (s, 1H), 8.01 (d, J=7.0 Hz, 1H), 7.86 (d, J=7.5 Hz, 1H), 7.73 (d, J=7.0 Hz, 1H), 7.58-7.51 (m, 1H), 7.40 (t, J=7.5 Hz, 1H), 7.32 (t, J=7.5 Hz, 1H), 7.21-7.12 (m, 1H), 5.16-4.63 (m, 2H), 4.51-4.49 (m, 2H), 3.94-3.92 (m 2H), 3.80-3.75 (m, 2H), 3.43-3.36 (m, 5H), 3.14-2.93 (m, 6H), 2.41 (s, 3H), 1.96-2.09 (m, 2H); MS (ESI) m/e 520 (M+H)$^+$.

Example 132

Preparation of (E)-N-(2-Ethoxy-3-methoxy-benzyl)-N-methyl-3-[3-(3-morpholin-4-yl-propyl)-2-oxo-1,2,3,4-tetrahydro-pyrido[2,3-d]pyrimidin-6-yl]acrylamide hydrochloride According to the procedure of Example 1, except substituting (2-ethoxy-3-methoxy-benzyl)methylamine for the methyl-(1-propyl-naphthalen-2-ylmethyl)amine, and substituting (E)-3-[3-(3-morpholin-4-yl-propyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.67 g, 62%) was prepared as an off-white solid: $^1$H NMR (500 MHz, DMSO-$d_6$) δ 11.16 (br s, 1H), 9.97 (d, J=11 Hz, 1H), 8.40-8.30 (m, 1H), 8.02-7.91 (m, 1H), 7.53-7.46 (m, 1H), 7.24-7.18 (m, 1H), 7.09-6.93 (m, 2H), 6.71-6.63 (m, 1H), 4.79-4.62 (m, 2H), 4.55-4.40 (m, 2H), 4.21-3.85 (m, 2H), 3.80-3.75 (m, 6H), 3.45-3.37 (m, 4H), 3.09-2.86 (m, 8H), 2.08-1.97 (m, 2H), 1.30-1.26 (m, 3H); MS (ESI) m/e 524 (M+H)$^+$.

Example 133

Preparation of (E)-N-(5-{2-Methyl-(3-methyl-benzo[b]thiophen-2-ylmethyl)carbamoyl]vinyl}pyridin-2-yl)-4-(4-methyl-piperazin-1-yl)-4-oxo-butyramide a) (E)-3-(6-Amino-pyridin-3-yl)-N-methyl-N-(3-methyl-benzo[b]thiophen-2-ylmethyl)acrylamide According to the procedure of Example 1, except substituting methyl-(3-methyl-benzo[b]thiophen-2-ylmethyl)amine for the methyl-(1-propyl-naphthalen-2-ylmethyl)amine, and substituting (E)-3-(6-amino-pyridin-3-yl)acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (2.2 g, 73%) was prepared as a yellow solid: $^1$H NMR (300 MHz, DMSO-$d_6$) 8.21 (s, 1H), 2.81-2.75 (m, 1H), 2.71-2.59 (m, 3H), 7.41-7.25 (m, 2H), 6.85-6.65 (m, 1H), 6.50-6.41 (m, 1H), 5.01-4.81 (m, 2H), 4.78-4.61 (m, 2H), 3.12 (s, 3H), 2.41 (s, 3H); MS (ESI) m/e 338 (M+H)$^+$.

b) (E)-3-[6-(2,5-Dioxo-pyrrolidin-1-yl)pyridin-3-yl]-N-methyl-N-(3-methyl-benzo[b]thiophen-2-ylmethyl)acrylamide According to the procedure of Example 109, except substituting (E)-3-(6-amino-pyridin-3-yl)-N-methyl-N-(3-methyl-benzo[b]thiophen-2-ylmethyl)acrylamide (2.2 g, 6.6 mmol) for the (E)-3-(6-aminopyridin-3-yl)-N-methyl-N-(1-methyl-1H-indol-2-ylmethyl)acrylamide, and succinic anhydride (0.80 g, 8.0 mmol) in 1,4-dioxane (119 mL) was heated to reflux for 15 h overnight. The title compound (1.7 g, 61%) was prepared as a yellow oil: $^1$H NMR (300 MHz, DMSO-$d_6$) δ 8.78 (s, 1H), 8.01-7.91 (m, 1H), 7.80-7.72 (m, 2H), 7.70-7.63 (m, 1H), 7.43-7.39 (m, 3H), 7.01-6.92 (m, 1H), 5.01-4.85 (m, 2H), 3.21-3.10 (m, 3H), 2.90-2.85 (m, 4H), 2.44 (s, 3H); MS (ESI) m/e 420 (M+H)$^+$ c) (E)-N-(5-{2-[Methyl-(3-methyl-benzo[b]thiophen-2-ylmethyl)carbamoyl]vinyl}pyridin-2-yl)-4(4-methyl-piperazin-1-yl)-4-oxo-butyramide According to the procedure of Example 110 except substituting 3-[6-(2,5-dioxo-pyrrolidin-1-yl)pyridin-3-yl]-N-methyl-N-(3-methyl-benzo[b]thiophen-2-ylmethyl)acrylamide for the (E)-3-[6-(2,5-dioxo-pyrrolidin-1-yl)-pyridin-3-yl]-N-methyl-N-(1-methyl-1H-indol-2-ylmethyl)acrylamide, and substituting 1-methylpiperazine for the ammonia, the title compound (0.53 g, 51%) was prepared as a light yellow solid: $^1$H NMR 300 MHz, DMSO-$d_6$) δ 10.71 (br s, 1H), 8.74-8.61 (m, 1H), 8.22-8.15 (m, 1H), 8.13-8.05 (m, 1H), 7.91-7.85 (m, 1H), 7.78-7.71 (m, 1H), 7.60-7.50 (m, 1H), 7.39-7.33 (m, 3H), 5.15-4.88 (m, 2H), 3.75-3.61 (m, 2H), 3.38-3.28 (m, 3H), 3.19-3.10 (m, 2), 3.05-2.75 (m, 4H), 2.71-2.51 (m, 7H), 2.41 (s, 3H); MS (ESI) m/e 520 (M+H)$^+$.

Example 134

Preparation of (E)-N-(2,3-Diethoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 2,3-diethoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.18 g, 56%) was prepared as an off-white solid: $^1$H NMR (300 MHz, DMSO-$d_6$) δ 10.63-10.49 (m, 1H), 10.14-10.12 (m, 1H), 8.41-8.31 (m, 1H), 8.03-7.91 (m, 1H), 7.52-7.45 (m, 1H), 7.38-7.19 (m, 1H), 7.03-6.90 (m, 2H), 6.70-6.51 (m, 1H), 4.63-4.51 (m, 4H), 4.02-3.91 (m, 6H), 3.81-3.68 (m, 4H), 3.60-3.50 (m, 2H), 3.40-3.28 (m, 2H), 3.20-2.85 (m, 5H), 1.40-1.31 (m, 6H); MS (ESI) m/e 524 (M+H)$^+$.

Example 135

Preparation of (E)-N-(2-Isopropoxy-3-methoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 2-isopropoxy-3-methoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.15 g, 47%) was prepared as an off-white solid: $^1$H NMR (500 MHz, DMSO-$d_6$) δ 10.41-10.21 (m, 1H), 10.13 (br s, 1H), 8.41-8.31 (m, 1H), 8.01-7.93 (m, 1H), 7.51-7.43 (m, 1H), 7.31-7.11 (m, 1H), 7.01-6.91 (m, 2H), 6.70-6.59 (m, 1H), 4.76-4.52 (m, 5H), 4.11-3.85 (m, 7H), 3.84-3.60 (m, 3H), 3.59-3.51 (m, 21), 3.40-3.31 (m, 2H), 3.07-2.86 (m, 4H), 1.23 (m, 6H); MS (ESI) m/e 524 (M+H)$^+$.

Example 136

Preparation of (E)-N-(3-Methoxy-2-propoxy-benzyl)-N-methyl-3-[3-(2-morpholin-4-yl-ethyl)-2-oxo-1,2,3,4-tetrahydro-pyrido[2,3-d]pyrimidin-6-yl]acrylamide hydrochloride According to the procedure of Example 1, except substituting 3-methoxy-2-propoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro- 1H-pyrido[2,3,-e][1,4]diazepin-7-yl)acrylic acid hydrochloride, the title compound (0.10 g, 35%) was prepared as an off-white solid: $^1$H NMR (300 MHz, DMSO-d$_6$) δ 10.68 (br s, 1H), 10.13 (m, 1H), 8.40-8.30 (m, 1H), 8.01-7.90 (m, 1H), 7.60-7.42 (m, 1H), 7.29-7.15 (m, 1H), 7.01-6.90 (m, 2H), 6.70-6.60 (m, 1H), 4.80-4.51 (m, 4H), 4.02-3.70 (m, 10H), 3.60-3.50 (m, 2H), 3.42-3.30 (m, 2H), 3.20-2.87 (m, 6H), 1.74-1.67 (m, 2H), 1.00-0.91 (m, 3H); MS (ESI) m/e 524 (M+H)$^+$.

Example 137

Preparation of (E)-N-Methyl-N-(3-methyl-benzofuran-2-ylmethyl)-3-[3-(2-morpholin-4-yl ethyl)-2-oxo-1,2,3,4-tetrahydro-pyrido[2,3-d]pyrimidin-6-yl] acrylamide hydrochloride According to the procedure of Example 1, except substituting methyl-(3-methyl-benzofuran-2-ylmethyl)amine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.26 g, 91%) was prepared as an off-white solid: $^1$H NMR (500 MHz, DMSO-d$_6$) δ 10.75 (br s, 1H), 10.11 (s, 1H), 8.39 (d, J=7.5 Hz, 1H), 7.99 (t, J=9.0 Hz, 1H), 7.59-7.47 (m, 3H), 7.29-7.17 (m, 3H), 5.01-4.57 (m, 4H), 3.97-3.95 (m, 2H), 3.81-3.71 (m, 4H), 3.60-3.51 (m, 2H), 3.41-3.31 (m, 2H), 3.21-2.91 (m, 5H), 2.26 (s, 3H); MS (ESI) m/e 490 (M+H)$^+$.

Example 138

Preparation of (E)-N-Methyl-N-(2-methyl-benzofuran-3-ylmethyl)-3-[3-(2-morpholin-4-yl-ethyl)-2-oxo-1,2,3,4-tetrahydro-pyrido[2,3-d]pyrimidin-6-yl] acrylamide hydrochloride According to the procedure of Example 1, except substituting methyl-(2-methyl-benzofuran-3-ylmethyl)amine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.17 g, 82%) was prepared as an off-white solid: $^1$H NMR (500 MHz, DMSO-d$_6$) δ 10.70-10.59 (m, 1H), 10.13 (s, 1H), 8.41-8.35 (m, 1H), 8.10-7.99 (m, 1H), 7.58-7.46 (m, 3H), 7.22-7.15 (m, 3H), 5.31-4.93 (m, 2H), 4.72-4.52 (m, 3H), 4.01-3.91 (m, 2H), 3.81-3.71 (m, 4H), 3.60-3.50 (m, 2H), 3.39-3.30 (m, 2H), 3.19-3.01 (m, 4H), 2.51 (s, 3H); MS (ESI) m/e 490 M+H)$^+$.

Example 139

Preparation of (E)-N-(3-Chloro-2-ethoxy-benzyl)-N-methyl-3-[3-(2-morpholin-4yl-ethyl)-2-oxo-1,2,3,4-tetrahydro-pyrido[2,3-d]pyrimidin-6-yl]acrylamide hydrochloride According to the procedure of Example 1, except substituting 3-chloro-2-ethoxy-benzyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.15 g, 60%) was prepared as an off-white solid: $^1$H NMR (500 MHz, DMSO-d$_6$) δ 10.82-10.69 (m, 1H), 10.11-10.09 (m, 1H), 8.41-8.33 (m, 1H), 8.01-7.91 (m, 1H), 7.58-7.48 (m, 1H), 7.47-7.36 (m, 1H), 7.28-7.01 (m, 3H), 4.86-4.68 (m, 2), 4.60-4.51 (m, 2H), 4.07-3.91 (m, 4H), 3.82-3.71 (m, 4H), 3.59-3.49 (m, 2H), 3.40-3.30 (m, 2H), 3.13-2.88 (m, 4H), 1.38 (t, J=7.0 Hz, 3H); MS (ESI) m/e 514 (M+I—)$^+$.

Example 140

Preparation of (E)-N-(4-Fluoro-naphthalen-1-ylmethyl)-N-methyl-3-[3-(2-morpholin-4-yl-ethyl)-2-oxo-1,2,3,4-tetrahydro-pyrido[2,3-d]pyrimidin-6-yl] acrylamide hydrochloride According to the procedure of Example 1, except substituting 4-fluoro-naphthalen-1-ylmethyl-methylamine for the methyl-(1-propyl-naphthalen-2-ylmethyl)amine, and substituting (E)-3-[3-(2-morpholin-4-yl-ethyl)-2-oxo-1,2,3,4-tetrahydro-pyrido[2,3-d]pyrimidin-6-yl]acrylic acid hydrochloride for the (E)-3-(4-methyl-2-oxo-2,3,4,5-tetrahydro-1H-pyrido[2,3,-e][1,4]diazepin-7-yl)acrylic acid hydrochloride, the title compound (0.13 g, 43%) was prepared as an off-white solid: $^1$H NMR (500 MHz, DMSO-d$_6$) δ 10.64-10.51 (m, 1H), 10.12 (m, 1H), 8.45-8.30 (m, 1H), 8.22-8.07 (m, 2H), 8.03-7.86 (m, 1H), 7.78-7.62 (m, 2H), 7.63-7.51 (m, 1H), 7.43 (t, J=7.5 Hz, 1H), 7.32 (t, J=8.6 Hz, 1H), 7.21-7.12 (m, 1H), 5.03-5.02 (m, 2H), 4.57-4.42 (m, 2H), 4.01-3.91 (m, 2H), 3.80-3.63 (m, 4H), 3.53-3.43 (m, 2H), 3.40-3.25 (m, 2H), 3.09-2.96 (m, 5H); MS (ESI) m/e 504 (M+H)$^+$.

Example 141

Preparation of (E)-N-(2,3-Dimethoxy-benzyl)-N-methyl-3-(7-oxo-5,6,7,8-tetrahydro-[1,8]naphthyridin-3-yl)acrylamide According to the procedure of Example 1 (a), except substituting (2,3-dimethoxy-benzyl)methylamine for the methyl-(1-propyl-naphthalen-2-ylmethyl)amine, and substituting (E)-3-(7-oxo-5,6,7,8-tetrahydro-[1,8]naphthyridin-3-yl)acrylic acid hydrochloride for the (E)-3-(4-methyl-2-oxo-2,3,4,5-tetrahydro-1H-pyrido[2,3-e][1,4]diazepin-7-yl) acrylic acid hydrochloride, the title compound (0.362 g, 61%) was prepared as an orange solid and as a mixture of amide rotamers: $^1$H NMR (300 MHz, DMSO-d$_6$) δ 10.67-10.64 (m, 1H), 8.36-8.32 (m, 1H), 8.09-8.02 (m, 1H), 7.52-7.47 (m, 1H), 7.31-7.22 (m, 1H), 7.08-6.95 (m, 2H), 6.69-6.64 (m, 1H), 4.78-4.62 (m, 2H), 3.80 (s, 3H), 3.73 (s, 3H), 3.01-2.85 (m, 5H), 2.56-2.49 (m, 2H); MS (ESI) m/e 382 (M+H)$^+$.

Example 142

Preparation of (E)-3-(6-Amino-5-morpholin-4-ylmethyl-pyridin-3-yl)-N-methyl-N-(1-methyl-1H-indol-3-ylmethyl acrylamide According to the procedure of Example 2(a), except substituting N-methyl-N-(1-methyl-1H-indol-3-ylmethyl)acrylamide for the N-methyl-N-(3-methyl-benzo[b]thiophen-2-ylmethyl)acrylamide, and substituting 5-bromo-3-morpholin-4-ylmethyl-pyridin-2-ylamine for the 7-bromo-3,3-dimethyl-1,3,4,5-tetrahydro-pyrido[2,3-e][1,4]diazepin-2-one, the title compound (510 mg, 38%) was prepared as an off-white powder: ¹H NMR (300 MHz, DMSO-$d_6$) δ 8.13 (s, 1H), 7.78 (s, 1H), 7.63-6.91 (m, 7H), 6.51 (s, 2H), 4.89-4.72 (m, 2H), 3.76 (s, 3H), 3.57 (br s, 4H), 3.42-3.34 (m, 2H), 3.02-2.90 (m, 3H), 2.33 (br s, 4H); MS (ESI) m/e 420 (M+H)⁺.

Example 143

Preparation of (E)-3-(6-Amino-pyridin-3-yl)-N-methyl-N-thieno[3,2-c]pyridin-2-ylmethyl-acrylamide EDC hydrochloride (118 mg, 0.62 mmol) was added to a solution of methyl-thieno[3,2-c]pyridine-2-ylmethyl-amine (100 mg, 0.56 mmol), (–3-(6-amino-pyridin-3-yl)acrylic acid (101 mg, 0.62 mmol), HOBt.H₂O (83 mg, 0.62 mmol) and triethylamine (235 μL, 1.68 mmol) in anhydrous DMF (5 mL). The mixture was stirred at room temperature overnight then diluted with H₂O (10 mL) and extracted with CH₂Cl₂ (3×50 mL). The combined organic fractions were dried over MgSO₄, filtered and evaporated to give a yellow residue which was subjected to flash chromatography on silica gel (10% MeOH: CH₂Cl₂) to yield the title compound (61.0%). ¹H-NMR (300 MHz, CDCl₃) δ 9.04 (s, 1H), 8.45 (d, J=5.3 Hz, 1H), 8.26 (s, 1H), 7.76-7.67 (m, 3H), 7.32 (d, J=15.0 Hz, 1H), 6.76 (d, J=15.2 Hz, 1H), 6.53 (d, J=8.3 Hz, 1H), 4.95 (s, 2H), 4.76 (br s, 2H), 3.22 (s, 3M); MS (ES) m/e 325.1 (M+H)⁺.

Example 144

Preparation of (E)-N-Methyl-3-(4-methyl-2-oxo-2,3,4,5-tetrahydro-1H-pyrido[2,3-e][1,4]diazepin-7-yl)-N-thieno[3,2-c]pyridin-2-ylmethyl-acrylamide EDC hydrochloride (118 mg, 0.62 mmol) was added to a solution of methyl-thieno[3,2-c]priding-2-ylmethyl-amine (100 mg, 0.56 mmol), (E)-3-(4-methyl-2-oxo-2,3,4,5-tetrahydro-1H-pyrido[2,3-e][1,4]diazepin-7-yl)acrylic acid dihydrochloride (198 mg, 0.62 mmol), HOBt.H₂O (83 mg, 0.62 mmol) and triethylamine (470 mL, 3.37 mmol) in anhydrous DMF (7 mL). The mixture was stirred at room temperature overnight; subsequent dilution with H₂O (10 mL) resulted in formation of a precipitate. The precipitate was filtered then subjected to flash chromatography on silica gel (10% MeOH: CH₂Cl₂) to yield the title compound (57.0%). ¹H-NMR (300 MHz, DMSO-$d_6$) a 1:1.8 mixture of amide rotamers δ 10.38 (s, 1H), 9.07 (s, 1H), 8.57 (d, J=2.0 Hz, 1H), 8.39 (d, J=5.6 Hz, 1H), 8.17 (s, 1H), 8.00 (m, 1H), 7.62-7.44 (m, 2H), 7.30 (d, J=15.5 Hz, 1H), 5.19 and 4.91 (2×s, 2H), 3.80 (br s, 2H), 3.45 (br s, 2H), 3.22 and 3.00 (2×s, 3H), 2.38 (s, 3H); MS (ES) m/e 408.4 (M+H)⁺.

Example 145

Preparation of (E)-N-Methyl-3-(7-oxo-5,6,7,8-tetrahydro-[1,8]naphthyridin-3-yl)-N-thieno[3,2-c]pyridin-2-ylmethyl-acrylamide According to the procedure for preparation of Example 144, except substituting (E)-3-(4-methyl-2-oxo-2,3,4,5-tetrahydro-1H-pyrido[2,3-e][1,4]diazepin-7-yl)acrylic acid dihydrochloride for (E)-3-(7-oxo-5,6,7,8-tetrahydro-[1,8]naphthyridin-3-yl)acyclic acid (246 mg, 0.62 mmol), the title compound (18.3%) was obtained as a white solid after purification by flash chromatography on silica gel (10% MeOH: CH₂Cl₂). ¹H-NMR (300 MHz, DMSO-$d_6$) a 1:1.8 mixture of amide rotamers δ 11.05 and 10.67 (2×s, 1H), 9.07 (s, 1H), 8.43-8.38 (m, 2H), 8.12 (d, J=11.7 Hz, 1H), 7.99-7.98 (m, 1H), 7.60-7.20 (m, 3H), 5.17 and 4.90 (2×s, 2H), 3.19 and 3.00 (2×s, 3H), 2.95-2.90 (m, 2H), 2.57-2.51 (m, 2H); MS (ES) m/e 379.4 (M+H)⁺.

Example 146

Preparation of (E)-3-(6-Amino-pyridin-3-yl)-N-(2-ethoxy-3-methoxy-benzyl)-N-methyl-acrylamide hydrochloride EDC (231 mg, 1.2 mmol) was added to a solution of (–3-(6-amino-pyridin-3-yl)acrylic acid (164 mg, 1.0 mmol), (2-ethoxy-3-methoxy-benzyl)methylamine (215 mg, 1.1 mmol), HOBt H₂O (149 mg, 1.1 mmol) and DIPEA (525 μL, 3.0 mmol) in dry DMF (10 mL). After 18 hr of stirring, the mixture was diluted with water (60 mL) and extracted with EtOAc (2×20 mL). The organic layer was washed with brine (2×30 mL), dried and evaporated. Flash chromatography (silica 1-3% MeOH in CH₂Cl₂) furnished pure free base which was dissolved in CH₂Cl₂ (10 mL). After addition of HCl (1.5 mL, 1M in ether), the solvents were evaporated and the residue was washed with ether and dried to afford the title compound (172 mg, 46%). ¹H NMR (300 MHz, DMSO-$d_6$) δ 8.28 (m, 3H), 7.48 and 7.45 (rotamers, 2d, J=15.4 Hz, 1H), 7.25 and 7.23 (rotamers, 2d, J=15.4 Hz, 11H), 7.00 (m, 3H), 6.62 (m, 1H), 4.78 and 4.63 (rotamers, 2s, 2H), 3.98 (m, 2H), 3.79 (s, 3H), 3.08 and 2.84 (rotamers, 2s, 3H), 1.28 (m, 3H). MS (ESI) m/e 342 (M+H)⁺.

Example 147

Preparation of (E)-3-(6-Amino-pyridin-3-yl)-N-(2-pro oxy-3-methoxy-benzyl)-N-methyl acrylamide hydrochloride EDC (231 mg, 1.2 mmol) was added to a solution of (E)-3-(6-amino-pyridin-3-yl)acrylic acid (164 mg, 1.0 mmol), (2-propoxy-3-methoxy-benzyl)methylamine (230 mg, 1.1 mmol), HOBt H₂O (149 mg, 1.1 mmol) and DIPEA (525 μL, 3.0 mmol) in dry DMF (10 mL). After 18 hr of stirring, the mixture was diluted with water (60 mL) and extracted with EtOAc (2×20 mL). The organic layer was washed with brine (2×30 mL), dried and evaporated. Flash chromatography (silica 1-3% MeOH in CH₂Cl₂) furnished pure free base which was dissolved in CH₂Cl₂ (10 mL). After addition of HCl (1.5 mL, 1M in ether), the solvents were evaporated; the residue was washed with ether and dried to afford the title compound (185 mg, 47%). ¹H NMR (300 MHz, DMSO-$d_6$) δ 8.16 (m, 3H), 7.48 and 7.45 (rotamers, 2d, J=15.4 Hz, 1H), 7.23 (d, J=15.4 Hz, 1H), 7.00 (m, 3H), 6.61 (m, 1H), 4.78 and 4.63 (rotamers, 2s, 2H), 3.87 (m, 2H), 3.79 (s, 3H), 3.09 and 2.85 (rotamers, 2s, 3H), 1.71 (m, 2H), 0.97 (m, 3H). MS (ESI) m/e 356 (M+H)⁺.

Example 148

Preparation of (E)-3-(6-amino-pyridin-3-yl)-N-(2-isopropoxy-3-methoxy-benzyl)-N-methyl-acrylamide hydrochloride EDC (231 mg, 1.2 mmol) was added to a solution of (E)-3-(6-amino-pyridin-3-yl)acrylic acid (164 mg, 1.0 mmol), (2-isopropoxy-3-methoxy-benzyl)methylamine (230 mg, 1.1 mmol), HOBt*H₂O (149 mg, 1.1 mmol) and DIPEA (525 μL, 3.0 mmol) in dry DMF (10. L). After 18 hr of stirring, the mixture was diluted with water (60 mL) and extracted with EtOAc (2×20 mL). The organic layer was washed with brine (2×30 mL), dried and evaporated. Flash chromatography (silica 1-3% MeOH in $CH_2Cl_2$) of the residue furnished pure free base which was dissolved in $CH_2Cl_2$ (10 mL). After addition of HCl (1.5 mL, 1M in ether) the solvents were evaporated; the residue was washed with ether and dried to afford the title compound (180 mg, 46%). $^1$H NMR (300 MHz, DMSO-$d_6$) 67 8.31 (m, 3H), 7.46 and 7.45 (rotamers, 2d, J=15.4 Hz, 1H), 7.23 and 7.17 (rotamers, 2d, J=15.4 Hz, 1H), 6.99 (m, 3H), 6.62 (m, 1H), 4.76 and 4.63 (rotamers, 2s, 2H), 4.51 (m, 1H), 3.79 (s, 3H), 3.06 and 2.85 (rotamers, 2s, 3H), 1.22 (d, J=6.1 Hz, 3H) 1.21 (d, J=6.1 Hz, 3H). MS (ESI) m/e 356 (M+H)$^+$.

Example 149

Preparation of (E)-3-(6-amino-pyridin-3-yl)-N-methyl-N-(3-methyl-benzofuran-2-ylmethyl)acrylamide hydrochloride EDC (231 mg, 1.2 mmol) was added to a solution of (E)-3-(6-amino-pyridin-3-yl)acrylic acid (164 mg, 1.0 mmol), methyl-(3-methyl-benzofuran-2-ylmethyl)amine (193 mg, 1.1 mmol), HOBt H$_2$O (149 mg, 1.1 mmol) and DIPEA (525 µL, 3.0 mmol) in dry DMF (10 mL). After 18 hr of stirring, the mixture was diluted with water (60 mL) and extracted with EtOAc (2×20 mL). The oraganic layer was washed with brine (2×30 mL), dried and evaporated. Flash chromatography (silica 1-3% MeOH in $CH_2Cl_2$) of the residue furnished pure free base which was dissolved in $CH_2Cl_2$ (10 mL). After addition of HCl (1.5 mL, 1M in ether), the solvents were evaporated, washed with ether and dried to afford the title compound (195 mg, 54%). $^1$H NMR (300 MHz, DMSO-$d_6$) δ 8.36 (m, 3H), 7.50 (m, 3H), 7.25 (m, 3H), 7.02 (m, 1H), 4.98 and 4.79 (rotamers, 2s, 2H), 3.17 and 2.92 (rotamers, 2s, 3H), 2.26 (s, 3H). MS (ESI) m/e 322 (M+H)$^+$.

Example 150

Preparation of (E)-N-Acenaphthen-5-ylmethyl-3-(6-amino-pyridin-3-yl)-N-methyl-acrylamide hydrochloride To a solution of acenaphthen-5-ylmethyl-methylamine (216 mg, 1.1 mmol), (E)-3-(6-amino-pyridin-3-yl)acrylic acid (164 mg, 1 mmol), HOBt (148 mg, 1.1 mmol) and diisopropylethylamine (0.8 mL, 4.4 mmol) in DMF (20 mL) was added EDC hydrochloride (210 mg, 1.1 mmol). The mixture was stirred overnight at room temperature. Water (100 mL) was added and the solution stirred for 1 hour. The precipitate was collected by filtration. The yellow solid was preabsorded onto silica gel and purified by column chromatography (95:5 $CH_2Cl_2$/MeOH). The residue was dissolved into methylene chloride followed by addition of 1M HCl/ether. The precipitate was collected by filtration to afford (E)-N-acenaphthen-5-ylmethyl-3-(6-amino-pyridin-3-yl)-N-methyl-acrylamide hydrochloride (120 mg, 32%) as a white solid and as a mixture of amide rotomers. $^1$H NMR (300 MHz, DMSO-$d_6$) δ 8.44-8.28 (m, 3H), 7.84-7.72 (m, 1H), 7.59-7.12 (m, 6H), 7.07-6.92 (m, 1H), 5.15-5.02 (2×s, 2H), 3.35-3.15 (bs, 2H), 3.18 (s, 4H), 3.07-2.90 (2×s, 3H); ESI MS m/z 344 [$C_{22}H_{21}N_3O$+H]$^+$.

Example 151

Preparation of (E)-N-(1H-Indol-5-ylmethyl)-N-methyl-3-(4-methyl-2-oxo-2,3,4,5-tetrahydro-1H-pyrido[2,3-e][1,4]diazepin-7-yl)acrylamide To a solution of (1H-indol-5-ylmethyl)methylamine (143 mg, 0.9 mmol), (E)-3-(4-methyl-2-oxo-2,3,4,5-tetrahydro-1H-pyrido[2,3-e][1,4]diazepin-7-yl)acrylic acid dihydrochloride (250 mg, 0.8 mmol), HOBt (121 mg, 0.9 mmol) and diisopropylethylamine (0.61 mL, 3.6 mmol) in DMF (25 mL) was added EDC hydrochloride (172 mg, 0.9 mmol). The mixture was stirred overnight at room temperature. Water (100 mL) was added and the solution was stirred for 1 hr. The precipitate was collected by filtration. The yellow solid was preabsorded onto silica gel and purified by column chromatography (95:5 $CH_2Cl_2$/MeOH) to afford (E)-N-(1H-indol-5-ylmethyl)-N-methyl-3-(4-methyl-2-oxo-2,3,4,5-tetrahydro-1H-pyrido[2,3-e][1,4]diazepin-7-yl)acrylamide (195 mg, 63%) as a white solid and as a mixture of amide rotomers. $^1$H NMR (300 MHz, DMSO-$d_6$) δ 11.07 (d, J=7.6 Hz, 1H), 10.37 (m, 1H), 8.52 (dd, J=7.0, 1.9 Hz, 1H), 8.15 (d, J=2.0 Hz, 1H), 7.59-7.26 (m, 5H), 7.07-6.92 (m, 11H), 6.38 (d, J=1.9 Hz, 1H), 4.66-4.85 (2×s, 2H), 3.74-3.77 (m, 2H), 3.42-3.38 (m, 2H), 3.08-2.90 (2×s, 3H), 2.37-2.32 (2×s, 3H); ESI MS m/z 390 [$C_{22}H_{23}N_5O_2$+H]$^+$.

Example 152

Preparation of (E)-N-Methyl-N-(1-methylindol-5-ylmethyl)-3-(4-methyl-2-oxo-2,3,4,5-tetrahydro-1H-Xyrido[2,3-e][1,4]diazepin-7-yl)acrylamide To a solution of (methyl-(1-methyl-1H-indol-5-ylmethyl)amine (103 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol), HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration.

The yellow solid was preabsorded onto silica gel and purified by column chromatography (95:5 $CH_2Cl_2$/MeOH) to give a yellow oil. Diethyl ether (100 mL) was added and the mixture was sonicated. The ether layer was decanted to afford (E)-N-methyl-N-(1methylindol-5-ylmethyl)-3-(4-methyl-2-oxo-2,3,4,5-tetrahydro-1H-pyrido[2,3-e][1,4]diazepin-7-yl) acrylamide (158 mg, 78%) as a white solid and as a mixture of amide rotomers. $^1$H NMR (300 MHz, DMSO-$d_6$) δ 10.33 (d, J=4.3 Hz, 1H), 8.51 (d, J=6.1 Hz, 1H), 8.13 (s, 1H), 7.59-7.25 (m, 5H), 7.09-7.02 (m, 1H), 6.37 (s 1H), 4.67-4.86 (2×s, 2H), 3.72-3.79 (m, 5H), 3.42-3.38 (m, 2H), 3.06-2.87 (2×s, 3H), 2.37-2.33 (2×s, 3H); ESI MS m/z 404 [$C_{23}H_{25}N_5O_2$+H]$^+$.

Example 153

Preparation of (E)-N-(1H-Indol-7-ylmethyl)-N-methyl-3-(4-methyl-2-oxo-2,34,5-tetrahydro-1H-pyrido[2,3-e][1,4]diazepin-7-yl)acrylamide To a solution of (1H-indol-7-ylmethyl)methylamine (103 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol), HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration and triturated with hexanes to afford (E)-N-(1H-indol-7-ylmethyl)-N-methyl-3-(4-methyl-2-oxo-2,3,4,5-tetrahydro-1H-pyrido[2,3-e][1,4]diazepin-7-yl)acrylamide (155 mg, 79%) as a white solid and as a mixture of amide rotamers. $^1$H NMR (300 MHz, DMSO-d$_6$) δ 10.78-11.23 (m, 1H), 10.34-10.30 (m, 1H), 8.54-8.45 (m, 1H), 8.14-8.00 (m, 1H), 7.64-7.27 (m, 4H), 6.99-6.75 (m, 2H), 6.47-6.45 (m, 1H), 5.10-4.82 (2×s, 2H), 3.79-3.71 (2×s, 2H), 3.42-3.38 (m, 2H), 3.15-2.95 (2×s, 3H), 2.36-2.31 (2×s, 3H); ESI MS m/z 390 [C$_{22}$H$_{23}$N$_5$O$_2$+H]$^+$.

Example 154

Preparation of (E)-N-Methyl-N-(1-methylindol-7-ylmethyl)-3-(4-methyl-2-oxo-2,3,4,5-tetrahydro-1H-pyrido[2,3-e][1,4]diazepin-7-yl)acrylamide To a solution of (methyl-(1-methyl-1H-indol-7-ylmethyl) amine (103 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol), HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration and triturated with hexanes to afford (E)-N-methyl-N-(1-methylindol-7-ylmethyl)-3-(4-methyl-2-oxo-2,3,4,5-tetrahydro-1H-pyrido[2,3-e][1,4]diazepin-7-yl)acrylamide (100 mg, 50%) as a white solid and as a mixture of amide rotamers. $^1$H NMR (300 MHz, DMSO-d$_6$) δ 10.33 (m, 1H), 8.54-8.47 (m, 1H), 8.16-7.97 (m, 1H), 7.62-7.19 (m, 4H), 6.92-6.97 (m, 1H), 6.78-6.58 (m, 1H), 6.39 (d, J=3.1 Hz, 1H) 5.48-5.19 (2×s, 2H), 3.99-4.11 (2×s, 3H), 3.79-3.70 (2×s, 2H), 3.42-3.36 (m, 2H), 3.30-3.13 (2×s, 3H), 2.36-2.30 (2×s, 3H); ESI MS m/z 404 [C$_{23}$H$_{25}$N$_5$O$_2$+H]$^+$.

Example 155

Preparation of (E)-N-(1H-Indol-6-ylmethyl)-N-methyl-3-(4-methyl-2-oxo-2,3,4,5-tetrahydro-1H-pyrido[2,3-e][1,4]diazepin-7-yl)acrylamide To a solution of (1H-indol-6-ylmethyl)methylamine (98 mg, 0.6 mmol), (E)-3-(4-methyl-2-oxo-2,3,4,5-tetrahydro-1H-pyrido[2,3-e][1,4]diazepin-7-yl)acrylic acid dihydrochloride (160 mg, 0.5 mmol) HOBt (81 mg, 0.5 mmol) and diisopropylethylamine (0.41 mL, 2 mmol) in DMF (12 mL) was added EDC hydrochloride (114 mg, 0.6 mmol). The mixture was stirred overnight at room temperature. Water (75 mL) was added and the solution stirred for 1 hr. The precipitate was collected by filtration and triturated with hexanes to afford (E)-N-(1H-indol-6-ylmethyl)-N-methyl-3-(4-methyl-2-oxo-2,3,4,5-tetrahydro-1H-pyrido[2,3-e][1,4]diazepin-7-yl)acrylamide (89 mg, 37%) as a white solid and as a mixture of amide rotamers. $^1$H NMR (300 MHz, DMSO-d$_6$) δ 11.03-11.01 (m, 1H), 10.33-10.30 (m, 1H), 8.52 (d, J=7.6 Hz, 1H), 8.13 (d, J=2.4 Hz, 1H), 7.60-7.22 (m, 5H), 6.92-6.86 (m, 1H), 6.37 (s, 1H), 4.88-4.68 (2×s, 2H), 3.78-3.74 (m, 2H), 3.08-2.89 (2×s, 3H), 2.36-2.33 (2×s, 3H); ESI MS m/z 390 [C$_{22}$H$_{23}$N$_5$O$_2$+H]$^+$.

Example 156

(E)-N-3-(6-Amino-pyridin-3-yl)-N-methyl-N-(2-methyl-benzofuran-3-ylmethyl)-acrylamide hydrochloride To a solution of methyl-(2-methylbenzofuran-3-ylmethyl)-amine (176 mg, 1.0 mmol), 3-(6-amino-pyridin-3-yl)-acrylic acid (150 mg, 0.91 mmol), HOBt (135 mg, 1.0 mmol) and diisopropylethylamine (0.46 mL, 2.7 mmol) in DMF (10 mL) was added EDC (209 mg, 1.1 mmol). The yellow solution was stirred overnight at room temperature. The reaction mixture was cooled to 0° C. then treated with H$_2$O (40 mL) to form a precipitate. The precipitate was filtered, washed with H$_2$O (20 mL) then with a 10% EtOAc:hexanes solution (10 mL). The solid was dissolved in a 10% MeOH:CH$_2$Cl$_2$ solution (20 mL), cooled to 0° C. then treated with 2 mL of a 1.0 M HCl in Et$_2$O. After stirring for 10 minutes, the yellow solution was concentrated to dryness then triturated with Et$_2$O (20 mL). The title compound was collected and dried under vacuo to yield the title compound (76.9%) as a mixture of amide rotamers. $^1$H NMR (300 MHz, DMSO-d$_6$) δ 8.41-8.33 (m, 3H), 7.58-7.02 (m, 6H), 4.93 and 4.74 (2×s, 2H), 3.05 and 2.82(2×s, 3H), 2.53 and 2.48 (2×s, 3H); MS (ESI) m/e 322 (M+H)$^+$.

Example 157

Preparation of (E)-3-(3,3-Dimethyl-2-oxo-2,3,4,5-tetrahydro-1H-pyrido[2,3-e][1,4]diazepin-7-yl)-N-methyl-N-(3-methyl-benzofuran-2-ylmethyl)acrylamide hydrochloride a) N-Methyl-N-(3-methyl-benzofuran-2-ylmethyl)acrylamide According to the procedure of Preparation 65, except substituting methyl-(3-methyl-benzofuran-2-ylmethyl)amine for the methyl-(3-methyl-benzo[b]thiophen-2-ylmethyl) amine, the title compound (0.95 g, 73%) was prepared as an white solid: $^1$H NMR (300 MHz, CDCl$_3$) δ 7.50-7.47 (m, 1H), 7.42-7.39 (m, 1H), 7.30-7.17 (m, 2H), 6.90-6.55 (m, 1H), 6.41-6.35 (m, 1H), 5.79-5.70 (m, 1H), 4.78-4.64 (m, 2H), 3.14-3.02 (m, 3H), 2.29-2.62 (m, 3H).

b) (E)-3-(3,3-Dimethyl-2-oxo-2,3,4,5-tetrahydro-1H-pyrido [2,3-e][1,4]diazepin-7-yl)-N-methyl-N-(3-methyl-benzofuran-2-ylmethyl)acrylamide According to the procedure of Example 2, except substituting N-methyl-N-(3-methyl-benzofuran-2-ylmethyl)acrylamide for the N-methyl-N-(3-methyl-benzo[b]thiophen-2-ylmethyl)acrylamide, the title compound (0.25 g, 60%) was prepared as a white solid and as a mixture of amide rotamers: $^1$H NMR (300 MHz, DMSO-d$_6$) δ 10.92 (s, 1H), 10.55 (br s, 2H), 8.68-8.65 (m, 1H), 8.39 (s, 1H), 7.60-7.24 (m, 6H), 5.01-4.81 (m, 2H), 4.40 (s, 2H), 3.20-2.93 (m, 3H), 2.27 (s, 3H), 1.63 (s, 6H); MS (ESI) m/e 419 (M+H)$^+$.

Example 158

Preparation of (E)-N-Methyl-N-(3-methyl-1H-inden-2-ylmethyl)-3-(4-methyl-2-oxo-2,3,4,5-tetrahydro-1H-pyrido[2,3-e][1,4]diazepin-7-yl)acrylamide hydrochloride According to the procedure of Example 1, except substituting methyl-(3-methyl-1H-inden-2ylmethyl)amine (0.237 g, 1.37 mmol) for methyl-(1-propyl-naphthalen-2ylmethyl) amine, the title compound (0.303 g, 60%) was prepared as light yellow solid and as a mixture of amide rotamers: $^1$H NMR (300 MHz, DMSO-d$_6$) δ 12.32 (br s, 1H), 11.21 (br s, 1H), 8.82-8.81 (m, 1H), 8.34 (s, 1H), 7.61-7.25 (m, 5H), 7.17-7.12 (m, 1H), 4.67-4.51 (m, 2H), 4.29 (br s, 2H), 3.80 (br s, 2H), 3.28-3.26 (m, 2H), 3.12-2.87 (m, 6H), 2.16-2.14 (m, 3H); MS (ESI) m/e 403 (M+H)$^+$.

Example 159

Preparation of (E)-3-(6-{2-[Methyl-(3-methyl-benzo[b]thiophen-2-ylmethyl)carbamoyl]vinyl}-2-oxo-1,4-dihydro-2H-pyrido[2,3-d]pyrimidin-3-yl)propionic acid ethyl ester According to the procedure of Example 2, except substituting 3-(6-bromo-2-oxo-1,4-dihydro-2H-pyrido[2,3-d]pyrimidin-3-yl)propionic acid ethyl ester for the 7-bromo-3,3-dimethyl-1,3,4,5-tetrahydro-pyrido[2,3-e][1,4]diazepin-2-one, the title compound (0.40 g, 38%) quantitative) was prepared as an off-white solid and as a mixture of amide rotamers: $^1$H NMR (300 MHz, DMSO-d$_6$) δ 9.97 (s, 1H), 8.36 (s, 1H), 8.00 (s, 1H), 7.87 (d, J=7.5 Hz, 1H), 7.73 (d, J=7.8 Hz, 1H), 7.55-7.50 (m, 1H), 7.41-7.31 (m, 3H), 7.19-7.14 (m, 1H), 5.10-4.88 (m, 2H), 4.50 (s, 2H), 4.08-4.01 (m, 2H), 3.55-3.46 (m, 2H), 3.15-2.93 (m, 3H), 2.62-2.58 (t, J=6.6 Hz, 2H), 2.41 (s, 3H), 1.23-1.03 (m, 3H); MS (ESI) m/e 493 (M+H)$^+$.

Example 160

Preparation of (E)-3-(6-amino-5-cyano-pyridin-3-yl)-N-methyl-N-(1-methyl-1H-indol-2-ylmethyl)-acrylamide hydrochloroide:

a) 2-amino-5-bromo-nicotinonitrile

Bromine (1.1 mL, 21 mmol) in AcOH (3 mL) was added dropwise to a solution of 2-amino-nicotinonitrile (1.00 g, 8.4 mmol) in AcOH (20 mL) at 10° C. The orange mixture was stirred for 22 hours at ambient temperature then diluted with ether (100 mL). The resultant precipitated salt was filtered, washed with ether and dried on air. The precipitate was suspended in water (100 mL), neutralized with 1N NaOH, filtered, washed with water and dried on air to give 1.29 g (78%) title compound. $^1$H NMR (300 MHz, DMSO-d$_6$) δ 8.27 (d, J=2.5 Hz, 1H), 8.14 (d, J=2.5 Hz, 1H), 7.13 (s, br, 2H). MS (ESI) m/e: 197.965 (M+H)$^+$.

b) N-methyl-N-(1-methyl-1H-indol-2-ylmethyl)-acrylamide

Acryloyl chloride (5.13 mL, 63.1 mmol) was added dropwise to a stirred CH$_2$Cl$_2$ (100 mL) solution of methyl-(1-methyl-1H-indol-2-ylmethyl)-amine (10.0 g, 57.4 mmol) and triethylamine (12 mL, 86.1 mmol) at −78° C. The reaction mixture was warmed to −30° C. over 30 min and quenched with water. The reaction mixture was diluted with CH$_2$Cl$_2$ (100 mL), washed with dilute NaHCO$_3$, HCl and water, dried and evaporated to afford 9.91 g (76%) title compound. $^1$H NMR (300 MHz, DMSO-d$_6$) 87.44 (m, 2H), 7.12 (t, J=7.2 Hz, 1H—), 7.00 (t, J=7.2 Hz, 1H), 6.81 (dd, J=7.4 and 16.7 Hz, 1H), 6.40 and 6.14 (rotamers, 2s, 1H), 6.20 (dd, J=2.5 and 16.7 Hz, 1H), 5.7 (m, 1H), 4.90 and 4.80 (rotamers, 2s, 2H), 3.68 and 3.66 (rotamers, 2s, 3H), 3.00 and 2.96 (rotamers, 2s, 3H). MS (ESI) m/e: 229.1 (M+H).

c) (E)-3-(6-amino-5-cyano-pyridin-3-yl)-N-methyl-N-(1-methyl-1H-indol-2-ylmethyl)-acryl-amide hydrochloride A propionitrile (15 mL) solution of 2-amino-5-bromo-nicotinonitrile (198 mg, 1 mmol), N-methyl-N-(1-methyl-1H-indol-2-ylmethyl)-acrylamide (457 mg, 2 mmol) and diisopropyl-ethylamine (523 μL, 3 mmol) was purged with Argon for 10 min. Pd(OAc)$_2$ (23 mg, 0.1 mmol) and P(o-Tol)$_3$ (61 mg, 0.2 mmol) was added and the Argon purge was repeated. The mixture was heated to 100° C. and stirred for 6 hr under Argon. Upon cooling, solvents were removed under vacuo and the residue was purified by Flash chromatography (silica, 2% MeOH in CH$_2$Cl$_2$). The purified free base was converted to its HCl salt by addition of HCl (1 mL, 1 mmol, IM in ether). The salt was washed with ether and dried to afford 162 mg (43%) of the title compound. $^1$H NMR (300 MHz, DMSO-d$_6$) δ 8.50 (m, 2H), 7.55-6.95 (m, 4H), 6.40 and 6.17 (rotamers, 2s, 1H), 5.03 and 4.83 (rotamers, 2s, 2H), 3.71 and 3.67 (rotamers, 2s, 3H), 3.09 and 2.96 (rotamers, 2s, 3H). MS (ESI) m/e: 346.1662 (M+H)$^+$.

Example 161

Preparation of (E)-N-methyl-N-(1-methyl-1H-indol-2-ylmethyl)-3-(2-oxo-1,2,3,4-tetrahydro-pyrido-[2,3-b]pyrazin-7-yl)-acrylamide a) 7-bromo-3,4-dihydro-1H-pyrido[2,3-b]pyrazin-2-one A mixture of 5-bromo-2,3-diaminopyridine (11.64 g, 61.9 mmol) and glyoxylic acid monohydrate (22.80 g, 247.7 mmol) in MeOH (200 mL) was stirred for 62 hours. The precipitate was filtered, washed with MeOH and dried at 110° C. to give 12.60 g (90%) of a regioisomeric mixture of the condensation products. The mixture (4.52 g, 20 mmol) was suspended in DME (300 mL) and, after addition of NaBH(OAc)$_3$ (11.87 g, 56 mmol), it was stirred for 88 hours at 60° C. Upon cooling, EtOAc (500 mL) and water (300 mL) was added and the pH was adjusted to 8.0 with 2N NaOH. The aqueous phase was separated and extracted with EtOAc (2×200 mL). The combined organic phases were washed with water and brine, dried and evaporated. The residue was stirred with CH$_2$Cl$_2$ (50 mL) for 24 hr then filtered. The solid cake was stirred with EtOAc (100 mL) at 75° C. for 14 hours, filtered and dried to afford the title compound (2.35 g, 52%). $^1$H NMR (300 MHz, DMSO-d$_6$) δ 10.47 (s, br, 1H), 7.65 (d, J=2.2 Hz, 1H), 7.01 (t, J=2.2 Hz, 1H), 6.99 (s, br, 1H), 3.93 (d, J=1.5 Hz, 2H). MS (ESI) m/e: 227.9764 (M+H)$^+$.

b) 7-bromo-2-oxo-2,3-dihydro-1H-pyrido[2,3-b]pyrazine-4-carboxylic acid tert-butyl ester Boc$_2$O (3.23 g, 14.8 mmol) was added to a stirred MeCN (120 mL) suspension containing 7-bromo-3,4-dihydro-1H-pyrido[2,3-b]pyrazin-2-one (2.25 g, 9.85 mmol), triethylamine (4.12 mL, 29.6 mmol) and N,N-dimethylaminopyridine (120 mg, 1 mmol). After 24 hr stirring, additional Boc$_2$O (3.23 g, 14.8 mmol) was added and the stirring was continued for 2 days. The solvent was removed in vacuo and the residue was purified by Flash Chromatography (silica, 1-2% MeOH in CH$_2$Cl$_2$) to afford the title compound (499 mg, 16%). $^1$H NMR (300 MHz, DMSO-d$_6$) δ 10.82 (s, br, 1H), 8.16 (d, J=2.3 Hz, 1H), 7.45 (t, J=2.3 Hz, 1H), 4.30 (s, 2H), 1.44 (s, 9H). MS (ESI) m/e: 328.0 (M+H)$^+$, 272.0 (M-tert-Bu)$^+$.

c) (E)-7-{2-[methyl-(1-methyl-1H-indol-2-ylmethyl)-carbamoyl]-vinyl}-2-oxo-2,3-dihydro-1H-pyrido[2,3-b]pyrazine-4-carboxylic acid tert-butyl ester A solution of 7-bromo-2-oxo-2,3-dihydro-1H-pyrido[2,3-b]pyrazine-4-carboxylic acid tert-butyl ester (494 mg, 1.5 mmol) in propionitrile (12 mL) was treated with N-methyl-N-(1-methyl-1H-indol-2-ylmethyl)-acrylamide (685 mg, 3 mmol) and diisopropylethylamine (788 μL, 4.5 mmol) and purged with Argon for 10 min. Pd(OAc)$_2$ (34 mg, 0.15 mmol) and P(o-Tol)$_3$ (92 mg, 0.3 mmol) was added and the Argon purge was repeated. The mixture was heated to 100° C. and stirred for 6 hours under Argon. Upon cooling, solvent was removed and the residue was purified by Flash chromatography (silica, 1-3% MeOH in CH$_2$Cl$_2$) to afford the title compound (480 mg, 67%). $^1$H NMR (300 MHz, DMSO-d$_6$) δ 10.81 and 10.73 (rotamers, 2s, br, 1H), 8.46 and 8.41 (rotamers, 2s, 1H), 7.58 (d, J=15.4 Hz, 1H), 7.51 (m, 3H), 7.23 (d, J=15.4 Hz, 1H), 7.11 (m, 1H), 7.03 (m, 1H), 6.45 and 6.20 (rotamers, 2s, 1H), 5.06 and 4.87 (rotamers, 2s, 2H), 4.32 and 4.28 (rotamers, 2s, 2H), 3.74 and 3.71 (rotamers, 2s, 3H), 3.16 and 3.05 (rotamers, 2s, 3H), 1.44 and 1.42 (rotamers, 2s, 9H). MS (ESI) in/e: 476.2 (M+H)$^+$, 420.2 (M-tert-Bu)$^+$.

d) (E)-N-methyl-N-(1-methyl-1H-indol-2-ylmethyl)-3-(2-oxo-1,2,3,4-tetrahydro-pyrido[2,3-b]pyrazin-7-yl)-acrylamide Trifluoroacetic acid (0.5 mL) was added to a solution of (E)-7-{2-[methyl-(1-methyl-1H-indol-2-ylmethyl)-carbamoyl]-vinyl}-2-oxo-2,3-dihydro-1H-pyrido[2,3-b]pyrazine-4-carboxylic acid tert-butyl ester in CH$_2$Cl$_2$ (1 mL) at 10° C. After stirring 1 hr, volatiles were removed in vacuo and the resulting residue was dissolved in EtOAc (2 mL). Upon addition of dilute NaOH, a precipitate formed. The solid was collected by filtration, washed with water (100 mL), MeOH (50 mL), EtOAc (50 mL) and CH$_2$Cl$_2$ (50 mL) to afford the title compound (170 mg). $^1$H NMR (300 MHz, DMSO-d$_6$) δ 10.42 and 10.33 (rotamers, 2s, br, 1H), 7.90 (m, 1H), 7.45 (m, 3H), 7.22 (m, 1H), 7.12 (m, 1H), 6.83 (d, J=15.4 Hz, 1H), 6.42 and 6.17 (rotamers, 2s, 1H), 4.98 and 4.84 (rotamers, 2s, 2H), 3.99 and 3.95 (rotamers, 2s, 2H), 3.72 and 3.68 (rotamers, 2s, 3H), 3.07 and 3.00 (rotamers, 2s, 3H). MS (ESI) m/e: 376 (M+H)$^+$.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

Heath, et al. *Nature* 406: 145 2000; Bergler, et al, 1994, *J. Biol. Chem.* 269, 5493-5496; Heath, et al, 1996, *J. Biol. Chem.* 271, 1833-1836; Grassberger, et al, 1984 *J. Med Chem* 27 947-953; Turnowsky, et al, 1989, *J. Bacteriol.*, 171, 6555-6565; McMurry, et al, 1998 *Nature* 394, 531-532; Levy, et al, 1999 *Nature* 398, 383-384; Ward, et al, 1999 *Biochem.* 38, 12514-12525; Heck, *Org. Reactions* 1982, 27, 345; *J. Het. Chem.* 1978, 15, 249-251; Morb. Mortal Wkly Rep. 1998; 46:71-80; Standards, N.C.f.C.L., Methods for Dilution Antimicrobial Susceptibility Tests for Bacteria that Grow Aerobically; Approved Standard—Fifth Edition. 2000; Baxter, D. F., et al., A novel membrane potential-sensitive fluorescent dye improves cell-based assays for ion channels. J Biomol Screen, 2002 7(1): p. 79-85; Ahmed, S. A., R. M. Gogal, Jr., and J. E. Walsh, A new rapid and simple non-radioactive assay to monitor and determine the proliferation of lymphocytes: an alternative to [3H]thymidine incorporation assay. J Immunol Methods, 1994 170(2): p. 211-24; http://bbrp.llnl.gov/bbrp/html/microbe.html; http://artedi.ebc.uu.se/Projects/Francisella/; U.S. patent application Ser. Nos. 08/790,043; 10/009,219, 10/089,019; 09/968,129; 09/968,123; 09/968, 236; 09/959,172; 09/979,560; 09/980,369; 10/089,755; 10/089,739; 10/089,740; PCT Application Nos. WO 0027628; WO 0210332; U.S. Provisional Application Nos. 60/431,406; 60/465,583; U.S. Pat. Nos. 6,531,126; 6,527,759; 6,518,270; 6,518,239; 6,517,827; 6,461,829; 6,448,054; 6,423,341; 6,495,551; 6,486,149; 6,441,162; 6,436,980; 6,399,629; 6,518,263; 6,503,881; 6,503,881; 6,486,148; 6,465,429; 6,388,070; 6,531,649; 6,531,465; 6,528,089; 6,521,408; 6,518,487; 6,531,508; 6,514,962; 6,503,953; 6,492,351; 6,486,148; 6,461,607; 6,448,054; 6,495,161; 6,495,158; 6,492,351; 6,486,165; 6,531,465; 6,514,535; 6,489,318; 6,497,886; 6,503,953; 6,503,539; 6,500,459; 6,492,351; 6,500,463; 6,461,829; 6,448,238; 6,432,444; 6,333,045; 6,291,462; 6,221,859; 6,514,986; 6,340,689; 6,309,663; 6,303,572; 6,277,836; 6,367,985; 6,468,964; 6,461,607; 6,448,449; 6,436,980; 6,423,741; 6,406,880; 6,395,746; 6,346,391; 6,294,192; 6,267,985; 6,235,908; 6,515,113; 6,509,327; 6,503,955; 6,525,066; 6,531,291; 6,517,827; 6,514,953; 6,514,541; 6,428,579; 6,451,339; 6,461,607; 6,461,829; 6,503,906; 6,518,239; 6,133,260; 6,174,878; 6,184,380; 6,187,341; 6,194,429; 6,194,441; 6,198,000; 6,221,859; 6,221,864; 6,239,113; 6,239,141; and 6,248,363.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound of formula I:

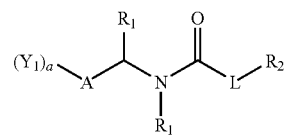

I wherein, independently for each occurrence,

L is a bond or L is alkyl, alkenyl, or cycloalkyl which may be substituted with one or more R$_1$;

A is a monocyclic ring of 4-7 atoms containing 0-2 heteroatoms, a bicyclic ring of 8-12 atoms containing 0-4 heteroatoms or a tricyclic ring of 12-16 atoms containing 0-6 heteroatoms wherein the rings are independently aliphatic, aromatic, heteroaryl, or heterocyclic; wherein the heteroatoms selected from N, S, and O, and wherein the rings are optionally substituted with one or more groups selected from C$_{1-4}$ alkyl, CH$_2$OH, OR", SR", CN, N(R")$_2$, CH$_2$N(R")$_2$, NO$_2$, CF$_3$, CO$_2$R", CON(R")$_2$, COR", NR"C(0)R", F, Cl, Br, I and —S(O)$_r$CF$_3$, wherein R" is H, alkyl or alkaryl;

R₁ is, independently for each occurrence, H, alkyl, cycloalkyl, aryl, or alkaryl;

R₂ is

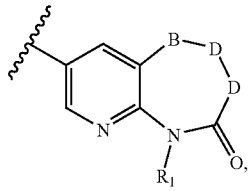

wherein the B adjacent to the D moiety, is selected from the group consisting of: C(R₁)₂ or C=O;

D is, independently for each occurrence, selected from the group consisting of:

C(R₁)₂, NR₁, C=O,

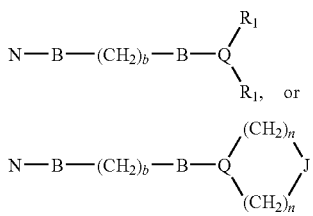

providing that the two Ds are different, and wherein for D, B is selected from the group consisting of a bond, C(R₁)₂ or C=O;

J is selected from the group consisting of NR₁, CH₂, CH₂CH₂, or O;

Q is N or CH;

r is 0, 1, or 2;

b is an integer from 0-4;

a is 0;

n is an integer from 0 to 4;

or a pharmaceutically acceptable salt thereof.

2. The compound of claim 1, wherein L is a C₂ alkenyl.

3. The compound of claim 1, wherein L is a C₂ alkenyl and R₂ is

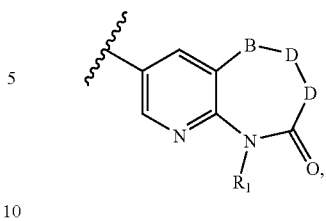

wherein R₁ is H.

4. The compound of claim 1, wherein L is a C₂ alkenyl and R₂ is

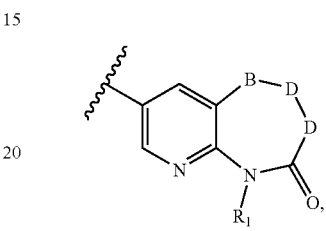

wherein R₁ is H and the D adjacent to B is NR₁.

5. The compound of claim 1, wherein A is a 9 membered bicyclic heteroaryl.

6. The compound of claim 1, wherein A comprises at least 1 heteroatom.

7. The compound of claim 1, wherein A comprises at least 1 oxygen atom.

8. A pharmaceutical composition comprising a compound of claim 1 and a pharmaceutically acceptable carrier or excipient.

9. The composition of claim 8, wherein the pharmaceutically acceptable carrier is suitable for intraveneous or injectable administration.

10. A tablet comprising the composition of claim 8.

11. The compound of claim 4, wherein B is CH₂.

12. The compound of claim 11, wherein A comprises a nine-membered bicyclic heteroaryl comprising at least one O.

13. The compound (E)-3-(3,3-Dimethyl-2-oxo-2,3,4,5-tetrahydro-1H-pyrido [2,3-e][1,4]diazepin-7-yl)-N-methyl-N-(3-methyl-benzofuran-2-ylmethyl)acrylamide, or pharmaceutically acceptable salts thereof.

14. A pharmaceutically acceptable composition comprising the compound of claim 13, and a pharmaceutically acceptable carrier.

* * * * *